(12) United States Patent
Crew et al.

(10) Patent No.: US 8,481,733 B2
(45) Date of Patent: Jul. 9, 2013

(54) SUBSTITUTED IMIDAZOPYR- AND IMIDAZOTRI-AZINES

(75) Inventors: Andrew P. Crew, North Babylon, NY (US); Meizhong Jin, Dix Hills, NY (US); Mridula Kadalbajoo, Farmingdale, NY (US); Andrew Kleinberg, East Meadow, NY (US); Mark J. Mulvihill, East Northport, NY (US); Jing Wang, Syosset, NY (US)

(73) Assignee: OSI Pharmaceuticals, LLC, Farmingdale, NY (US)

( * ) Notice: Subject to any disclaimer, the term of this patent is extended or adjusted under 35 U.S.C. 154(b) by 521 days.

(21) Appl. No.: 12/468,188

(22) Filed: May 19, 2009

(65) Prior Publication Data

US 2009/0286768 A1  Nov. 19, 2009

Related U.S. Application Data

(60) Provisional application No. 61/054,345, filed on May 19, 2008.

(51) Int. Cl.
    *C07D 487/04*  (2006.01)
    *C07D 403/04*  (2006.01)
    *A61K 31/4985* (2006.01)
    *A61P 11/06*   (2006.01)

(52) U.S. Cl.
    USPC ......................................... 544/350; 514/249

(58) Field of Classification Search
    USPC .................................. 544/350, 359; 514/249
    See application file for complete search history.

(56) References Cited

U.S. PATENT DOCUMENTS

| | | | |
|---|---|---|---|
| 5,217,999 A | 6/1993 | Levitzki | |
| 5,302,606 A | 4/1994 | Spada | |
| 5,397,787 A | 3/1995 | Buzzetti | |
| 5,556,874 A | 9/1996 | Dobrusin | |
| 6,194,439 B1 | 2/2001 | Dow | |
| 6,265,411 B1 | 7/2001 | Thomas | |
| 6,337,338 B1 | 1/2002 | Kozlowski | |
| 6,362,336 B1 | 3/2002 | Lohmann | |
| 6,486,179 B2 | 11/2002 | Jirousek | |
| 6,939,874 B2 | 9/2005 | Harmange | |
| 7,087,602 B2 | 8/2006 | Thomas | |
| 7,087,613 B2 | 8/2006 | Norris | |
| 7,115,617 B2 | 10/2006 | Buchanan | |
| 7,202,243 B2 | 4/2007 | Hendrix | |
| 7,244,733 B2 | 7/2007 | Hunt et al. | |
| 7,271,262 B2 | 9/2007 | La Greca et al. | |
| 7,326,699 B2 | 2/2008 | Capraro | |
| 7,332,497 B2 | 2/2008 | Hirst | |
| 7,345,038 B2 | 3/2008 | Bright | |
| 7,514,444 B2 * | 4/2009 | Honigberg et al. | 514/263.22 |
| 7,534,797 B2 * | 5/2009 | Arnold et al. | 514/255.05 |
| 7,651,687 B2 * | 1/2010 | Buck et al. | 424/130.1 |
| 7,700,594 B2 * | 4/2010 | Chen et al. | 514/243 |
| 7,772,231 B2 * | 8/2010 | Sheppard et al. | 514/234.2 |
| 7,820,662 B2 * | 10/2010 | Arnold et al. | 514/243 |
| 2002/0076408 A1 | 6/2002 | Buchsbaum | |
| 2003/0108545 A1 | 6/2003 | Rockwell | |
| 2003/0114467 A1 | 6/2003 | Shakespeare | |
| 2003/0144252 A1 | 7/2003 | Furr | |
| 2003/0153752 A1 | 8/2003 | Hirst | |
| 2003/0157104 A1 | 8/2003 | Waksal | |
| 2003/0175763 A1 | 9/2003 | Degenhardt | |
| 2004/0014774 A1 | 1/2004 | Myers | |
| 2004/0052785 A1 | 3/2004 | Goodman | |
| 2004/0057950 A1 | 3/2004 | Waksal | |
| 2004/0106605 A1 | 6/2004 | Carboni | |
| 2004/0180911 A1 | 9/2004 | Capraro | |
| 2004/0220189 A1 | 11/2004 | Sun | |
| 2005/0032759 A1 | 2/2005 | Massimini | |
| 2005/0037999 A1 | 2/2005 | La Greca | |
| 2005/0054638 A1 | 3/2005 | Barlaam | |
| 2005/0153966 A1 | 7/2005 | Gangloff | |
| 2005/0215530 A1 | 9/2005 | Ryan | |
| 2005/0215564 A1 | 9/2005 | Stiles | |
| 2005/0271747 A1 | 12/2005 | Higgins | |
| 2006/0019957 A1 | 1/2006 | Crew | |

(Continued)

FOREIGN PATENT DOCUMENTS

WO  97/28161 A1  8/1997
WO  01/12227 A1  2/2001

(Continued)

OTHER PUBLICATIONS

Akio et al (1995), Abstract of JP 07133280.
Akio, et al. (1995) Machine English Translation of JP 071333280.
Adachi, et al. (2004) CAS Accession #2005:366557, corresponding to Novartis Foundation Symposium 262 (biology of IGF-1), 177-192.
Albert, A. et al. (1970) Journal of the Chemical Society, vol. 11, pp. 1540-1547.
Albert, A. et al. (1969) Chem. Biol. Pterdines.Proc.Int.Symp., 4th, 4:1-5.
Arteaga, C.L. and Johnson, D.H. (2001) Current Opinion Oncol. 13:491-498.
Baserga R. (1999) Exp.Cell.Res, vol. 253, pp. 1-6.

(Continued)

*Primary Examiner* — Venkataraman Balasubramanian
(74) *Attorney, Agent, or Firm* — Frank W. Forman; Astellas US LLC

(57) ABSTRACT

Fused pyridine-based bicyclic compounds having the structure of Formula I, as defined herein, pharmaceutically acceptable salts thereof, preparation, compositions, and disease treatment therewith. This abstract does not define or limit the invention.

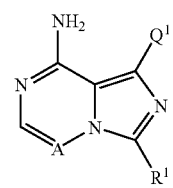

16 Claims, No Drawings

U.S. PATENT DOCUMENTS

| | | | |
|---|---|---|---|
| 2006/0046977 A1 | 3/2006 | Nunes | |
| 2006/0069084 A1 | 3/2006 | Burns | |
| 2006/0084654 A1 | 4/2006 | Beck | |
| 2006/0154982 A1 | 7/2006 | Larsson | |
| 2006/0166992 A1 | 7/2006 | Hendrix | |
| 2006/0235031 A1 | 10/2006 | Arnold | |
| 2007/0087613 A1 | 4/2007 | Schumacher | |
| 2007/0112005 A1* | 5/2007 | Chen et al. | 514/243 |
| 2007/0149521 A1 | 6/2007 | Crew | |
| 2007/0202101 A1 | 8/2007 | Rosen | |
| 2007/0203143 A1* | 8/2007 | Sheppard et al. | 514/243 |
| 2007/0238734 A1 | 10/2007 | Nemecek | |
| 2007/0280928 A1* | 12/2007 | Buck et al. | 424/130.1 |
| 2008/0014200 A1 | 1/2008 | Arnold | |
| 2008/0076921 A1* | 3/2008 | Honigberg et al. | 544/184 |
| 2008/0139582 A1 | 6/2008 | Honigberg | |
| 2008/0267957 A1 | 10/2008 | Arnold | |

FOREIGN PATENT DOCUMENTS

| | | |
|---|---|---|
| WO | 01/72751 A1 | 10/2001 |
| WO | 02/79192 A1 | 10/2002 |
| WO | 03/080064 A1 | 10/2003 |
| WO | 2006004703 A2 | 1/2006 |
| WO | 2007079164 A2 | 6/2007 |
| WO | 2007/075554 A2 | 7/2007 |
| WO | 2008/076143 A1 | 6/2008 |
| WO | 2008/106168 A1 | 9/2008 |

OTHER PUBLICATIONS

Bertino J. R. et al., Cecil Textbook of Medicine, XIV Oncology 198, pp. 1060-1074.
"Bevacizumab and Gemcitabine Combined with either Cetuximab or Erlotinib in Treating Patients with Advanced Pancreatic Cancer" Internet Citation, [Online] Sep. 7, 2004, XP002410261. Retrieved from the Internet: URL: http://www.clinicaltrials.gov/ct/gui/show/NCT00091026> [retrieved on Dec. 1, 2006] the whole document.
Bulgaru, A.M. et al. (2003) Expert Rev. Anticancer Ther.3:269-279.
Chakravarti, A. et al. Cancer Research 62: 200-207.
Ciardiello, F. et al. (2000) Clin. Cancer Res. 6:2053-2063.
Ciardiello, F. et al. (2000) Clin. Cancer Res. 6:3739-3747.
Ciardiello, F. et al. (2003) Clin. Cancer Res. 9:1546-1556.
Contessa, J. N. et al. (1999) Clin. Cancer Res. 5:405-411.
Dancey, J. and Sausville, E.A. (2003) Nature Rev. Drug Discovery 2:296-313.
de Bono, J.S. and Rowinsky, E.K. (2002) Trends in Mol. Medicine 8:S19-S26.
Grunwald, V. and Hidalgo, M. (2003) J. Nat. Cancer Inst. 95:851-867.
Gupta, R.A. and DuBois, R.N. (2000) Nature Med. 6:974-975.
Gura, et al. (1997) Science 278:1041-1042.
Hartz, R.A. et al (2002) Bioorganic & Medicinal Chemistry Letters, vol. 12, pp. 291-294.
Herbst, R.S. et al. (2001) Expert Opin. Biol. Ther. 1:719-732.
Holbro, T. and Hynes, N.E. (2004) Annu Rev Pharmacol Toxicol 44:195-217.
Huang, S. et al. (1999) Cancer Res. 59:1935-1940.
Hurbin, A. et al. (2003) Ann. N.Y. Acad. Sci 1010:354-357.
Johnson, et al. (2001) British Journal of Cancer 84:1424-1431.
Jones, H.E. et al. (2004) Endocr Relat Cancer 11:793-814.
Khalil, M.Y. et al. (2003) Expert Rev. Anticancer Ther. 3:367-380.
Kim, E.S. et al. (2001) Current Opinion Oncol. 13:506-513.
Knowlden, J. M. (2005) Endocrinology 146(11):4609-4618.
Krishnan, S. et al. (2003) Frontiers in Bioscience 8, e1-13.
Kurmasheva, R. T. and Houghton, P. J. (2006) Biochim Biophys Acta 1766:1-22.
Levitzki, A. (2003) Lung Cancer 41 Suppl 1, S9-14.
Li, M. et al. (2002) Clin.Cancer Res. 8:3570-3578.
Liu, B. (2001) Oncogene 20:1913-1922.
Lu, Y. at al. (2001) Journal of the National Cancer Institute 93: 1852-1857.
Magne, N. et al. (2002) British Journal of Cancer 86:819-827.
Magne, N. et al. (2003) Clin. Can. Res. 9:4735:4732.
Morgillo, F. et al. (2006) Cancer Res 66(20):10100-10111.
Nahta, R. (2005) Cancer Research 65:11118-111128.
National Library of Medicine—Medical Subject Headings definition of Sarcoma (http://www.nlm.nih.gov/mesh/2008/MBrowser.html, then type "sarcoma"); last accessed Jul. 1, 2008.
Parrizas et al (1997) Endocrinology, vol. 138, pp. 1427-1433.
Raben, D. et al. (2002) Semin. Oncol. vol. 29, No. 1, suppl 4 (Feb.): 37-46.
Roskoski, R., Jr. (2004) Biochem Biophys Res Commun 319:1-11.
Seymour, L. (2003) Current Opin. Investig. Drugs 4(6):658-666.
Solomon, B. et al (2003) Int. J. Radiat. Oncol. Biol. Phys. 55:713-723.
Stein, J.H. et al (1994) Internal Medicine 4th Edition, Chapters 71 and 72, pp. 699-729.
Thomas, et al. (1998) Expert Opinion Ther. Pat., vol. 8, pp. 475-478.
Torrance, C.J. et al. (2000) Nature Med. 6:1024-1028.
Tortora, et al. (2003) Clin. Cancer Res. 9:1566-1572.
Austrian Search Report and Written Opinion in Singapore 200606863-9 on Dec. 23, 2008.
Breault, Gloria A, et al., Cyclin-Dependent Kinase 4 Inhibitors as a Treatment for Cancer. Part 2: Identification and Optimisation of Substitiuted 2,4-Bis Anilino Pyrimidines. Bioorganic & Medicinial Chemistry Letters 13 (2003) 2961-2966.
Blair, Joseph B et al., Thieno[3,2-b]- and Thieno[2,3-b]pyrrole Bioisoteric Analogues of the Hallucinogen and Serotonin Agonist N,N-Dimethyltryptamine. J. Chem. Med. 1999, 42, 1106-1111.
Galisteo, M.L. et al. (2006) PNAS 103 (26): 9796-9801.
Gundisch, Daniela et al., Synthesis and Evaluation of Pyridazine and Pyrimidine Containing Bioisoteres of (+)-Pyrido [3,4-b]homotropane and Pyrido-]3,4-b]tropane as Novel nAChR Ligands. Bioorganic & Medicinal Chemistry 10 (2002) 1-9.
Kopecky, D.J. et al. (2008) Bioorganic & Medicinal Chemistry Letters 18(24):6352-6356.
Mahajan, N. P.(2005) Cancer Research 65 (22):10514-10523.
Mahajan, N. P.(2007) PNAS 104 (20): 8438-8443.
Manser, E. et al. (1993) Nature 363 (6427):364-367.
Mulvihill, M.J. et al (2007) Bioorganic & Medicinal Chemistry 17(4): 1091-1097.
Mulvihill, M.J. (2007) Bioorganic & Medicinal Chemistry Letters 16(3): 1359-1375.
Robertson, David et al., Imidazole-Pyridine Bioisosterism: Comparison of the Intropis Activities of Pyridine- and Imidazole-Subsitituted 6-Phenyldihydropyridazinone Cardiotonics. J. Med. Chem. 1988, vol. 31, pp. 461-465.
Smalley Jr., Terrence L. et al., Synthesis and evaluation of a novel heterocyclic inhibitors of GSK-3. Bioorganic & Medicinal Letters 16 (2006) 2091-2094.
Valeriote, et al. (1975) Cancer Chemotherapy Reports (5):895-900.
van der Horst, E.T. et al. (2005) PNAS 102 (44):15901-15906.
Yang, et al. (1999) The Journal of Biological Chemistry 274 (13): 8524-8530.
International Search Report & Written Opinion of the International Searching Authority in PCT/US2009/044325, Sep. 18, 2009.

* cited by examiner

SUBSTITUTED IMIDAZOPYR- AND IMIDAZOTRI-AZINES

This application claims priority of U.S. Appl. No. 61/054,345, filed May 19, 2008, the entire content of which is incorporated herein by way of this reference.

FIELD AND BACKGROUND

The present invention relates to pharmaceuticals, tyrosine kinase inhibitors, ACK1 inhibitors, substituted imidazopyrazines and imidazotriazines, preparation thereof, pharmaceutical formulations and compositions, disease treatment therewith, and cancer treatment.

The activated p21cdc42Hs-associated kinase (ACK1) gene encodes an intracellular, non-receptor tyrosine kinase that binds cdc42Hs in its GTP-bound form and inhibits both the intrinsic and GTPase-activating protein (GAP)-stimulated GTPase activity of p21cdc42, a Ras-like protein involved in cell growth. This binding is mediated by a polypeptide of 47 amino acids C-terminal to an SH3 domain.

The ACK1 gene contains a tyrosine kinase domain and is reported to possess tyrosine kinase activity. ACK1 is activated by multiple extracellular stimuli (e.g., EGF, PDGF, IGF, TGFb, Gas6, ECM, stress, etc.). Upon activation, ACK1 mediates signaling cascade by direct interacting with and phosphorylating downstream effectors via its SH3, CRIB or/and proline-rich domains.

ACK1 kinase activity is regulated in the context of cell attachment and detachment, and certain cancer cells depend on ACK1's kinase activity for adhesion, anchorage independent growth and survival. ACK1 is implicated in cell motility, receptor endocytosis, and enhancement of tumorigenesis/metastasis & tumor cell survival. ACK1 is amplified and overexpressed in primary human tumors. ACK1 is amplified and overexpressed in several types of metastatic tumors and promotes prostate tumorigenesis; and phosphorylates tumor suppressor Wwox. Down regulation of ACK1 kinase activity or ACK1 expression levels can result in reduced tumor growth.

It is desirable to identify effective inhibitors of ACK1 for use in proliferative diseases, such as, but not limited to, cancer. There is a continuing need for new anticancer pharmaceuticals. Various publications refer to imidazopyrazines, triazines, and other compounds as tyrosine kinase inhibitors.

Additional background may be found in Nature 363(6427): 364-367 (1993); JBC 274:8524 (1999); Cancer Res 65:10514 (2005); PNAS 102:15901 (2005); PNAS 103:9796 (2006); PNAS 104:8438 (2007); Bioorg. & Med. Chem. Lett. 17:1091-97 (2007); US2003/0175763; US200610019957; US2006/0084654; US2006/0235031; US2007/0112005; US2007/0149521; US2007/0280928; US2008/0014200; US200810076921; US2008/0139582; US 2008/0108636; and WO2007/079164.

SUMMARY DESCRIPTION

The present invention includes certain substituted imidazopyrazines and imidazotriazines described herein, their salts, preparation thereof, pharmaceutical compositions and formulations thereof, and methods of treating disease such as cancers therewith.

The present invention includes compounds of the Formula I and pharmaceutically acceptable salts thereof:

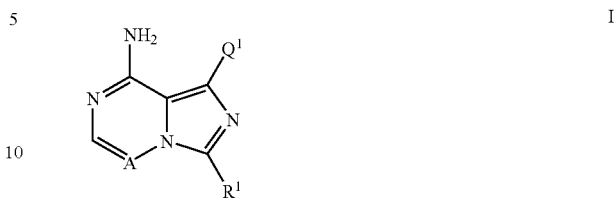

wherein A can be N or CH; $Q^1$ can be $—X_1—Y^1—Z^1$; $X^1$ can be a ring-containing moiety such as aryl or heterocyclic; $Y^1$ can be a bond or other linker such as carbon, nitrogen, oxygen, or sulfur; $Z^1$ can be a ring-containing moiety; and $R^1$ can be a ring-containing moiety, alkyl, or other group. Any of the above can be further substituted. Compounds of the invention inhibit ACK1.

DETAILED DESCRIPTION

Compounds

The invention includes Formula I, described above, and further includes Subgenus 1 thereof, wherein:
A is CH or N;
$Q^1$ is $—X^1—Y^1—Z^1$;
or $Q^1$ is:

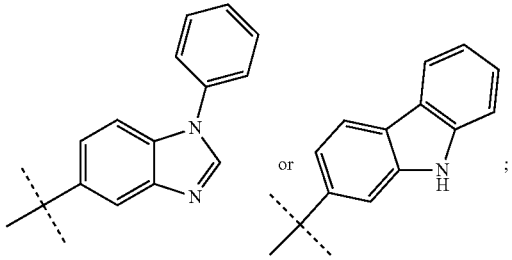

$X^1$ is $_{5-10}$cyclic, which can be substituted by one or more independently selected $G^1$ groups;
$Y^1$ is selected from $>C(R^2)R^3$, $>C(OR^2)R^3$, $>C=O$, $>C=C(R^2)R^3$, $>C=NR^2$, $>C=NOR^2$, $>NR^2$, $>O$, $>S(O)_m$, or a single bond;
$Z^1$ is selected from $_{5-10}$cyclic or $C_{1-6}$alkoxy, either of which can be substituted by one or more independently selected $G^1$ groups;
and wherein when Y is $>O$ and $R^1$ is cyclobutyl, at least one of X or Z is substituted;
each instance of $G^1$ is independently selected from halo, —CN, —CF$_3$, —OCF$_3$, —NO$_2$, $C_{1-6}$alkyl, $_{3-6}$cyclic $C_{0-6}$alkyl, —OR$^4$, —NR$^4$R$^5$, C(O)R$^4$, —C(O)NR$^4$R$^5$, —C(O)OR$^4$, or —NR$^4$C(O)R$^5$, any of which can be substituted with one or more independently selected $G^2$ groups;
each instance of $G^2$ is independently selected from halo, —CN, —OH, —NH$_2$, —NO$_2$, oxo, —CF$_3$, —OCF$_3$, or $C_{1-6}$alkyl, any of which can be substituted with one or more groups independently selected from halo, —CN, —OH, —NH$_2$, $C_{1-6}$alkyl (wherein any of the following can be partially or fully halogenated), —OC$_{1-6}$alkyl, or —N(C$_{1-6}$alkyl) $C_{1-6}$alkyl;
each instance of $G^3$ is independently selected from halo, oxo, —CN, —CF$_3$, —OCF$_3$, $C_{1-6}$alkyl, $_{3-6}$cyclic$C_{0-6}$alkyl, —OR$^8$, —NR$^8$R$^9$, —C(O)R$^8$, C(O)NR$^8$R$^9$, O(O)OR$^8$, —NR$^8$C(O)R$^9$, —(CR$^8$R$^9$)$_n$NR$^6$R$^7$, —(CR$^8$R$^9$)$_n$OR$^6$, —NR$^8$C(O)OR$^9$, —O(CR$^8$R$^9$)$_n$NR$^6$R$^7$, —N(CR$^8$R$^9$)$_n$OR$^6$ or —(CR$^8$R$^9$)$_n$NR$^6$C(O)OR$^7$, any of which can be substituted with one or more independently selected G$^2$ substituents;

R$^1$ is selected from —SR$^2$, C$_{1-6}$alkyl, 5,6-bicyclicaryl, or $_{3-6}$cyclic, any of which can be substituted by one or more independently selected G$^3$ groups;

each instance of R$^2$ and R$^3$ is independently selected from H, halo, or —C$_{1-6}$alkyl;

each instance of R$^4$, R$^5$, R$^6$, R$^7$, R$^8$, R$^9$ is independently selected from H, C$_{1-6}$alkyl, or $_{3-6}$cyclicC$_{0-6}$alkyl; wherein any R$^4$/R$^5$, R$^6$/R$^7$, R$^8$/R$^9$ pair, together with the atom to which they are attached, can form a $_{3-6}$cyclic that can include one or more heteroatoms selected from O, N(C$_{0-3}$alkyl), or S(O)$_m$;

each m is independently selected from 0-2; and each n is independently selected from 0-4; or a pharmaceutically acceptable salt thereof.

In other embodiments, Subgenus 2 includes Formula I and Subgenus 1, wherein:

X$^1$ is phenyl which can be substituted by 1 to 3 independently selected G$^1$ groups;

Z$^1$ is phenyl which can be substituted by 1 to 3 independently selected G$^1$ groups;

each instance of G$^1$ is independently selected from halo, —CN, —CF$_3$, —OCF$_3$, —NO$_2$, C$_{1-4}$alkyl, phenylC$_{0-3}$alkyl, $_{5-6}$heteroarylC$_{0-3}$alkyl, —OR$^4$, —NR$^4$R$^5$, —C(O)R$^6$, —C(O)NR$^4$R$^5$, —C(O)OR$^4$, or —NR$^4$C(O)R$^5$, any of which can be substituted by 1 to 3 independently selected G$^2$ groups;

each instance of G$^2$ is independently selected from halo, —CN, —OH, —NH$_2$, oxo, —CF$_3$, —OCF$_3$, or C$_{1-4}$alkyl, any of which can be substituted by 1 to 3 groups independently selected from halo, —CN, —OH, —NH$_2$, C$_{1-4}$alkyl (which may be partially or fully halogenated), —N(C$_{1-6}$alkyl)C$_{1-6}$alkyl (which may be partially or fully halogenated), or —OC$_{1-4}$alkyl (which may be partially or fully halogenated);

each instance of G$^3$ is independently selected from halo, oxo, —CN, —CF$_3$, —OCF$_3$, C$_{1-4}$alkyl, $_{5-6}$heterocyclicC$_{0-3}$alkyl, phenylC$_{0-3}$alkyl, —OR$^8$, —NR$^8$R$^9$, —C(O)R$^8$, —C(O)NR$^8$R$^9$, —C(O)OR$^8$, —NR$^8$C(O)R$^9$, —(CR$^8$R$^9$)$_n$NR$^6$R$^7$, —(CR$^8$R$^9$)$_n$OR$^6$, —NR$^8$C(O)OR$^9$, —O(CR$^8$R$^9$)$_n$NR$^6$R$^7$, —N(OR$^8$R$^9$)$_n$OR$^6$, or (OR$^8$R$^9$)$_n$NR$^6$C(O)OR$^7$, any of which can be substituted by 1 to 3 independently selected G$^2$ substituents;

R$^1$ is selected from C$_{3-12}$alkyl, $_{3-6}$cycloalkyl, phenyl, $_{5-6}$heterocyclic, any of which can be substituted by 1 to 3 independently selected G$^3$ groups;

each instance of R$^4$ and R$^5$ can be independently selected from H, C$_{1-4}$alkyl, $_{5-6}$cyclicC$_{0-3}$alkyl; and each n is independently selected from 0-3; or a pharmaceutically acceptable salt thereof.

In other embodiments, Subgenus 3 includes Formula I and any of Subgenuses 1-2, wherein:

A is CH;

X$^1$ is phenyl, which can be substituted by 1 to 2 independently selected G$^1$ groups;

Y$^1$ is selected from >O, >C(O), >NH, >N(CH$_3$), >C(OR$^2$)(R$^3$), >C(R$^2$)(R$^3$), S(O)$_m$;

Z$^1$ is phenyl which can be substituted by 1 to 2 independently selected G$^1$ groups;

each instance of G$^1$ is independently selected from halo, —CN, —CF$_3$, —OCF$_3$, —NO$_2$, C$_{1-4}$alkyl, —OR$^4$, —NR$^4$R$^5$, —C(O)R$^4$, —C(O)NR$^4$R$^5$, —C(O)OR$^4$, or —NR$^4$C(O)R$^5$, any of which can be substituted by 1 to 2 independently selected G$^2$ groups;

each instance of G$^2$ is independently selected from halo, —CN, OH, —NH$_2$, —NO$_2$, oxo, —CF$_3$, —OCF$_3$, or C$_{1-4}$alkyl;

R$^1$ is selected from phenyl, $_{5-6}$heteroaryl, $_{3-6}$cycloalkyl, or C$_{3-6}$alkyl, any of which can be substituted by 1 to 2 independently selected G$^3$ groups;

each instance of R$^2$ and R$^3$ is independently selected from H, halo, or C$_{1-3}$alkyl;

each instance of R$^4$ and R$^5$ is independently selected from H or C$_{1-4}$alkyl;

each instance of R$^6$, R$^7$, R$^8$, R$^9$ is independently selected from H or C$_{1-4}$alkyl; wherein any R$^8$/R$^9$ or R$^6$/R$^7$ pair, together with the atom to which they are attached, can form a $_{3-6}$cyclic that can include one or more heteroatoms selected from O, N(C$_{0-3}$alkyl), or S(O)$_m$; and each n is independently selected from 0-2; or a pharmaceutically acceptable salt thereof.

In other embodiments, Subgenus 4 includes Formula I and any of Subgenuses 1-3 herein, wherein:

X$^1$ is phenyl which can be substituted by 1 to 2 of —OH, C$_{1-3}$alkyl, halo, C$_{1-3}$alkoxy, or NH$_2$;

Y$^1$ is selected from >S, >O, >C(O), >C(OR$^2$)R$^3$, or >C(R$^2$)R$^3$;

Z$^1$ is phenyl which can be substituted by 1 to 2 independently selected from halo, methyl, —OH, or NH$_2$;

R$^1$ is selected from $_{5-6}$heteroaryl, phenyl, or $_{3-6}$cycloalkyl, any of which can be substituted with 1 to 2 independently selected from —OH, —C(O)NH$_2$, C$_{1-2}$alkyl, —(CH$_2$)$_{0-2}$NH$_2$, —C$_{1-2}$alkoxyNH$_2$, or piperazin-1-yl, wherein any amine hydrogen or hydroxy hydrogen can be replaced with methyl, ethyl, or with —(CH$_2$)$_2$N(CH$_3$)$_2$; and each instance of R$^2$ and R$^3$ is independently selected from H, halo, methyl, or OH; or a pharmaceutically acceptable salt thereof.

In other embodiments, Subgenus 5 includes Formula I and any of Subgenuses 1-4 herein, wherein:

A is CH;

X$_1$ is phenyl which can be substituted with 1 to 2 of halo, NH$_2$, ethoxy, or methoxy;

R$^2$ and R$^3$ are independently selected from H, halo, hydroxy, or methyl;

Z$^1$ is phenyl which can be substituted by 1-2 of halo, —OH, or NH$_2$; and

R$^1$ is C$_{4-6}$cycloalkyl which can be substituted with 1 to 2 independently selected from methyl, hydroxy, aminomethyl, or hydroxymethyl; or a pharmaceutically acceptable salt thereof.

In other embodiments, Subgenus 6 includes Formula I and any of Subgenuses 1-5 herein, wherein:

X$^1$ is phenyl which can be substituted with 1 to 2 independently selected from halo, NH$_2$, or methoxy;

Y$^1$ is selected from >O, >C(OR$^2$)R$^3$ or >C(R$^2$)R$^3$; and

R$^2$ and R$^3$ are independently selected from H, F or methyl;

Z$^1$ is phenyl; or a pharmaceutically acceptable salt thereof.

In other embodiments, Subgenus 7 includes Formula I and any of Subgenuses 1-6 herein, wherein each instance of G$^1$ is independently selected from halo, —CN, —CF$_3$, —OCF$_3$, C$_{1-6}$alkyl, phenylC$_{0-6}$alkyl, $_{5-6}$heteroarylC$_{0-6}$alkyl, —OR$^4$, —NR$^4$R$^5$, —C(O)R$^4$, —C(O)NR$^4$R$^5$, —C(O)OR$^4$, —NR$^4$C(O)R$^5$, any of which is optionally substituted with one or more independent G$^2$ substituents;

each instance of G$^2$ can be independently selected from halo, —CN, —OH, —NH$_2$, —NO$_2$, oxo, —CF$_3$, —OCF$_3$, C$_{2-4}$alkenyl, C$_{2-4}$alkynyl, or C$_{1-4}$alkyl, any of which can be substituted by 1 to 3 groups independently selected from halo, —CN, —OH, —NH$_2$, C$_{1-4}$alkyl (which may be partially or fully halogenated), or —OC$_{1-4}$alkyl (which may be partially or fully halogenated);

or a pharmaceutically acceptable salt thereof.

In other embodiments, Subgenus 8 includes Formula I and any of Subgenuses 1-7 herein, wherein:

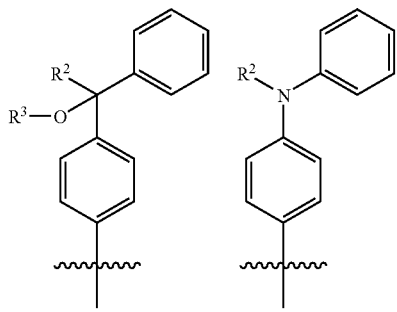

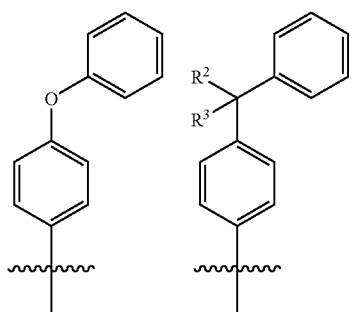

wherein each phenyl group in Q$^1$ can be substituted by up to two G$^1$ substituents; or a pharmaceutically acceptable salt thereof.

In other embodiments, Subgenus 9 includes Formula I and any of Subgenuses 1-8 herein, wherein R$^1$ is cyclobutyl which can be substituted with 1 to 2 independent hydroxy or methyl; or a pharmaceutically acceptable salt thereof.

In other embodiments, Subgenus 10 includes Formula I and any of Subgenuses 1-8 herein, wherein R$^1$ is optionally substituted $_{3-6}$cycloalkyl; or a pharmaceutically acceptable salt thereof.

In other embodiments, Subgenus 11 includes Formula I and any of Subgenuses 1-8 herein, wherein R$^1$ is cyclohexyl or phenyl, either optionally substituted with 4-methylpiperazin-1-yl, —(CH$_2$)$_{1-3}$N(CH$_2$)$_2$, or —O(CH$_2$)$_{1-3}$N(CH$_2$)$_2$, or a pharmaceutically acceptable salt thereof.

In other embodiments, Subgenus 12 includes Formula I and any of Subgenuses 1-8 herein, wherein R$^1$ is phenyl or $_{5-6}$heteroaryl, either optionally substituted by G$^3$; or a pharmaceutically acceptable salt thereof.

In other embodiments, Subgenus 13 includes Formula I and any of Subgenuses 1-8 herein, wherein R$^1$ is $_{4-6}$heterocyclyl; or a pharmaceutically acceptable salt thereof.

In other embodiments, Subgenus 14 includes Formula I and any of Subgenuses 1-8 herein, wherein R$^1$ is:

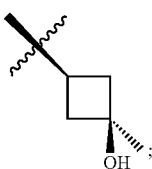

or a pharmaceutically acceptable salt thereof.

In other embodiments, Subgenus 15 includes Formula I and any of Subgenuses 1-14 herein, wherein each G$^3$ is independently selected from halo, —CN, —CF$_3$, C$_{1-12}$alkyl, heterocycloalkylC$_{0-12}$alkyl, arylC$_{0-12}$alkyl, heteroarylC$_{0-12}$alkyl, —OR$^4$, —NR$^4$R$^5$, —C(O)R$^4$, —C(O)NR$^4$R$^5$, —C(O)OR$^4$, —NR$^4$C(O)R$^5$, —(CR$^4$R$^5$)$_n$NR$^6$R$^7$, —(CR$^4$R$^5$)$_n$OR$^6$, —NR$^4$C(O)OR$^5$, or —(CR$^4$R$^5$)$_n$NR$^6$C(O)OR$^7$, any of which is optionally substituted with 1 to 3 independent G$^2$ substituents; or a pharmaceutically acceptable salt thereof.

In other embodiments, Subgenus 16 includes Formula I and any of Subgenuses 1-15 herein, wherein each instance of R$^2$ and R$^3$ is independently selected from H, halo, or C$_{1-3}$alkyl; or a pharmaceutically acceptable salt thereof.

In other embodiments, Subgenus 17 includes Formula I and Subgenus 1, wherein:

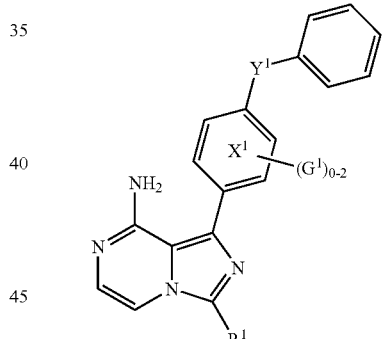

wherein Y$^1$ is >O or >C(CH$_3$)OH or >CF$_2$; each G$^1$ group is independently selected from C$_{1-3}$alkyl, halo or C$_{1-3}$alkoxy; and R$^1$ is selected from:

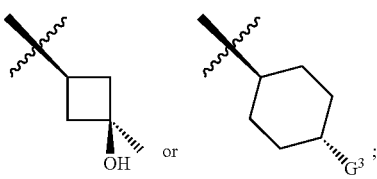

wherein G$^3$ is —CH$_2$NR$^6$R$^7$; and R$^6$ and R$^7$ are independently selected from H, C$_{1-4}$alkyl, or a pharmaceutically acceptable salt thereof.

In other embodiments, Subgenus 18 includes Formula I and Subgenus 1, wherein:

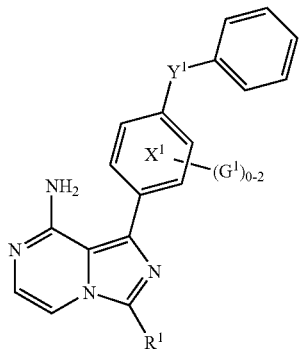

wherein $Y^1$ is >O or >C(CH$_3$)OH or >CF$_2$; each $G^1$ group is independently selected from C$_{1-3}$alkyl, halo or C$_{1-3}$alkoxy; and $R^1$ is selected from phenyl or $_{5-6}$heteroaryl; or a pharmaceutically acceptable salt thereof.

In some embodiments, the compound is one of the examples disclosed herein or a pharmaceutically acceptable salt thereof.

In some embodiments of any the above recitations, the compound or pharmaceutically acceptable salt thereof is present in substantially pure form.

In any of these recitations, A can be selected from CH or N.

Each variable definition above is taken to include any subset thereof and the compounds of Formula I include any combination of such variables or variable subsets.

The invention includes the compounds described herein, including the Examples, and any pharmaceutically acceptable salts thereof.

Compounds described can contain one or more asymmetric centers and may thus give rise to stereoisomers. The present invention includes any stereoisomers, even if not specifically shown, individually as well as mixtures, geometric isomers, and pharmaceutically acceptable salts thereof. Where a compound or stereocenter is described or shown without definitive stereochemistry, it is to be taken to embrace all possible isomers and mixtures thereof. Thus, a material sample containing a mixture of stereoisomers would be embraced by a recitation of either of the stereoisomers or a recitation without definitive stereochemistry. Also envisioned art N-oxides of the compounds in cases where such can be prepared. Also contemplated are any cis/trans isomers or tautomers of the compounds described.

The compounds may be amorphous or may exist or be prepared in various crystal forms or polymorphs, including solvates and hydrates. A recitation of a compound per se is taken to embrace that compound regardless of form and whether or not associated with solvent or water.

The invention includes compounds described which exhibit a biochemical assay IC$_{50}$ against ACK1 as described herein of about 0.05 μM or lower, 0.1 μM or lower, 0.2 μM or lower, 0.5 μM or lower, 1 μM or lower, or 10 μM or lower.

The invention includes the intermediates and methods described herein.

General Synthetic Methods

Compounds of the invention may be prepared by the methods described below, together with synthetic methods known in the art of organic chemistry, or modifications and derivatizations that are familiar to those of ordinary skill in the art. See, e.g., US2006/0084654; US2006/0235031, US2007/0129547; and US2007/0149521, which are incorporated herein in their entireties for all purposes, including synthetic methods. Compounds of Formula I, or their pharmaceutically acceptable salts, can be prepared according to the reaction Schemes discussed hereinbelow. Unless otherwise indicated, the substituents in the Schemes are defined as above. Isolation and purification of the products is accomplished by standard procedures, which are known to a chemist of ordinary skill.

Method A was used to prepare compounds of Formula I-AA as shown below in Scheme 1:

Scheme 1

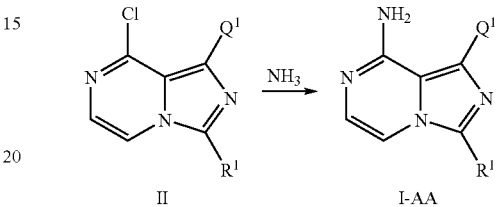

where $Q^1$ and $R^1$ are as defined previously for compound of Formula I.

In a typical preparation of compounds of Formula I-AA, compound of Formula II was reacted with ammonia in a suitable solvent. Suitable solvents for use in the above process included, but were not limited to, ethers such as THF, glyme, and the like; DMF; DMSO; MeCN; alcohols such as MeOH, EtOH, isopropanol, trifluoroethanol, and the like; and chlorinated solvents such as DCM or chloroform (CHCl$_3$). If desired, mixtures of these solvents were used, however, the preferred solvents were isopropanol and a mixture of THF and isopropanol. The above process was carried out at temperatures between about −78° C. and about 120° C. Preferably, the reaction was carried out between 80° C. and about 120° C. The above process to produce compounds of the present invention was preferably carried in a sealed reaction vessel such as but not limited to a thick walled glass reaction vessel or a stainless steel Parr bomb. An excess amount of the reactant, ammonia, was preferably used.

The compounds of Formula II of Scheme 1 were prepared as shown below in Scheme 2.

Scheme 2

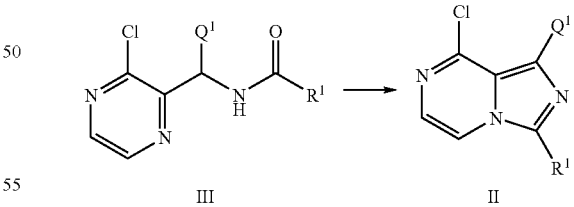

where $Q^1$ and $R^1$ are as defined previously for compound of Formula I.

In a typical preparation of a compound of Formula II, an intermediate of Formula III was treated with POCl$_3$ in a suitable solvent at a suitable reaction temperature. Suitable solvents for use in the above process included, but were not limited to, ethers such as THF, glyme, and the like; MeCN; and chlorinated solvents such as DCM or chloroform (CHCl$_3$). If desired, mixtures of these solvents were used or no solvent was used. The preferred solvents included DCM and MeCN. The above process was carried out at temperatures between about −78° C. and about 120° C. Preferably, the reaction was carried out between 20° C. and about 95° C. The above process to produce compounds of the present invention was preferably carried out at about atmospheric pressure although higher or lower pressures were used if desired. Substantially, equimolar amounts of reactants were preferably used although higher or lower amounts were used if desired.

The compounds of Formula III of Scheme 2 were prepared as shown below in Scheme 3:

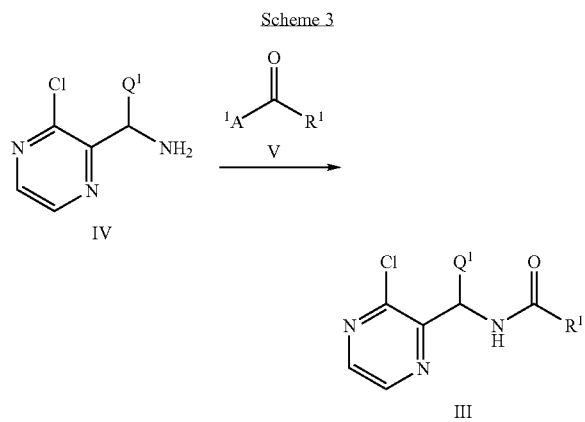

where $Q^1$ and $R^1$ are as defined previously for compound of Formula I and $A^1$=OH, alkoxy, or a leaving group such as chloro or imidazole.

In a typical preparation, of a compound of Formula II, a compound of Formula IV and compound of Formula V were reacted under suitable amide coupling conditions. Suitable conditions include but are not limited to treating compounds of Formula IV and V (when $A^1$=OH) with coupling reagents such as DCC or EDC in conjunction with DMAP, HOBt, HOAt and the like. Suitable solvents for use in the above process included, but were not limited to, ethers such as THF, glyme, and the like; DMF; DMSO; MeCN; halogenated solvents such as chloroform or DCM. If desired, mixtures of these solvents were used, however the preferred solvents were DCM and DMF. The above process was carried out at temperatures between about 0° C. and about 80° C. Preferably, the reaction was carried out at about rt. The above process to produce compounds of the present invention was preferably carried out at about atmospheric pressure although higher or lower pressures were used if desired. Substantially, equimolar amounts of reactants were preferably used although higher or lower amounts were used if desired. Alternatively, compounds of Formula IV and V (where $A^1$=F, Cl, Br, I) were reacted with bases such as TEA or ethyldiisopropylamine and the like in conjunction with DMAP and the like. Suitable solvents for use in this process included, but were not limited to, ethers such as THF, glyme, and the like; DMF; DMSO; MeCN; halogenated solvents such as chloroform or DCM. If desired, mixtures of these solvents were used, however the preferred solvent was DCM. The above process was carried out at temperatures between about −20° C. and about 40° C. Preferably, the reaction was carried out between 0° C. and 25° C. The above process to produce compounds of the present invention was preferably carried out at about atmospheric pressure although higher or lower pressures were used if desired. Substantially, equimolar amounts of compounds of Formula IV and V (where $A^1$=F, Cl, Br, I) and base and substoichiometric amounts of DMAP were preferably used although higher or lower amounts were used if desired. Additionally, other suitable reaction conditions for the conversion of a compound of Formula IV to a compound of Formula III can be found in Larock, R. C. Comprehensive Organic Transformations, $2^{nd}$ ed.; Wiley and Sons: New York, 1999, pp 1941-1949.

The compounds of Formula IV of Scheme 3 were prepared as shown below in Scheme 4:

Scheme 4

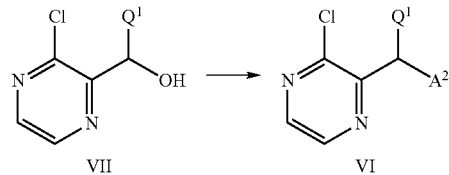

where $Q^1$ is as defined previously for compound of Formula I and $A^2$=phthalimido or $N^3$.

In a typical preparation, of a compound of Formula IV, a compound of Formula VI is reacted under suitable reaction conditions in a suitable solvent. When $A^2$=phthalimido, suitable conditions include treatment of compound of Formula VI with hydrazine in a suitable solvent. Suitable solvents for use in the above process included, but were not limited to, ethers such as THF, glyme, and the like; DMF; DMSO; MeCN; halogenated solvents such as chloroform or DCM; alcoholic solvents such as MeOH and EtOH. If desired, mixtures of these solvents may be used, however the preferred solvent was EtOH. The above process was carried out at temperatures between about 0° C. and about 80° C. Preferably, the reaction was carried out at about 22° C. The above process to produce compounds of the present invention was preferably carried out at about atmospheric pressure although higher or lower pressures were used if desired. Substantially, equimolar amounts of reactants were preferably used although higher or lower amounts were used if desired. In the transformation of compound of Formula VI to IV, if $A^2$=$N_3$, then one skilled in the art would recognize that typical azide reduction conditions could be employed, including but not limited to $PPh_3$ and water or hydrogenation in the presence of a metal catalyst such as palladium.

The compounds of Formula VI of Scheme 4 were prepared as shown below in Scheme 5:

Scheme 5 where $Q^1$ is as defined previously for compound of Formula I and $A^2$=phthalimido or $N^3$.

In a typical preparation of a compound of Formula VI (when $A^2$=phthalimido), a compound of Formula VII was reacted with a phthalimide under typical Mitsunobu conditions in a suitable solvent in the presence of suitable reactants. Suitable solvents for use in the above process included, but were not limited to, ethers such as THF, glyme, and the like;

DMF; DMSO; MeCN(CH$_3$CN); chlorinated solvents such as DCM or chloroform (CHCl$_3$). If desired, mixtures of these solvents were used, however, the preferred solvent was THF. Suitable reactants for use in the above process included, but were not limited to, triphenylphosphine and the like, and an azodicarboxylate (DIAD, DEAD, DBAD). The preferred reactants were triphenylphosphine or resin-bound triphenylphosphine (PS—PPh$_3$), and DIAD. The above process may be carried out at temperatures between about −78° C. and about 100° C. Preferably, the reaction was carried out at about 22° C. The above process to produce compounds of the present invention was preferably carried out at about atmospheric pressure although higher or lower pressures were used if desired. Substantially, equimolar amounts of reactants were preferably used although higher or lower amounts were used if desired. Generally, one equivalent or a slight excess, 1.1 equivalents, of triphenylphosphine, DIAD and phthalimide was used per equivalent of compound of Formula VII. Additionally, compound of Formula VII can be reacted with Ts$_2$O, MS$_2$O, Tf$_2$O, TsCl, MsCl, or SOCl$_2$ in which the hydroxy group is converted to a leaving group such as its respective tosylate, mesylate, triflate, or halogen such as chloro and subsequently reacted with an amine equivalent such as NH(Boc)$_2$, phthalimide, potassium phthalimide, or sodium azide. Conversion of the amine equivalents by known methods such as by treating under acidic conditions (NH(Boc)$_2$), with hydrazine (phthalimide) as shown in Scheme 4, or with triphenylphosphine/water (azide) will afford the desired amine as shown in Scheme 4.

The compounds of Formula VII of Scheme 5 were prepared from aldehydes Q$^1$-CHO and a 2-chloropyrazine VIII as shown below in Scheme 6:

Scheme 6

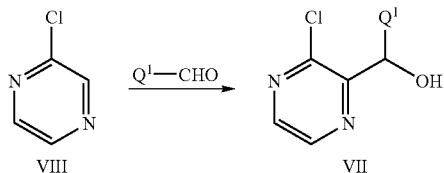

VIII      VII where Q$^1$ is as defined previously for compound of Formula I.

In a typical preparation, of a compound of Formula VII, a compound of Formula VIII was reacted under suitable reaction conditions in a suitable solvent with a compound of Formula Q$^1$-CHO. Suitable conditions included but were not limited to treating compounds of Formula VIII with a base such as lithium tetramethylpiperidide (Li-TMP) followed by treating with compounds of Formula Q$^1$-CHO. Lithium tetramethylpiperidide may be prepared by reacting tetramethylpiperidine with n-butyllithium at −78° C. and warming up to 0° C. Suitable solvents for use in the above process included, but were not limited to, ethers such as THF, glyme, and the like. Polar solvents such as hexamethylphosphoramide (HMPA), 1,3-dimethyl-3,4,5,6-tetrahydro-2(1H)-pyrimidinone (DMPU), and the like may be added if necessary. If desired, mixtures of these solvents were used, however, the preferred solvent was THF. The above process may be carried out at temperatures between about −80° C. and about 20° C. Preferably, the reaction was carried out at −78° C. to 0° C. The above process to produce compounds of the present invention was preferably carried out at about atmospheric pressure although higher or lower pressures were used if desired. Substantially, equimolar amounts of reactants were preferably used although higher or lower amounts were used if desired.

The compounds of Formula I of this invention and the intermediates used in the synthesis of the compounds of this invention were prepared according to the following methods. Method B was used when preparing compounds of Formula I-AA from compound of Formula I-BB as shown below in Scheme 7:

Scheme 7

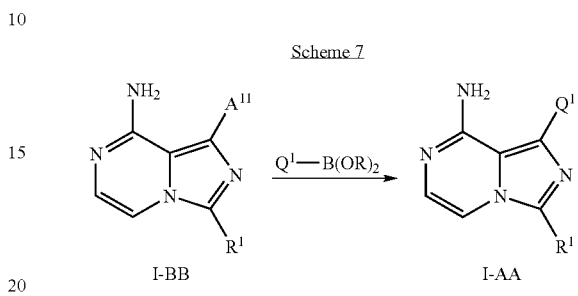

I-BB      I-AA where Q$^1$ and R$^1$ are as defined previously for compound of Formula I, A$^{11}$=halogen such as Cl, Br, or I and B(OR)$_2$=suitable boronic acid/ester.

In a typical preparation of compounds of Formula I-AA, compound of Formula I-BB was reacted with a suitable boronic acid/ester (Q$^1$-B(OR)$_2$) in a suitable solvent via typical Suzuki coupling procedures. Suitable solvents for use in the above process included, but were not limited to, ethers such as THF, glyme, dioxane, dimethoxyethane; and the like; DMF; DMSO, MeCN; alcohols such as MeOH, EtOH, isopropanol, trifluoroethanol, and the like; and chlorinated solvents such as DCM or chloroform (CHCl$_3$). If desired, mixtures of these solvents were used, however, the preferred solvent was dimethoxyethane/water. The above process was carried out at temperatures between about −78° C. and about 120° C. Preferably, the reaction was carried out between 60° C. and about 100° C. The above process to produce compounds of the present invention was preferably carried out at about atmospheric pressure although higher or lower pressures were used if desired. Substantially, equimolar amounts of reactants were preferably used although higher or lower amounts were used if desired.

One skilled in the art will appreciate that alternative methods may be applicable for preparing compounds of Formula I-AA from I-BB. For example, compound of Formula I-BB could be reacted with a suitable organotin reagent Q$^1$-SnBu$_3$ or the like in a suitable solvent via typical Stille coupling procedures.

The compounds of Formula I-BB of Scheme 7 were prepared as shown below in Scheme 8.

Scheme 8

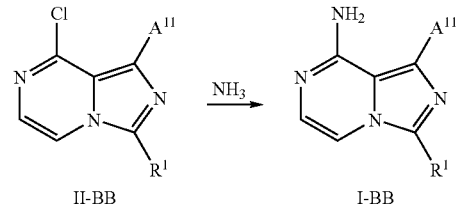

II-BB      I-BB where R$^1$ is as defined previously for compound of Formula I and A$^{11}$=halogen such as Cl, Br, or I.

In a typical preparation of compounds of Formula I-BB, compound of Formula II-BB was reacted with ammonia in a suitable solvent. Suitable solvents for use in the above process included, but were not limited to, ethers such as THF, glyme, and the like; DMF; DMSO; MeCN; alcohols such as MeOH, EtOH, isopropanol, trifluoroethanol, and the like; and chlorinated solvents such as DCM or chloroform ($CHCl_3$). If desired, mixtures of these solvents were used, however, the preferred solvents were isopropanol and a mixture of THF and isopropanol. The above process was carried out at temperatures between about −78° C. and about 120° C. Preferably, the reaction was carried out between 80° C. and about 120° C. The above process to produce compounds of the present invention was preferably carried in a sealed reaction vessel such as but not limited to a thick walled glass reaction vessel or a stainless steel Parr bomb. An excess amount of the reactant, ammonia, was preferably used.

The compounds of Formula II-BB of Scheme 8 were prepared as shown below in Scheme 9.

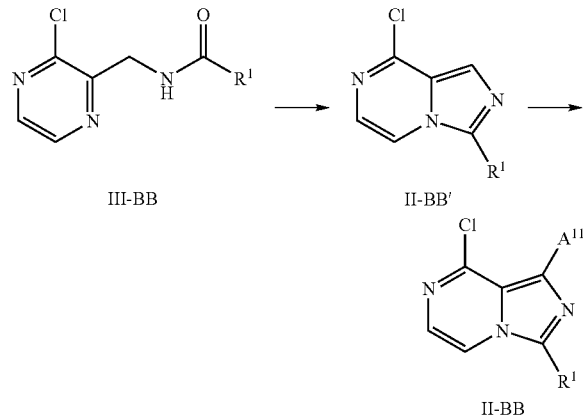

where $R^1$ is as defined previously for compound of Formula I and $A^{11}$=halogen such as Cl, Br, or I.

In a typical preparation of a compound of Formula II-BB, intermediate III-BB was converted to compound of Formula II-BB'. Intermediate of Formula III-BB was treated with $POCl_3$ in a suitable solvent at a suitable reaction temperature. Suitable solvents for use in the above process included, but were not limited to, ethers such as THF, glyme, and the like; MeCN; and chlorinated solvents such as DCM or chloroform ($CHCl_3$). If desired, mixtures of these solvents were used. The preferred solvents included DCM and MeCN. The above process was carried out at temperatures between about −78° C. and about 120° C. Preferably, the reaction was carried out between 20° C. and about 95° C. The above process to produce compounds of the present invention was preferably carried out at about atmospheric pressure although higher or lower pressures were used if desired. Substantially, equimolar amounts of reactants were preferably used although higher or lower amounts were used if desired. In the conversion of compound of Formula III-BB to II-BB', suitable halogenating agent were used, but were not limited to, $Br_2$, $I_2$, $Cl_2$, N-chlorosuccinimide, N-bromosuccinimide, or N-iodosuccinimide. The preferred halogenating agent was N-iodosuccinimide. Suitable solvents for use in the above process included, but were not limited to, ethers such as THF, glyme, and the like; DMF; DMSO; MeCN; alcohols such as MeOH, EtOH, isopropanol, trifluoroethanol, and the like; and chlorinated solvents such as DCM or chloroform ($CHCl_3$). If desired, mixtures of these solvents were used, however, the preferred solvent was DMF. The above process was carried out at temperatures between about −78° C. and about 120° C. Preferably, the reaction was carried out between 40° C. and about 75° C. The above process to produce compounds of the present invention was preferably carried out at about atmospheric pressure although higher or lower pressures were used if desired. Substantially, equimolar amounts of reactants were preferably used although higher or lower amounts were used if desired.

The compounds of Formula III-BB of Scheme 9 were prepared as shown below in Scheme 10:

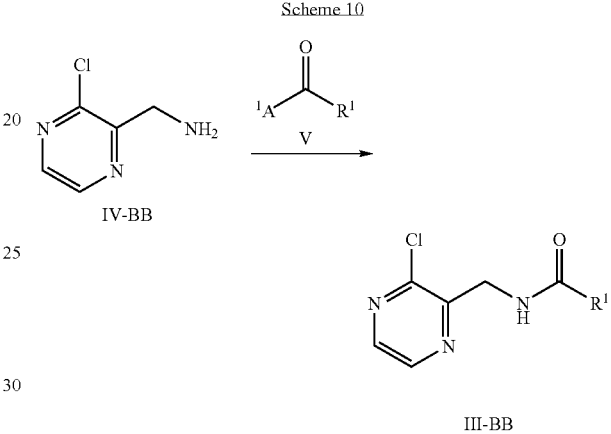

where $R^1$ is as defined previously for compound of Formula I and $A^1$=OH, alkoxy, or a leaving group such as chloro or imidazole.

In a typical preparation, of a compound of Formula III-BB, a compound of Formula IV-BB and compound of Formula V were reacted under suitable amide coupling conditions Suitable conditions include but are not limited to treating compounds of Formula IV-BB and V (when $A^1$=OH) with coupling reagents such as DCC or EDC in conjunction with DMAP, HOBt, HOAt and the like. Suitable solvents for use in the above process included, but were not limited to, ethers such as THF, glyme, and the like; DMF; DMSO; MeCN; halogenated solvents such as chloroform or DCM. If desired, mixtures of these solvents were used, however the preferred solvent was DCM. The above process was carried out at temperatures between about 0° C. and about 80° C. Preferably, the reaction was carried out at about 22° C. The above process to produce compounds of the present invention was preferably carried out at about atmospheric pressure although higher or lower pressures were used if desired. Substantially, equimolar amounts of reactants were preferably used although higher or lower amounts were used if desired. Additionally, if compound of Formula IV-BB was a salt or bis-salt, a suitable base was required and included, but was not limited to, DMF or TEA. Alternatively, compounds of Formula IV-BB and V (where $A^1$=F, Cl, Br, I) were reacted with bases such as TEA or ethyldiisopropylamine and the like in conjunction with DMAP and the like. Suitable solvents for use in this process included, but were not limited to, ethers such as THF, glyme, and the like; DMF; DMSO; MeCN; halogenated solvents such as chloroform or DCM. If desired, mixtures of these solvents were used, however the preferred solvent was DCM. The above process was carried out at temperatures between about −20° C. and about 40° C. Preferably, the reaction was carried out between 0° C. and 25° C. The above process to produce compounds of the present invention was preferably carried out at about atmospheric pressure although higher or lower pressures were used if desired. Substantially, equimolar amounts of compounds of Formula IV-BB and V (where $A^1$=F, Cl, Br, I) and base and substoichiometric amounts of DMAP were preferably used although higher or lower amounts were used if desired. Additionally, other suitable reaction conditions for the conversion of an amine (compound of Formula IV-BB) to an amide (compound of Formula III-BB) can be found in Larock, R. C. Comprehensive Organic Transformations, $2^{nd}$ ed.; Wiley and Sons: New York, 1999, pp 1941-1949.

The compounds of Formula IV-BB of Scheme 10 were prepared as shown below in Scheme 11:

Scheme 11

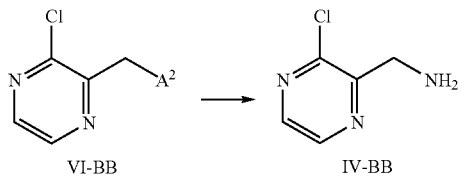

VI-BB            IV-BB where $A^2$ is phthalimido or $N^3$.

In a typical preparation of a compound of Formula IV-BB, a compound of Formula VI-BB is reacted under suitable reaction conditions in a suitable solvent, When $A^2$=phthalimido, suitable conditions include treatment of compound of Formula VI-BB with hydrazine in a suitable solvent, Suitable solvents for use in the above process included, but were not limited to, ethers such as THF, glyme, and the like; DMF; DMSO; MeCN; halogenated solvents such as chloroform or DCM; alcoholic solvents such as MeOH and EtOH, If desired, mixtures of these solvents may be used, however the preferred solvent was EtOH. The above process was carried out at temperatures between about 0° C. and about 80° C. Preferably, the reaction was carried out at about 22° C. The above process to produce compounds of the present invention was preferably carried out at about atmospheric pressure although higher or lower pressures were used if desired. Substantially, equimolar amounts of reactants were preferably used although higher or lower amounts were used if desired.

The compounds of Formula VI-BB of Scheme 11 were prepared as shown below in Scheme 12:

Scheme 12

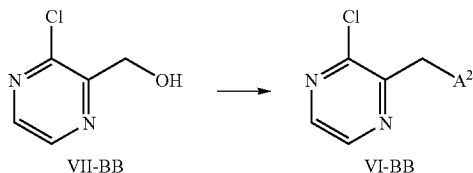

VII-BB            VI-BB where $A^2$=phthalimido or $N^3$.

In a typical preparation of a compound of Formula VI-BB (when $A^2$=phthalimido), a compound of Formula VII-BB was reacted with a phthalimide under typical Mitsunobu conditions in a suitable solvent in the presence of suitable reactants. Suitable solvents for use in the above process included, but were not limited to, ethers such as THF, glyme, and the like; DMF; DMSO; MeCN(CH$_3$CN); chlorinated solvents such as DCM (CH$_2$Cl$_2$) or chloroform (CHCl$_3$). If desired, mixtures of these solvents were used, however, the preferred solvent was THF. Suitable reactants for use in the above process included, but were not limited to, triphenylphosphine and the like, and an azodicarboxylate (DIAD, DEAD, DBAD). The preferred reactants were triphenylphosphine or resin-bound triphenylphosphine (PS—PPh$_3$) and DIAD. The above process may be carried out at temperatures between about –78° C. and about 100° C. Preferably, the reaction was carried out at about 22° C. The above process to produce compounds of the present invention was preferably carried out at about atmospheric pressure although higher or lower pressures were used if desired. Substantially, equimolar amounts of reactants were preferably used although higher or lower amounts were used if desired. Generally, 1.0 or 1.1 equivalents of triphenylphosphine, DIAD and phthalimide was used per equivalent of compound of Formula VII-BB. Additionally, compound of Formula VII-BB can be reacted with Ts$_2$O, Ms$_2$O, Tf$_2$O, TsCl, MsCl, or SOCl$_2$ in which the hydroxy group is converted to a leaving group such as its respective tosylate, mesylate, triflate, or halogen such as chloro and subsequently reacted with an amine equivalent such as NH(Boc)$_2$, phthalimide, potassium phthalimide or sodium azide. Conversion of the amine equivalents by known methods such as by treating under acidic conditions (NH(Boc)$_2$), with hydrazine (phthalimide) as shown in Scheme 11, or with triphenyl-phosphine/water (azide) will afford the desired amine as shown in Scheme 11.

The compounds of Formula VII-BB of Scheme 12 were prepared from 2-chloropyrazine VIII as shown below in Scheme 13:

Scheme 13

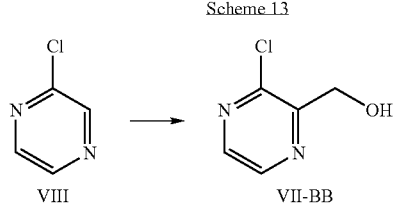

VIII            VII-BB

In a typical preparation, of a compound of Formula VIII-BB, a compound of Formula VIII was reacted under suitable reaction conditions in a suitable solvent. Suitable reaction conditions included, but were not limited to, treating compounds of Formula VIII with a base such as lithium tetramethylpiperidide (Li-TMP) followed by treatment with a reagent containing a carbonyl equivalent followed by treatment with a suitable reducing agent. Lithium tetramethylpiperidide may be prepared by reacting tetramethylpiperidine with n-butyllithium at –78° C. and warming up to 0° C. Suitable solvents for use in the above process included, but were not limited to, ethers such as THF, glyme, and the like. Polar solvents such as hexamethylphosphoramide (HMPA), 1,3-dimethyl-3,4,5,6-tetrahydro-2(1H)-pyrimidinone (DMPU), and the like may be added if necessary. If desired, mixtures of these solvents were used, however, the preferred solvent was THF. Suitable carbonyl equivalent reagents include, but are not limited to, formamides such as DMF or suitable chloroformate such as methyl or ethyl chloroformate. After addition of the suitable carbonyl equivalent reagent, the reaction if charged with a polar protic solvent such as, but not limited to, MeOH or EtOH followed by treatment with a suitable reducing agent such as sodium borohydride. The above process may be carried out at temperatures between about 80° C. and about 20° C. Preferably, the reaction was carried out at –78° C. to 0° C. The above process to produce compounds of the present invention was preferably carried out at about atmospheric pressure although higher or lower pressures were used if desired. Substantially, equimolar amounts of reactants were preferably used although higher or lower amounts were used if desired.

The compounds of Formula I of this invention and the intermediates used in the synthesis of the compounds of this invention were prepared according to the following methods. Method C was used when preparing compounds of Formula I-AA from compound of Formula I-CC as shown below in Scheme 14:

Scheme 14

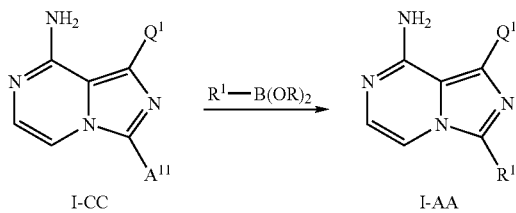

where $Q^1$ and $R^1$ are as defined previously for compound of Formula I, $A^{11}$=halogen such as Cl, Br, or I and $B(OR)_2$=suitable boronic acid/ester.

In a typical preparation of compounds of Formula I-AA, compound of Formula I-CC was reacted with a suitable boronic acid/ester ($R^1$—$B(OR)_2$) in a suitable solvent via typical Suzuki coupling procedures. Suitable solvents for use in the above process included, but were not limited to, ethers such as THF, glyme, dioxane, dimethoxyethane, and the like; DMF; DMSO; MeCN; alcohols such as MeOH, EtOH, isopropanol, trifluoroethanol, and the like; and chlorinated solvents such as DCM ($CH_2Cl_2$) or chloroform ($CHCl_3$). If desired, mixtures of these solvents were used, however, the preferred solvent was dimethoxyethane/water. The above process was carried out at temperatures between about −78° C. and about 120° C. Preferably, the reaction was carried out between 60° C. and about 100° C. The above process to produce compounds of the present invention was preferably carried out at about atmospheric pressure although higher or lower pressures were used if desired. Substantially, equimolar amounts of reactants were preferably used although higher or lower amounts were used if desired.

One skilled in the art will appreciate that alternative methods may be applicable for preparing compounds of Formula I-AA from I-CC. For example, compound of Formula I-CC could be reacted with a suitable organotin reagent $R^1$—$SnBu_3$ or the like in a suitable solvent via typical Stille coupling procedures.

The compounds of Formula I-CC of Scheme 14 were prepared as shown below in Scheme 15:

Scheme 15

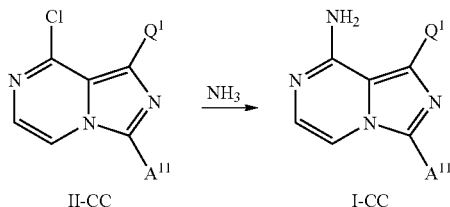

where $Q^1$ is as defined previously for compound of Formula I.

In a typical preparation of compounds of Formula I-CC, compound of Formula II-CC was reacted with ammonia in a suitable solvent. Suitable solvents for use in the above process included, but were not limited to, ethers such as THF, glyme, and the like; DMF; DMSO; MeCN; alcohols such as MeOH, EtOH, isopropanol, trifluoroethanol, and the like; and chlorinated solvents such as DCM ($CH_2Cl_2$) or chloroform ($CHCl_3$). If desired, mixtures of these solvents were used, however, the preferred solvents were isopropanol and a mixture of THF and isopropanol. The above process was carried out at temperatures between about −78° C. and about 120° C. Preferably, the reaction was carried out between 80° C. and about 120° C. The above process to produce compounds of the present invention was preferably carried in a sealed reaction vessel such as but not limited to a thick walled glass reaction vessel or a stainless steel Parr bomb. An excess amount of the reactant, ammonia, was preferably used.

The compounds of Formula II-CC of Scheme 15 were prepared as shown below in Scheme 16:

Scheme 16

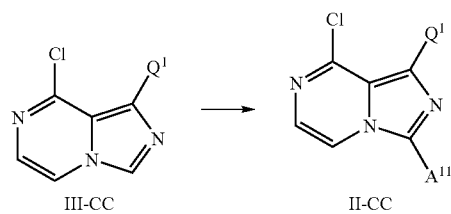

In the typical preparation of compound of Formula II-CC, compound of Formula III-CC was first treated with halogenating agent. Suitable halogenating agent were used, but were not limited to, $Br_2$, $I_2$, $Cl_2$, N-chlorosuccinimide, N-bromosuccinimide, or N-iodosuccinimide. The preferred halogenating agent was N-bromosuccinimide. Suitable solvents for use in the above process included, but were not limited to, ethers such as THF, glyme, and the like; DMF; DMSO; MeCN; alcohols such as MeOH, EtOH, isopropanol, trifluoroethanol, and the like; and chlorinated solvents such as DCM or chloroform ($CHCl_3$). If desired, mixtures of these solvents were used, however, the preferred solvent was DMF. The above process was carried out at temperatures between about −78° C. and about 120° C. Preferably, the reaction was carried out between −20° C. and about 45° C. The above process to produce compounds of the present invention was preferably carried out at about atmospheric pressure although higher or lower pressures were used if desired. Substantially, equimolar amounts of reactants were preferably used although higher or lower amounts were used if desired.

The compounds of Formula III-CC of Scheme 16 were prepared as shown below in Scheme 17.

Scheme 17

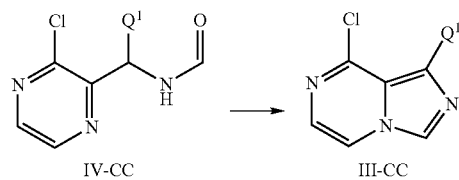

where $Q^1$ is as defined previously for compound of Formula I.

In a typical preparation of a compound of Formula III-CC, an intermediate of Formula IV-CC was treated with $POCl_3$ in a suitable solvent at a suitable reaction temperature. Suitable solvents for use in the above process included, but were not limited to, ethers such as THF, glyme, and the like; MeCN; and chlorinated solvents such as DCM or chloroform (CHCl$_3$). If desired, mixtures of these solvents were used or no solvent was used. The preferred solvents included DCM and MeCN. The above process was carried out at temperatures between about −78° C. and about 120° C. Preferably, the reaction was carried out between 20° C. and about 95° C. The above process to produce compounds of the present invention was preferably carried out at about atmospheric pressure although higher or lower pressures were used if desired. Substantially, equimolar amounts of reactants were preferably used although higher or lower amounts were used if desired.

The compounds of Formula IV-CC of Scheme 17 were prepared as shown below in Scheme 18:

Scheme 18

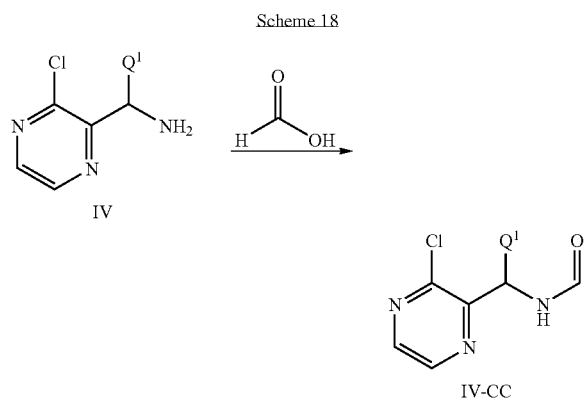

where $Q^1$ is as defined previously for compound of Formula I

In a typical preparation of a compound of Formula IV-CC, a compound of Formula IV and formic acid were reacted under suitable amide coupling conditions. Suitable conditions include but are not limited to treating compounds of Formula IV and formic acid with coupling reagents such as DCC or EDC in conjunction with DMAP, HOBt, HOAt and the like. Suitable solvents for use in the above process included, but were not limited to, ethers such as THF, glyme, and the like; DMF; DMSO; MeCN; halogenated solvents such as chloroform or DCM. If desired, mixtures of these solvents were used, however the preferred solvents were DCM and DMF. The above process was carried out at temperatures between about 0° C. and about 80° C. Preferably, the reaction was carried out at about rt. The above process to produce compounds of the present invention was preferably carried out at about atmospheric pressure although higher or lower pressures were used if desired. Substantially, equimolar amounts of reactants were preferably used although higher or lower amounts were used if desired. Additionally, other suitable reaction conditions for the conversion of a compound of Formula IV to a compound of Formula IV-CI can be found in Larock, R. C. Comprehensive Organic Transformations, 2$^{nd}$ ed., Wiley and Sons: New York, 1999, pp 1941-1949.

The compounds of Formula I of this invention and the intermediates used in the synthesis of the compounds of this invention were prepared according to the following methods. Method D was used when preparing compounds of Formula I-AA from compound of Formula I-DD as shown below in Scheme 19:

Scheme 19

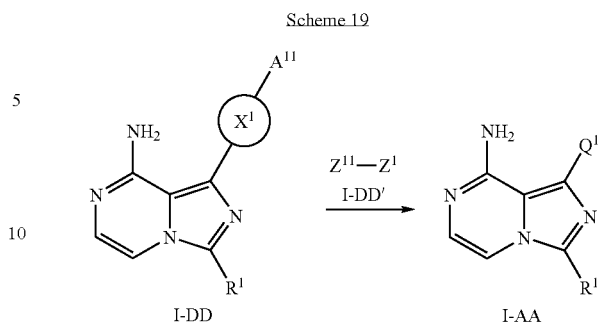

where $X^1$, $Z^1$, $Q^1$ and $R^1$ are as defined previously for compound of Formula I, $A^{11}$=halogen such as Cl, Br, or I. $Z^{11}$=OH, SH.

In a typical preparation of compounds of Formula I-AA, compound of Formula I-DD was reacted with a suitable coupling partner I-DD' in a suitable solvent under presence of a base and catalysis of a copper salt. Suitable solvents for use in the above process included, but were not limited to, ethers such as THF, glyme, dioxane, dimethoxyethane, and the like; DMF; DMSO; MeCN; alcohols such as MeOH, EtOH, isopropanol, trifluoroethanol, and the like; and chlorinated solvents such as DCM or chloroform (CHCl$_3$). If desired, mixtures of these solvents were used, however, the preferred solvent was DMF/dioxane. Suitable catalyst for use in the above process included, but were not limited to, CuI, CuBr, CuCl, CuSO$_4$, Cu(OAc)$_2$. However, the preferred catalyst was CuI. A ligand was added to the system to facilitate reaction if necessary. Suitable ligands for use in the above process included, but were not limited to, L-proline, N,N-dimethylglycine Hydrochloride. However, the preferred ligand was N,N-dimethylglycine Hydrochloride. Suitable bases for use in the above process included, but were not limited to, Cs$_2$CO$_3$, K$_2$CO$_3$, t-BuOK, t-BuONa, K$_3$PO$_4$. However, the preferred base was Cs$_2$CO$_3$. The above process was carried out at temperatures between about −78° C. and about 150° C. Microwave irradiation was applied if necessary. Preferably, the reaction was carried out between 60° C. and about 130° C. under microwave irradiation. The above process to produce compounds of the present invention was preferably carried out at about atmospheric pressure although higher or lower pressures were used if desired. Substantially, equimolar amounts of reactants were preferably used although higher or lower amounts were used if desired. Additionally, other suitable reaction conditions for the conversion of a compound of Formula I-DD to a compound of Formula I-AA were described in Ma, D. et al, Org. Lett. 2003, 3799.

The compounds of Formula I-DD of Scheme 19 were prepared as shown below in Scheme 20:

Scheme 20

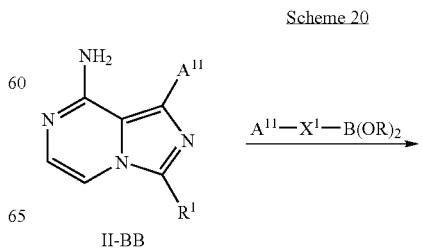

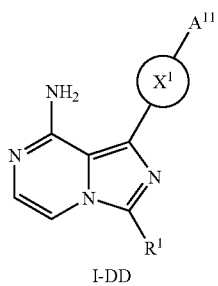

where $A^{11}$=halogen such as Cl, Br, or I and $B(OR)_2$=suitable boronic acid/ester.

In a typical preparation of compounds of Formula I-DD, compound of Formula II-BB was reacted with a suitable boronic acid/ester in a suitable solvent via typical Suzuki coupling procedures. Suitable solvents for use in the above process included, but were not limited to, ethers such as THF, glyme, dioxane, dimethoxyethane, and the like; DMF; DMSO; MeCN; alcohols such as MeOH, EtOH, isopropanol, trifluoroethanol, and the like; and chlorinated solvents such as DCM or chloroform ($CHCl_3$). If desired, mixtures of these solvents were used, however, the preferred solvent was dimethoxyethane/water. The above process was carried out at temperatures between about −78° C. and about 120° C. Preferably, the reaction was carried out between 60° C. and about 100° C. The above process to produce compounds of the present invention was preferably carried out at about atmospheric pressure although higher or lower pressures were used if desired. Substantially, equimolar amounts of reactants were preferably used although higher or lower amounts were used if desired.

One skilled in the art will appreciate that alternative methods may be applicable for preparing compounds of Formula I-DD from II-BB. For example, compound of Formula II-BB could be reacted with a suitable organotin reagent or the like in a suitable solvent via typical Stille coupling procedures.

The compounds of Formula I of this invention and the intermediates used in the synthesis of the compounds of this invention were prepared according to the following methods. Method E was used when preparing compounds of Formula I-AA from compound of Formula I-EE as shown below in Scheme 21:

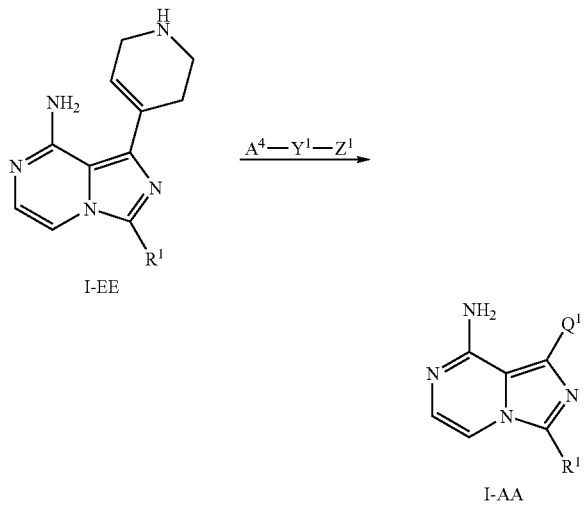

where $Q^1$ and $R^1$ are as defined previously for compound of Formula I, $A^4$=Leaving group such as OTs, OMs, OTf, or halo such as chloro, bromo, or iodo.

In a typical preparation of compounds of Formula I-AA, compound of Formula I-EE was reacted with a suitable $A^4$-$Y^1$—$Z^1$ in a suitable solvent under presence of a suitable base. Suitable solvents for use in the above process included, but were not limited to, alcoholic solvents such as EtOH, butanol and the like, esters such as EtOAc, methyl acetate and the like, DMF, MeCN, acetone DMSO. If desired, mixtures of these solvents were used. The preferred solvent was DMF. Suitable bases for use in the above process included, but were not limited to, $Cs_2CO_3$, $K_2CO_3$, t-BuOK, t-BuONa, $K_3PO_4$, TEA, diisopropylethyl amine. However, the preferred base was diisopropylethyl amine. The above process was carried out at temperatures between about −78° C. and about 120° C. Preferably, the reaction was carried out between 0° C. and about 25° C. The above process to produce compounds of the present invention was preferably carried out at about atmospheric pressure although higher or lower pressures were used if desired. Alternatively, Substantially, equimolar amounts of reactants were preferably used although higher or lower amounts were used if desired.

The compounds of Formula I-EE of Scheme 19 were prepared as shown below in Scheme 22:

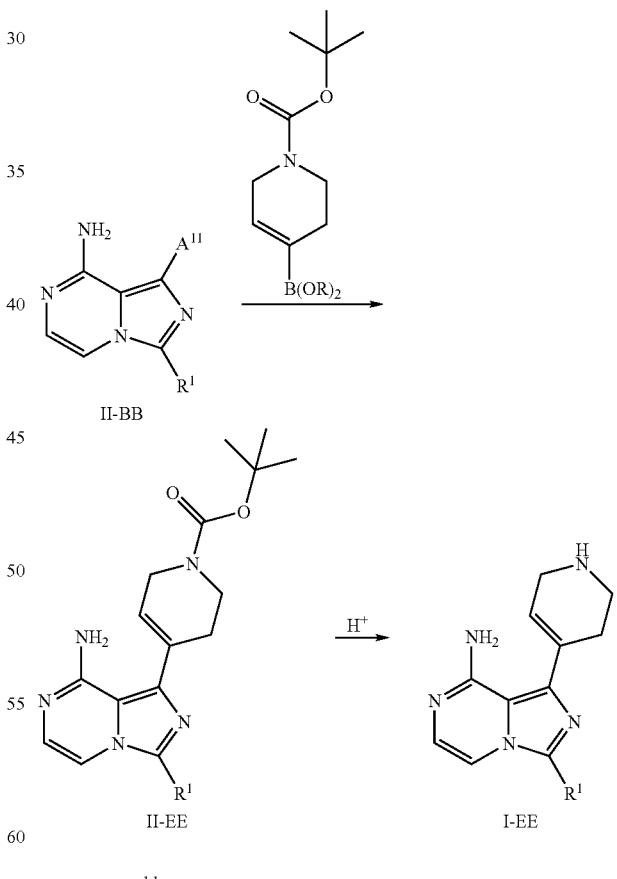

where $A^{11}$=halogen such as Cl, Br, or I and $B(OR)_2$ suitable boronic acid/ester.

In a typical preparation of compounds of Formula II-EE, compound of Formula I'-BB was reacted with a suitable boronic acid/ester in a suitable solvent via typical Suzuki coupling procedures. Suitable solvents for use in the above process included, but were not limited to, ethers such as THF, glyme, dioxane, dimethoxyethane, and the like; DMF; DMSO; MeCN; alcohols such as MeOH, EtOH, isopropanol, trifluoroethanol, and the like; and chlorinated solvents such as DCM or chloroform (CHCl$_3$). If desired, mixtures of these solvents were used, however, the preferred solvent was dimethoxyethane/water. The above process was carried out at temperatures between about −78° C. and about 120° C. Preferably, the reaction was carried out between 60° C. and about 100° C. The above process to produce compounds of the present invention was preferably carried out at about atmospheric pressure although higher or lower pressures were used if desired. Substantially, equimolar amounts of reactants were preferably used although higher or lower amounts were used if desired.

One skilled in the art will appreciate that alternative methods may be applicable for preparing compounds of Formula II-BB from II-EE. For example, compound of Formula III-BB could be reacted with a suitable organotin reagent or the like in a suitable solvent via typical Stille coupling procedures.

In a typical preparation of compounds of Formula I-EE, compound of Formula II-EE was treated with a suitable acid in a suitable solvent. Suitable solvents for use in the above process included, but were not limited to, ethers such as THF, glyme, dioxane, dimethoxyethane, and the like; DMF; DMSO; MeCN; alcohols such as MeOH, EtOH, isopropanol, trifluoroethanol, and the like; and chlorinated solvents such as DCM or chloroform (CHCl$_3$). If desired, mixtures of these solvents were used, however, the preferred solvent was dioxane. Suitable acids for use in the above process included, but were not limited to, hydrochloride in water, hydrochloride in dioxane, TFA. however, the preferred acid was hydrochloride in dioxane. The above process was carried out at temperatures between about −78° C. and about 120° C. Preferably, the reaction was carried out between 10° C. and about 25° C. The above process to produce compounds of the present invention was preferably carried out at about atmospheric pressure although higher or lower pressures were used if desired. Substantially, equimolar amounts of reactants were preferably used although higher or lower amounts were used if desired.

The compounds of Formula I of this invention and the intermediates used in the synthesis of the compounds of this invention were prepared according to the following methods. Method F was used when preparing compounds of Formula I-AA from compound of Formula I-FF as shown below in Scheme 23:

Scheme 23

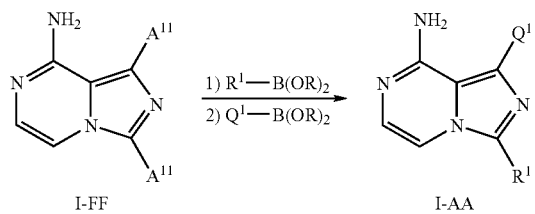

I-FF          I-AA where A$^{11}$=halogen such as Cl, Br, or I and B(OR)$_2$=suitable boronic acid/ester.

In a typical preparation of compounds of Formula I-AA, compound of Formula I-FF was reacted with a suitable boronic acid/ester R$^1$—B(OR)$_2$ in a suitable solvent via typical Suzuki coupling procedures. Suitable solvents for use in the above process included, but were not limited to, ethers such as THF, glyme, dioxane, dimethoxyethane, and the like; DMF; DMSO; MeCN; alcohols such as MeOH, EtOH, isopropanol, trifluoroethanol, and the like; and chlorinated solvents such as DCM or chloroform (CHCl$_3$). If desired, mixtures of these solvents were used, however, the preferred solvent was dimethoxyethane/water. The above process was carried out at temperatures between about −78° C. and about 120° C. Preferably, the reaction was carried out between 60° C. and about 100° C. The reaction was monitored by LC-MS. After completion of first coupling reaction, another suitable boronic acid/ester Q$^1$-B(OR)$_2$ was added to the reaction system for second coupling reaction. The above process to produce compounds of the present invention was preferably carried out at about atmospheric pressure although higher or lower pressures were used if desired. Substantially, equimolar amounts of reactants were preferably used although higher or lower amounts were used if desired.

One skilled in the art will appreciate that alternative methods may be applicable for preparing compounds of Formula I-AA from I-FF. For example, compound of Formula I-FF could be reacted with a suitable organotin reagent or the like in a suitable solvent via typical Stille coupling procedures.

The compounds of Formula I-FF of Scheme 23 were prepared as shown below in Scheme 24:

Scheme 24

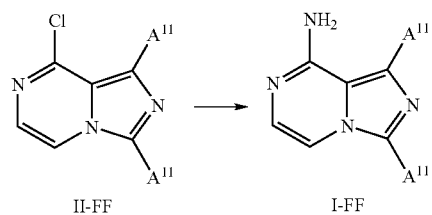

II-FF          I-FF

Where A$^{11}$=halogen such as Cl, Br, or I.

In a typical preparation of compounds of Formula I-FF, compound of Formula II-FF was reacted with ammonia in a suitable solvent. Suitable solvents for use in the above process included, but were not limited to, ethers such as THF, glyme, and the like; DMF; DMSO; MeCN; alcohols such as MeOH, EtOH, isopropanol, trifluoroethanol, and the like; and chlorinated solvents such as DCM or chloroform (CHCl$_3$). If desired, mixtures of these solvents were used, however, the preferred solvents were isopropanol and a mixture of THF and isopropanol. The above process was carried out at temperatures between about −78° C. and about 120° C. Preferably, the reaction was carried out between 80° C. and about 120° C. The above process to produce compounds of the present invention was preferably carried in a sealed reaction vessel such as but not limited to a thick walled glass reaction vessel or a stainless steel Parr bomb. An excess amount of the reactant, ammonia, was preferably used.

The compounds of Formula I'-FF of Scheme 24 were prepared as shown below in Scheme 25:

Scheme 25

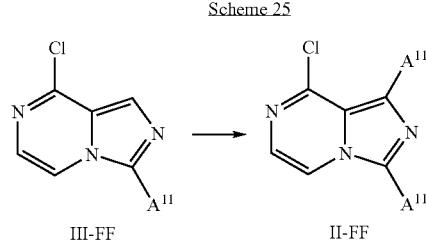

III-FF          II-FF

Where A$^{11}$=halogen such as Cl, Br, or I.

In a typical preparation of compounds of Formula II-FF, compound of Formula III-FF was reacted a suitable halogenating agent in a suitable solvent. Suitable halogenating agent for use in the above process included, but were not limited to, Br$_2$, I$_2$, Cl$_2$, N-chlorosuccinimide, N-bromosuccinimide, or N-iodosuccinimide. The preferred halogenating agent was N-bromosuccinimide. Suitable solvents for use in the above process included, but were not limited to, ethers such as THF, glyme, and the like; DME; DMSO; MeCN; alcohols such as MeOH, EtOH, isopropanol, trifluoroethanol, and the like; and chlorinated solvents such as DCM or chloroform (CHCl$_3$). If desired, mixtures of these solvents were used, however, the preferred solvent was DMF. The above process was carried out at temperatures between about −78° C. and about 120° C. Preferably, the reaction was carried out between 0° C. and about 45° C. The above process to produce compounds of the present invention was preferably carried out at about atmospheric pressure although higher or lower pressures were used if desired. Substantially, equimolar amounts of reactants were preferably used although higher or lower amounts were used if desired.

The compounds of Formula III-FF of Scheme 25 were prepared as shown below in Scheme 26:

Scheme 26

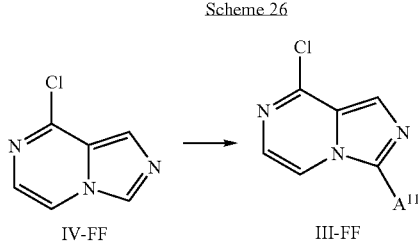

IV-FF    III-FF

Where A$^{11}$ halogen such as Cl, Br, or I

In a typical preparation of a compound of Formula II-FF, a compound of Formula IV-FF was treated under suitable reaction conditions in a suitable solvent with a suitable halogenating agent. Suitable conditions included but were not limited to treating compounds of Formula IV-FF with a suitable base followed by treating with a suitable halogenating agent. Suitable base for use in the above process included, but were not limited to, organolithium base such as n-butyllithium, LDA, lithium tetramethylpiperidide (Li-TMP). Suitable halogenating agent for use in the above process included, but were not limited to, Br$_2$, I$_2$, Cl$_2$, N-chlorosuccinimide, N-bromosuccinimide, or N-iodosuccinimide. The preferred halogenating agent was N-iodosuccinimide. Suitable solvents for use in the above process included, but were not limited to, ethers such as THF, glyme, and the like. Polar solvents such as hexamethylphosphoramide (HMPA), 1,3-dimethyl-3,4,5,6-tetrahydro-2(1H)-pyrimidinone (DMPU), and the like may be added if necessary. If desired, mixtures of these solvents were used, however, the preferred solvent was THF. The above process may be carried out at temperatures between about −80° C. and about 20° C. Preferably, the reaction was carried out at −78° C. to 0° C. The above process to produce compounds of the present invention was preferably carried out at about atmospheric pressure although higher or lower pressures were used if desired. Substantially, equimolar amounts of reactants were preferably used although higher or lower amounts were used if desired.

The compounds of Formula IV-FF in scheme 26 equals to compound of Formula II-BB' in scheme 9 where R$^1$=H.

The compounds of Formula XIV-Z (Q$^1$-B(OR)$_2$) of Scheme 7 were prepared as shown below in Scheme 27:

Scheme 27

XIII-Z    XIV-Z where Q$^1$ is as defined previously for compound of Formula I, A$^{111}$=OTf or halogen such as Cl, Br, or I and B(OR)$_2$=suitable boronic acid/ester.

In a typical preparation of a compound of Formula XIV-Z (Q$^1$-B(OR)$_2$), a compound of Formula XIII-Z (Q$^1$-A$^{111}$) was reacted with a suitable metal catalyst and a suitable boronating agent under suitable reaction conditions. Suitable metal catalyst agents included, but were not limited to, Pd(OAc)$_2$ in the presence of 1,3-bis(2,6-diisopropylphenyl)imidazolium chloride. Suitable boronating agents included, but were not limited to, bis(pinacolato)diboron. Suitable reaction conditions for use in the above process included, but were not limited to, heating a mixture of Pd(OAc)$_2$, 1,3-bis(2,6-diisopropylphenyl)imidazolium chloride, KOAc, and bis(pinacol)borane in a suitable solvent such as, but not limited to, THF. The above process may be carried out at temperatures between about 20° C. and about 100° C. Preferably, the reaction was carried out at 60° C. to 80° C. The above process to produce compounds of the present invention was preferably carried out at about atmospheric pressure although higher or lower pressures were used if desired. Preferably, 2-3 equivalents of KOAc, 1-1.5 equivalents of bis(pinacol)borane, 0.03-1 equivalent of Pd(OAc)$_2$, and 0.09-3 equivalents of 1,3-bis(2,6-diisopropylphenyl)imidazolium chloride were used although higher or lower amounts were used if desired. Additionally, other suitable reaction conditions for the conversion of Q$^1$-A$^{111}$ to Q$^1$-B(OR)$_2$ can be found in the literature which involve a variety of Q$^1$-A$^{111}$ or aryl/heteroarylhalides and a variety of conditions (Biooganic & Medicinal Chemistry Letters, 2003, 12(22), 4001; Biooganic & Medicinal Chemistry Letters, 2003, 13(18), 3059; Chemical Communications (Cambridge, UK), 2003, 23, 2924; Synthesis, 2002, 17, 2503; Angewandte Chemie, International Ed., 2002, 41(16), 3056; Journal of the American Chemical Society, 2002, 124(3), 390; Organic Letters, 2002, 4(4), 541; Tetrahedron, 2001, 57(49), 9813; Journal of Organic Chemistry, 2000, 65(1), 164; Journal of Organic Chemistry, 1997, 62(19), 6458; Journal of Organometallic Chemistry, 1983, 259(3), 269). In some cases, compounds of Formula XIII-Z (Q$^1$-A$^{111}$) and XIV-Z (Q$^1$-B(OR)$_2$) are commercially available or synthesized according to literature procedures. In cases where neither are available, compounds of Formula XIII-Z (Q$^1$-A$^{111}$) and XIV-Z (Q$^1$-B(OR)$_2$) were synthesized via procedures described in the experimental section herein.

Both R$^1$ and Q$^1$ in the compounds described herein in some instances contain functional groups which can be further manipulated. It would be appreciated by those skilled in the art that such manipulation of functional groups can be accomplished with key intermediates or with late stage compounds. Such functional group transformations are exemplified in the following Schemes 28-36 as well as in the experimental section but are in no way meant to limit the scope of such transformations. Additionally, the chemistry shown in Schemes 28-36 can also be applied to compounds of I-BB, II-BB, and II-BB'.

The compounds of Formula I-A (compounds of Formula I-AA where $R^1$=Z—$CONR^2R^3$) were prepared as shown below in Scheme 28:

Scheme 28

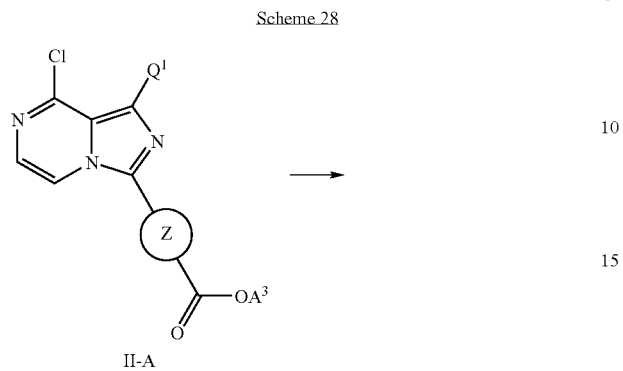

II-A where $Q^1$, $R^2$, and $R^3$ are as defined previously for compound of Formula I and $A^3$=hydrogen or alkyl such as methyl or ethyl.

In a typical preparation of compound of Formula I-A, when $A^3$=alkyl and $R^2$ and $R^3$ were both equal to H, reaction of compound of Formula II-A (compounds of Formula II where $R^1$=Z—$CO_2A^3$) with ammonia in a suitable solvent, afforded compound of Formula I-A. Suitable solvents for use in the above process included, but were not limited to, ethers such as THF, glyme, and the like; DMF; DMSO; MeCN; alcohols such as MeOH, EtOH, isopropanol, trifluoroethanol, and the like; and chlorinated solvents such as DCM or chloroform ($CHCl_3$). If desired, mixtures of these solvents were used, however, the preferred solvents were isopropanol and a mixture of isopropanol/THF. The above process was carried out at temperatures between about −78° C. and about 120° C. Preferably, the reaction was carried out between 80° C. and about 120° C. The above process to produce compounds of the present invention was preferably carried out at about atmospheric pressure although higher or lower pressures were used if desired. Substantially, equimolar amounts of reactants were preferably used although higher or lower amounts were used if desired. Additionally, in a typical preparation of compound of Formula I-A, compound of Formula II-A (when $A^3$H) was reacted with $HNR^2R^3$ followed by ammonia in a suitable solvent. When $A^3$=H, typical coupling procedures as described in Scheme 3 (conversion of $CO_2H$ to COCl via treatment with $SOCl_2$ or oxalyl chloride followed by reaction with $HNR^2R^3$ or treatment of $CO_2H$ and $HNR^2R^3$ with EDC or DCC in conjunction with DMAP, HOBT, or HOAt and the like) were employed to afford the transformation of a carboxylic acid to an amide. When $A^3$=alkyl such as methyl or ethyl, treatment of the ester with $Al(NR^2R^3)$ afforded conversion of $CO_2A^3$ to $CO(NR^2R^3)$. Subsequent treatment with ammonia afforded compounds of Formula I-A.

The compounds of Formula I-A' (compounds of Formula I-AA where $R^1$=Z—$CO_2A^3$) and I-A" (compounds of Formula I-AA where $R^1$=Z—$CO_2H$) were prepared as shown below in Scheme 29:

Scheme 29

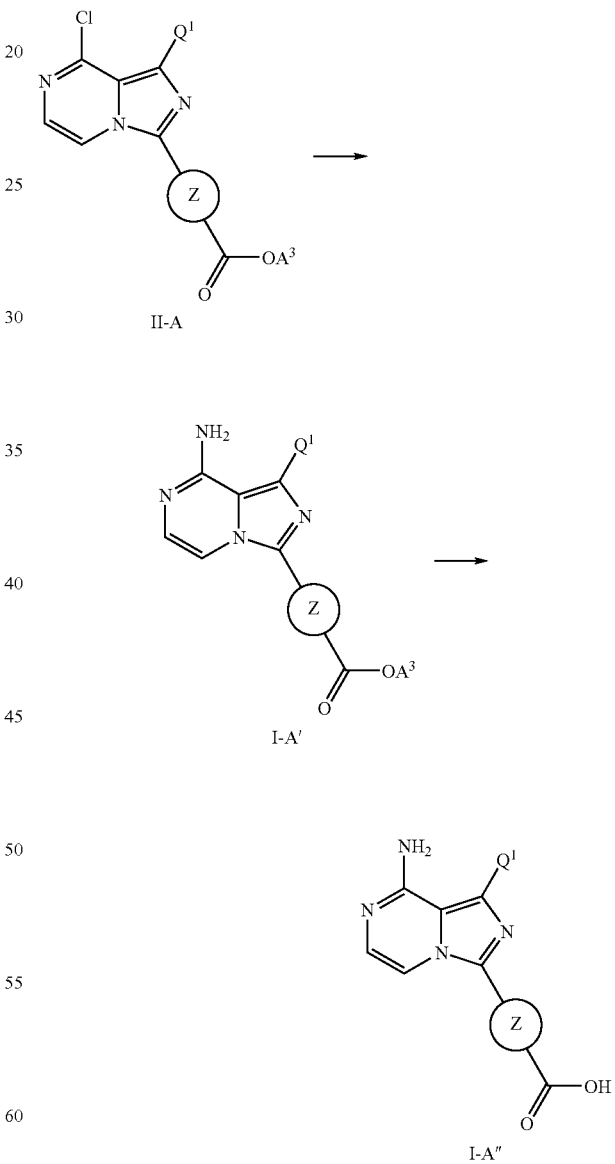

where $Q^1$ is as defined previously for compounds of Formula I and $A^3$=alkyl such as methyl or ethyl.

In a typical preparation of compound of Formula I-A', compound of Formula II-A was reacted with ammonia in a suitable solvent. Suitable solvents for use in the above process included, but were not limited to, ethers such as THF, glyme, and the like; DMF; DMSO; MeCN; alcohols such as MeOH, EtOH, isopropanol, trifluoroethanol, and the like; and chlorinated solvents such as DCM or chloroform ($CHCl_3$). If desired, mixtures of these solvents were used, however, the preferred solvent was isopropanol. The above process was carried out at temperatures between about −78° C. and about 120° C. Preferably, the reaction was carried out between 100° C. and about 120° C. The above process to produce compounds of the present invention was preferably carried out at about atmospheric pressure although higher or lower pressures were used if desired. In most cases, the reactions were run in a sealed tube. Substantially, equimolar amounts of reactants were preferably used although higher or lower amounts were used if desired. Typically, an excess of ammonia was used and the reaction was monitored in order to ensure that additional of ammonia to the ester moiety did not occur to an appreciable extent. Additionally, in a typical preparation of compound of Formula I-A″, compound of Formula I-A′ was reacted under typical saponification conditions such as NaOH in $THF/H_2O/MeOH$. Suitable solvents for use in the above process included, but were not limited to, ethers such as THF, glyme, and the like; DMF; DMSO; MeCN; alcohols such as MeOH, EtOH, isopropanol, trifluoroethanol, and the like; and chlorinated solvents such as DCM or chloroform ($CHCl_3$). If desired, mixtures of these solvents were used, however, the preferred solvent was a mixture of $THF/H_2O/MeOH$. The above process was carried out at temperatures between about −78° C. and about 120° C. Preferably, the reaction was carried out between rt and about 60° C. The above process to produce compounds of the present invention was preferably carried out at about atmospheric pressure although higher or lower pressures were used if desired. Substantially, equimolar amounts of reactants were preferably used although higher or lower amounts were used if desired.

The compounds of Formula II-B (compounds of Formula II where $R^1$=Z—$CH_2OH$) and I-B (compounds of Formula I-AA where $R^1$=Z—$CH_2OH$) were prepared as shown below in Scheme 30:

Scheme 30

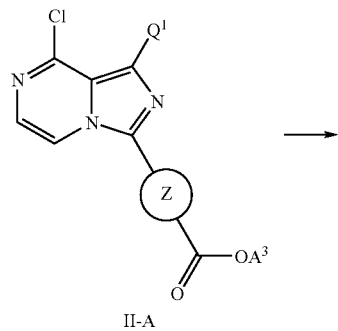

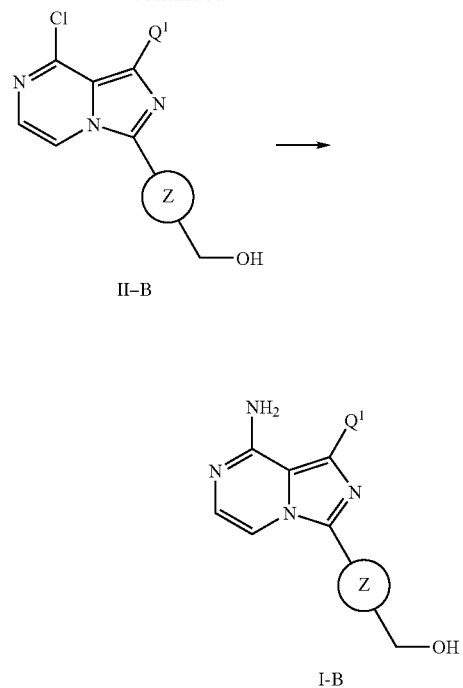

where $Q^1$ is as defined previously for compound of Formula I and $A^3$=hydrogen or alkyl such as methyl or ethyl.

In a typical preparation of compound of Formula I-B, compound of Formula II-A is treated with a suitable reducing agent such as lithium aluminum hydride in a suitable solvent, such as THF to afford compound of Formula II-B. Suitable solvents for use in the above process included, but were not limited to, ethers such as THF, glyme, and the like; DMF; DMSO; MeCN; alcohols such as MeOH, EtOH, isopropanol, trifluoroethanol, and the like; and chlorinated solvents such as DCM or chloroform ($CHCl_3$). If desired, mixtures of these solvents were used. The preferred solvent was THF. The above process was carried out at temperatures between about −78° C. and about 120° C. Preferably, the reaction was carried out between 0° C. and about 50° C. The above process to produce compounds of the present invention was preferably carried out at about atmospheric pressure although higher or lower pressures were used if desired. Substantially, equimolar amounts of reactants were preferably used although higher or lower amounts were used if desired. Subsequent treatment of compound of Formula I′-B under previously described ammonolysis conditions (ammonia in isopropanol in a sealed tube at 120° C.), afforded compound of Formula I-B.

The compounds of Formula II-C (compounds of Formula II where $R^1$=Z—$CH_2A^4$) II-D (compounds of Formula II where $R^1$=Z—$CH_2A^5(R^2)(R^3)_d$), I-B (compounds of Formula I-AA where $R^1$=Z—$CH_2OH$) and I-C (compounds of Formula I-AA where $R^1$=Z—$CH_2A^5(R^2)(R^3)_d$) were prepared as shown below in Scheme 31:

Scheme 31

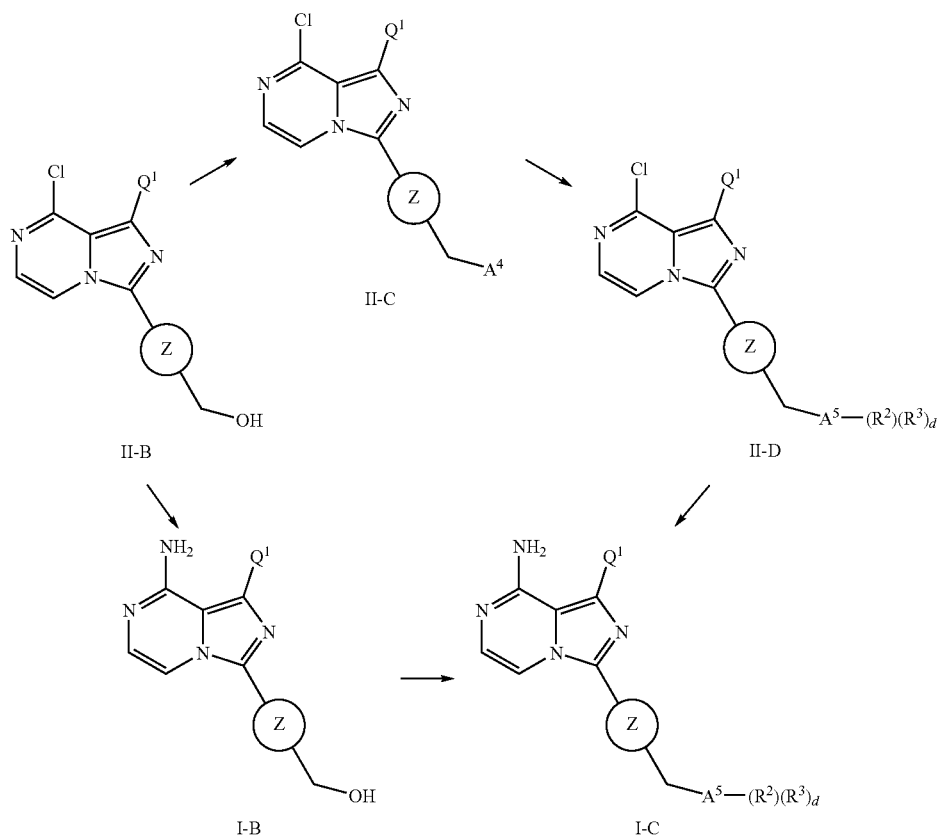

where $Q^1$, $R^2$, and $R^3$ are as defined previously for compound of Formula I; $A^4$ suitable leaving group such as OTs, OMs, OTf, or halo such as chloro, bromo, or iodo; d=0 or 1; and $A^5$=N, O or S.

In a typical preparation of compound of Formula I-C, the hydroxy group of compound of Formula II-B was converted to a suitable leaving group, $A^4$, such as Cl or OTs, OMs, or OTf, by reaction with $SOCl_2$ or $Ts_2O$, $Ms_2O$, or $Tf_2O$ to afford compound of Formula II-C. Reaction of compound of Formula II-C with $HA^5(R^2)(R^3)_d$ afforded compound of Formula II-D. Subsequent reaction of compound of Formula II-D under previously described ammonolysis conditions afforded compound of Formula I-C. Additionally, compound of Formula II-B was converted to compound of Formula I-B as described previously in Scheme 30. Further conversion of compound of Formula I-B to compound of Formula I-C was accomplished by following the previously described conditions for the conversion of compound of Formula II-B to compound of Formula II-C and the further conversion of compound of Formula II-C to compound of Formula II-D (in the net conversion of OH to $A^5(R^2)(R^3)_d$). Furthermore, compound of Formula II-B can be directly converted to compound of Formula II-D by treating compound of Formula II-B with various alkylating agent or with phenols via the Mitsunobu reaction to afford compounds Formula II-D (compounds of Formula II where $R^1$=$CH_2$—Z—$A^5(R^2)(R^3)_d$) in which $A^5$=O, d=0, and $R^2$=alkyl or aryl).

The compounds of Formula I-C' (compounds of Formula I-AA where $R^1$=Z—$CH_2$-$A^2$), I-C" (compounds of Formula I-AA where $R^1$=Z—$CH_2$—$NH_2$), and I-C''' (compounds of Formula I-AA where $R^1$=Z—$CH_2$—N($R^2$)($R^3$)) were prepared as shown below in Scheme 32:

Scheme 32

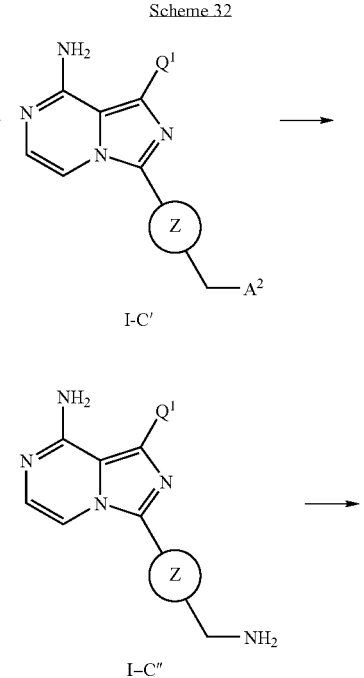

-continued

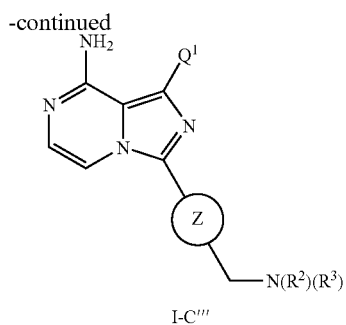

I-C''' where $Q^1$, $R^2$, and $R^3$ are as defined previously for compound of Formula I and $A^2$=phthalimido or $N_3$.

In a typical preparation of compounds of Formula I-C', I-C'', and I-C''', the hydroxy group of compound of Formula I-B was converted to $A^2$, following the procedures as described in Scheme 5 for the conversion of compound of Formula VII to compound of Formula VI. Reaction of compound of Formula I-C' under conditions described in Scheme 4 afforded compound of Formula I-C''. Reaction of compound of Formula I-C'' with, but not limited to various alkylating agents, various aldehydes/ketones under reductive amination conditions, various acylating agents such as acetic anhydride, benzoyl chlorides, or with carboxylic acids in the presence of EDC or DCC with HOBT or HOAT, or with sulfonylating agents such as $Ts_2O$ or $MeSO_2Cl$ afforded compounds of Formula I-C'''. For example, in a typical preparation of compounds of Formula I-C''', a compound of Formula I-C'' is treated with a suitable acylating agent in the presence of a suitable base in a suitable solvent. Suitable solvents for use in the above process included, but were not limited to, ethers such as THF, glyme, and the like; and chlorinated solvents such as DCM or chloroform ($CHCl_3$). If desired, mixtures of these solvents were used, however; the preferred solvent was chloroform. Suitable bases for use in the above process included, but were not limited to, trialkylamines such as DMF, TEA, or resin bound trialkylamines such as PS-DIEA. The preferred base was PS-DIEA. In the case where the suitable acylating agent was acetic anhydride, the conversion of compound of Formula I-C'' to compound of Formula I-C''' where $R^2$H and $R^3$=$COCH_3$ was accomplished. The above process was carried out at temperatures between about −78° C. and about 120° C. Preferably, the reaction was carried out between 0° C. and about 20° C. The above process to produce compounds of the present invention was preferably carried out at about atmospheric pressure although higher or lower pressures were used if desired. Substantially, equimolar amounts of reactants were preferably used although higher or lower amounts were used if desired.

The compounds of Formula II-G (compounds of Formula II where $R^1$=$Z^3$—OH), II-H (compounds of Formula II where $R^1$=Z-$A^5(R^2)(R^3)_d$), I-F (compounds of Formula I-AA where $R^1$=Z—OH), and I-G (compounds of Formula I-AA where $R^1$=Z-$A^5(R^2)(R^3)_d$) were prepared as shown below in Scheme 33:

Scheme 33

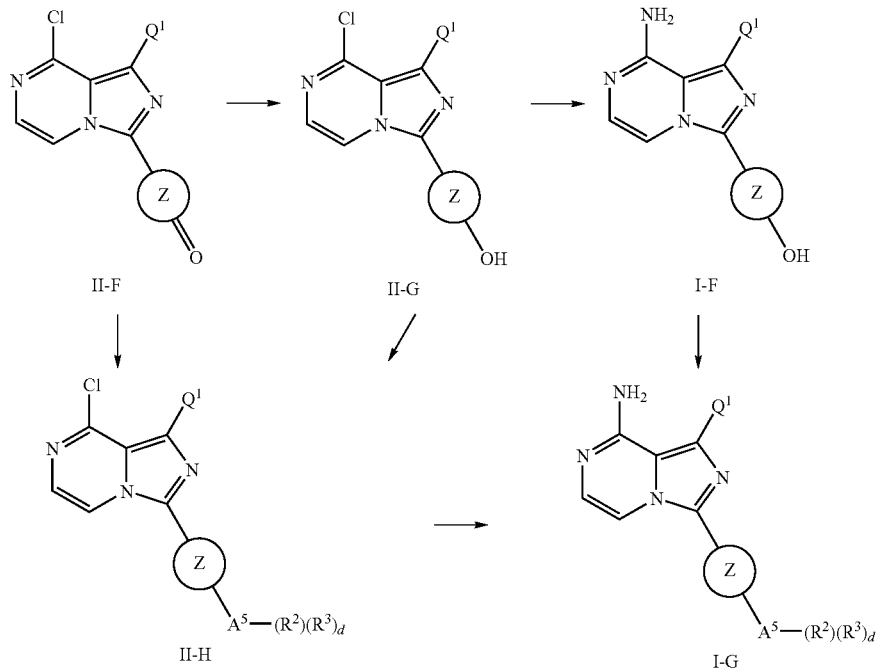

where $Q^1$, $R^2$, and $R^3$ are as defined previously for compound of Formula I; d=0 or 1; and $A^5$=N, O or S.

In a typical preparation of compound of Formula I-F and I-G, the following transformations occurred: Compound of Formula II-F was reduced with a suitable reducing agent in a suitable solvent, such as sodium borohydride in MeOH to afford compound of Formula II-G. Compound of Formula II-G was subjected to previously described ammonolysis conditions to afford compound of Formula I-F. Additionally, compounds of Formula II-F can be reacted with various amines under reductive amination conditions ($NaBH_3CN$ or $NaBH(OAc)_3$ with $HA^5(R^2)(R^3)_d$ where d=0, $A^5$=N, and $R^2$ and $R^3$ are as previously described for compound of Formula I) to afford compounds of Formula II-H where d=0, $A^5$=N, and R² and R³ are as previously described for compound of Formula I. Subsequent reaction of compounds of Formula II-H (compounds of Formula I where R¹=Z-A⁵(R²)(R³)$_d$ where d=0, A⁵=N, and R² and R³ are as previously described for compound of Formula I) with previously described ammonolysis conditions afforded compounds of Formula I-G. Furthermore, compounds of Formula II-H from II-G and I-G from I-F can be synthesized according to the conditions described in Scheme 31 for the transformations of II-B to II-D and I-B to I-C, respectively.

The compounds of Formula I-C''' (compounds of Formula I-AA where R¹=Z—CH₂—N(R²)(R³)) were prepared as shown below in Scheme 34:

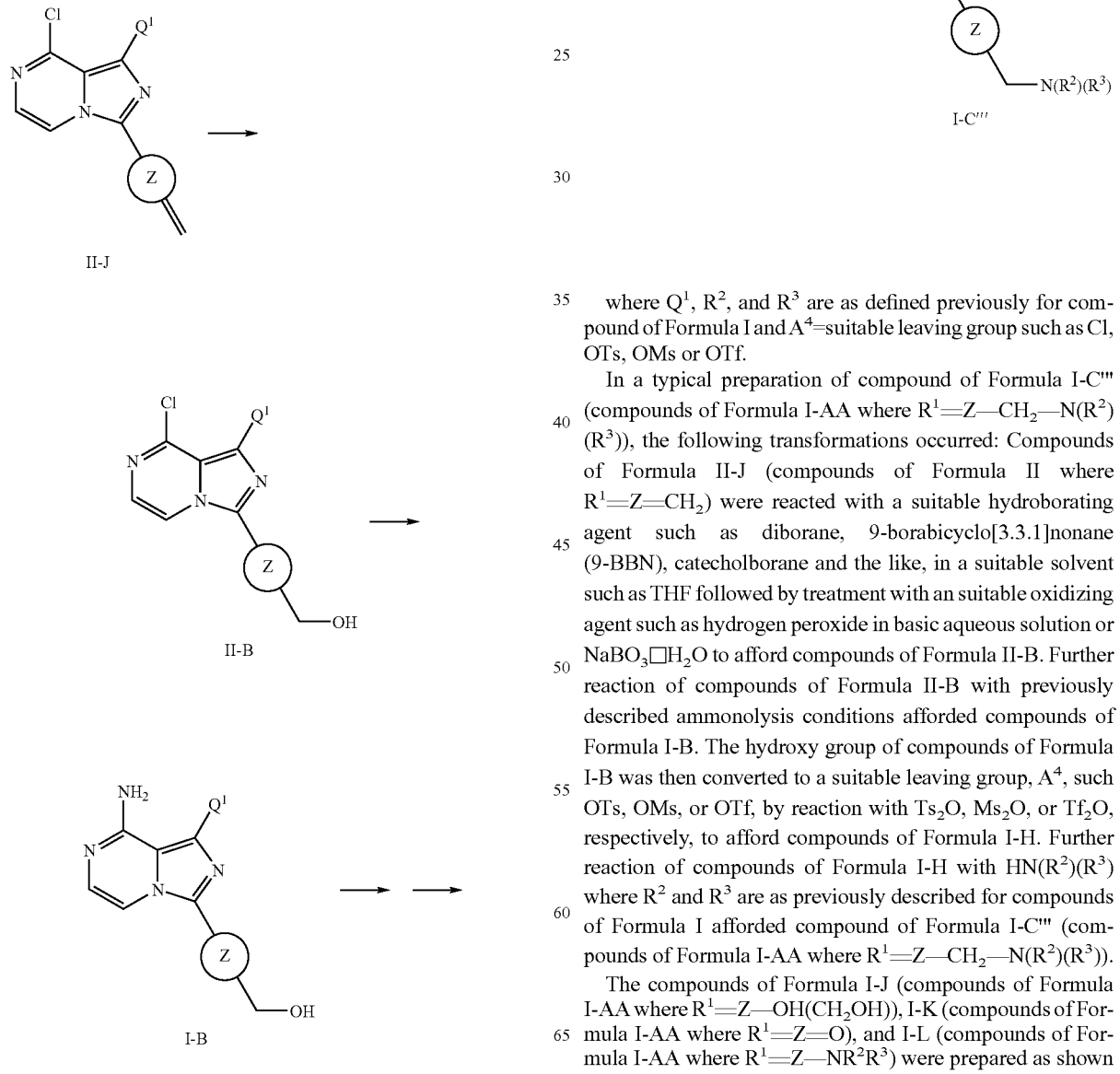

where Q¹, R², and R³ are as defined previously for compound of Formula I and A⁴=suitable leaving group such as Cl, OTs, OMs or OTf.

In a typical preparation of compound of Formula I-C''' (compounds of Formula I-AA where R¹=Z—CH₂—N(R²)(R³)), the following transformations occurred: Compounds of Formula II-J (compounds of Formula II where R¹=Z=CH₂) were reacted with a suitable hydroborating agent such as diborane, 9-borabicyclo[3.3.1]nonane (9-BBN), catecholborane and the like, in a suitable solvent such as THF followed by treatment with an suitable oxidizing agent such as hydrogen peroxide in basic aqueous solution or NaBO₃□H₂O to afford compounds of Formula II-B. Further reaction of compounds of Formula II-B with previously described ammonolysis conditions afforded compounds of Formula I-B. The hydroxy group of compounds of Formula I-B was then converted to a suitable leaving group, A⁴, such OTs, OMs, or OTf, by reaction with Ts₂O, Ms₂O, or Tf₂O, respectively, to afford compounds of Formula I-H. Further reaction of compounds of Formula I-H with HN(R²)(R³) where R² and R³ are as previously described for compounds of Formula I afforded compound of Formula I-C''' (compounds of Formula I-AA where R¹=Z—CH₂—N(R²)(R³)).

The compounds of Formula I-J (compounds of Formula I-AA where R¹=Z—OH(CH₂OH)), I-K (compounds of Formula I-AA where R¹=Z=O), and I-L (compounds of Formula I-AA where R¹=Z—NR²R³) were prepared as shown below in Scheme 35:

Scheme 35

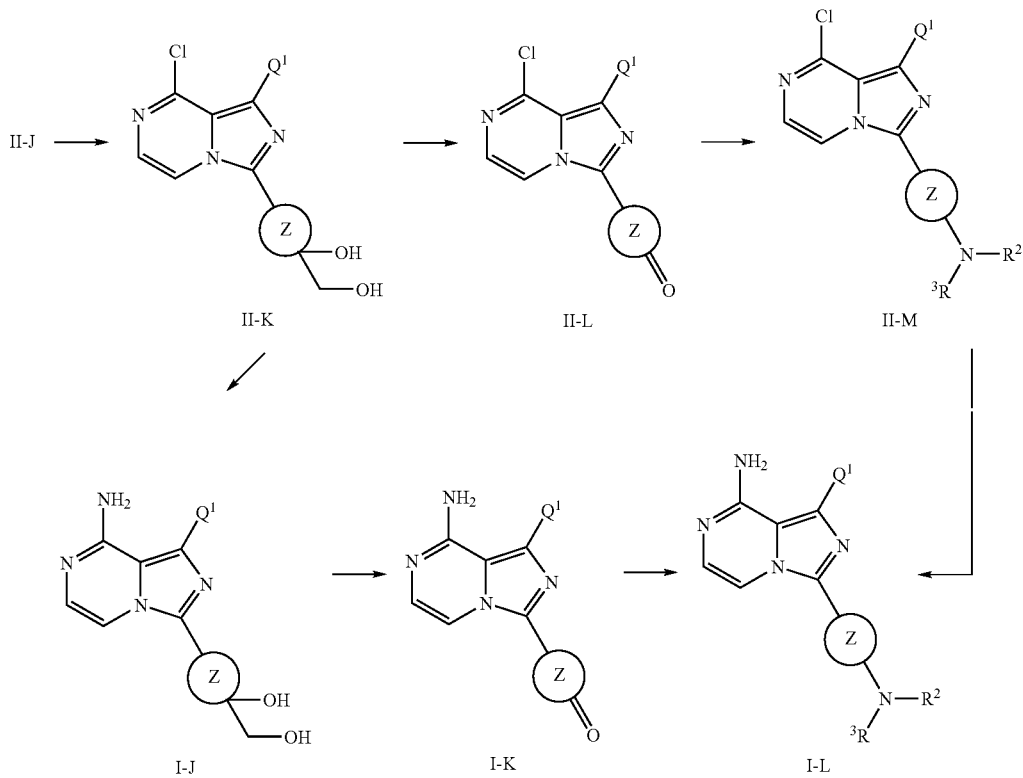

where $Q^1$, $R^2$ and $R^3$ are as defined previously for compound of Formula I.

In a typical preparation of compound of Formula I-J (compounds of Formula I-AA where $R^1=Z-OH(CH_2OH)$), I-K (compounds of Formula I-AA where $R^1=Z=O$), and I-L (compounds of Formula I-AA where $R^1=Z-NR^2R^3$) compound of Formula II-J was treated under (compounds of Formula II where $R^1=Z=CH_2$) was reacted with a suitable dihydroxylating agent such as osmium tetraoxide in the presence of NMO in a suitable solvent such as THF to afford compound of Formula II-K (compounds of Formula II where $R^1=Z-OH(CH_2OH)$) as a mixture of cis and trans isomers. Compounds of Formula I'-K (compounds of Formula II where $R^1=Z-OH(CH_2OH)$) were treated with a suitable oxidizing agent, such as but not limited to, $NaIO_4$, converting the diol into a ketone moiety, affording compound of Formula I'-L (compounds of Formula II where $R^1=Z=O$). Compound of Formula I'-L (compounds of Formula II where $R^1=Z=O$) was then treated under typical reductive amination conditions, involving a suitable amine, $HNR^2R^3$ and a suitable reducing agent, such as but not limited to, $NaBH(OAc)_3$ or $NaBH(CN)_3$, affording compound of Formula II-M (compounds of Formula II where $R^1=Z-NR^2R^3$). Compound of Formula II-M (compounds of Formula II where $R^1=Z-NR^2R^3$) was treated under ammonolysis conditions, ammonia in isopropanol in a stainless steel bomb at 110° C., to afford compound of Formula I-L (compounds of Formula I-AA where $R^1=Z-NR^2R^3$). Moreover, compound of Formula II-K (compounds of Formula II where $R^1=Z-OH(CH_2OH)$) was treated under the ammonolysis conditions described above to afford compound of Formula I-J (compounds of Formula I-AA where $R^1=Z-OH(CH_2OH)$) as a mixture of isomers. Compound of Formula I-J (compounds of Formula I-AA where $R^1=Z-OH(CH_2OH)$) was treated with a suitable oxidizing agent, such as but not limited to, $NaIO_4$, converting the diol into a ketone moiety, affording compound of Formula I-K (compounds of Formula I-AA where $R^1=Z=O$), which was treated under the typical reductive amination conditions described above to afford compound of Formula I-L (compounds of Formula I-AA where $R^1=Z-NR^2R^3$).

The compounds of Formula I-O (compounds of Formula I where $R^1=Z^3-OH(G^{11})$) were prepared as shown below in Scheme 36:

Scheme 36

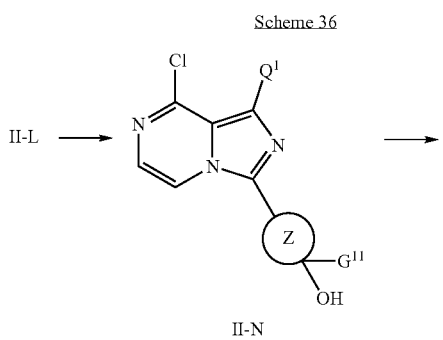

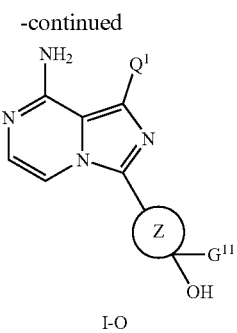

I-O where $Q^1$ and $G^{11}$ are as defined previously for compound of Formula I.

In a typical preparation of compounds of Formula I-O (compounds of Formula I where $R^1$=Z—OH($G^{11}$)), the ketone moiety of compound of Formula II-L (compounds of Formula II where $R^1$=Z=O) was reacted with a suitable nucleophilic reagent such as MeMgBr or MeLi in a suitable solvent such as THF to afford compound of Formula II-N (compounds of Formula II where $R^1$=Z—OH($G^{11}$)). Compound of Formula II-N (compounds of Formula II where $R^1$=Z—OH($G^{11}$)) was reacted under ammonolysis conditions, ammonia in isopropanol in a stainless steel bomb at 110° C., to afford compound of Formula I-O (compounds of Formula I where $R^1$=Z—OH($G^{11}$)). Additionally, compound of Formula I-O (compounds of Formula I where $R^1$=Z—OH($G^{11}$)) was prepared by reacting compound of Formula I-K (compounds of Formula I-AA where $R^1$=Z=O) with a suitable nucleophilic reagent such as MeMgBr or MeLi in a suitable solvent such as THF.

It would be appreciated by those skilled in the art that in some situations, a substituent that is identical or has the same reactivity to a functional group which has been modified in one of the above processes, will have to undergo protection followed by deprotection to afford the desired product and avoid undesired side reactions. Alternatively, another of the processes described within this invention may be employed in order to avoid competing functional groups. Examples of suitable protecting groups and methods for their addition and removal may be found in the following reference: "Protective Groups in Organic Syntheses", T. W. Greene and P. G. M. Wuts, John Wiley and Sons, 1989.

Compound of Formula I-AQ is equal to compound of Formula I wherein $X_1$ CH; $X_2$, $X_3$ and $X_5$=N; $X_4$, $X_6$, and $X_7$=C and J=H or $NH_2$

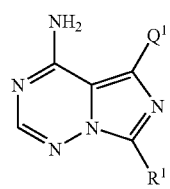

I-AQ

Method AQ was used when preparing compounds of Formula I-AQ as shown below in Scheme 37:

Method AQ:

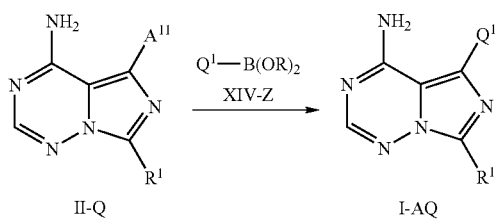

where $Q^1$ and $R^1$ are as defined previously for compound of Formula I, $A^{11}$=halogen such as Cl, Br, or I; $B(OR)_2$=suitable boronic acid/ester.

In a typical preparation of compounds of Formula I-AQ, compound of Formula II-Q was reacted with a suitable boronic acid/ester ($Q^1$-$B(OR)_2$) in a suitable solvent via typical Suzuki coupling procedures. Suitable solvents for use in the above process included, but were not limited to, water, ethers such as THF, glyme, and the like; DMF; DMSO; MeCN; alcohols such as MeOH, EtOH, isopropanol, trifluoroethanol, and the like; and chlorinated solvents such as DCM or chloroform ($CHCl_3$). If desired, mixtures of these solvents were used, however, the preferred solvent was glyme/water. The above process was carried out at temperatures between about −78° C. and about 120° C. Preferably, the reaction was carried out between 80° C. and about 100° C. The above process to produce compounds of the present invention was preferably carried out at about atmospheric pressure although higher or lower pressures were used if desired. Substantially equimolar amounts of reactants were preferably used although higher or lower amounts were used if desired.

One skilled in the art will appreciate that alternative methods may be applicable for preparing compounds of Formula I-AC from II-Q. For example, compound of Formula II-Q could be reacted with a suitable organotin reagent $Q^1$-$SnBu_3$ or the like in a suitable solvent via typical Stille coupling procedures.

The compounds of Formula II-Q of Scheme 37 were prepared as shown below in Scheme 38:

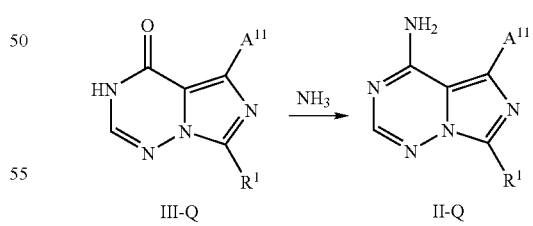

where $R^1$ is as defined previously for compound of Formula I and $A^{11}$=halogen such as Cl, Br, or 1.

In a typical preparation of compounds of Formula II-Q, compound of Formula III-Q was reacted with phosphorus oxychloride ($POCl_3$) and triazole, and pyridine followed by ammonia ($NH_3$) in a suitable solvent. Suitable solvents for use in the above process included, but were not limited to, ethers such as THF, glyme, and the like; DMF; DMSO; MeCN; alcohols such as MeOH, EtOH, isopropanol, trifluoroethanol, and the like, and chlorinated solvents such as DCM or chloroform (CHCl$_3$). If desired, mixtures of these solvents were used, however, the preferred solvent was isopropanol. The above process was carried out at temperatures between about −20° C. and about 50° C. Preferably, the reaction was carried out between 0° C. and about 25° C. The above process to produce compounds of the present invention was preferably carried out at about atmospheric pressure although higher or lower pressures were used if desired. Substantially equimolar amounts of reactants were preferably used although higher or lower amounts were used if desired.

The compounds of Formula III-Q of Scheme 38 were prepared as shown below in Scheme 39:

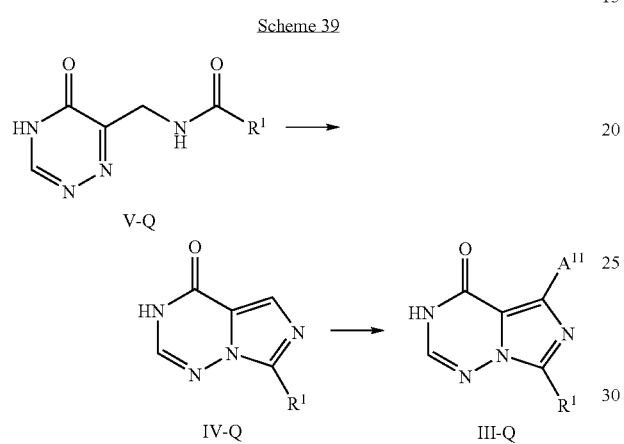

where R$^1$ is as defined previously for compound of Formula I; A$^{11}$=halogen such as Cl, Br, or I.

In a typical preparation of a compound of Formula III-Q, intermediate V-Q was converted to compound of Formula IV-Q. Intermediate of Formula V-Q was treated with phosphorus oxychloride (POCl$_3$) in a suitable solvent at a suitable reaction temperature. Suitable solvents for use in the above process included, but were not limited to, ethers such as THF, glyme, and the like, chlorinated solvents such as DCM or chloroform (CHCl$_3$), and MeCN. If desired, mixtures of these solvents were used. The preferred solvent was MeCN. The above process was carried out at temperatures between about −78° C. and about 120° C. Preferably, the reaction was carried out between 40° C. and about 95° C. The above process to produce compounds of the present invention was preferably carried out at about atmospheric pressure although higher or lower pressures were used if desired. Intermediate for Formula III-Q was prepared by reacting intermediate of Formula IV-Q with a suitable halogenating agent. Suitable halogenating agents included, but were not limited to, Br$_2$, I$_2$, Cl$_2$, N-chlorosuccinimide, N-bromosuccinimide, or N-iodosuccinimide. The preferred halogenating agent was N-iodosuccinimide. Suitable solvents for use in the above process included, but were not limited to, ethers such as THF, glyme, and the like; DMF; DMSO; MeCN; alcohols such as MeOH, EtOH, isopropanol, trifluoroethanol, and the like; and chlorinated solvents such as DCM or chloroform (CHCl$_3$). If desired, mixtures of these solvents were used, however, the preferred solvent was DMF. The above process was carried out at temperatures between about −78° C. and about 120° C. Preferably, the reaction was carried out between 40° C. and about 75° C. The above process to produce compounds of the present invention was preferably carried out at about atmospheric pressure although higher or lower pressures were used if desired. Substantially equimolar amounts of reactants were preferably used although higher or lower amounts were used if desired.

Compounds of Formulae IV-Q and II-Q where J=NH$_2$ can be respectively converted into the compounds of Formulae IV-Q and III-Q where J=H, by diazotization procedures known to those skilled in the art. A typical procedure includes the treatment of a compound of Formula IV-Q or III-Q where J=NH$_2$ with tert-butylnitrite in a suitable solvent such a THF or DMF.

The compounds of Formula V-Q of Scheme 39 were prepared as shown below in Scheme 40:

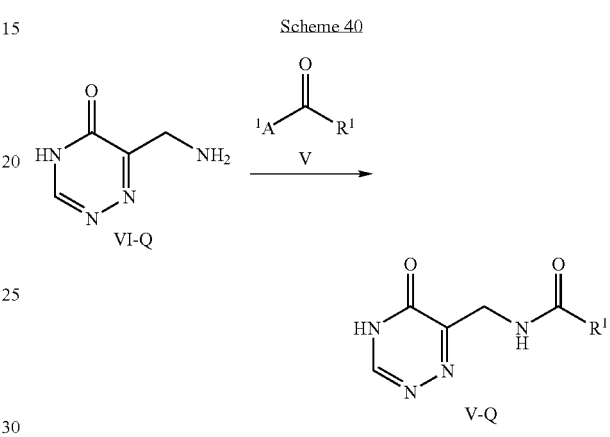

where R$^1$ is as defined previously for compound of Formula I; A$^1$=OH, alkoxy, or a leaving group such as chloro or imidazole.

In a typical preparation, of a compound of Formula V-Q, a compound of Formula VI-Q and compound of Formula V were reacted under suitable amide—coupling conditions. Suitable conditions include but are not limited to treating compounds of Formula VI-Q and V (when A$^1$=OH) with coupling reagents such as DCC or EDC in conjunction with DMAP, HOBt, HOAt and the like, or reagents like EEDQ. Suitable solvents for use in the above process included, but were not limited to, ethers such as THF, glyme, and the like; DMF; DMSO; MeCN; halogenated solvents such as chloroform or DCM. If desired, mixtures of these solvents used, however the preferred solvent was DCM. The above process was carried out at temperatures between about 0° C. and about 80° C. Preferably, the reaction was carried out at about 22° C. The above process to produce compounds of the present invention was preferably carried out at about atmospheric pressure although higher or lower pressures were used if desired. Substantially equimolar amounts of reactants were preferably used although higher or lower amounts were used if desired. Alternatively, compounds of Formula VI-Q and V (where A$^1$=F, Cl, Br, I) were reacted with bases such as TEA or ethyldiisopropylamine and the like in conjunction with DMAP and the like. Suitable solvents for use in this process included, but were not limited to, ethers such as THF, glyme, and the like; DMF; DMSO; MeCN; pyridine; halogenated solvents such as chloroform or DCM. If desired, mixtures of these solvents were used, however the preferred solvent was DMF. The above process was carried out at temperatures between about −20° C. and about 40° C. Preferably, the reaction was carried out between 0° C. and 25° C. The above process to produce compounds of the present invention was preferably carried out at about atmospheric pressure although higher or lower pressures were used if desired. Substantially equimolar amounts of compounds of Formula VI-Q and V (where $A^1$=F, Cl, Br, I) and base and substoichiometric amounts of DMAP were preferably used although higher or lower amounts were used if desired. Additionally, other suitable reaction conditions for the conversion of an amine (compound of Formula VI-Q) to an amide (compound of Formula V-Q) can be found in Larock, R. C. Comprehensive Organic Transformations, $2^{nd}$ ed.; Wiley and Sons: New York, 1999, pp 1941-1949.

The compounds of Formula VI-Q of Scheme 40 were prepared as shown below in Scheme 41:

Scheme 41

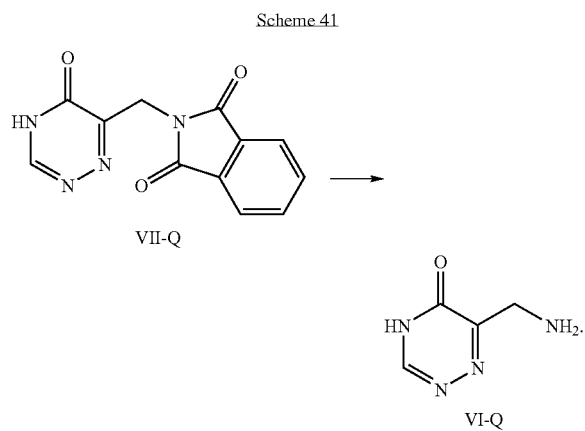

In a typical preparation, of a compound of Formula VI-Q, a compound of Formula VII-Q is reacted under suitable reaction conditions in a suitable solvent. Suitable conditions include treatment of compound of Formula VII-Q with hydrazine or methyl hydrazine in a suitable solvent. Suitable solvents for use in the above process included, but were not limited to, ethers such as THF, glyme, and the like; DMF; DMSO; MeCN; halogenated solvents such as chloroform or DCM; alcoholic solvents such as MeOH and EtOH. If desired, mixtures of these solvents may be used, however the preferred solvents were EtOH and DCM. The above process was carried out at temperatures between about 0° C. and about 80° C. Preferably, the reaction was carried out at about 22° C. The above process to produce compounds of the present invention was preferably carried out at about atmospheric pressure although higher or lower pressures were used if desired. Substantially equimolar amounts of reactants were preferably used although higher or lower amounts were used if desired.

Compounds of Formula VI-Q where J=NH$_2$ may be prepared according to the procedures described in J. Het. Chem., (1984), 21, 697.

The compounds of Formula VII-Q of Scheme 41 were prepared as shown below in Scheme 42:

Scheme 42

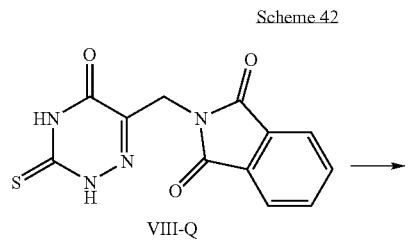

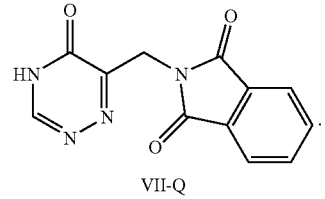

In a typical preparation of a compound of Formula VII-Q, a compound of Formula VIII-Q was reacted with Raney Nickel in a suitable solvent. Suitable solvents for use in the above process included, but were not limited to, ethers such as THF, glyme, and the like; DMF; DMSO; MeCN(CH$_3$CN); alcohols such as MeOH, EtOH, isopropanol, trifluoroethanol, and the like; chlorinated solvents such as DCM or chloroform (CHCl$_3$). If desired, mixtures of these solvents were used, however, the preferred solvent was EtOH. The above process may be carried out at temperatures between about rt and about 100° C. Preferably, the reaction was carried out at about 80° C. The above process to produce compounds of the present invention was preferably carried out at about atmospheric pressure although higher or lower pressures were used if desired. Substantially equimolar amounts of reactants were preferably used although higher or lower amounts were used if desired. Additionally a compound of Formula VII-Q can be prepared by reacting a compound of Formula VIII-Q with a suitable oxidizing agent in a suitable solvent: A suitable oxidizing agent includes, but is not limited to hydrogen peroxide (H$_2$O$_2$), 3-chloro peroxybenzoic acid (mCPBA) and the like. Suitable solvents for use in the above process included, but were not limited to, ethers such as THF, glyme, and the like; DMF; DMSO; CH$_3$CN; and DMA; chlorinated solvents such as CH$_2$Cl$_2$ or CHCl$_3$ If desired, mixtures of these solvents were used, however, the preferred solvent was DMA. The above process may be carried out at temperatures between about 0° C. and 100° C. Preferably, the reaction was carried out at about rt to 70° C. The above process to produce compounds of the present invention was preferably carried out at about atmospheric pressure although higher or lower pressures were used if desired. Substantially equimolar amounts of reactants were preferably used although higher or lower amounts were used if desired.

The compounds of Formula VIII-Q of Scheme 42 were prepared as shown below in Scheme 43:

Scheme 43

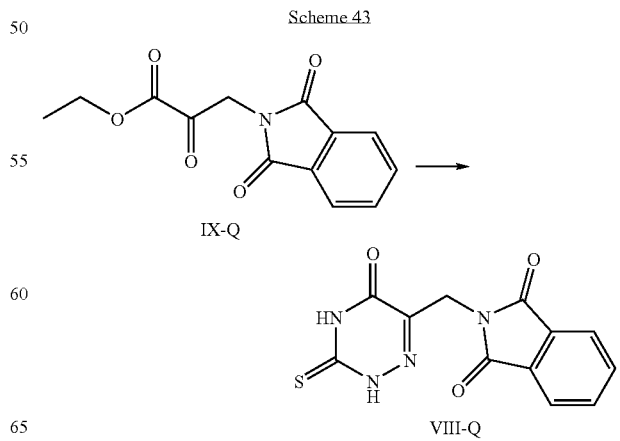

In a typical preparation of a compound of Formula VIII-Q, a compound of Formula IX-Q was reacted with thiosemicarbazide and a suitable base in a suitable solvent. Suitable bases include, but were not limited to TEA, ethyldiisopropylamine and the like. Suitable solvents for use in the above process included, but were not limited to, ethers such as THF, glyme, and the like; DMF; DMA; DMSO; MeCN (CH$_3$CN); alcohols such as MeOH, EtOH, isopropanol, trifluoroethanol, and the like; chlorinated solvents such as DCM or chloroform (CHCl$_3$). If desired, mixtures of these solvents were used, however, the preferred solvent was EtOH. The above process may be carried out at temperatures between about rt and about 100° C. Preferably, the reaction was carried out between about 40° C. and 80° C. The above process to produce compounds of the present invention was preferably carried out at about atmospheric pressure although higher or lower pressures were used if desired. Substantially equimolar amounts of reactants were preferably used although higher or lower amounts were used if desired. Compound of Formula IX-Q can be prepared according to literature procedures Knutsen, Lars J. S. et. al., J. Chem. Soc. Perkin Trans 1: Organic and Bio-Organic Chemistry (1972-1999), 1984, 229-238.

It would be appreciated by those skilled in the art that in some situations, a substituent that is identical or has the same reactivity to a functional group which has been modified in one of the above processes, will have to undergo protection followed by deprotection to afford the desired product and avoid undesired side reactions. Alternatively, another of the processes described within this invention may be employed in order to avoid competing functional groups. Examples of suitable protecting groups and methods for their addition and removal may be found in the following reference: "Protective Groups in Organic Syntheses", T. W. Greene and P. G. M. Wuts, John Wiley and Sons, 1989.

Method AW was also used when preparing compounds of Formula II-Q as shown below in Scheme 44:

Method AW:

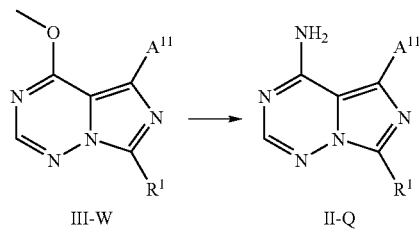

III-W          II-Q where Q$^1$ and R$^1$ are as defined previously for compound of Formula I, and A$^{11}$=halogen such as Cl, Br, or I.

In a typical preparation of compounds of Formula II-Q, compound of Formula III-W was reacted with ammonia in a suitable solvent. Suitable solvents for use in the above process included, but were not limited to, ethers such as THF, glyme, and the like; alcohols such as MeOH, EtOH, isopropanol, trifluoroethanol, and the like; and chlorinated solvents such as DCM or chloroform (CHCl$_3$). If desired, mixtures of these solvents were used, however, the preferred solvent was isopropanol. The above process was carried out at temperatures between about 0° C. and about 50° C. Preferably, the reaction was carried out at between 0° C. and about 22° C. The above process to produce compounds of the present invention was preferably carried out at about atmospheric pressure although higher or lower pressures were used if desired. Substantially equimolar amounts of reactants were preferably used although higher or lower amounts were used if desired.

The compounds of Formula III-W of Scheme 44 were prepared as shown below in Scheme 45.

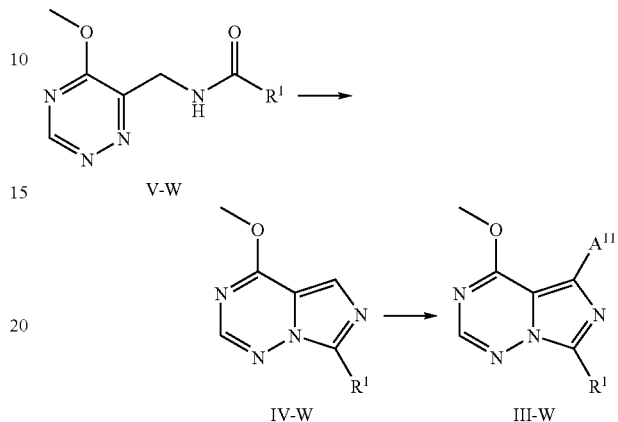

IV-W          III-W where R$^1$ is as defined previously for compound of Formula I and A$^{11}$ halogen such as Cl, Br, or I.

In a typical preparation of a compound of Formula III-W, compound V-W was converted to compound of Formula IV-W. Compound of Formula V-W was treated with phosphorus oxychloride (POCl$_3$) or the isolated "Vilsmeir salt" [CAS#33842-02-3] in a suitable solvent at a suitable reaction temperature. Suitable solvents for use in the above process included, but were not limited to, ethers such as THF, glyme, and the like, chlorinated solvents such as DCM or chloroform (CHCl$_3$), and MeCN (CH$_3$CN). If desired, mixtures of these solvents were used. The preferred solvent was MeCN. The above process was carried out at temperatures between about −78° C. and about 120° C. Preferably, the reaction was carried out between 40° C. and about 95° C. The above process to produce compounds of the present invention was preferably carried out at about atmospheric pressure although higher or lower pressures were used if desired. Compounds of Formula III-W were prepared by reacting compound of Formula IV-W with a suitable halogenating agent. Suitable halogenating agents included, but were not limited to, Br$_2$, I$_2$, Cl$_2$, N-chlorosuccinimide, N-bromosuccinimide, or N-iodosuccinimide. The preferred halogenating agent was N-iodosuccinimide. Suitable solvents for use in the above process included, but were not limited to, ethers such as THF, glyme, and the like; DMF; DMSO; MeCN; alcohols such as MeOH, EtOH, isopropanol, trifluoroethanol, and the like; and chlorinated solvents such as DCM or chloroform (CHCl$_3$). If desired, mixtures of these solvents were used, however, the preferred solvent was DMF. The above process was carried out at temperatures between about −78° C. and about 120° C. Preferably, the reaction was carried out between 40° C. and about 75° C. The above process to produce compounds of the present invention was preferably carried out at about atmospheric pressure although higher or lower pressures were used if desired. Substantially equimolar amounts of reactants were preferably used although higher or lower amounts were used if desired.

The compounds of Formula V-W of Scheme 45 were prepared as shown below in Scheme 46.

Scheme 46

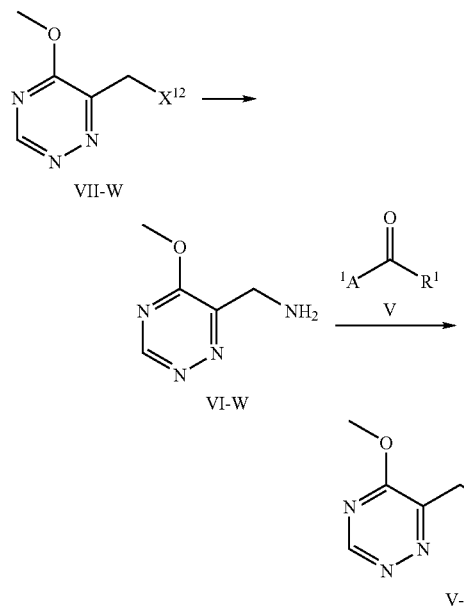

VII-W

VI-W

V-W where R¹ is as defined previously for compound of Formula I, $X^{12}$=azido, or mono- or di-protected amino and $A^1$=OH, alkoxy or a leaving group such as chloro or imidazole.

In a typical preparation of a compound of Formula V-W, compound VI-W was reacted with compound V under suitable amide coupling conditions. Suitable conditions include but are not limited to those described for the conversion of compound XIII to compound XII as shown in Scheme 10. Compounds of Formula VI-W were prepared from compounds of Formula VII-W. A typical procedure for the conversion of compounds of Formula VIII-W to compounds of Formula VI-W involves subjecting a compound of Formula VII-W, where $X^{12}$=azido, to reducing conditions such as, but not limited to, catalytic hydrogenation in a suitable solvent at a suitable reaction temperature. Suitable solvents for use in the above process included, but were not limited to, ethers such as THF, glyme, and the like, alcoholic solvents such as MeOH, EtOH and the like, esters such as EtOAc, methyl acetate and the like. If desired, mixtures of these solvents were used. The preferred solvents were EtOAc and MeOH. The above process was carried out at temperatures between about −78° C. and about 120° C. Preferably, the reaction was carried out between 40° C. and about 95° C. The above process to produce compounds of the present invention was preferably carried out at about atmospheric pressure although higher or lower pressures were used if desired. Alternatively, when $X^{12}$=azido, the reduction to compounds of Formula VI-W could be achieved by treatment of a compound of Formula VII-W with triaryl- or trialkylphosphines in the presence of water in a suitable solvent at a suitable reaction temperature. Suitable solvents for use in the above process included, but were not limited to, ethers such as THF, dioxane and the like, alcoholic solvents such as MeOH, EtOH and the like, esters such as EtOAc, methyl acetate and the like, DMF, MeCN, and pyridine. If desired, mixtures of these solvents were used. The preferred solvents were THF and MeCN. The above process was carried out at temperatures between about −78° C. and about 120° C. Preferably, the reaction was carried out between 40° C. and about 95° C. The above process to produce compounds of the present invention was preferably carried out at about atmospheric pressure although higher or lower pressures were used if desired.

Where $X^{12}$ mono- or di-protected amino, the deprotection could be effected by the procedures known to those skilled in the art and as disclosed in: "Protective Groups in Organic Syntheses", T. W. Greene and P. G. M. Wuts, John Wiley and Sons, 1989.

The compounds of Formula VII-W of Scheme 46 were prepared as shown below in Scheme 47:

Scheme 47

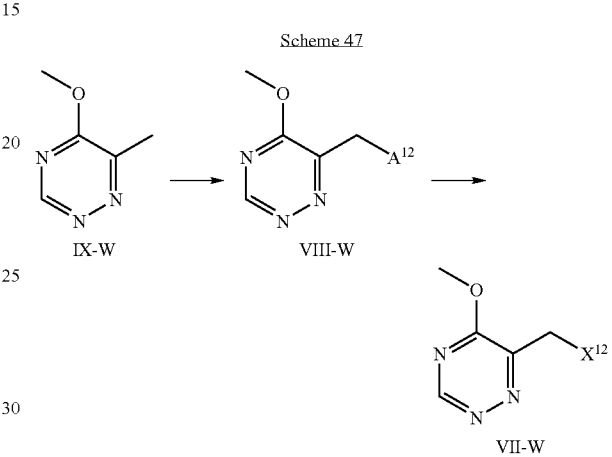

IX-W

VIII-W

VII-W where $X^{12}$ is as defined for a compound of formula VII-W and $A^{12}$=iodo, bromo, chloro, tosylate, mesylate or other leaving group.

In a typical preparation of a compound of Formula VII-W where $X^{12}$=azide, compound VIII-W was reacted with an azide salt, such as lithium or sodium azide in suitable solvent at a suitable reaction temperature. Suitable solvents for use in the above process included, but were not limited to, alcoholic solvents such as EtOH, butanol and the like, esters such as EtOAc, methyl acetate and the like, DMF, MeCN, acetone DMSO. If desired, mixtures of these solvents were used. The preferred solvents were acetone and DMF. The above process was carried out at temperatures between about −78° C. and about 120° C. Preferably, the reaction was carried out between 40° C. and about 95° C. The above process to produce compounds of the present invention was preferably carried out at about atmospheric pressure although higher or lower pressures were used if desired. Alternatively, where $X^{12}$ mono- or di-protected amino, compounds of Formula VII-W were reacted with suitably protected amines where the protecting group is chosen such that the nucleophilic nature of the nitrogen is either retained or where it can be enhanced by the action of a reagent such as a base. Those skilled in the art will recognize that such protecting groups include, but are not limited to, benzyl, trityl, allyl, and alkyloxycarbonyl derivatives such as BOC, CBZ and FMOC.

Compounds of Formula VII-W where $A^{12}$=halogen, are prepared from compounds of Formula XI-W. In a typical procedure, compounds of Formula XI-W are treated with halogenating reagents such as but not limited to N-iodosuccinimide, N-bromosuccinimide, N-chlorosuccinimide, trichloroisocyanuric acid, N,N'-1,3-dibromo-5,5-dimethylhydantoin, bromine and iodine, preferably in the presence of one or more radical sources such as dibenzoyl peroxide, azobisisobutyronitrile or light in suitable solvent at a suitable reaction temperature. Suitable solvents for use in the above process included, but were not limited to, chlorinated solvents such as carbon tetrachloride, DCM, α,α,α-trifluorotoluene and the like, esters such as methyl formate, methyl acetate and the like, DMF, MeCN. If desired, mixtures of these solvents were used. The preferred solvents were carbon tetrachloride and α,α,α-trifluorotoluene. The above process was carried out at temperatures between about −78° C. and about 120° C. Preferably, the reaction was carried out between 40° C. and about 95° C. The above process to produce compounds of the present invention was preferably carried out at about atmospheric pressure although higher or lower pressures were used if desired.

Alternatively, compounds of Formula VIII-W where $A^{12}$=tosylate or mesylate were prepared from compounds of Formula X-W as shown in Scheme 48. In a typical preparation of a compound of Formula VIII-W, a compound of Formula X-W was reacted with a sulfonylating reagent such as methanesulfonyl chloride or p-toluenesulfonyl chloride in the presence of a base such as, but not limited to DIEA or TEA in a suitable solvent at a suitable reaction temperature. Suitable solvents for use in the above reaction included, but were not limited to, chlorinated solvents such as DCM, 1,2-dichloroethane and the like, ethers such THF, diethylether and the like, DMF and MeCN. If desired, mixtures of these solvents were used. The preferred solvents were THF and DCM. The above process was carried out at temperatures between about −78° C. and about 120° C. Preferably, the reaction was carried out between 40° C. and about 95° C. The above process to produce compounds of the present invention was preferably carried out at about atmospheric pressure although higher or lower pressures were used if desired.

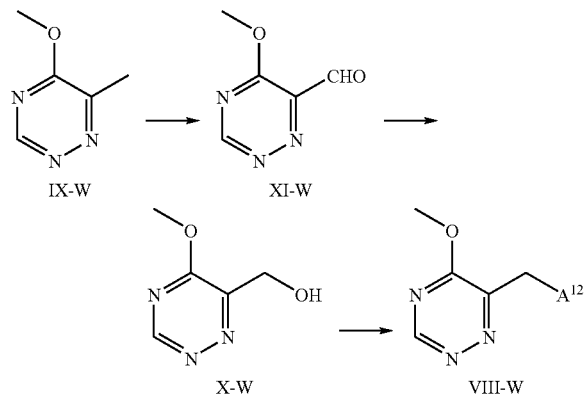

Scheme 48

Compounds of Formula X-W were prepared from compounds of Formula XI-W. In a typical preparation of a compound of Formula X-W, a compound of Formula XI-W was reacted with a reducing reagent such as, but not limited to, sodium borohydride, lithium borohydride or lithium aluminum hydride in a suitable solvent at a suitable reaction temperature. Suitable solvents for use in the above reaction included, but were not limited to, ethers such THF, diethylether and the like, and alcohols such as EtOH, MeOH, isopropanol and the like. If desired, mixtures of these solvents were used. The preferred solvents were THF and MeOH. The above process was carried out at temperatures between about −78° C. and about 120° C. Preferably, the reaction was carried out between 40° C. and about 95° C. The above process to produce compounds of the present invention was preferably carried out at about atmospheric pressure although higher or lower pressures were used if desired.

Compounds of Formula XI-W were prepared from compounds of Formula XI-W. In a typical preparation of a compound of Formula XI-W, a compound of Formula IX-W was reacted with an oxidizing reagent such as, but not limited to, selenium dioxide, manganese dioxide, potassium permanganate and the like, in a suitable solvent at a suitable reaction temperature. Suitable solvents for use in the above reaction included, but were not limited to, chlorinated solvents such as DCM, 1,2-dichloroethane and the like, water, acetic acid and sulfolane. If desired, mixtures of these solvents were used. The above process was carried out at temperatures between about −78° C. and about 120° C. Preferably, the reaction was carried out between 40° C. and about 95° C. The above process to produce compounds of the present invention was preferably carried out at about atmospheric pressure although higher or lower pressures were used if desired.

Those skilled in the art will appreciate that compounds of Formula IX-W can be made by routes disclosed in the literature, for example as in Bulletin de la Societe Chimique de France, (1973), (6)(Pt. 2), 2126.

Compounds of Formula I-AQ and/or their precursors may be subjected to various functional group interconversions as a means to access some functionalities that may not be introduced directly as a result of incompatible chemistries. Examples of such functional group manipulations applicable to compounds of Formula I-AQ and their precursors are similar, but not limited to, those described in Schemes 28-36.

Preparations

8-Chloro-3-cyclobutyl-imidazo[1,5-a]pyrazine was prepared using procedures analogous to that described for trans-methyl 4-(8-chloroimidazo[1,5-a]pyrazin-3-yl)cyclohexanecarboxylate and its precursor trans-methyl 4-({[(3-chloropyrazin-2-yl)methyl]amino}carbonyl)cyclohexanecarboxylate, using cyclobutanecarboxylic acid in place of 4-(methoxycarbonyl)cyclohexanecarboxylic acid 8-Chloro-3-cyclobutyl-1-iodoimidazo[1,5-a]pyrazine 8-Chloro-3-cyclobutylimidazo[1,5-a]pyrazine (1058 mg, 5.1 mmol) and NIS (1146 mg, 5.1 mmol) in anh DMF (10 mL) were stirred at 60° C. under Ar for 6 h. The reaction was diluted with DCM (~400 mL), washed ($H_2O$, brine), dried ($Na_2SO_4$) and concentrated under reduced pressure. Purification of the crude material by flash chromatography on silica gel (50 g cartridge, 10:1-8:1-7:1-6:1 hexanes:EtOAc) afforded the title compound as a pale yellow solid; $^1$H NMR (400 MHz, $CDCl_3$) δ 7.51 (d, J=4.8 Hz, 1H), 7.26 (d, J=4.8 Hz, 1H), 3.75 (quintet, J=1.2 Hz, 8.4 Hz, 1H), 2.62-2.42 (m, 4H), 2.32-1.98 (m, 2H); MS (ES+): m/z 334.0 (100) [MH+]; HPLC: $t_R$=3.38 min (OpenLynx, polar_5 min).

3-Cyclobutyl-1-iodoimidazo[1,5-a]pyrazin-8-amine

A Parr bomb containing 8-chloro-3-cyclobutyl-1-iodoimidazo[1,5-a]pyrazine (759 mg, 2.3 mmol) in IPA (100 mL) was saturated with $NH_3$(g) for 5 min at 0° C. then sealed and heated at 115° C. for 38 h. The reaction mixture was then concentrated under reduced pressure, partitioned between DCM (200 mL) and $H_2O$ (50 mL) and extracted with DCM (50 mL). Combined organic fractions were washed with brine, dried ($Na_2SO_4$) and concentrated under reduced pressure to provide the title compound as a white solid; $^1$H NMR (400 MHz, $CDCl_3$) δ 7.13 (d, J=4.8 Hz, 1H), 7.01 (d, J=5.2 Hz, 1H), 5.63 (br, 2H), 3.68-3.73 (m, 1H), 2.60-2.38 (m, 4H), 2.20-1.90 (m, 2H); MS (ES+): m/z 315.9 (100) [MH+]; HPLC: $t_R$=1.75 min (OpenLynx, polar_5 min).

trans-4-(8-Amino-1-iodo-imidazo[1,5-a]pyrazin-3-yl)-cyclohexanecarboxylic acid methyl ester Prepared according to the procedure described above for 3-cyclobutyl-1-iodoimidazo[1,5-a]pyrazin-8-amine, except using trans-4-(8-Chloro-1-iodo-imidazo[1,5-a]pyrazin-3-yl)-cyclohexanecarboxylic acid methyl ester. $^1$H NMR ($d_6$-DMSO): δ 7.65 (d, J=4.8 Hz, 1H), 6.96 (d, J=4.8 Hz, 1H), 6.52 (br s, 2H), 3.65 (s, 3H), 3.16 (m, 1H), 2.71 (m, 1H), 2.15-2.00 (m, 2H), 1.80-1.60 (m, 6H) MS (ES+): m/z 400.98 (100) [M+1].

trans-4-(8-Chloro-1-iodo-imidazo[1,5-a]pyrazin-3-yl)-cyclohexanecarboxylic acid methyl ester Prepared according to the procedure described above for 8-chloro-3-cyclobutyl-1-iodoimidazo[1,5-a]pyrazin-8-amine, except using trans-methyl 4-(8-chloroimidazo[1,5-a]pyrazin-3-yl)cyclohexanecarboxylate. $^1$H NMR (400 MHz, CDCl$_3$) δ 1.62-1.69 (m, 2H), 1.79-1.94 (m, 2H), 2.01-2.26 (m, 5H), 2.30-2.51 (m, 1H), 3.71 (s, 3H), 7.32 (d, J=5.05 Hz, 1H), 7.65 (d, J=5.05 Hz, 1H). MS (ES+): m/z 419.71, 421.73 [MH+].

trans-Methyl 4-(8-chloroimidazo[1,5-a]pyrazin-3-yl)cyclohexanecarboxylate trans-Methyl 4-({[(3-chloropyrazin-2-yl)methyl]amino}carbonyl)-cyclohexane carboxylate (29.00 g, 93.02 mmol) was dissolved in anhydrous MeCN (930 mL), anhydrous DMF (9 mL) and POCl$_3$ (10.4 mL, 110 mmol) and heated at 55° C. under nitrogen for 3 h. The reaction mixture was concentrated in vacuo, then, the solid residue was taken up in DCM, then, basified to pH 10 with 2M ammonia in isopropanol. The mixture was concentrated in vacuo, re-dissolved in DCM, and then loaded onto TEA-basified silica gel. The crude product was purified by a silica gel column chromatography (eluted with 2:3 EtOAc/DCM) to obtain the title compound as a yellow powder; $^1$H NMR (CDCl$_3$, 400 MHz) δ 1.63 (ddd, J=13.2, 13.2, 13.2, 3.2 Hz, 2H), 1.85 (ddd, J=13.2, 13.2, 13.2, 2.8 Hz, 2H), 2.10 (dd, J=14.4, 3.2 Hz, 2H), 2.19 (dd, J=14.0, 3.2 Hz, 2H), 2.46 (tt, J=12.4, 3.6 Hz, 1H), 2.96 (tt, J=11.6, 3.2 Hz, 1H), 3.70 (s, 3H), 7.33 (dd, J=5.2, 1.2 Hz, 1H), 7.61 (d, J=4.8 Hz, 1H), 7.79 (s, 1H). MS (ES+): m/z 294.17/296.14 (100/86) [MH+]. HPLC: $t_R$=2.85 min (OpenLynx, polar_5 min).

trans-Methyl 4-({[(3-chloropyrazin-2-yl)methyl]amino}carbonyl)cyclohexanecarboxylate A THF (370 mL) solution of 4-(methoxycarbonyl)cyclohexanecarboxylic acid (15.14 g, 81.30 mmol) and CDI (13.18 g, 81.30 mmol) was placed under a nitrogen atmosphere and stirred at 60° C. for 4 h. The reaction mixture was cooled to rt, then, (3-chloropyrazin-2-yl)methylamine bis-hydrochloride salt (16.00 g, 73.91 mmol) and DIEA (31.52 g, 244.00 mmol, 42.5 mL) was added. After stirring at 60° C. for 20 h, the reaction was concentrated in vacuo. The crude reaction mixture was purified by a silica gel glass column chromatography (eluted with 3:2 DCM/EtOAc) to obtain the pure desired product as a slightly yellowish creamy white powder; $^1$H NMR (CDCl$_3$, 400 MHz) δ 1.43-1.65 (m, 4H), 2.01-2.14 (m, 4H), 2.25 (tt, J=12.0, 3.6 Hz, 1H), 2.34 (tt, J=11.6, 3.2 Hz, 1H), 3.68 (s, 3H), 4.70 (d, J=4.4 Hz, 2H), 6.81 (s, br, —NH), 8.32-8.36 (m, 1H), 8.46 (d, J=2.4 Hz, 1H); MS (ES+): m/z 312.17/314.12 (84/32) [MH+]; HPLC: $t_R$=2.44 min (OpenLynx, polar_5 min).

[3-(8-Amino-1-iodoimidazo[1,5-a]pyrazin-3-yl)-cyclobutyl]methanol

[3-(8-Chloro-1-iodoimidazo[1,5-a]pyrazin-3-yl)cyclobutyl]methanol (6.9 g) in i-PrOH (200 mL) was saturated with NH$_{3(g)}$, by passing a slow a slow stream of ammonia for 10 min at −20° C., and then heated in a Parr bomb at 110° C. for 2 d. The reaction mixture was then cooled to rt, filtered through a sintered glass and the solid residue and the Parr vessel were rinsed with i-PrOH several times. The filtrate was concentrated under reduced pressure to provide an orange solid still containing NH$_4$Cl. The material was taken up into refluxing MeCN (250 mL) and filtered hot. The step was repeated with another portion of hot MeCN (200 mL). The combined MeCN filtrates were concentrated under reduced pressure to give the title compound as an orange solid; HPLC: (polar5 min) 0.53 and 1.51 min; MS (ES+): 345.1 (100, M$^+$+1); $^1$H NMR (400 MHz, DMSO-d6) δ 7.50 (d, J=5.2 Hz, 1H), 7.44 (d, J=5.2 Hz, 0.27H, minor isomer), 6.95 (d, J=5.2 Hz, 1.29H overlapped with the minor isomer) 6.63 (br, 2H), 4.61 (t, J=5.2 Hz, 0.27H, minor isomer), 4.52 (t, J=5.2 Hz, 1H), 3.69 (quintet, J=5.6 Hz, 0.32H, minor isomer), 3.54 (quintet, J=5.6 Hz, 1H), 2.52-2.25 (m, 4H), 2.10-2.00 (m, 1H).

[3-(8-Chloro-1-iodo-imidazo[1,5-a]pyrazin-3-yl)-cyclobutyl]-methanol

To a solution of NIS (6.31 g, 28.0 mmol) in anhydrous DMF (100 mL) under Ar was added dry [3-(8-chloroimidazo[1,5-a]pyrazin-3-yl)cyclobutyl]methanol (6.67 g) dissolved in anh DMF (30 mL). The flask containing [3-(8-chloroimidazo[1,5-a]pyrazin-3-yl)cyclobutyl]methanol was rinsed with another portion of anh DMF (20 mL) and the rinse was added to the reaction mixture. The reaction was heated to 60° C. (rt-60° C.~30 min) and the stirred at this temperature for 3 h. The mixture was then cooled to rt, partitioned between 1M aq Na$_2$S$_2$O$_3$ (60 mL), brine (60 mL) and DCM (160 mL). The aq layer was extracted with DCM (3×100 mL). The combined organics were dried (Na$_2$SO$_4$), concentrated under reduced pressure and purified by flash chromatography on SiO$_2$ (0-8% MeOH in DCM) to provide a material, homogenous by UV on both TLC and HPLC, still containing DMF. The material was dissolved in DCM (200 mL) and washed with water (3×40 mL), dried (Na$_2$SO$_4$) and concentrated under reduced pressure to provide the title compound as a pale yellow solid; HPLC (polar5 min) 2.52 min; MS (ES+): m/z (rel. int.) 364.0 (100, M$^+$+1); $^1$H NMR (400 MHz, CDCl$_3$) δ 7.59 (d, J=4.8 Hz, 1H), 7.49 (d, J=4.8 Hz, 0.22H, minor isomer), 7.29 (d, J=4.8 Hz, 1H), 7.28 (d, J=5.2 Hz, 0.23H, minor isomer), 3.83-3.80 (m, 0.7H), 3.72-3.62 (m, 3H), 2.75-2.55 (m, 4H), 2.42-2.32 (m, 1-2H).

[3-(8-Chloro-imidazo[1,5-a]pyrazin-3-yl)-cyclobutyl]-methanol

To a solution of 8-chloro-3-(3-methylenecyclobutyl)imidazo[1,5-a]pyrazine (4.48 g, 20.4 mmol) in anh THF (255 mL) at −78° C. under Ar, 9-BBN (61.2 mL, 0.5M in THF, 30.6 mmol) was added dropwise over 8 min (a suspension). The cooling bath was replaced with ice-H$_2$O and the reaction was allowed to warm slowly to rt. After being stirred for 17 h, H$_2$O (100 mL) was added followed by, after ~5 min, NaBO$_3$.H$_2$O (12.2 g, 122.3 mmol) added in one lot. The reaction was stirred at rt for 5 h and then filtered through Celite. The Celite and residual solids were washed with DCM and EtOAc. The filtrate was concentrated under reduced pressure to yield an aq solution, which was saturated with NaCl and extracted with EtOAc (3×). The extracts were dried ($Na_2SO_4$) and concentrated under reduced pressure to yield a light yellow oil which was purified by flash chromatography on $SiO_2$ (9:1 DCM:MeOH) to afford the title compound as a light yellow oil; HPLC: $t_R$ (mass-directed HPLC, polar7 min) 2.52 min; MS ($ES^+$): 238.0. The addition may be carried out at 0° C. Suspension quickly clears up after the exchange of cooling baths. The final product contained 1,5-cis-octanediol derived from 9-BBN. Based on $^1H$ NMR estimated roughly to be 66% target material and 33% of the byproduct. The crude product was taken onto next step crude, stereoselectivity of the product was 4-5:1 as judged by $^1H$ NMR.

(8-Chloro-3-(3-methylene-cyclobutyl)-imidazo[1,5a]pyrazine)

3-Methylene-cyclobutanecarboxylic acid (3-chloropyrazin-2-ylmethyl)-amide (52.1 g, 219.2 mmol) was dissolved in 1.0 L of anhydrous MeCN. Followed by the addition of DMF (1.0 mL) and $POCl_3$ (100 mL, 1.09 mol). The reaction was heated to 55° C. for 30 min. with a slow $N_2$ bubbling the reaction. The reaction was then concentrated in vacuo, basified with cold 2.0M $NH_3$ in IPA with $CH_2Cl_2$. The IPA/$CH_2Cl_2$ was concentrated in vacuo and the salts were dissolved with minimal water and extracted with $CH_2Cl_2$ (4×). The organic layers where combined and washed with sat. $NaHCO_3$ (1×), dried over sodium sulfate, filtered and concentrated in vacuo. The crude product was purified via silica gel column chromatography [eluting with 2:1 Hex: EtOAc] to yield the title compound as a light yellow solid; $^1H$ NMR (400 MHz, $CDCl_3$) δ 3.24-3.30 (4H, m), 3.78-3.85 (1H, m), 4.89-4.94 (2H, m), 7.33 (1H, d, J=4.99 Hz), 7.53 (1H, d, J=5.09 Hz), 7.82 (1H, s); MS (ES+): m/z 220.28/222.30 (100/80) [$MH^+$]; HPLC: $t_R$=2.87 min (OpenLynx, polar__5 min).

3-Methylene-cyclobutanecarboxylic acid (3-chloropyrazin-2-ylmethyl)amide

C-(3-Chloropyrazin-2-yl)-methylamine bis-HCl (1.0 g, 4.62 mmol), N-ethyl-N'-(3-dimethylaminopropyl)carbodiimide (EDC) (1.31 g, 6.47 mmol, 1.4 eq.), 4-dimethylamino pyridine (DMAP) (0.141 g, 1.15 mmol, 0.25 eq.), and DIEA (2.42 mL, 1.79 g, 13.9 mmol, 3.0 eq.) were dissolved in anhydrous $CH_2Cl_2$ (25 mL). To this solution, a solution of 3-methylenecyclobutanecarboxylic acid (0.622 g, 5.54 mmol, 1.2 eq.) in anhydrous $CH_2Cl_2$ (25 mL) was added under $N_2$ and the reaction was allowed to stir overnight at rt. Reaction mixture was concentrated in vacuo and the resulting residue was dissolved in EtOAc, washed with water (2×), $NaHCO_3$ (1×), water (1×), and brine (1×), dried over $Na_2SO_4$, filtered, and concentrated in vacuo, giving crude title compound, as a brown oil. The crude material was purified by chromatography on silica gel [Jones Flashmaster, 20 g/70 mL cartridge, eluting with 10% hexane in ethyl acetate, affording the title compound as a pale yellow solid. Additionally, the title compound could be prepared by the following route: 1,1'-Carbonyldiimidazole (CDI) (0.824 g, 5.08 mmol, 1.1 eq.) and 3-methylenecyclobutanecarboxylic acid (0.570 g, 5.08 mmol, 1.1 eq.) were dissolved in anhydrous THF (12 mL) and allowed to stir at 60° C. for 2 h. A solution of C-(3-chloropyrazin-2-yl)-methylamine bis-HCl (1.0 g, 4.62 mmol) and DIEA (2.42 mL, 1.79 g, 13.9 mmol, 3.0 eq.) in anhydrous $CH_2Cl_2$ (13 mL) was added to the acid mixture and the reaction was allowed to stir at 60° C., under $N_2$, overnight. The reaction mixture was concentrated in vacuo and the resulting residue was dissolved in EtOAc, washed with $NaHCO_3$ (2×) and brine (1×), dried over $Na_2SO_4$, filtered, and concentrated in vacuo, giving crude title compound, as a brown oil. The crude material was purified by chromatography on silica gel [Jones Flashmaster, 20 g/70 mL cartridge, eluting with 10% hexane in ethyl acetate, affording the title compound as a pale yellow solid; $^1H$ NMR ($CDCl_3$, 400 MHz) δ 2.86-2.96 (m, 2H), 3.03-3.19 (m, 3H), 4.72 (dd, J=4.4, 0.8 Hz, 2H), 4.79-4.84 (m, 2H), 6.78 (s, —NH), 8.32-8.34 (m, 1H), 8.46 (d, J=2.8 Hz, 1H); MS (ES+): m/z 238.19 (90) [$MH^+$]; HPLC: $t_R$=2.67 min (OpenLynx, polar 7 min).

cis-3-(8-Amino-1-iodoimidazo[1,5-a]pyrazin-3-yl)cyclobutanol

In a Parr pressure reactor 3-(8-chloro-1-iodo-imidazo[1,5-a]pyrazin-3-yl)-cyclobutanol (4.159 g, 0.0119 mol) was dissolved with 2.0M ammonia in isopropyl alcohol (40 mL). The mixture was cooled to −20° C. and saturated with ammonia. The reaction was heated at 110° C. for 63 h at which point it was cooled and concentrated in vacuo. The crude product was purified using HPFC Jones 25 g silica gel column eluting with 5-8% MeOH: $CH_2Cl_2$ to yield the title compounds; MS (ES+): m/z 330.88 (100) [$MH^+$], 331.89 (10) [$MH^{++}$]; HPLC: $t_R$=0.48 min (OpenLynx, polar__5 min); $^1H$ NMR ($CDCl_3$, 400 MHz) δ 2.55-2.76 (m, 2H) 3.06-3.22 (m, 2H) 3.32-3.50 (m, 1H) 4.51-4.69 (m, 1H) 6.15 (br. s., 2H) 7.24 (d, J=5.05 Hz, 1H) 7.39 (d, J=5.05 Hz, 1H).

cis-3-(8-Chloro-1-iodoimidazo[1,5-a]pyrazin-3-yl)cyclobutanol 3-(8-Chloro-1-iodo-imidazo[1,5-a]pyrazin-3-yl)-cyclobutanone (5.0 g, 14 mmol) was dissolved in a 1:1 mixture of MeOH (35.0 mL) and $CH_2Cl_2$ (35.0 mL). To the solution mixture sodium tetrahydroborate (560 mg, 14.0 mmol) was added slowly, gas evolution was observed. After 4.5 h at rt under nitrogen, the reaction was concentrated in vacuo. The crude mix was dissolved in EtOAc and washed with water. The organic layer was dried over sodium sulfate, filtered and concentrated in vacuo. The crude product was purified using HPFC Jones 50 gram silica gel column eluting with 50% EtOAc in Hexane to 100% EtOAc, to yield the title compound as a light yellow solid; MS (ES+): m/z 349.81 (100) [$MH^+$], 351.50 (30) [$MH^{+++}$]; HPLC: $t_R$=2.49 min (OpenLynx, polar__5 min); $^1H$ NMR ($CDCl_3$, 400 MHz) δ 2.41-2.54 (m, 2H) 2.78-3.05 (m, 1H) 3.12-3.32 (m, 1H) 4.08-4.75 (m, 1H) 5.30 (s, 1H) 7.31 (d, J=5.05 Hz, 1H) 7.57 (d, J=4.80 Hz, 1H)

(1-Iodo-3-[3-(4-methyl-piperazin-1-yl)-cyclobutyl]-imidazo[1,5-a]pyrazin-8-ylamine)

A solution of 2N ammonia in isopropyl alcohol (350 mL) and THF (30 mL, 0.4 mol) was added to 8-chloro-1-iodo-3-[3-(4-methyl-piperazin-1-yl)-cyclobutyl]-imidazo[1,5-a]pyrazine (19.91 g, 0.04612 mol) in a Parr bomb and cooled to −78° C. Ammonia was bubbled into the solution for 8-10 min. The bomb was sealed, stirred and heated to at 110° C. over 3 d. The solvent was then evaporated in vacuo and purified by flash silica gel chromatography (wetted with $CHCl_3$, dried loaded with silica, and eluted with 8% (7N $NH_3$) MeOH in $CHCl_3$), which afforded the title compound; $^1H$ NMR ($CDCl_3$, 400 MHz) δ 7.31 (1H, d, J=5.01), 7.16 (1H, d, J=6.25), 5.83 (2H, s), 3.49 (1H, m), 3.06 (1H, m), 2.76 (4H, m), 2.64 (8H, m), 2.46 (3H, s); MS (ES+): m/z 412.89/413.91 (50/10) [MH+]; HPLC: $t_R$=0.31 min. (OpenLynx, polar_5 min.).

(8-Chloro-1-iodo-3-[3-(4-methylpiperazin-1-yl)cyclobutyl]imidazo[1,5-a]pyrazine)

1-Methyl piperazine (5.75 mL, 0.0514 mol) in 1,2-dichloroethane (1096.7 mL, 13.892 mol) was added to 3-(8-chloro-1-iodoimidazo[1,5-a]pyrazin-3-yl)cyclobutanone (1700 g, 0.04892 mol) and sodium triacetoxyborohydride (21.8 g, 0.0978 mol). The reaction stirred at rt for 3 h. The reaction was concentrated, dissolved in $CH_2Cl_2$, and then washed with saturated $NaHCO_3$ solution and brine. The product was dried over sodium sulfate, filtered, and concentrated in vacuo. The product was flushed through a quick silica gel plug (wetted with 100% $CHCl_3$, eluted with 8% (7N $NH_3$) MeOH in $CHCl_3$), to afford the title compound; $^1H$ NMR ($CDCl_3$, 400 MHz) δ 7.63 (1H, d), 7.30 (1H, d), 3.42 (1H, m), 2.94 (1H, m), 2.65 (4H, m), 2.44 (8H, m), 2.32 (3H, s); MS (ES+): m/z 431.85/433.87 (100/45) [MH+]; HPLC: $t_R$=1.82 min. (OpenLynx, polar_5 min.).

cis-3-(8-Chloroimidazo[1,5-a]pyrazin-3-yl)-1-methylcyclobutanol 3-(8-Chloroimidazo[1,5-a]pyrazin-3-yl)cyclobutanone (1.95 g, 8.80 mmol) in anhydrous THF (77.78 mL) at −78° C. under an atmosphere of nitrogen was treated slowly with a 3.0 M solution of methylmagnesium chloride in THF (5.9 mL). The solution stirred for 3 hr at −78° C. then quenched with 40 mL of semi-saturated aqueous $NH_4Cl$ ($NH_4Cl$ dilution in 1:1 mixture with water) at −78° C. and allowed to warm up to rt. The mixture was then extracted with EtOAc (3×40 mL) and the combined extracts washed with brine (30 mL), dried over magnesium sulfate, filtered and concentrated in vacuo. The crude solid was purified by chromatography over silica gel eluting with 1:1 EtOAc/DCM to 4% MeOH in (1:1) EtOAc/DCM to afford desired product. $^1$H-NMR (400 MHz, $CDCl_3$) δ ppm 1.54 (s, 3H), 2.74-2.60 (m, 4H), 3.75-3.39 (m, 1H), 7.35 (d, J=5.04 Hz, 1H), 7.71 (d, J=5.00 Hz, 1H) and 7.86 (s, 1H). MS (ES+): m/z 238.15 and 240.17 [MH+].

cis-3-(8-Chloro-1-iodoimidazo[1,5-a]pyrazin-3-yl)-1-methylcyclobutanol cis-3-(8-Chloroimidazo[1,5-a]pyrazin-3-yl)-1-methylcyclobutanol (2.20 g, 9.26 mmol) and NIS (2.71 g, 12.0 mmol) were dissolved in DMF (36.6 mL, 0.472 mol) and stirred at 60° C. for 4 h. The mixture was then concentrated in vacuo and the residue reconstituted in EtOAc (100 mL). This solution was washed with sodium bicarbonate (2×20 mL) and these washes back-extracted with EtOAc (2×20 mL). The organic layers were combined, dried with sodium sulfate, filtered and concentrated in vacuo. The crude solid was purified by chromatography over silica gel eluting with 1:1 EtOAc:hexanes to afford desired product. $^1$H-NMR (400 MHz, $CDCl_3$) δ ppm 1.53 (s, 3H), 2.72-2.59 (m, 4H), 3.37-3.29 (m, 1H), 7.32 (d, J=4.91 Hz, 1H) and 7.60 (d, J=4.96 Hz, 1H). MS (ES+): m/z 363.95 and 365.91 [MH+].

cis-3-(8-Amino-1-iodoimidazo[1,5-a]pyrazin-3-yl)-1-methylcyclobutanol

A solution of 2M ammonia in isopropanol (80 mL) and THF (5 mL) was added to cis-3-(8-chloro-1-iodoimidazo[1,5-a]pyrazin-3-yl)-1-methylcyclobutanol (2.77 g, 7.62 mmol) in a Parr pressure reactor. The mixture was cooled to at −78° C. then ammonia gas was bubbled into the solution for 4-6 min. The reactor was sealed then heated at 110° C. for 15 h. The solvent was then removed in vacuo and the residue purified by chromatography over silica gel eluting with 7% MeOH in DCM to afford desired product. $^1$H NMR (400 MHz, DMSO-d6) δ ppm 1.44 (s, 3H), 2.32-2.51 (m, 4H), 3.33-3.52 (m, 1H), 6.61 (br.s., 2H), 7.03 (d, J=5.05 Hz, 1H) and 7.62 (d, J=5.05 Hz, 1H).

3-(3,3-Difluoro-cyclobutyl)-1-iodo-imidazo[1,5-a]pyrazin-8-ylamine

Prepared according to the procedure described above for 3-cyclobutyl-1-iodoimidazo[1,5-a]pyrazin-8-amine, except using 8-chloro-3-(3,3-difluoro-cyclobutyl)-1-iodo-imidazo[1,5-a]pyrazine. HPLC: $t_R$=1.87 min. (Open Lynx polar_5 min). MS (ES+): m/z 350.74 (100) [MH+].

8-Chloro-(3,3-difluoro-cyclobutyl)-1-iodo-imidazo[1,5-a]pyrazine

To a stirred mixture of 3-(8-chloro-1-iodo-imidazo[1,5-a]pyrazin-3-yl)-cyclobutanone (150.00 mg, 0.43 mmol) in DCM (10.00 mL) was added solution of diethylaminosulfur trifluoride (0.12 mL, 0.94 mmol) in DCM (2 ml) slowly at 0° C. The stirred mixture was allowed to warm up to rt. in 1 hour and was stirred at rt. overnight. The reaction was then quenched by aq. $NaHCO_3$ and extracted by DCM. The solvent was then removed to give a crude product which was carried onto the next step without any further purification.

3-(3-Dimethylamino-cyclobutyl)-1-iodo-imidazo[1,5-a]pyrazin-8-ylamine

Prepared according to the procedure described above for 3-cyclobutyl-1-iodoimidazo[1,5-a]pyrazin-8-amine, except using [3-(8-Chloro-1-iodo-imidazo[1,5-a]pyrazin-3-yl)-cyclobutyl]-dimethyl-amine. $^1$H NMR (400 MHz, $CDCl_3$): δ 2.25 (br.s, 6H), 2.47 (br.s, 2H), 2.63 (q, J=8.17 Hz, 2H), 2.93 (br.s, 1H), 3.30-3.41 (m, 1H), 5.64 (br.s, 2H), 7.03 (d, J=4.80 Hz, 1H), 7.22 (d, J=4.80 Hz, 1H). HPLC: $t_R$=0.36 min. (Open Lynx polar_5 min.). MS (ES+): m/z 357.73 (100) [MH+].

[3-(8-Chloro-1-iodo-imidazo[1,5-a]pyrazin-3-yl)-cyclobutyl]-dimethyl-amine

To a dry flask loaded with 3-(8-chloro-1-iodo-imidazo[1,5-a]pyrazin-3-yl)-cyclobutanone (400.0 mg, 1.15 mmol) in THF (9.0 mL) was added DIEA (0.42 ml, 2.42 mmol), dimethylamine hydrochloride (0.19 g, 2.30 mmol) followed by sodium triacetoxyborohydride (539 mg, 2.42 mmol) at rt. The resulting mixture was stirred at room temperature overnight. The reaction mixture was extracted with aq. Solution of $NaHCO_3$ (2×30 mL). The aq.—layer was back-extracted with EtOAc (2×100 mL), dried ($Na_2SO_4$) and concentrated in vacuo to a solid. The material was carried onto the next step without any further purification. MS (ES+): m/z 344.73/345.81 (100/10) [MH+]

(3-(8-Chloro-1-iodoimidazo[1,5-a]pyrazin-3-yl)cyclobutanone)

A solution of 3-(8-chloro-1-iodoimidazo[1,5-a]pyrazin-3-yl)-1-hydroxymethylcyclobutanol (4.08 g, 0.011 mol) in THF (120 mL) and water (40 mL) was charged with sodium periodate (2.8 g, 0.013 mol) at 0° C. The reaction warmed to rt and stirred for 5 h. The reaction mixture was diluted with EtOAc and then washed with brine. The organic phase was dried over Na$_2$SO$_4$, filtered, and concentrated in vacuo to afford the title compound as a yellow solid; $^1$H NMR (CDCl$_3$, 400 MHz) δ 7.56 (1H, d, J=4.94 Hz), 7.32 (1H, d, J=4.98 Hz), 3.64 (5H, m); MS (ES+): m/z 347.82 and 349.85 [MH$^+$]; HPLC: t$_R$=2.89 min. (OpenLynx, polar_5 min.).

3-(8-Chloro-1-iodoimidazo[1,5-a]pyrazin-3-yl)-1-hydroxymethylcyclobutanol

Under inert atmosphere N-iodosuccinimide. (3.6 g, 0.016 mol) and 3-(8-chloroimidazo[1,5-a]pyrazin-3-yl)-1-hydroxymethylcyclobutanol (3.16 g, 0.012 mol) were dissolved in DMF (30 mL) and heated at 60° C. for 3.0 h. The reaction mixture was then concentrated in vacuo to a dark oil and purified by HPFC Jones 20 g silica gel column, eluting with 5% MeOH: CH$_2$Cl$_2$ to yield a light brown fluffy solid which was triturated with diethyl ether and hexanes to afford the title compound; MS (ES+): m/z 379.85 and 381.80 [MH$^+$]; HPLC: t$_R$=2.30 min (OpenLynx, polar_5 min).

3-(8-Chloroimidazo[1,5-a]pyrazin-3-yl)-1-hydroxymethylcyclobutanol

To a THF solution (170 mL) of 8-chloro-3-(3-methylenecyclobutyl)imidazo[1,5-a]pyrazine (3.1 g, 14 mmol), water (18 mL), 50% N-methylmorpholine-N-oxide in water (3.2 mL) and potassium osmate, dehydrate (200 mg, 0.70 mmol) were added and the reaction was allowed to stir at rt for 4 h. Sodium sulfite (8.0 g, 70.0 mmol) was added to the reaction mixture and allowed to stir for 30 min at which point the reaction was concentrated in vacuo. The crude product was extracted from the aqueous with EtOAc. The organics were washed with brine and the combined aqueous washes were back extracted with EtOAc (5×50 mL). The combined organics were dried over sodium sulfate, filtered, and concentrated in vacuo to yield the title compounds as a sticky tan/off-white solid; MS (ES+): m/z 254.17 (100) [MH$^+$], HPLC: t$_R$=1.95 min (OpenLynx, polar_5 min).

3-Methylene-cyclobutanecarboxylic acid

To a solution of 3-methylenecyclobutanecarbonitrile (100.0 g, 1.042 mol) in EtOH (1.00 L) and water (1.00 L) was added potassium hydroxide (230.0 g, 4.2 mol). The resulting mixture was heated at reflux for 7 hr then the EtOH was removed in vacuo and the solution was cooled to 0° C. and acidified with (300.0 mL) of conc. HCl to pH=1. The mixture was extracted with diethyl ether (4×1 L) and the combined organic phases were dried over sodium sulfate, filtered and concentrated in vacuo to yield desired product. $^1$H NMR (400 MHz, CDCl$_3$) δ 2.64-3.44 (m, 5H), 4.60-4.98 (m, 2H) and 10.64 (br. s., 1H).

Ethyl 3-methylenecyclobutanecarboxylate

Iodoethane (7.5 mL, 93.0 mol) was added at rt to a mixture of 3-methylenecyclobutanecarboxylic acid (10.0 g, 80.0 mmol) and cesium carbonate (56.0 g, 170.0 mmol) in anhydrous DMF (500.00 mL) under an atmosphere of nitrogen. The reaction was stirred for 16 hr then partitioned between diethyl ether (1 L) and brine (1 L). The aqueous layer was extracted with diethyl ether (3×500 mL) and the combined organic phases washed with water (2×1 L), dried over sodium sulfate, filtered and concentrated in vacuo to yield desired product $^1$H NMR (400 MHz, CDCl$_3$) δ 1.26 (t, 3H), 2.71-3.27 (m, 5H), 4.15 (q, J=7.07 Hz, 2H) and 4.53-4.96 (m, 2H).

N-[(3-chloropyrazin-2-yl)methyl]-3-methylenecyclobutanecarboxamide 1,1'-Carbonyldiimidazole (CDI) (8.24 g, 50.81 mmol) and 3-methylenecyclobutanecarboxylic acid (5.70 g, 50.81 mmol) were dissolved in anhydrous THF (100 mL) and allowed to stir at 60° C. for 4 h. A solution of C-(3-Chloropyrazin-2-yl)methylamine bis-hydrochloride (10.0 g, 46.19 mmol) and DIEA (32.30 mL, 184.76 mmol) in anhydrous CH$_2$Cl$_2$ (150 mL) was added to the mixture and the reaction was allowed to stir at rt for 24 h. The mixture was concentrated in vacuo, the residue dissolved in EtOAc and the resulting solution washed with saturated NaHCO$_3$ (aq.) water H$_2$O and Brine. The combined organic layers were dried over sodium sulfate, filtered and concentrated in vacuo to afford crude product, which was purified by chromatography over silica gel eluting with 50-70% EtOAc/hexane to yield desired product. $^1$H NMR (400 MHz, CDCl$_3$) δ ppm 2.92-2.94 (2H, m), 3.05-3.14 (2H, m), 4.60 (2H, d, J=4.24 Hz), 4.80-4.84 (2H, m), 6.75 (1H, brs), 8.33 (1H, d, J=4.22 Hz), 8.45 (1H, d, J=2.54 Hz). MS (ES+): m/z 238 and 240 [MH$^+$].

8-Chloro-3-(3-methylenecyclobutyl)imidazo[1,5-a]pyrazine

N-[(3-Chloropyrazin-2-yl)methyl]-3-methylenecyclobutanecarboxamide (52.1 g, 219.2 mmol) in anhydrous MeCN (1.0 L) was treated with DMF (1.0 mL) and POCl$_3$ (100 mL, 1.09 mol) and the mixture was stirred at 55° C. for 30 min. under a gentle stream of N$_2$. The reaction was then concentrated in vacuo and the residue reconstituted in CH$_2$Cl$_2$ and treated with cold 2.0 M NH$_3$ in IPA. This mixture was concentrated in vacuo, water added to dissolve the salts, and then extracted with CH$_2$Cl$_2$ (4×60 mL). The organic layers where combined and washed with sat. NaHCO$_3$ (1×70 mL) dried over sodium sulfate, filtered and concentrated in vacuo. The crude material was purified by chromatography over silica gel eluting with hexane: EtOAc (v:v=2:1) to yield desired product. $^1$H NMR (400 MHz, CDCl$_3$) δ ppm 3.24-3.30 (4H, m), 3.78-3.85 (1H, m), 4.89-4.94 (2H, m), 7.33 (1H, d, J=4.99 Hz), 7.53 (1H, d, J=5.09 Hz) and 7.82 (1H, s). MS (ES$^+$): m/z 220.28, 222.30 [MH$^+$].

1-Bromo-3-iodo-imidazo[1,5-a]pyrazin-8-ylamine

To a stirred solution of 1-bromo-8-chloro-3-iodo-imidazo[1,5-a]pyrazine (250.00 mg, 0.696 mmol) in i-PrOH (8 mL) in a Parr bomb was added 7 mL ammonia in water (35%). The resulting solution was stirred at 95° C. overnight. The solvent was removed under reduced pressure and the crude material was passed through a short silica gel column (5% MeOH in DCM as eluent). The fractions were collected and combined, solvent was removed under reduced pressure to give a residue which was used in next step without further purification. MS (ES$^+$): m/z: 338.80, 340.81 [MH$^+$]. HPLC: t$_R$=1.64 min (OpenLynx: polar_5 min).

1-Bromo-8-chloro-3-iodo-imidazo[1,5-a]pyrazine

To a stirred solution of 8-chloro-3-iodo-imidazo[1,5-a]pyrazine (730.0 mg, 2.61 mmol) in DMF (8.00 mL) was added NBS (557.9 mg, 3.13 mol) in 3 portions at 0° C. The resulting mixture was allowed to warm up to rt. and stirred at rt. for 2 hours. To the mixture was added 30 mL saturated NaHCO₃ aq. solution, extracted with DCM (20 mL×3). Organic phase was combined and dried (Na₂SO₄) and evaporated to give crude material which was used in next step without further purification. ¹H NMR (400 MHz, MeOD) δ 7.48 (d, J=5.1 Hz, 1H) 8.02 (d, J=5.1 Hz, 1H). MS (ES: m/z: 357.68, 359.67, 361.68 [MH⁺]. HPLC: $t_R$=3.22 min (OpenLynx: polar_5 min).

8-Chloro-3-iodo-imidazo[1,5-a]pyrazine

To a stirred solution of 8-chloro-imidazo[1,5-a]pyrazine (200.00 mg, 1.30 mmol) in THF (10.0 mL) was slowly added n-BuLi in hexane (2.5 M, 0.62 mL, 1.55 mmol) at −78° C. under nitrogen. The resulting mixture was stirred at the same temperature for 15 min. Then to this mixture a solution of iodine (429.7 mg, 1.693 mol) in 3 mL of THF was slowly added. The mixture was allowed to warm up to 30° C. in 1 hour. Reaction was quenched by 2 mL saturated aq. solution of NH₄Cl. The reaction mixture was extracted with DCM. The solvent was removed under reduced pressure and the residue was used in next step without further purification. ¹H NMR (400 MHz, CDCl₃) δ 7.48 (d, J=5.05 Hz, 1H), 7.71 (dd, J=5.05, 1.01 Hz, 1H), 7.94 (d, J=1.01 Hz, 1H). MS (ES⁺): m/z 279.86/281.90 [MH⁺]; HPLC: $t_R$=2.70 min (OpenLynx, polar_5 min).

8-Chloro-imidazo[1,5-a]pyrazine

To an oven dried flask filled with nitrogen was added N-(3-chloro-pyrazin-2-ylmethyl)-formamide (3.000 g, 0.01748 mol) followed by MeCN (60 mL). POCl₃ (4.89 mL, 0.0524 mol) was added to the reaction mixture dropwise at 0° C. and the reaction mixture was stirred at 0° C. for 5 min before DMF (0.2 mL) was added. The mixture was then warmed up to rt and stirred at rt for overnight. The excess of POCl₃ was removed under reduced pressure and the residue was quenched with solution of 2N NH₃ in i-PrOH at 0° C. with vigorous stirring to adjust the pH to 9. The crude reaction mixture was then charged with water and the aqueous layer was washed with DCM. The combined organic layer was dried over Na₂SO₄, filtered and concentrated under reduced pressure to obtain the titled compound. ¹H NMR (400 MHz, CDCl₃) δ 7.38 (d, J=4.80 Hz, 1H) 7.80 (d, J=5.05 Hz, 1H) 7.87 (s, 1H) 8.28 (s, 1H). MS (ES+): m/z 154.13, 156.02 [MH⁺]; HPLC: $t_R$=2.02 min (OpenLynx, polar_7 min).

N-(3-Chloro-pyrazin-2-ylmethyl)-formamide

To a solution of C-(3-chloro-pyrazin-2-yl)-methylamine bis-hydrochloride (6.0 g, 0.027 mol) in DMF (50 mL) was added N-(3-dimethylaminopropyl)-N'-ethylcarbodiimide hydrochloride (7.9 g, 0.041 mol), diisopropyl ethylamine (24.2 mL, 0.139 mol), hydrate (400.0 mg, 0.003 mol) and formic acid (1.57 mL, 0.041 mol). The reaction was left to stir at rt for 16 h under an atmosphere of nitrogen. The solvent was then removed under reduced pressure and the residue was purified by chromatography (5% DCM in hexane. ¹H NMR (400 MHz, CD₃OD) δ ppm 4.72 (s, 2H), 8.26 (s, 1H), 8.39 (d, J=1.77 Hz, 1H), 8.57 (d, J=2.53 Hz, 1H). MS (ES+): m/z 172.11, 174.09 [MH⁺]; HPLC: $t_R$=1.57 min (OpenLynx, polar_7 min).

C-(3-Chloropyrazin-2-yl)methylamine bis-hydrochloride

A solution of 2-(3-chloropyrazin-2-ylmethyl)-isoindole-1,3-dione (10.0 g, 36.5 mmol) in anhydrous CH₂Cl₂ (200 mL) was charged with hydrazine (2.87 mL, 2.93 g, 91.3 mmol, 2.5 eq.) at rt, under N₂ atmosphere. After 2.5 h, MeOH (300 mL) was added and the reaction was heated until the solution was homogenous. The reaction mixture was allowed to stir for 19 h. The white ppt that had formed (2,3-dihydrophthalazine-1,4-dione byproduct), was filtered off and washed several times with ether. The clear filtrate was concentrated in vacuo and the concentrate was dissolved in EtOAc and filtered again to remove white ppt. All solvent was removed, giving a yellow oil, which was dissolved into EtOAc and ether and charged with HCl (g). The title compound, a pale yellow solid, instantly precipitated. The title compound was dried in a 40° C. oven for 72 h, affording the title compound, as a dark yellow solid; ¹H NMR (400 MHz, CD₃OD) δ 4.55 (2H, s), 8.27 (1H, d, J=2.52 Hz), 8.54 (1H, d, J=2.56 Hz); MS (ES+): m/z 143.96/145.96 (100/60) [MH⁺]; HPLC: $t_R$=0.41 min (OpenLynx, polar 7 min).

1-{[(3-Oxocyclobutyl)carbonyl]oxy}pyrrolidine-2,5-dione

Into a 5 L reactor equipped with a nitrogen flow and an overhead stirrer was added N-hydroxysuccinimide (250.0 g, 2.172 mol) and 3-oxo-cyclobutanecarboxylic acid (248 g, 2.17 mol). EtOAc (3.4 L) was added and the reaction was cooled to 16° C. A solution of 25% DCC in EtOAc (2.17 mol) was added slowly via an addition funnel to the reaction mixture over 7 minutes then the mixture was then heated at 45° C. After 2 h, the mixture was filtered and the filtrate was washed once with EtOAc (1 L×1) and evaporated to dryness in vacuo to afford the desired product. ¹H NMR (400 MHz, DMSO-d₆) δ 2.83 (bs, 4H), 3.30-3.39 (m, 2H), 3.52-3.60 (m, 2H) and 3.67-3.73 (m, 1H).

3-(8-Chloroimidazo[1,5-a]pyrazin-3-yl)cyclobutanone

Into a round bottom 1-neck flask (5 L), 3-oxo-cyclobutanecarboxylic acid 2,5-dioxo-pyrrolidin-1-yl ester (217.2 g, 0.937 mol), C-(3-chloro-pyrazin-2-yl)-methylamine hydrochloride salt (153.3 g, 0.852 mol), and THF (760 mL) were added. A solution of 10% NaHCO3 (1.07 kg) was then added and after 20 min, the layers were allowed to separate and the aqueous layer was removed. The aqueous layer was back extracted with EtOAc (1×700 mL, 1×300 mL). The combined organics were washed with brine (350 mL), dried over MgSO₄, filtered, and concentrated in vacuo to provide the title compound. This solid was resuspended in EtOAc (915 mL) and DMF (132 mL) and the solution was put under an atmosphere of nitrogen and cooled to 10.5° C. Phosphorus oxychloride (159 mL, 1.70 mol) was then added over 15 minutes and the reaction was allowed to stir for 45 min. The reaction solution was then poured slowly into a 22% aqueous Na₂CO₃ solution at 10° C. Water (1 L) was added and the layers were allowed to separate. The organic layer was removed and the aqueous was back extracted with EtOAc (1×μL, 1×0.5 L). The combined organic phases were dried over MgSO₄, filtered, and concentrated in vacuo until about 0.5 L of solvent remained. Heptane was added and the slurry was concentrated in vacuo until most of the EtOAc was removed. The resultant slurry was filtered to give desired product. ¹H NMR (400 MHz, CDCl₃) δ3.59-3.68 (m, 2H), 3.72-3.79 (m, 2H), 3.86-3.94 (m, 1H), 7.40 (d, 1H, J=5.2 Hz), 7.60 (d, 1H, J=5.2 Hz) and 7.85 (s, 1H).

3-(1-Bromo-8-chloroimidazo[1,5-a]pyrazin-3-yl)cyclobutanone 3-(8-Chloroimidazo[1,5-a]pyrazin-3-yl)cyclobutanone (47.7 g, 215 mmol) was dissolved in DMF (200 mL) under an atmosphere of nitrogen and cooled to −4° C. N-Bromosuccinimide (40.3 g, 226 mmol) was dissolved in DMF (140 mL) and slowly added to the reaction mixture. After 5 min, water (400 mL) was added and the resulting solid isolated by filtration and washed with solid with water to give the title compound. $^1$H NMR (DMSO-d6, 400 MHz): δ 3.45-3.53 (m, 2H), 3.58-3.67 (m, 2H), 4.08-4.16 (m, 1H), 7.45 (d, 1H, J=5.2 Hz) and 8.30 (d, 1H, J=4.8 Hz).

cis-3-(1-Bromo-8-chloroimidazo[1,5-a]pyrazin-3-yl)-1-methylcyclobutanol 3-(1-Bromo-8-chloroimidazo[1,5-a]pyrazin-3-yl)cyclobutanone (51.988 g, 0.17 mol) in anhydrous THF (550 g, 620 mL) under nitrogen at −78° C. was treated with a 3.0 M solution of methyl magnesium chloride in THF (130 mL, 0.38 mol) over 30 min. The mixture was stirred at −78° C. for 30 min and then the cooling bath was removed and the mixture quenched with 14% NH$_4$Cl (132 g). EtOAc was added to the aqueous phase and the pH was adjusted to ~5 with 20% HCl and the layers separated. The combined organic phases were concentrated in vacuo to a slurry and 0.5 L of toluene was added and the mixture concentrated in vacuo until the EtOAc was removed. The slurry was heated at reflux until homogeneous then allowed to cool to provide desired product, which was isolated by filtration and dried in vacuo. $^1$H NMR (DMSO-d$_6$, 400 MHz): δ 1.37 (s, 3H), 2.35-2.49 (m, 4H), 3.52 (dddd, 1H, J=9.6, 9.6, 9.6, 9.6 Hz), 5.18 (bs, 1H), 7.37 (d, 1H, J=5.2 Hz) and 8.26 (d, 1H, J=5.2 Hz).

cis-3-(8-Amino-1-bromoimidazo[1,5-a]pyrazin-3-yl)-1-methylcyclobutanol

A 35% ammonia solution (132 ml, 2.9 moles) was added to a suspension of cis-3-(1-bromo-8-chloroimidazo[1,5-a]pyrazin-3-yl)-1-methylcyclobutanol (22.0 g, 0.06463 mol) in 2-butanol (81 ml). The mixture was heated at 90° C. in a pressure vessel for 15 hr then concentrated to ~130 ml, cooled to room temperature and the solid collected by filtration. This material was washed with water (3×22 mL) and dried at 40° C. under vacuum. To afford the desired product. $^1$H NMR (DMSO-d$_6$, 400 MHz): 67.5 (m, 1H), 7.0 (m, 1H), 6.6 (bs, 2H), 5.1 (s, 1H), 3.4 (m, 1H), 2.3-2.4 (m, 4H) and 1.4 (s, 3H).

7-Cyclobutyl-5-iodoimidazo[5,1-f][1,2,4]triazin-4-ylamine

To a solution of 1,2,4-triazole (1.28 g, 18.59 mmol) in anhydrous pyridine (10 mL) was added phosphorus oxychloride (POCl$_3$) (0.578 mL, 6.20 mmol) and stirred at rt for 15 min. This mixture was dropwise charged (3.5 min) with a solution of 7-cyclobutyl-5-iodo-3H imidazo[5,1f][1,2,4]triazin-4-one (0.653 mg, 2.07 mmol) in anhydrous pyridine (14 mL) and stirred for 1.5 h. The reaction mixture was cooled to 0° C. quenched with 2M NH$_3$ in isopropanol (IPA) until basic then allowed to reach rt and stirred for an additional 2 h. The reaction mixture was filtered through a fritted Büchner funnel and washed with DCM. The filtrate was concentrated in vacuo and purified by chromatography on silica gel [eluting with 30% EtOAc in DCM] resulting in the title compound as an off-white solid; $^1$H NMR (CDCl$_3$, 400 MHz) δ 1.93-2.04 (m, 1H), 2.05-2.18 (m, 1H), 2.35-2.45 (m, 2H), 2.49-2.62 (m, 2H), 4.00-4.12 (m, 1H), 7.82 (s, 1H); MS (ES+): m/z 316.08 (100) [MH$^+$], HPLC: t$_R$=2.59 min (MicromassZQ, polar_5 min).

7-Cyclobutyl-5-iodo-3H-imidazo[5,1-f][1,2,4]triazin-4-one

A solution of 7-cyclobutyl-3H-imidazo[5,1-f][1,2,4]triazin-4-one (789 mg, 4.15 mmol) and N-iodosuccinimide (NIS, 933 mg, 4.15 mmol) in anhydrous DMF (40 mL) was stirred overnight at rt. An additional 4 eq. of NIS was added and reaction was heated to 55° C. for 6 h. The reaction mixture was concentrated in vacuo and partitioned between DCM and H$_2$O and separated. The aqueous layer was washed with DCM (3×) and the combined organic fractions were washed with 1M sodium thiosulfate (Na$_2$S$_2$O$_3$) (1×), brine (1×), dried over sodium sulfate (Na$_2$SO$_4$), filtered, and concentrated in vacuo. The solid was triturated with 20% EtOAc in DCM and filtered through a fritted Büchner funnel resulting in the title compound as an off-white solid; $^1$H NMR (DMSO-d$_6$, 400 MHz) δ 1.84-1.96 (m, 1H), 1.98-2.13 (m, 1H), 2.25-2.43 (m, 4H), 3.84-3.96 (m, 1H), 7.87 (s, 1H); MS (ES+): m/z 317.02 (100) [MH$^+$], HPLC: t$_R$=2.62 min (MicromassZQ, polar_5 min).

7-Cyclobutyl-3H-imidazo[5,1-f][1,2,4]triazin-4-one

A crude solution of cyclobutanecarboxylic acid (5-oxo-4,5-dihydro-[1,2,4]triazin-6-ylmethyl)amide (1.33 g, 6.39 mmol) in phosphorus oxychloride (POCl$_3$) (10 mL) was heated to 55° C. The reaction was heated for 2 h then concentrated in vacuo and the crude oil was cooled to 0° C. in an ice-bath and quenched with 2M NH$_3$ in isopropanol (IPA) until slightly basic. This crude reaction mixture was concentrated in vacuo and was partitioned between DCM and H$_2$O and separated. The aqueous layer was extracted with DCM (3×) and the combined organic fractions were dried over sodium sulfate (Na$_2$SO$_4$), filtered and concentrated in vacuo. The crude material was purified by chromatography on silica gel [eluting with 5% MeOH in DCM], resulting in the title compound as an off-white solid; $^1$H NMR (DMSO-d$_6$, 400 MHz) δ 1.86-1.96 (m, 1H), 2.00-2.13 (m, 1H); 2.26-2.46 (m, 4H); 3.87-4.00 (m, 1H); 7.71 (s, 1H); 7.87 (d, J=3.6 Hz, 1H); 11.7 (brs, 1H); MS (ES+): m/z 191.27 (100) [MH$^+$], HPLC: t$_R$=2.06 min (MicromassZQ, polar_5 min).

Cyclobutanecarboxylic acid (5-oxo-4,5-dihydro-[1,2,4]triazin-6-ylmethyl)amide

To a solution of 6-aminomethyl-4H-[1,2,4]triazin-5-one (500 mg, 3.96 mmol) and DIEA (0.829 mL, 4.76 mmol) in anhydrous N,N-DMF (20 mL) and anhydrous pyridine (2 mL) was dropwise charged with cyclobutanecarbonyl chloride (0.451 mL, 3.96 mmol) at 0° C. then warmed to rt and stirred for an additional 1.5 h. The reaction mixture was quenched with H$_2$O (2 mL) and concentrated in vacuo and was purified by chromatography on silica gel [eluting with 5% MeOH in DCM (200 mL)×10% MeOH in DCM (800 mL)], affording the title compound; $^1$H NMR (DMSO-d$_6$, 400 MHz) δ 1.7-1.82 (m, 1H), 1.70-1.92 (m, 1H); 1.97-2.07 (m, 2H); 2.07-2.19 (m, 2H); 3.55-3.67 (m, 1H); 4.19 (d, 2H); 7.97 (br. t, J=5.6 Hz, 1H); 8.67 (s, 1H); MS (ES+): m/z 209.25 (100) [MH$^+$], HPLC: t$_R$=1.56 min (MicromassZQ, polar_5 min).

6-Aminomethyl-4H-[1,2,4]triazin-5-one

A slurry of 2-(5-oxo-4,5-dihydro-[1,2,4]triazin-6-ylmethyl)isoindole-1,3-dione (4 g, 15.6 mmol) in DCM/EtOH (1:1) (150 mL) was charged with anhydrous hydrazine (1.23 mL, 39.0 mmol) and stirred at rt for 18 h. The reaction mixture was concentrated in vacuo and the off-white solid was triturated with warm CHCl$_3$ and filtered through a fritted funnel. The solid was then triturated with hot boiling MeOH and filtered through a fritted funnel resulting in an off-white solid. The material was triturated a second time as before and dried overnight resulting in the title compound as a white solid, which was taken on to the next step without further purification; $^1$H NMR (DMSO-d$_6$, 400 MHz) δ 3.88 (s, 2H), 8.31 (s, 1H); MS (ES+): m/z 127.07 (100) [MH$^+$], HPLC: t$_R$=0.34 min (MicromassZQ, polar_5 min).

2-(5-Oxo-4,5-dihydro-[1,2,4]triazin-6-ylmethyl) isoindole-1,3-dione

A slurry of 2-(5-oxo-3-thioxo-2,3,4,5-tetrahydro-[1,2,4] triazin-6-ylmethyl)isoindole-1,3-dione (1.0 g, 3.47 mmol) in EtOH (40 mL) was charged with excess Raney Ni (3 spatula) and heated to reflux for 2 h. The reaction mixture was filtered hot through a small pad of celite and washed with a hot mixture of EtOH/THF (1:1) (100 mL) and the filtrate was concentrated in vacuo resulting in the title compound as an off-white solid; $^1$H NMR (DMSO-d$_6$, 400 MHz) δ 4.75 (s, 2H), 7.84-7.98 (m, 4H), 8.66 (s, 1H); MS (ES+): m/z 257.22 (100) [MH$^+$].

2-(5-Oxo-3-thioxo-2,3,4,5-tetrahydro-[1,2,4]triazin-6-ylmethyl)indan-1,3-dione

A slurry of 3-(1,3-dioxo-1,3-dihydroisoindol-2-yl)-2-oxopropionic acid ethyl ester (20 g, 76.6 mmol) in anhydrous EtOH (300 mL) was charged with thiosemicarbazide (6.98 g, 76.6 mmol) in one portion and heated to 80° C. for 2 h. The reaction mixture was charged with N,N-diisopropylethylamine (DIEA) (26.7 mL, 76.56 mmol) and heated to 40° C. for 6 h then stirred at rt for an additional 10 h. The reaction mixture was concentrated in vacuo and solid was triturated with hot EtOH/EtOAc filtered and washed with EtOAc. The solid was dried overnight in a vacuum oven (40° C.) resulting in the title compound as an off-white solid; $^1$H NMR (DMSO-d$_6$, 400 MHz) δ 4.68 (s, 2H), 7.85-7.95 (m, 4H); MS (ES+): m/z 289.2 (100) [MH$^+$].

trans-4-({[(Benzyloxy)carbonyl]amino}methyl)cyclohexanecarboxylic acid trans-4-(Aminomethyl)cyclohexanecarboxylic acid (10.00 g, 0.06361 mol), in a 10% aq solution of NaOH (5.60 g in 55 mL) was cooled to 0° C. and treated over 15 min with vigorous stirring, with benzyl chloroformate (11 mL, 0.076 mol). After one hour the solution was acidified (1M HCl(aq)) and the resulting the white precipitate collected by filtration, washed with water and hexane then dried in vacuo oven overnight to afford 17.23 g of the title compound. $^1$H NMR (400 MHz, CDCl$_3$): δ 0.93-0.99 (m, 2H), 1.38-1.46 (m, 2H), 1.82-1.85 (m, 2H), 2.03-2.06 (m, 2H), 2.25 (m, 1H), 3.06 (t, J=5.6 Hz, 2H), 4.83 (m, 1H), 5.09 (s, 2H), 7.31-7.36 (m, 5H). MS (ES+): m/z 292 [MH$^+$].

Benzyl[(trans-4-{[(3-chloropyrazin-2-yl)methyl] carbamoyl}cyclohexyl)methyl]carbamate To a solution of C-(3-chloropyrazin-2-yl)methylamine hydrochloride salt (0.100 g, 0.533 mmol) in DCM (1.35 mL) was added N-(3-dimethylaminopropyl)-N'-ethylcarbodiimide hydrochloride (0.16 g, 0.83 mmol), N,N-diisopropylethylamine (0.14 mL, 0.83 mmol), (0.075 g, 0.56 mmol) and trans-4-({[(benzyloxy)carbonyl]amino}methyl)cyclohexanecarboxylic acid (0.21 g, 0.70 mmol). The reaction was stirred at rt overnight then diluted with DCM, washed with sat. NaHCO$_3$ (aq) and brine, then dried over Na$_2$SO$_4$ and the solvent removed in vacuo. The residue thus isolated was chromatographed over silica gel eluting with EtOAc/hexane (1:1) to afford 0.173 g of the title compound. $^1$H NMR (400 MHz, CDCl$_3$): δ 1.00-1.03 (m, 2H), 1.45-1.51 (m, 2H), 1.83-1.89 (m, 2H), 1.99-2.03 (m, 2H), 2.20 (m, 1H), 3.05-3.12 (m, 3H), 4.68 (d, J=4.4 Hz, 2H), 4.79 (br, 1H), 5.10 (s, 2H), 6.79 (br, 1H), 7.31-7.37 (m, 5H), 8.33 (d, J=2.8 Hz, 1H), 8.46 (d, J=2.8 Hz, 1H). MS (ES+): m/z 417.14 [MH+].

Benzyl{[trans-4-(8-chloroimidazo[1,5-a]pyrazin-3-yl)cyclohexyl]methyl}carbamate

To a suspension of benzyl[(trans-4-{[(3-chloropyrazin-2-yl)methyl]carbamoyl}cyclohexyl)methyl]carbamate (0.100 g, 0.220 mmol) in EtOAc (0.9 mL) and DMF (0.068 mL) at 0° C. was added slowly POCl$_3$ (0.082 mL, 0.88 mmol). After stirring at rt for an hour, the mixture was cooled to 0° C. and solid NaHCO$_3$ was added. After a further 10 min at 0° C. and 20 min at rt, the mixture was re-cooled to 0° C. and water (20 mL) was added. The reaction mixture was extracted with EtOAc (3×20 mL) and the extracts washed with water (2×30 mL) and brine (30 mL) and then dried over Na$_2$SO$_4$ and concentrated in vacuo to afford 0.096 g of the title compound. $^1$H NMR (400 MHz, CDCl$_3$): δ 1.15-1.19 (m, 2H), 1.76-1.87 (m, 3H), 1.93-2.00 (m, 2H), 2.04-2.08 (m, 2H), 3.07 (m, 1H), 3.15 (t, J=6.4 Hz, 2H), 4.84 (br, 1H), 5.09 (s, 2H), 7.31-7.40 (m, 6H), 7.61 (d, J=4.8 Hz, 1H), 7.79 (s, 1H). MS (ES+): m/z 399.26 [MH$^+$].

Benzyl{[trans-4-(8-chloro-1-iodoimidazo[1,5-a] pyrazin-3-yl)cyclohexyl]methyl}carbamate To a solution of benzyl{[trans-4-(8-chloroimidazo[1,5-a] pyrazin-3-yl)cyclohexyl]methyl}carbamate (1.49 g, 0.00374 mol) in DMF (0.6 mL) was added NIS (1.0 g, 0.0045 mol). The reaction mixture was stirred at 55° C. overnight then diluted with EtOAc (20 mL), washed with water (2×40 mL) and brine (20 mL), then dried over Na$_2$SO$_4$ and concentrated in vacuo. The crude mixture thus isolated was chromatographed over silica gel eluting with hexane→hexane:EtOAc 1:1 to afford 1.7 g of the title compound. MS (ES+): m/z 525.01 [MH$^+$].

Benzyl{[trans-4-(8-amino-1-iodoimidazo[1,5-a] pyrazin-3-yl)cyclohexyl]methyl}carbamate A solution of benzyl{[trans-4-(8-chloro-1-iodoimidazo[1, 5-a]pyrazin-3-yl)cyclohexyl]methyl}carbamate (1.70 g, 0.00324 mol) in IPA (30 mL) was cooled to −78° C., treated with a stream of ammonia gas over 3 min. and then heated at 110° C. in a Parr vessel overnight. The reaction solution was concentrated in vacuo and residue washed with water to afford 1.37 g of desired product. $^1$H NMR (400 MHz, CDCl$_3$): δ=1.08-1.17 (m, 2H), 1.88 (m, 1H), 1.71-1.81 (m, 2H), 1.91-1.94 (m, 2H), 2.00-2.04 (m, 2H), 2.90 (m, 1H), 3.13 (t, J=6.4 Hz, 2H), 4.86 (br, 1H), 5.11 (s, 2H), 5.76 (br, 2H), 7.00 (d, J=5.2 Hz, 1H), 7.22 (d, J=5.2 Hz, 1H), 7.31-7.37 (m, 5H). MS (ES+): m/z 5.7.36 [MH$^+$].

Benzyl 4-{[(3-chloropyrazin-2-yl)methyl] carbamoyl}piperidine-1-carboxylate

A solution of C-(3-Chloropyrazin-2-yl)methylamine bishydrochloride (2.00 g, 0.0107 mol) and N,N-diisopropylethylamine (2.2 g, 0.017 mol) in DCM (27.0 mL) was treated with and N-(3-dimethylaminopropyl)-N'-ethylcarbodiimide hydrochloride (3.2 g, 0.017 mol), (1.5 g, 0.011 mol) and 1-[(benzyloxy)carbonyl]-4-piperidine carboxylic acid (3.8 g, 0.014 mol). The mixture was stirred at rt overnight then diluted with DCM (30 mL), washed with sat. NaHCO$_3$ (20 mL) and brine (20 mL), then dried over Na$_2$SO$_4$ and concentrated in vacuo. The crude material thus obtained was chromatographed over silica gel eluting with EtOAc:hexane 1:1 yielding 3.38 g of the title compound. $^1$H NMR (400 MHz, CDCl$_3$); δ 1.68-1.78 (m, 2H), 1.91-1.94 (m, 2H), 2.44 (m, 1H), 2.89-2.92 (m, 2H), 4.24-4.26 (m, 2H), 4.70 (d, J=4.8 Hz, 2H), 5.14 (s, 2H), 6.85 (br, 1H), 7.30-7.37 (m, 5H), 8.34 (d, J=2.8 Hz, 1H), 8.45 (d, J=2.8 Hz, 1H). MS (ES+): m/z 389.17 [MH$^+$].

Benzyl 4-(8-chloroimidazo[1,5-a]pyrazin-3-yl)piperidine-1-carboxylate

To a suspension of benzyl 4-{[(3-chloropyrazin-2-yl)methyl]carbamoyl}piperidine-1-carboxylate (0.100 g, 0.220 mmol) in EtOAc (0.9 mL) and DMF (0.068 mL) at 0° C. was slowly added POCl$_3$ (0.082 mL, 0.88 mmol). After stirring at rt for an hour the mixture was cooled to 0° C. then treated with solid NaHCO$_3$ The mixture was stirred for 20 min at rt, diluted with water and extracted with EtOAc (3×20 mL). The combined extracts were washed with water (2×30 mL) and brine (30 mL), then dried over Na$_2$SO$_4$, and concentrated in vacuo to yield 2.07 g of desired product. $^1$H NMR (400 MHz, CDCl$_3$): δ1.98-2.04 (m, 4H), 3.03-3.20 (m, 3H), 4.30-4.33 (m, 2H), 5.16 (s, 2H), 7.33 (d, J=5.2 Hz, 1H), 7.35-7.38 (m, 5H), 7.26 (d, J=4.4 Hz, 1H), 7.79 (s, 1H). MS (ES+): m/z 371.22 [MH+].

Benzyl 4-(8-chloro-1-iodoimidazo[1,5-a]pyrazin-3-yl)piperidine-1-carboxylate To a solution of benzyl 4-(8-chloroimidazo[1,5-a]pyrazin-3-yl)piperidine-1-carboxylate (1.31 g, 0.00354 mol) in DMF (0.6 mL) was added NIS (1.6 g, 0.0071 mol). The reaction mixture was left to stir at 55° C. for 20 h. then the mixture was diluted with EtOAc (20 mL), washed with water (2×40 mL) and brine, then dried over Na$_2$SO$_4$ and concentrated in vacuo. The crude reaction mixture was chromatographed over silica gel eluting with hexane hexane:EtOAc 1:1 yielding 1.63 g of desired product. $^1$H NMR (400 MHz, CDCl$_3$): δ 1.95-2.04 (m, 4H), 3.02-3.15 (m, 3H), 4.29-4.32 (m, 2H), 5.15 (s, 2H), 7.32 (d, J=5.2 Hz, 1H), 7.34-7.37 (m, 5H), 7.66 (d, J=5.2 Hz, 1H). MS (ES+): m/z 497.03 [MH$^+$].

Benzyl 4-(8-amino-1-iodoimidazo[1,5-a]pyrazin-3-yl)piperidine-1-carboxylate

A mixture of benzyl 4-(8-chloro-1-iodoimidazo[1,5-a]pyrazin-3-yl)piperidine-1-carboxylate (0.500 g, 0.00101 mol) in IPA (20 mL) was cooled to at −78° C. and treated with a stream of ammonia gas over 3 minutes. The resulting solution was heated at 110° C. in a Parr vessel prior to concentration in vacuo, suspension in DCM and filtration through a bed of Celite. The filtrate was concentrated in vacuo to afford 0.504 g of desired product. $^1$H NMR (400 MHz, CDCl$_3$): δ 1.88-2.02 (m, 2H), 2.99-3.10 (m, 3H), 4.24-4.41 (m, 2H), 5.15 s, 2H), 6.03 (br, 2H), 7.03 (d, J=4.8 Hz, 1H), 7.24 (d, J=5.2 Hz, 1H), 7.31-7.40 (m, 5H). MS (ES+): m/z 479.33 [MH$^+$].

1-Iodo-3-piperidin-4-yl-imidazo[1,5-a]pyrazin-8-ylamine

Benzyl 4-(8-amino-1-iodoimidazo[1,5-a]pyrazin-3-yl)piperidine-1-carboxylate (1.00 g. 2.10 mmol) was dissolved in concentrated HCl (30 mL) at 0° C. The reaction was stirred at rt. overnight. The reaction mixture was diluted with water (30 mL) and washed with EtOAc (30 mL×3), the aqueous phase was removed under reduced pressure to give a residue which was used for next step without further purification. MS (ES+): m/z 343.78 [MH$^+$].

1-[4-(8-Amino-1-iodo-imidazo[1,5-a]pyrazin-3-yl)-piperidin-1-yl]-2-dimethylamino-ethanone To a stirred mixture of 1-iodo-3-piperidin-4-yl-imidazo[1,5-a]pyrazin-8-ylamine (1.000 g, 2.91 mmol) and dimethylamino-acetyl chloride (0.38967 g, 3.20 mmol) in DMF (10.00 mL) was added DIEA (2.58 mL, 14.57 mmol) at 0° C. The resulting mixture was stirred at rt. overnight. The mixture was diluted with sat. aq. NaHCO$_3$ and extracted with DCM (50 ml×3). The extracts were combined, dried (Na$_2$SO$_4$). Solvent was then removed under reduced pressure and the resulting residue was used for next step without further purifications. MS (ES+): m/z 428.74 [MH$^+$].

1-Iodo-3-methylsulfanyl-imidazo[1,5-a]pyrazin-8-ylamine

To a suspension of 8-chloro-1-iodo-3-methylsulfanyl-imidazo[1,5-a]pyrazine (2.68 g, 0.00823 mol) in i-PrOH (50 mL) was bubbled NH$_3$ gas for 5 min at −78° C., the mixture was heated at 110° C. overnight. LC-MS showed the reaction was complete. The mixture was cooled to rt and water (10 mL) was added. The off-white solid was collected by filtration, 1.20 g as the first batch. The filtrate was diluted with EtOAc (200 mL), washed with brine (30 mL), and dried over anhydrous sodium sulfate. The crude material was suspended in EtOAc (20 mL), and the off-white solid was collected by filtration, 700 mg as the second batch. Totally 1.90 g, 75% yield. LC-MS (ES+.): 307 [MH$^+$], $^1$H-NMR (DMSO-d$_6$): δ 2.55 (s, 3H), 6.64 (br s, 2H), 7.08 (d, J=4.8 Hz, 1H), 7.53 (d, J=4.8 Hz, 1H).

8-Chloro-1-iodo-3-methylsulfanyl-imidazo[1,5-a]pyrazine

P To a solution of 8-chloro-3-methylsulfanyl-imidazo[1,5-a]pyrazine (1.75 g, 0.00876 mol) in DMF (15 mL) was added N-iodosuccinimide (3.94 g, 0.0175 mol), the resulting mixture was stirred at 55° C. for 6 hrs. The mixture was diluted with EtOAc (200 mL), washed with sat. aq. NaHCO$_3$ (40 mL), water (2×40 mL), brine (40 mL), and dried over anhydrous sodium sulfate. The crude material was purified by silica gel chromatography to give the title compound as a yellow solid, 2.68 g, 94% yield. $^1$H NMR (CDCl$_3$, 400 MHz): δ 2.72 (s, 3H), 7.36 (d, J=4.8 Hz, 1H), 7.76 (d, J=4.8 Hz, 1H).

8-Chloro-3-methylsulfanyl-imidazo[1,5-a]pyrazine

To a solution of (3-chloro-pyrazin-2-ylmethyl)-thiocarbamic acid S-methyl ester (3.05 g, 0.0140 mol) in MeCN (70 mL) were added DMF (4.3 mL, 0.056 mol) and POCl$_3$ (5.2 mL, 0.056 mol) at 0° C. under nitrogen. The reaction mixture was slowly warmed to rt and stirred at rt overnight. LC-MS showed the SM was completely consumed. The solvent was evaporated under reduced pressure and the residue was cooled at 0° C. and diluted with EtOAc (250 mL), then quenched with sat. aq. NaHCO$_3$ (100 mL). The mixture was washed brine (50 mL), and dried over anhydrous sodium sulfate. The crude material was purified by silica gel chromatography (Hexane EtOAc=80:20→70:30) to give the title compound as a light-yellow solid, 1.75 g, 63% yield. LC-MS (ES+): 200/202 (3/1) [MH$^+$], and $^1$H NMR (CDCl$_3$, 400 MHz): δ 2.71 (s, 3H), 7.40 (d, J=5.1 Hz, 1H), 7.74 (dd, J=5.1, 1.0 Hz, 1H), 7.90 (s, 1H).

(3-Chloro-pyrazin-2-ylmethyl)-thiocarbamic acid S-methyl ester

To a suspension of C-(3-chloro-pyrazin-2-yl)-methylamine hydrochloride salt (5.13 g, 0.0285 mol) in DCM (60 mL) were added N,N-diisopropylethylamine (15 mL, 0.085 mol) and carbonochloridothioic acid, S-methyl ester (3.15 g, 0.0285 mol) at 0° C. 5 min later, the mixture was warmed to rt and kept at rt overnight. The mixture was diluted with DCM (50 mL), washed with water (30 mL), sat. aq. NaHCO$_3$ (2×30 mL), brine (30 mL), and dried over anhydrous sodium sulfate. The crude product was purified by silica gel chromatography (Hex EtOAc=70:30→50:50) to give the title compound as a light-yellow solid, 4.4 g, 71% yield. $^1$H NMR (CDCl$_3$, 400 MHz) δ 2.41 (s, 3H), 4.76 (d, J=4.6 Hz, 2H), 6.67 (br s, 1H), 8.34 (d, J=2.5 Hz, 1H), 8.48 (d, J=2.5 Hz, 1H).

Methyl trans-4-{[(2,5-dioxopyrrolidin-1-yl)oxy]carbonyl}cyclohexanecarboxylate A solution of N-hydroxysuccinimide (6.18 g, 0.0537 mol) and trans-4-(methoxycarbonyl)cyclohexanecarboxylic acid (10.00 g, 0.05370 mol) in THF (100.00 mL) was charged with (N,N'-dicyclohexylcarbodiimide (11.08 g, 0.0537 mol) in THF (16 mL). This reaction was stirred at rt for an additional 16 h then stirred at 45° C. for 1 h. The reaction mixture was filtered while still warm through a fritted funnel. The cake was washed with 3 more portions of THF and the filtrate was concentrated in vacuo and was crystallized from i-PrOH (300 mL) and filtered through a fritted funnel resulting in 11.8 g, (78% yield) of the title compound as a white crystals. $^1$H NMR (400 MHz, CDCl3) δ ppm 1.45-1.69 (m, 4H), 2.07-2.16 (m, 2H), 2.18-2.28 (m, 2H), 2.29-2.39 (m, 1H), 2.59-2.71 (m, 1H) 2.84 (br. s., 4H) and 3.68 (s, 3H); MS (ES+): m/z 284.09 [MH$^+$].

Methyl trans-4-{[(3-amino-5-oxo-4,5-dihydro-1,2,4-triazin-6-yl)methyl]carbamoyl}cyclohexanecarboxylate A solution of 3-amino-6-(aminomethyl)-1,2,4-triazin-5 (4H)-one [J.Heterocyclic Chem., (1984), 21 (3), 697](2.00 g, 0.0113 mol) in H$_2$O (60.0 mL, 3.33 mol) was cooled to 0° C. and drop wise charged with 1.00 M of NaHCO$_3$ in H$_2$O (22.5 mL) and allowed to warm to rt. This mixture was charged with methyl trans-4-[(2,5-dioxopyrrolidin-1-yl)oxy]carbonyl}cyclohexanecarboxylate (3.8 g, 0.012 mol) in 1:1 THF/MeCN (40 mL). After 30 min a precipitate began to form in the reaction. This was allowed to stir at rt for an additional 16 h and was filtered through a fritted funnel and washed with H$_2$O (2x), diethyl ether (2x), and dried in vacuo resulting in the title compound 2.92 g, (84% yield) as an off-white solid. $^1$H NMR (400 MHz, DMSO-d$_6$) δ ppm 1.24-1.55 (m, 4H), 1.83 (s, 2H), 1.98 (d, J=10.61 Hz, 2H), 2.27 (s, 2H), 3.64 (s, 3H), 4.10 (d, J=5.81 Hz, 2H), 6.81 (br. s., 2H), 7.91 (t, J=5.56 Hz, 1H) and 11.98 (br. s., 1H); MS (ES+): m/z 310.05 [MH$^+$].

Methyl trans-4-(2-amino-4-oxo-3,4-dihydroimidazo[5,1-f][1,2,4]triazin-7-yl)cyclohexanecarboxylate A solution of methyl trans-4-{[(3-amino-5-oxo-4,5-dihydro-1,2,4-triazin-6-yl)methyl]carbamoyl}cyclohexanecarboxylate (2.00 g, 0.00646 mol) in 1,2-dichloroethane (130 mL) was charged with POCl$_3$ (4.2 mL, 0.045 mol) and heated to reflux for 3 h. The reaction mixture was concentrated in vacuo then partitioned between EtOAc and sat. NaHCO$_3$ and separated. The aqueous was re-extracted with EtOAc (3x) and the combined organic fractions were dried over Na$_2$SO$_4$, filtered, and concentrated in vacuo resulting in 1.43 g, (76% yield) of the title compound as an off-white solid. $^1$H NMR (400 MHz, DMSO-d$_6$) δ ppm 1.43 (q, J=11.79 Hz, 2H), 1.61 (q, J=12.55 Hz, 2H), 1.85-2.11 (m, 4H), 2.38 (t, J=11.87 Hz, 1H), 2.98 (t, J=11.75 Hz, 1H), 3.61 (s, 3H), 6.17 (br. s., 2H), 7.49 (s, 1H) and 10.90 (br. s., 1H); MS (ES+): m/z 292.25 [MH$^+$].

Methyl trans-4-(2-amino-5-iodo-4-oxo-3,4-dihydroimidazo[5,1-f][1,2,4]triazin-7-yl)cyclohexanecarboxylate A solution of methyl trans-4-(2-amino-4-oxo-3,4-dihydroimidazo[5,1-f][1,2,4]triazin-7-yl)cyclohexanecarboxylate (0.200 g, 0.000686 mol) and N-iodosuccinimide (0.278 g, 0.00124 mol) in anhydrous DMF (4.0 mL) was stirred at rt for 48 h. The reaction was concentrated in vacuo then partitioned between H$_2$O and EtOAc. The aqueous material was re-extracted with EtOAc (3x) and the combined organic fractions were washed with H$_2$O (2x), Na$_2$S$_2$O$_3$ (2x) and brine (1x). The aqueous was re-extracted with CHCl$_3$ and combined with the EtOAc fractions dried over Na$_2$SO$_4$, filtered and concentrated in vacuo resulting in 229 mg, (79.9% yield) of the title compound as a light orange solid. $^1$H NMR (400 MHz, DMSO-de) δ ppm 1.34-1.65 (m, 4H), 1.88-2.06 (m, 4H), 2.33-2.45 (m, 1H), 2.91-3.01 (m, 1H), 3.61 (s, 3H), 6.17 (s, 2H), 10.82 (br. s., 1H); MS (ES+): m/z 417.82 [MH$^+$].

Methyl trans-4-(5-iodo-4-oxo-3,4-dihydroimidazo[5,1-f][1,2,4]triazin-7-yl)cyclohexanecarboxylate A solution of methyl trans-4-(2-amino-5-iodo-4-oxo-3,4-dihydroimidazo[5,1-f][1,2,4]triazin-7-yl)cyclohexanecarboxylate (0.880 g, 0.00211 mol) in anhydrous THF (74 mL) and DMF (13.2 mL) was charged with tert-butyl nitrite (1.2 mL, 0.010 mol) and stirred at rt for 2 h. The reaction was concentrated in vacuo and was purified by chromatography over silica gel [eluting with 5% MeOH in CHCl$_3$] resulting in 570 mg, (67% yield) of the title compound as a pale orange solid. ($^1$H NMR (400 MHz, DMSO-de) δ ppm 1.40-1.54 (m, 2H), 1.56-1.69 (m, 2H), 1.92-2.06 (m, 4H), 2.36-2.46 (m, 1H), 3.02-3.14 (m, 1H), 3.61 (s, 3H), 7.89 (d, J=3.28 Hz, 1H) and 11.79 (br. s., 1H); MS (ES+): m/z 402.86 [MH$^+$].

Methyl trans-4-(4-amino-5-iodoimidazo[5,1-f][1,2,4]triazin-7-yl)cyclohexanecarboxylate A solution of 1H-1,2,4-triazole (0.881 g, 0.0128 mol) in pyridine (3.00 mL) was charged with POCl$_3$ (0.396 mL, 0.00425 mol) and stirred at rt for 15 min. To this mixture was drop wise added methyl trans-4-(5-iodo-4-oxo-3,4-dihydroimidazo[511-f][1,2,4]triazin-7-yl)cyclohexanecarboxylate (0.570 g, 0.00142 mol) in pyridine (6.00 mL) and stirred at rt for an additional 2.45 h. The reaction was quenched with excess 2 M of NH$_3$ in i-PrOH (40.00 mL) at 0° C. and allowed to stir at rt for an additional 3 h. The reaction was concentrated in vacuo and partitioned between EtOAc and sat. NaHCO$_3$ and separated. The aqueous was washed with EtOAc (3x) and the combined organic fractions were washed with brine (1x). The aqueous was re-extracted with CHCl$_3$ (3x) and the organic was added to the EtOAc fractions. The combined organic fractions were dried over Na$_2$SO$_4$, filtered and concentrated in vacuo. The crude brown/red solid was purified by chromatography over silica gel [eluting with 5% MeOH in CHCl$_3$] resulting in 438 mg, (76% yield) of the title compound as a light yellow solid. $^1$H NMR (400 MHz, DMSO-$d_6$) δ ppm 1.39-1.54 (m, 2H), 1.55-1.71 (m, 2H), 1.92-2.07 (m, 4H), 2.35-2.46 (m, 1H), 3.06-3.19 (m, 1H), 3.61 (s, 3H), 6.77 (br. s., 1H) 7.86 (s, 1H) and 8.44 (br. s., 1H); MS (ES+): m/z 401.85 [MH$^+$].

cis-3-(4-Amino-5-bromo-imidazo[5,1-f][1,2,4]triazin-7-yl)-1-methyl-cyclobutanol cis-3-(5-bromo-4-methoxyimidazo[5,1-f][1,2,4]triazin-7-yl)-1-methylcyclobutanol (0.22 g, 0.70 mmol) in 2 M of NH$_3$ in i-PrOH (30 mL) was heated at 60° C. in a Parr bomb overnight. The reaction was concentrated in vacuo and purified by silica gel chromatography [eluted with 5% MeOH in EtOAc] which afforded the desired product. $^1$H NMR (400 MHz, MeOD) δ 1.48 (s, 3H), 2.41-2.62 (m, 4H), 3.54-3.68 (m, 1H), 7.79 (s, 1H)

cis-3-(5-Bromo-4-methoxy-imidazo[5,1-f][1,2,4]triazin-7-yl)-1-methyl-cyclobutanol To a round bottom flask, 3-(5-bromo-4-methoxyimidazo[5,1-f][1,2,4]triazin-7-yl)cyclobutanone (1.32 g, 4.44 mmol) was added and dissolved in anhydrous THF (40.0 mL) under nitrogen. The flask was cooled to −78° C., at which 3.00 M of methylmagnesium bromide in THF (3.0 mL) was added to the reaction via a syringe. The solution stirred for 3 h at −78° C. The reaction was quenched with 10 mL of saturated aqueous NH$_4$Cl at −78° C. and allowed to warm to rt in a water bath. A white precipitate formed. The solution was a faint yellowish color. The product was and extracted with EtOAc (2×15 mL). The aqueous layer was back-extracted with DCM several times. The organic layers were combined, dried, filtered and concentrated in vacuo. The crude product was purified by silica gel column chromatography [eluted with 1:1 EtOAc/DCM], which afforded desired product. MS (ES+): m/z 312.91/314.93 (100/10) [MH+]. HPLC: $t_R$=2.62 min. (OpenLynx, polar_5 min).

3-(5-Bromo-4-methoxy-imidazo[5,1-f][1,2,4]triazin-7-yl)-cyclobutanone

NBS (2.00 g, 0.01 mol) was added in one portion to a stirred, cooled solution of 3-(4-methoxyimidazo[5,1-f][1,2,4]triazin-7-yl)cyclobutanone (6.0 g, 0.027 mol) in DMF (40 mL) at 0° C. under N$_2$. Two other portions of NBS (2.00 g, 0.01 mol) were added after 15 and 30 min respectively. The reaction was stirred with cooling for 5 h. The reaction mixture was partitioned between EtOAc (1 L) and brine (200 mL) and then 83 of 219 organic layer was washed with brine (2×150 mL), dried (Na$_2$SO$_4$) and concentrated under reduced pressure. The crude material was purified by flash chromatography on silica gel using hexanes:EtOAc (1:1) as the eluent. $^1$H NMR (400 MHz, Chloroform-d) δ 3.45-3.60 (m, 3H), 3.66-3.77 (m, 2H), 4.19 (s, 3H), 8.01 (s, 1H).

3-(4-Methoxy-imidazo[5,1-f][1,2,4]triazin-7-yl)-cyclobutanone

In an oven-dried flask filled with N$_2$ was added N-[(5-methoxy-1,2,4-triazin-6-yl)methyl]-3-oxocyclobutanecarboxamide (2.40 g, 0.00833 mol) followed by MeCN (200 mL) and DMF (40 mL). The reaction mixture was treated with POCl$_3$ (3.1 mL, 0.033 mol) dropwise at 0° C. under N$_2$ over 10 min. The reaction was stirred at rt overnight. The reaction mixture was concentrated and poured into ice, saturated aqueous NaHCO$_3$ solution was added to adjust the pH to 7. The mixture was extracted with DCM (150×3). The organic extracts were combined, dried (Na$_2$SO$_4$) and concentrated under reduced pressure to give a crude residue, which was then purified by flash chromatography on silica gel using hexanes:EtOAc (1:1) as the eluent.

3-Oxo-cyclobutanecarboxylic acid (5-methoxy-[1,2,4]triazin-6-ylmethyl)-amide

A flask filled with N$_2$ was charged with 6-(azidomethyl)-5-methoxy-1,2,4-triazine (15.0 g, 0.0903 mol) and Pd/C (10%) (3.20 g) followed by MeOH (480 mL). The suspension was purged with N$_2$. The reaction was then stirred under H$_2$ (1 atm) at rt for 5 h. The inorganics were filtered off, the solvent was removed under reduced pressure to give 1-(5-methoxy-[1,2,4]triazin-6-yl)-methylamine which was used for next step without any further purification.

A flask filled with N$_2$ was charged with 1-(5-methoxy-1,2,4-triazin-6-yl)methylamine (3.0 g, 0.021 mol), 1-{[(3-oxocyclobutyl)carbonyl]oxy}pyrrolidine-2,5-dione (5.0 g, 0.024 mol) and THF (50 mL). Sodium carbonate (20 g, 0.2 mol) dissolved in water was added to the reaction mixture slowly at 0° C. The reaction was then stirred at rt for 3 h. The reaction mixture was then concentrated under reduced pressure to give a residue. To this residue brine (500 mL) was added and the mixture was extracted with EtOAc (100 mL×3). The organics were combined, dried (Na$_2$SO$_4$) and concentrated under reduced pressure to give a crude residue, which was then purified by flash chromatography on silica gel using hexanes:EtOAc (2:1) as the eluent. $^1$H NMR (400 MHz, Chloroform-d) δ 3.12-3.33 (m, 3H), 3.44-3.58 (m, 2H), 4.11 (s, 3H), 4.75 (d, J=4.80 Hz, 2H), 7.11 (br. s., 1H), 9.08 (s, 1H).

EXAMPLES

Examples 1-8 were synthesized according to Method A:

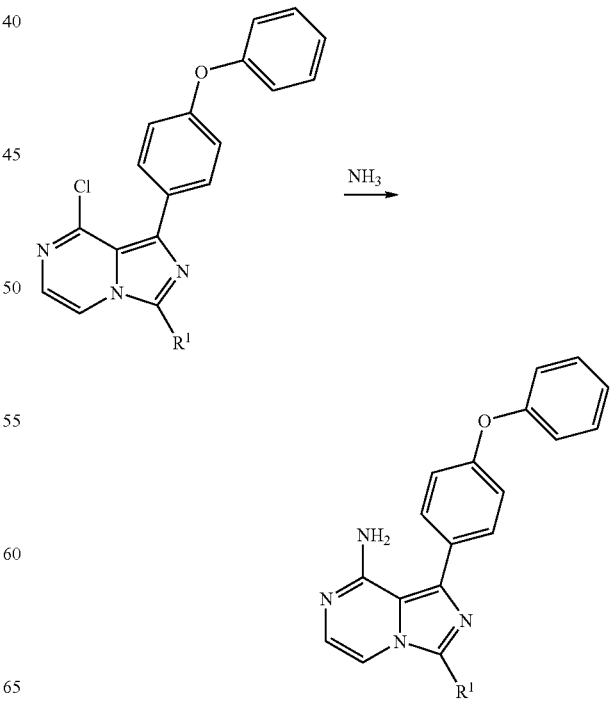

Example 1

3-Cyclohexyl-1-(4-phenoxyphenyl)-imidazo[1,5-a]pyrazin-8-ylamine

20 M NH$_3$ in H$_2$O (4 mL) was added to a suspension of 8-chloro-3-cyclohexyl-1-(4-phenoxyphenyl)-imidazo[1,5-a]pyrazine (82 mg, 0.20 mmol) in 2-butanol (0.9 mL). The mixture was heated in an oil bath set at 105° C. overnight. The reaction was stopped at this time and concentrated in vacuo. Purification by prep TLC using 3% NH$_3$ in MeOH in DCM afforded 41.4 mg of the title compound as an off white solid. $^1$H NMR (400 MHz, CDCl$_3$): δ=1.27-1.52 (m, 3H), 1.73-1.96 (m, 5H), 1.99-2.10 (m, 2H), 2.84-3.02 (m, 1H), 5.28 (br. s., 2H), 7.01-7.08 (m, 3H), 7.09-7.14 (m, 3H), 7.23 (d, J=5.31 Hz, 1H), 7.32-7.40 (m, 2H), 7.58-7.65 (m, 2H). MS (ES+): m/z 385.03 (100)[MH$^+$]. HPLC: t$_R$=2.83 min (Open Lynx polar__5 min).

8-Chloro-3-cyclohexyl-1-(4-phenoxyphenyl)-imidazo[1,5-a]pyrazine

In an oven-dried flask filled with N$_2$ was added cyclohexanecarboxylic acid [(3-chloro-pyrazin-2-yl)-(4-phenoxyphenyl)-methyl]-amide (100 mg, 0.0002 mol), MeCN (6 mL) and DMF (1 mL, 0.01 mol). POCl$_3$ was added dropwise at 0° C. The reaction mixture was allowed to warm up to rt and stirred at that temp overnight. The excess of POCl$_3$ was removed under reduced pressure and the residue was quenched with 2 N NH$_3$ in i-PrOH at 0° C. with vigorous stirring to adjust pH to 9. The crude reaction mixture was then charged with water and the aqueous layer was washed with DCM. The combined organic layer was dried over Na$_2$SO$_4$, filtered and concentrated under reduced pressure to obtain 82 mg of the title compound as a yellow oil. The compound was carried over to the next step. MS (ES+): m/z 404.09 (100)[MH$^+$]. HPLC: t$_R$=4.49 min (Open Lynx polar__5 min).

Cyclohexanecarboxylic acid [(3-chloropyrazin-2-yl)-(4-phenoxyphenyl)-methyl]-amide In a 10 mL flask were added C-(3-chloropyrazin-2-yl)-C-(4-phenoxyphenyl)-methylamine (110 mg, 0.35 mmol), cyclohexanecarboxylic acid (0.090 g, 0.00070 mol), DIEA (0.55 mL, 0.0032 mol), TBTU (0.17 g, 0.00053 mol) and DMF (5 mL, 0.07 mol) and the reaction mixture is stirred at rt for 10 min. Reaction mixture was stirred at rt over weekend. The reaction mixture was concentrated in vacuo dissolved in DCM and washed with sat. aq NaHCO$_3$ followed by brine. The organics were collected and concentrated in vacuo to give 160 mg of the compound as a yellow solid. Purification by prep TLC in 60% EtOAc:hexanes afforded 110 mg of the title compound as a light yellow solid. Compound was carried on to the next step. MS(ES+): m/z 422.15 (100)[MH$^+$]. HPLC: t$_R$=3.97 min (Open Lynx polar__5 min).

C-(3-Chloropyrazin-2-yl)-C-(4-phenoxyphenyl)-methylamine

A solution of 2-[(3-chloropyrazin-2-yl)-(4-phenoxyphenyl)-methyl]-isoindole-1,3-dione (1.04 g, 0.0023 mol) and anhydrous hydrazine (0.247 mL, 0.0078 mol) in DCM (8.8 mL)/EtOH (6 mL) was stirred at rt overnight. The white precipitate (phthalic hydrazide) was filtered and washed with DCM. The filtrate was collected and concentrated in vacuo and purified by flash column chromatography using 10%-30% EtOAc in hexanes to afford 570 mg of the title compound as an orange oily solid. $^1$H NMR (400 MHz, CDCl$_3$): δ 2.38 (br. s., 2H), 5.54 (s, 1H), 6.89-7.01 (m, 4H), 7.09 (t, J=7.45 Hz, 1H), 7.27-7.36 (m, 4H), 8.26 (d, J=2.27 Hz, 1H), 8.53 (d, J=2.53 Hz, 1H). MS (ES+): m/z 294.72 (90) [MH$^+$]. HPLC: t$_R$=2.15 min (Open Lynx, polar__5 min).

2-[(3-Chloropyrazin-2-yl)-(4-phenoxyphenyl)-methyl]-isoindole-1,3-dione

To a mixture of (3-chloropyrazin-2-yl)-(4-phenoxyphenyl)-methanol (12.0 g, 38.4 mmol), phthalimide (11.30 g, 76.8 mmol) and triphenylphosphine (20.10 g, 76.8 mmol) in THF (150 mL) in a flame-dried flask was added diisopropylazodicarboxylate (15.2 mL, 76.8 mmol) drop wise under nitrogen atmosphere. The reaction mixture was stirred at 60° C. for 16 h. TLC (EtOAc/Hexanes, 1:1) showed no starting material left. Solvent was then evaporated to give a crude residue which was purified through column on silica gel using EtOAc/Hexanes (1:1). Yield: 10.5 g (61%); $^1$H NMR (CDCl$_3$, 300 MHz) δ 6.91 (s, 1H), 7.01-7.22 (m, 5H), 7.39-7.43 (m, 4H), 7.78-7.82 (m, 2H), 7.89-7.94 (m, 2H), 8.40 (d, J=2.4 Hz, 1H), 8.58 (d, J=2.4 Hz, 1H).

(3-Chloropyrazin-2-yl)-(4-phenoxyphenyl)-methanol

To a solution of 2.5 M of n-BuLi in hexanes (10 mL) in THF (50 mL) was added 2,2,66-tetramethyl-piperidine (5.3 mL, 0.031 mol) slowly at −78° C. The cooling bath was replaced by an ice-water bath for 30 min and the solution was re-cooled to −78° C. After 5 min a solution of 2-chloropyrazine (2.3 mL, 0.026 mol) in THF (10 mL) is added. The reaction mixture turned brown in color. After 10 min, 4-formyldiphenyl ether (6.2 g, 0.031 mol) was added slowly. The reaction mixture was stirred at −78° C. for 2.5 h. The reaction mixture was quenched using sat. aq. NH$_4$Cl at −78° C. After warming up to rt, the reaction mixture was concentrated under vacuo and purified by flash column chromatography (eluting with 10% EtOAc in hexanes) to afford the title compound. $^1$H NMR (400 MHz, CDCl$_3$): δ 6.02 (s, 1H), 6.93-6.98 (m, 2H), 7.00 (d, J=7.58 Hz, 2H), 7.12 (t, J=7.33 Hz, 1H), 7.29-7.37 (m, 4H), 8.39 (d, J=2.53 Hz, 1H), 8.58 (d, J=2.53 Hz, 1H). MS (ES+): m/z 295.08 (100)[M-18]. HPLC: t$_R$=3.46 min (Open lynx, polar__5 min).

Example 2

3-Cyclopropyl-1-(4-phenoxyphenyl)-imidazo[1,5-a]pyrazin-8-ylamine

A solution of NH$_3$ in H$_2$O (20 M, 2 mL) was added to a suspension of 8-chloro-3-cyclopropyl-1-(4-phenoxyphenyl)-imidazo[1,5-a]pyrazine (33 mg, 0.091 mmol) in 2-butanol (0.4 mL). The mixture was heated in an oil bath set at 105° C. overnight. Reaction mixture was concentrated in vacuo and purification by prep TLC (4% MeOH in DCM as eluent) afforded the title compound as a solid. $^1$H NMR (400 MHz, CDCl$_3$): δ 0.95-1.22 (m, 4H), 1.93-2.09 (m, 1H), 5.10 (br. s., 2H), 7.02-7.18 (m, 6H), 7.32-7.44 (m, 3H), 7.55-7.62 (m, 2H). MS (ES$^+$): m/z 343.15 (100)[MH$^+$]. HPLC: t$_R$=2.52 min (Open Lynx polar__5 min).

8-Chloro-3-cyclopropyl-1-(4-phenoxyphenyl)-imidazo[1,5-a]pyrazine

In an oven-dried flask filled with N2 was added cyclopropanecarboxylic acid [(3-chloropyrazin-2-yl)-(4-phenoxyphenyl)-methyl]-amide (55 mg, 0.00014 mol), MeCN (4 mL, 0.07 mol) and DMF (0.7 mL, 0.009 mol). $POCl_3$ was added dropwise at 0° C. The reaction mixture was warmed up to rt and stirred at that temperature overnight. The excess of $POCl_3$ was removed under reduced pressure and the residue was quenched with solution of $NH_3$ in i-PrOH (2 N) at 0° C. with vigorous stirring to adjust pH to 9. The crude reaction mixture was then charged with water and the aqueous layer was washed with DCM. The combined organic layer was dried over $Na_2SO_4$, filtered and concentrated under reduced pressure to give the title compound, which was used in next step without further purification.

Cyclopropanecarboxylic acid [(3-chloropyrazin-2-yl)-(4-phenoxyphenyl)-methyl]-amide In a 10 mL flask were added C-(3-chloropyrazin-2-yl)-C-(4-phenoxyphenyl)-methylamine (110 mg, 0.00035 mol), cyclopropanecarboxylic acid (0.056 mL, 0.00070 mol), DIEA (0.55 mL, 0.0032 mol), TBTU (0.17 g, 0.00053 mol) and DMF (5 mL, 0.07 mol). The reaction mixture was stirred at rt for 10 min. Reaction was left to stir over weekend. The reaction mixture was concentrated in vacuo, dissolved in DCM and washed with sat aq $NaHCO_3$ followed by brine. The organics were collected and concentrated in vacuo to give 160 mg of the compound as a yellow solid. Purification by prep TLC in 60% EtOAc: hexanes afforded 55 mg of the title compound as a yellow solid. The compound was carried on to the next step. MS ($ES^+$): m/z 380.08 (20)[$MH^+$]. HPLC: $t_R$=3.56 min (Open lynx polar_5 min).

Example 3

3-Cyclopentyl-1-(4-phenoxyphenyl)-imidazo[1,5-a]pyrazin-8-ylamine

20 M $NH_3$ in $H_2O$ (2 mL) was added to a suspension of 8-chloro-3-cyclopentyl-1-(4-phenoxyphenyl)-imidazo[1,5-a]pyrazine (21 mg, 0.054 mmol) in i-PrOH (2 mL). The mixture was heated in an oil bath set at 105° C. overnight. Reaction mixture was concentrated in vacuo and purification by prep TLC using 10% MeOH in DCM afforded 9 mg of the title compound as an off white solid. The compound was registered as OSIP 700099. $^1$H NMR (400 MHz, $CDCl_3$): δ=1.61-1.95 (m, 4H), 2.02-2.23 (m, 4H), 3.30-3.43 (m, 1H), 5.07 (br. s., 2H), 7.03-7.08 (m, 3H), 7.08-7.16 (m, 3H), 7.23 (d, J=5.05 Hz, 1H), 7.30-7.41 (m, 2H), 7.61 (d, 2H). MS ($ES^+$): m/z 370.83 (100)[$MH^+$]. HPLC: $t_R$=2.61 min (Open Lynx polar_5 min).

8-Chloro-3-cyclopentyl-1-(4-phenoxyphenyl)-imidazo[1,5-a]pyrazine

In an oven-dried flask filled with $N_2$ was added cyclopentanecarboxylic acid [(3-chloropyrazin-2-yl)-(4-phenoxyphenyl)-methyl]-amide (80 mg, 0.2 mol), MeCN (5 mL) and DMF (0.9 mL). $POCl_3$ was added dropwise at 0° C. The reaction was warmed up to rt and stirred at that temp overnight. The excess of $POCl_3$ was removed under reduced pressure and the residue was quenched with 2 N $NH_3$ in i-PrOH at 0° C. with vigorous stirring to adjust pH to 9. The crude reaction mixture was then charged with water and the aqueous layer was washed with DCM. The combined organic layer was dried over $Na_2SO_4$, filtered and concentrated under reduced pressure to obtain 42 mg of the title compound as a yellow oil. Compound was carried over to the next step. MS ($ES^+$): m/z 389.88 (30)[$MH^+$]. HPLC: $t_R$=4.29 min (Open Lynx, polar_5 min).

Cyclopentanecarboxylic acid [(3-chloropyrazin-2-yl)-(4-phenoxyphenyl)-methyl]-amide In a 10 mL flask were added C-(3-chloropyrazin-2-yl)-C-(4-phenoxyphenyl)-methylamine (75 mg, 0.24 mmol), DIEA (0.38 mL, 0.0022 mol), TBTU (0.12 g, 0.00036 mol) and DMF (4 mL, 0.05 mol) and the reaction mixture is stirred at rt overnight. Reaction mixture was concentrated in vacuo and washed with sat $NaHCO_3$, brine extracting with DCM. The organic layer was concentrated to give a dark yellow solid. Purification by prep TLC using 50% EtOAc: hexanes afforded 80 mg of the title compound as an off white solid. MS ($ES^+$): m/z 407.86 (50)[$MH^+$]. HPLC: $t_R$=3.75 min (Open Lynx, polar_5 min).

Example 4

3-Azetidin-3-yl-1-(4-phenoxyphenyl)-imidazo[1,5-a]pyrazin-8-ylamine

Into a round bottom flask at 0° C. was added 3-[8-amino-1-(4-phenoxyphenyl)-imidazo[1,5-a]pyrazin-3-yl]-azetidine-1-carboxylic acid tert-butyl ester (30 mg, 0.00006 mol) and 4 M of HCl in 1,4-Dioxane (2 mL) and the suspension was stirred at 0° C.→RT for 3-4 h. The solvent was concentrated in vacuo and purification by prep TLC using 10% $NH_3$ in MeOH in DCM afforded the compound as a yellow solid. The compound was dissolved in MeOH and passed through an SPE cartridge. The compound was registered as OSIP 700588 AA. $^1$H NMR (400 MHz, $CDCl_3$): δ=4.17-4.28 (m, 2H), 4.42 (d, J=3.03 Hz, 3H), 7.05-7.10 (m, 2H), 7.10-7.15 (m, 3H), 7.15-7.19 (m, 1H), 7.20 (d, J=5.05 Hz, 1H), 7.34-7.41 (m, 2H), 7.55-7.65 (m, 2H). MS ($ES^+$): m/z 358.12 [$MH^+$]. HPLC: $t_R$=0.65 min (Open Lynx, polar_5 min).

3-[8-Amino-1-(4-phenoxyphenyl)-imidazo[1,5-a]pyrazin-3-yl]-azetidine-1-carboxylic acid tert-butyl ester 20 M of $NH_3$ in $H_2O$ (3 mL) was added to a suspension of 3-[8-chloro-1-(4-phenoxyphenyl)-imidazo[1,5-a]pyrazin-3-yl]-azetidine-1-carboxylic acid tert-butyl ester in i-PrOH (4 mL, 0.05 mol). The mixture was heated in an oil bath set at 105° C. overnight. The solvent was removed under reduced pressure and the residue was carried on to the next step without further purification. MS ($ES^+$): m/z 467.82 (100) [$MH^+$]. HPLC: $t_R$=2.66 min (Open Lynx, polar_5 min).

3-[8-Chloro-1-(4-phenoxyphenyl)-imidazo[1,5-a]pyrazin-3-yl]-azetidine-1-carboxylic acid tert-butyl ester In an oven-dried flask filled with $N_2$ was added 3-[(3-chloropyrazin-2-yl)-(4-phenoxyphenyl)-methyl]-carbamoylazetidine-1-carboxylic acid tert-butyl ester (110 mg, 0.00022 mol), MeCN (3 mL, 0.07 mol) and DMF (0.3 mL, 0.004 mol). $POCl_3$ was added dropwise at 0° C. The reaction was warmed up to rt and stirred at that temp overnight. The excess of $POCl_3$ was removed under reduced pressure and the residue was quenched with 2 N $NH_3$ in i-PrOH at 0° C. with vigorous stirring to adjust pH to 9. The crude reaction mixture was then charged with water and the aqueous layer was washed with DCM. The combined organic layer was dried over $Na_2SO_4$, filtered and concentrated under reduced pressure. Purification by prep TLC using 3% $NH_3$ in MeOH in DCM afforded 45 mg of the title compound as a yellow oil.

The compound was carried on to the next step. MS (ES+): m/z 477.02 (100)[MH+]. HPLC: $t_R$=4.17 min (Open Lynx, polar_5 min).

3-[(3-Chloropyrazin-2-yl)-(4-phenoxyphenyl)-methyl]-carbamoyl-azetidine-1-carboxylic acid tert-butyl ester In a 10 mL flask was added C-(3-chloropyrazin-2-yl)-C-(4-phenoxyphenyl)-methylamine (85 mg, 0.00027 mol), DIEA (0.24 mL, 0.0014 mol), TBTU (0.13 g, 0.00041 mol) and DMF (4 mL, 0.05 mol) and the reaction mixture is stirred at rt for 10 min. The reaction mixture was concentrated in vacuo and purified by prep TLC using 5% MeOH in DCM afforded 110 mg of the title compound as a yellow oil. The compound was carried on to the next step. MS (ES+): m/z 438.95 (40)[MH+]. HPLC: $t_R$=3.79 min (Open Lynx, polar_5 min).

Example 5

3-Ethyl-1-(4-phenoxyphenyl)-imidazo[1,5-a]pyrazin-8-ylamine $^1$H NMR (400 MHz, CDCl$_3$): δ=1.44 (t, J=7.58 Hz, 3H), 2.99 (q, J=7.66 Hz, 2H), 5.09 (br. s., 2H), 7.03-7.09 (m, 3H), 7.09-7.15 (m, 3H), 7.15-7.20 (m, 1H), 7.32-7.40 (m, 2H), 7.58-7.65 (m, 2H), MS(ES+): m/z 331.79 (100)[MH+]. HPLC: $t_R$=3.13 min (Open Lynx, polar_5 min).

Example 6

3-isopropyl-1-(4-phenoxyphenyl)-imidazo[1,5-a]pyrazin-8-ylamine $^1$H NMR (400 MHz, CDCl$_3$): δ=1.47 (d, J=6.82 Hz, 6H), 3.17-3.37 (m, 1H), 5.23 (br. s., 2H), 7.02-7.09 (m, 3H), 7.09-7.16 (m, 3H), 7.22 (d, J=5.05 Hz, 1H), 7.32-7.40 (m, 2H), 7.59-7.66 (m, 2H). MS (ES+): m/z 345.89 (100)[MH]. HPLC: $t_R$=3.41 min (Open Lynx, polar_5 min).

Example 7

1-(4-Phenoxyphenyl)-3-(tetrahydropyran-4-yl)-imidazo[1,5-a]pyrazin-8-ylamine $^1$H NMR (400 MHz, CDCl$_3$): δ=1.94 (dd, J=13.26, 1.89 Hz, 2H), 2.11-2.27 (m, 2H), 3.12-3.30 (m, 1H), 3.50-3.67 (m, 2H), 4.06-4.20 (m, 2H), 5.08 (br. s., 2H), 7.04-7.09 (m, 3H), 7.09-7.17 (m, 3H), 7.24 (d, J=5.05. Hz, 1H), 7.32-7.40 (m, 2H), 7.58-7.64 (m, 2H). MS (ES+): m/z 386.70 (100)[MH+]. HPLC: $t_R$=2.26 min (Open Lynx, polar_5 min).

Example 8

3-tert-Butyl-1-(4-phenoxyphenyl)-imidazo[1,5-a]pyrazin-8-ylamine $^1$H NMR (400 MHz, CDCl$_3$): δ=1.57 (s, 9H), 5.03 (br. s., 2H), 6.97-7.17 (m, 6H), 7.32-7.40 (m, 2H), 7.47 (d, J=5.05 Hz, 1H), 7.57-7.65 (m, 2H). MS (ES+): m/z 359.11 (100) [MH+]. HPLC: $t_R$=2.58 min. (Open Lynx, polar_5 min).

Examples 9-133 were synthesized according to Method B:

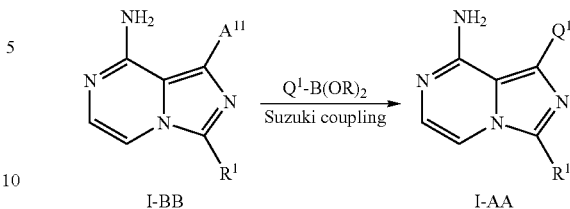

Example 9

3-[3-(4-Methyl-piperazin-1-yl)-cyclobutyl]-1-(4-phenoxy-phenyl)-imidazo[1,5-a]pyrazin-8-ylamine To a stirred mixture of 1-iodo-3-[3-(4-methyl-piperazin-1-yl)-cyclobutyl]-imidazo[1,5-a]pyrazin-8-ylamine (30.0 mg, 0.072 mmol), potassium carbonate (35.2 mg, 0.25 mmol) in DME (2.0 mL) and H$_2$O (0.50 mL, 28 mmol) in a microwave reactor vessel was added 4-phenoxyphenylboronic acid (18.69 mg, 0.087 mmol). The solution was bubbled with nitrogen for 5 min. Then Pd(PPh$_3$)$_4$ (4.2 mg, 0.0036 mmol) was added and the resulting mixture was irradiated by microwave at 300 watt, at 100° C. for 30 min. The solvent was then removed under reduced pressure and the resulting residue was purified by flash chromatography (5% MeOH in DCM). $^1$H NMR (400 MHz, MeOD) δ 2.29 (s, 3H), 2.30-2.78 (m, 12H), 2.91-3.03 (m, 1H), 3.53-3.66 (m, 1H), 6.97 (d, J=5.1 Hz, 1H), 7.05-7.20 (m, 5H), 7.36-7.45 (m, 3H), 7.56-7.63 (m, 2H). MS (ES+): m/z: 455.24, [MH+]. HPLC: $t_R$=1.94 min (OpenLynx, polar_5 min).

Examples 10-13, Examples 15-18 were synthesized according procedure described for synthesis of Example 9 using corresponding I-BB and boronic acids or boronates.

Examples 20-87 were synthesized from 3-cyclobutyl-1-iodo-imidazo[1,5-a]pyrazin-8-ylamine and corresponding boronic acids or boronates according to the procedure described for Comparator 5.

Example 88 cis-{4-[8-amino-3-(3-hydroxy-3-methyl-cyclobutyl)-imidazo[1,5-a]pyrazin-1-yl]-phenyl}-phenyl-methanone To a mixture of cis-3-(8-amino-1-bromo-imidazo[1,5-a]pyrazin-3-yl)-1-methyl-cyclobutanol (50.0 mg, 0.168 mmol), 4-benzoyl phenyl boronic acid (41.8 mg, 0.185 mmol), potassium carbonate (69.8 mg, 0.505 mmol) in DME/water (v:v=5:1, 2 mL) was added Pd(PPh$_3$)$_4$ (20 mg, 0.015 mmol) under nitrogen. The resulting mixture was then microwaved at 300 watt, 100° C. for 30 min. The solvent was removed under reduced pressure, and the material was dissolved in DCM (5 mL). The insolubles were removed by filtration. The solvent was removed under reduced pressure to give a crude product which was then purified by Gilson HPLC. MS (ES+): m/z 398.78 [MH+]. HPLC: $t_R$=2.08 min. (Open Lynx, polar_5 min).

Example 94 cis-3-[8-Amino-1-(2-methoxy-4-phenoxy-phenyl)-imidazo[1,5-a]pyrazin-3-yl]-1-methyl-cyclobutanol To a stirred mixture of 2-(2-methoxy-4-phenoxy-phenyl)-4,4,5,5-tetramethyl-[1,3,2]dioxaborolane (82.0 mg, 0.25 mmol), cis-3-(8-amino-1-bromo-imidazo[1,5-a]pyrazin-3-yl)-1-methyl-cyclobutanol (65.00 mg, 0.21 mmol), potassium carbonate (105.8 mg, 0.76 mmol) in DME (4.00 mL) and H$_2$O (1.00 mL) was added 1,1'bis-(diphenylphosphino)-ferrocene)palladium dichloride (9.60 mg, 0.013 mmol) under Nitrogen. The resulting mixture was stirred at 100° C., for 2 h. LC-MS indicated completion of coupling reaction. The solvent was then removed under reduced pressure and the resulting residue was purified by flash chromatography (5% MeOH in DCM). $^1$H NMR (400 MHz, MeOD) δ ppm 1.49 (s, 3H), 2.48-2.65 (m, 4H), 3.41-3.51 (m, 1H), 3.75 (s, 3H), 6.62-6.70 (m, 1H), 6.83 (d, J=2.27 Hz, 1H), 6.94 (d, J=5.05 Hz, 1H), 7.08-7.22 (m, 3H), 7.31-7.47 (m, 4H). MS (ES$^+$): m/z 416.91 (M+H). HPLC: t$_R$=2.25 min (OpenLynx, polar_5 min).

Example 106 cis-3-{8-Amino-1-[4-(1-hydroxy-1-phenyl-ethyl)-phenyl]-imidazo[1,5-a]pyrazin-3-yl}-1-methyl-cyclobutanol, (1:1 mixture of two enantiomers)

To a stirred mixture of 1-Phenyl-1-[4-(4,4,5,5-tetramethyl-[1,3,2]dioxaborolan-2-yl)-phenyl]-ethanol (81.0 mg, 0.25 mmol), cis-3-(8-amino-1-bromo-imidazo[1,5-a]pyrazin-3-yl)-1-methyl-cyclobutanol (65.00 mg, 0.21 mmol), potassium carbonate (105.8 mg, 0.76 mmol) in DME (4.00 mL) and H$_2$O (1.00 mL) was added 1,1'bis-(diphenylphosphino)-ferrocene)palladium dichloride (9.60 mg, 0.013 mmol) under nitrogen. The resulting mixture was stirred at 100° C., for 3 h. LC-MS indicated completion of coupling reaction. The solvent was then removed under reduced pressure and the resulting residue was purified by flash chromatography (5% MeOH in DCM). $^1$H NMR (400 MHz, DMSO-d$_6$) μ 1.37 (s, 3H), 1.87 (s, 3H), 2.39 (d, J=8.8 Hz, 4H), 3.41 (m, 1H), 5.09 (s, 1H), 5.76 (s, 1H), 5.94 (br s, 2H), 6.99 (d, J=4.80 Hz, 1H), 7.18 (m, 1H), 7.28 (m, 2H), 7.45-7.55 (m, 7H), MS (ES$^+$): m/z 415.02 (M+H). HPLC: t$_R$=2.20 min (OpenLynx, polar_5 min).

Examples 106A and 106B

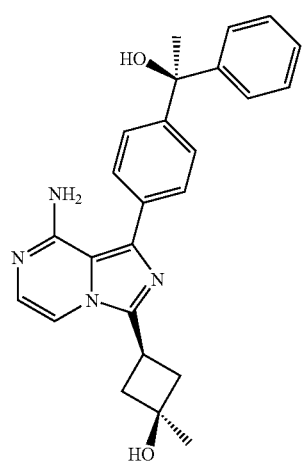

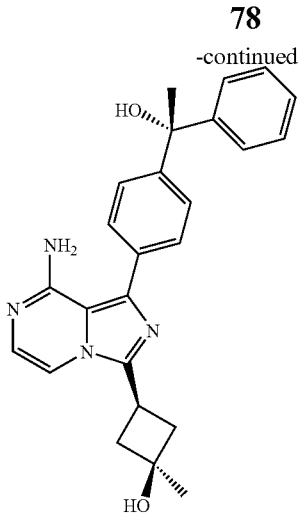

The Example 106 material prepared above was subjected to supercritical fluid chromatography-mass spectrometry system (Thar's Prep30 SFC equipped with a Waters 3100 SQD mass spectrometer controlled by MassLynx with Fractonlynx software) for chiral resolution. Example 106A and Example 106B were identified by electrospray ionization and collected by mass directed triggering of the fraction collector which gave enantiomerically pure Example 106A (t$_R$=9.5 min) and enantiomerically pure Example 106B (t$_R$=11.9 min).

The SFC conditions for this study were the following: SFC column: ChiralPack IA 21×250 mm, 5 u from Chiral Technologies, Inc. (West Chester, Pa.); Modifier: 60% of HPLC grade IPA/MeOH 80/20 mixture; Flow Rate: 30 mL/min; Column Temp: 40 C.; Backpressure: 150 bar. The MS conditions for this study were the following: Capillary voltage 3.0 kV; Cone voltage 30 V; Source temperature 150° C.; Desolvation temperature 475° C.; Desolvation gas flow 650 L/hr; Cone gas flow 60 L/hr.

$^1$H NMR and MS of both Example 106A and Example 106B were identical to $^1$H NMR of Example 106.

Example 14, Examples 89-117 and Examples 119-133 were synthesized from cis-3-(8-amino-1-bromo-imidazo[1,5-a]pyrazin-3-yl)-1-methyl-cyclobutanol and corresponding boronic acids or boronates according to the procedure described for Example 88.

Example 118 cis-3-{8-Amino-1-[4-(difluoro-phenyl-methyl)-phenyl]-imidazo[1,5-a]pyrazin-3-yl}-1-methyl-cyclobutanol To a stirred mixture of 2-[4-(difluoro-phenyl-methyl)-phenyl]-4,4,5,5-tetramethyl-[1,3,2]dioxaborolane (82.5 mg, 0.25 mmol), cis-3-(8-amino-1-bromo-imidazo[1,5-a]pyrazin-3-yl)-1-methyl-cyclobutanol (65.00 mg, 0.21 mmol), potassium fluoride (45 mg, 0.76 mmol) in DME (4.00 mL) and H$_2$O (1.00 mL) was added 1,1'bis-(diphenylphosphino)-ferrocene) palladium dichloride (9.60 mg, 0.013 mmol) under nitrogen. The resulting mixture was stirred at 100° C., for 2 h. LC-MS indicated completion of coupling reaction. The solvent was then removed under reduced pressure and the resulting residue was purified by flash chromatography (5% MeOH in DCM). $^1$H NMR (400 MHz, MeOD) 1.52 (s, 3H), 2.51-2.68 (m, 4H), 3.43-3.56 (m, 1H), 7.03 (d, J=5.31 Hz, 1H), 7.44-7.53 (m, 4H), 7.55-7.63 (m, 2H), 7.66-

7.73 (m, 2H), 7.75-7.80 (m, 2H). MS (ES⁺): m/z 420.99 (M+H). HPLC: $t_R$=2.51 min (OpenLynx, polar__5 min).

Examples 134-170 were synthesized according to Method C.

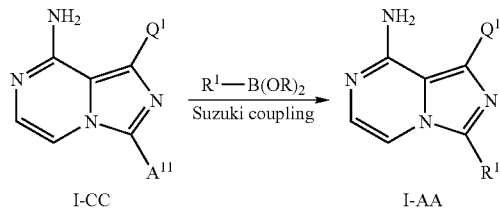

Representative examples for synthesis:

Example 134

1-(4-Phenoxyphenyl)-3-(1H-pyrazol-3-yl)-imidazo [1,5-a]pyrazin-8-ylamine

A mixture of 3-bromo-1-(4-phenoxyphenyl)-imidazo[1,5-a]pyrazin-8-ylamine (20.0 mg, 0.052 mmol), 1H-pyrazol-3-yl boronic acid (6.46 mg, 0.057 mmol), Pd(PPh₃)₄ (10 mg, 0.01 mmol), potassium carbonate (21.8 mg, 0.157 mmol) and DME/H₂O (v:v=5:1, 2 mL) was microwaved at 300 watt, 100° C. for 30 min. The solution was transferred to a 20 mL vial, and 1 mL of DMF was added. The solution was concentrated in vacuo until only DMF remained. The mixture was passed through a syringe filter pad, and prepared for Gilson HPLC separation. The fractions containing the pure product were collected and concentrated in vacuo to afford the title compound as a yellow solid. ¹H NMR (400 MHz, CDCl₃): δ=6.99 (d, J=2.5 Hz, 1 H), 7.07-7.13 (m, 3H), 7.13-7.20 (m, 3H), 7.37-7.45 (m, 2H), 7.63-7.69 (m, 2H), 7.76 (d, J=2.5 Hz, 1H), 8.65 (br. s., 1H). MS (ES⁺): m/z 369.10 (100) [MH⁺]. HPLC: $t_R$=20.39 min (ZQ3, polar__5 min).

3-Bromo-1-(4-phenoxy-phenyl)-imidazo[1,5-a] pyrazin-8-ylamine

3-Bromo-8-chloro-1-(4-phenoxy-phenyl)-imidazo[1,5-a]pyrazine (2.05 g, 5.0 mmol) and NH₃ in ⁱPrOH (9 M, 20 mL, 180 mmol) in a bomb apparatus were heated at 110° C. for 24 h. Cooled to rt., and evaporated. The residue was dissolved in EtOAc (20 mL), washed with water (10 mL) and dried (Na₂SO₄). Evaporation of solvent gave a residue, which was triturated with diisopropyl ether (30 mL). ¹H NMR (DMSO-d₆, 400 MHz), δ 6.23 (bs, 2H), 7.09-7.19 (m, 6H), 7.39-7.43 (m, 3H), 7.58 (d, J=8.4 Hz, 2H).

3-Bromo-8-chloro-1-(4-phenoxy-phenyl)-imidazo[1, 5-a]pyrazine

To a solution of 8-chloro-1-(4-phenoxy-phenyl)-imidazo [1,5-a]pyrazine (2.10 g, 6.5 mmol) in DMF (12 mL) at 0° C. was added NBS (1.40 g, 7.84 mmol) and stirred for 2 h. DMF was removed under pressure and added water (75 mL). Solid formed was extracted with EtOAc (3×50 mL), washed with water (40 mL) and dried (Na₂SO₄). Evaporation of solvent gave crude material, which was purified by column chromatography on silica gel using CH₂Cl₂/MeOH (98:2). Yield: 2.05 g (77%); ¹H NMR (CDCl₃, 300 MHz) δ 7.11-7.21 (m, 5H), 7.28-7.32 (m, 3H), 7.61-7.64 (m, 2H), 7.70 (d, J=2.4 Hz, 1H).

8-Chloro-1-(4-phenoxy-phenyl)-imidazo[1,5-a]pyrazine

A solution of formamide N-[(3-chloro-pyrazin-2-yl)-(4-phenoxy-phenyl)-methyl]-formamide (1.85 g, 5.45 mmol) in CH₃CN (50 mL) at 0° C. was added DMF (0.4 mL) and POCl₃ (1.52 mL, 16.3 mmol). The mixture was allowed to warm to rt over 16 h. TLC (EtOAc/CH₂Cl₂, 1:1) showed no starting material. Reaction mixture was evaporated to remove solvents. To the residue was added aq. satd. NaHCO₃ (100 mL) and extracted with EtOAc (3×50 mL). Organic layer was washed with water (30 mL) and dried (Na₂SO₄). Evaporation of solvent gave titled compound (1.62 g, 92%). ¹H NMR (CDCl₃, 300 MHz) δ 7.13-7.21 (m, 5H), 7.29-7.31 (m, 3H), 7.60-7.64 (m, 2H), 7.68 (d, J=2.4 Hz, 1H), 8.30 (s, 1H).

N-[(3-Chloro-pyrazin-2-yl)-(4-phenoxy-phenyl)-methyl]-formamide

To a mixture of formic acid. (0.38 mL, 9.6 mmol), EDC (1.84 g, 9.6 mmol) and HOBt (0.2 g, 1.3 mmol) in CH₂Cl₂ (25 mL) under nitrogen were added compound C-(3-chloropyrazin-2-yl)-C-(4-phenoxyphenyl)-methylamine (2.0 g, 6.4 mmol), followed by DIEA (2.2 mL, 12.8 mmol). The mixture was stirred for 16 h at rt. TLC (EtOAc/CH₂Cl₂, 1:1) showed no starting material. The reaction mixture was diluted with CH₂Cl₂ (75 mL), washed with water (3×50 mL) and dried (Na₂SO₄). Evaporation of solvent gave desired product, which was used for next step without any further purification. Yield: 1.85 g (84%). ¹H NMR (CDCl₃, 300 MHz) δ 6.61 (d, J=6.8 Hz, 1H), 6.70-6.99 (m, 4H), 7.16 (t, J=7.2 Hz, 1H), 7.27-7.32 (m, 4H), 8.29 (s, 1H), 8.38 (d, J=2.4 Hz, 1H), 8.61 (d, J=2.4 Hz, 1H).

Example 135

1-(4-Phenoxyphenyl)-3-thiophen-3-yl-imidazo[1,5-a]pyrazin-8-ylamine

A mixture of 3-bromo-1-(4-phenoxyphenyl)-imidazo[1,5-a]pyrazin-8-ylamine (20.0 mg, 0.0525 mmol), 3-thiophenyl-boronic acid (7.38 mg, 0.0577 mmol), Pd(PPh₃)₄ (10 mg, 0.01 mmol), potassium carbonate (21.8 mg, 0.157 mmol) and DME/Water (5:1) was microwaved at 300 watt, 100° C. for 30 min. The solution was transferred to a 20 mL vial, and 1 mL of DMF was added. The solution was concentrated in vacuo until only DMF remained. The mixture was passed through a syringe filter pad, and prepared for Gilson HPLC separation. The fractions containing the pure product were collected and concentrated in vacuo to afford the title compound as a yellow solid. ¹H NMR (400 MHz, CDCl₃): δ=6.96 (d, J=5.3 Hz, 1H), 7.07-7.12 (m, 2H), 7.14-7.22 (m, 3H), 7.38-7.43 (m, 2H), 7.55-7.67 (m, 5H), 7.86 (dd, J=3.0, 1.3 Hz, 1H). MS (ES+): m/z 384.94 (100) [MH⁺]. HPLC: $t_R$=2.58 min (polar__5 min).

Example 171-216 were synthesized according to Method D:

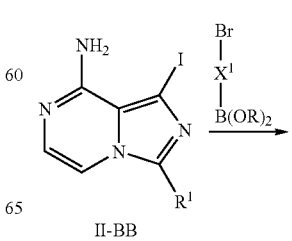

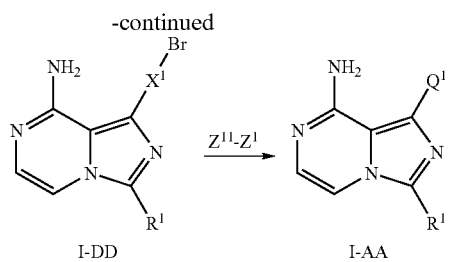

Example 171

3-Cyclobutyl-1-[4-(4-fluorophenoxy)-phenyl]-imidazo[1,5-a]pyrazin-8-ylamine

A mixture of 1-(4-bromo-phenyl)-3-cyclobutyl-imidazo[1,5-a]pyrazin-8-ylamine (30.0 mg, 0.0874 mmol), 4-fluorophenol (29.4 mg, 0.262 mmol), copper(I) iodide (5 mg, 0.03 mmol), $Cs_2CO_3$ (114 mg, 0.350 mmol), N,N-dimethylglycine hydrochloride (10 mg, 0.08 mmol) and 5:1 dioxane:DMF (1 mL) was microwaved at 120° C. for 4 h (CEM; PowerMAX). The mixture was filtered through a syringe filter pad to remove any solid particles, then concentrated in vacuo. DMF (1 mL) was added to bring the mixture to a homogeneous solution, and Gilson HPLC was used to purify. The fractions containing the product were passed through a benzene-sulfonic acid SPE cartridge, washed with MeOH (10 mL), and flushed out using 2M $NH_3$ in MeOH. The material was concentrated in vacuo to afford the title compound as a yellow solid. $^1$H NMR (400 MHz, $CDCl_3$): δ=1.99-2.09 (m, 1H), 2.11-2.24 (m, 1H), 2.45-2.55 (m, 2H), 2.58-2.69 (m, 2H), 3.77-3.87 (m, 1H), 5.12 (br. s., 2H), 7.01-7.13 (m, 8H), 7.61-7.65 (m, 2H). MS (ES+): m/z 374.98 (100) [MH$^+$]. HPLC: $t_R$=2.55 min (ZQ3, polar__5 min).

1-(4-Bromophenyl)-3-cyclobutylimidazo[1,5-a]pyrazin-8-ylamine

In 10 mL RBF, 3-cyclobutyl-1-iodo-imidazo[1,5-a]pyrazin-8-ylamine (100.0 mg, 0.318 mmol), 4-bromobenzenebronic acid (63.9 mg, 0.318 mmol), potassium carbonate (0.132 g, 0.955 mmol) and Pd(PPh$_3$)$_4$ (20 mg, 0.02 mmol) were added. In a separate RBF, DME (7.2 mL, 0.070 mol) and $H_2O$ (2.4 mL, 0.13 mol) were combined, mixed and degassed with Nitrogen. The reaction was refluxed at 90-95° C. for 3 h. For the workup, the mixture was cooled to rt and concentrated in vacuo. The crude product was purified by silica gel chromatography [Jones Flashmaster; 10 g column; dried loaded; wetted with 4:6 EtOAc/DCM; eluted with 4:6 EtOAc/DCM→5% MeOH in 4:6 EtOAc/DCM], which afforded 51 mg (46.7%) of the desired product as a yellow solid. $^1$H NMR (400 MHz, $CDCl_3$): δ=2.15-2.27 (m, 1H), 2.45-2.57 (m, 2H), 2.57-2.70 (m, 2H), 3.75-3.87 (m, 1H), 6.97 (d, J=5.31 Hz, 1H), 7.13 (d, J=5.31 Hz, 1H), 7.56 (d, J=8.59 Hz, 2H), 7.67 (d, J=8.34 Hz, 2H). MS (ES+): m/z 342.79, 344.64 [MH$^+$]. HPLC: $t_R$=2.23 min. (Open Lynx, polar__5 min).

Examples 175-207 were synthesized from 1-(4-bromophenyl)-3-cyclobutylimidazo[1,5-a]pyrazin-8-ylamine according to the procedure described for synthesis of Example 171.

Example 172

3-Cyclobutyl-1-[2-fluoro-4-(2-fluoro-phenoxy)-phenyl]-imidazo[1,5-a]pyrazin-8-ylamine Prepared according to a procedure analogous to that described for Example 171, except using 1-(4-bromo-3-fluoro-phenyl)-3-cyclobutyl-imidazo[1,5-a]pyrazin-8-ylamine and 2-fluoro-phenol. $^1$H NMR (400 MHz, $CDCl_3$): δ=2.01-2.07 (m, 1H), 2.12-2.22 (m, 1H), 2.45-2.54 (m, 2H), 2.57-2.67 (m, 2H), 3.77-3.87 (m, 1H), 5.01 (br. s., 2H), 6.81 (dd, J=10.7, 2.4 Hz, 1H), 6.89 (dd, J=8.5, 2.7 Hz, 1H), 7.04 (d, J=5.1 Hz, 1H), 7.13 (d, J=5.1 Hz, 1H), 7.16-7.25 (m, 4H), 7.49 (t, J=8.5 Hz, 1H). MS (ES+): m/z 392.85 (100) [MH$^+$].

1-(4-Bromo-2-fluoro-phenyl)-3-cyclobutyl-imidazo[1,5-a]pyrazin-8-ylamine

Prepared according to a procedure analogous to that described for 1-(4-bromophenyl)-3-cyclobutylimidazo[1,5-a]pyrazin-8-ylamine except using 4-bromo-2-fluoro-phenyl-boronic acid. MS (ES+): m/z 360.98, 362.91 [MH$^+$].

Examples 215 and 216 were synthesized from 1-(4-bromo-2-fluoro-phenyl)-3-cyclobutyl-imidazo[1,5-a]pyrazin-8-ylamine according to the procedure described for synthesis of Example 172.

Example 173

3-Cyclobutyl-1-[4-(2-fluoro-phenoxy)-3-methoxy-phenyl]-imidazo[1,5-a]pyrazin-8-ylamine Prepared according to a procedure analogous to that described for synthesis of Example 171, except using 1-(4-bromo-3-methoxy-phenyl)-3-cyclobutyl-imidazo[1,5-a]pyrazin-8-ylamine and 2-fluoro-phenol. $^1$H NMR (400 MHz, $CDCl_3$): δ=2.01-2.11 (m, 1H), 2.14-2.25 (m, 1H), 2.46-2.55 (m, 2H), 2.59-2.71 (m, 2H), 3.83 (t, J=8.6 Hz, 1H), 3.95 (s, 3H), 6.95-7.04 (m, 3H), 7.07-7.22 (m, 5H), 7.33 (d, J=2.0 Hz, 1H). MS (ES+): m/z 404.94 (100) [MH$^+$].

1-(4-Bromo-3-methoxy-phenyl)-3-cyclobutyl-imidazo[1,5-a]pyrazin-8-ylamine

Prepared according to a procedure analogous to that described for 1-(4-bromophenyl)-3-cyclobutylimidazo[1,5-a]pyrazin-8-ylamine except using 2-(4-bromo-3-methoxy-phenyl)-4,4,5,5-tetramethyl-[1,3,2]dioxaborolane. MS (ES+): m/z 372.99, 374.96 [MH$^+$].

2-(4-Bromo-3-methoxy-phenyl)-4,4,5,5-tetramethyl-[1,3,2]dioxaborolane

A mixture of 4-bromo-3-methoxyphenylamine (1.00 g, 4.95 mmol) and $H_2O$ (4.01 mL) were treated with concentrated HCl (3.03 mL) where upon the reactants turned into a slurry. The mixture was cooled at −20° C. by keeping the dry ice bath with acetone and treated dropwise with 5 M of sodium nitrite in $H_2O$ (1.0 mL). After 10 min, tetrafluoroboric acid solution (48% wt. % in water) (52:48, tetrafluoroboric acid:$H_2O$, 3.18 mL) was added to the reaction mixture. The reaction mixture was concentrated to a solid on the freeze drying system for 16 h to give a crude material. It was then dissolved in anhydrous THF (20 mL). To this solution was added bis(pinacolato)diboron (1.26 g, 4.95 mmol), 1,3-bis(2,6-diisopropylphenyl)imidazol-2-ylidene hydrochloride (0.11 g, 0.26 mmol) and Pd(OAc)$_2$ (0.048 g, 0.21 mmol). The resulting mixture was stirred at rt. under argon for 16 h. The reaction mixture was diluted with DCM and passed through a short silica gel column. The solvent was removed under reduced pressure to give a crude material which was used for next step without further purification. Similar procedures were described in literature. Org. Lett., 2003, 5(24), 4635-4638.

Example 174

3-Cyclobutyl-1-(3-methoxy-4-phenylsulfanyl-phenyl)-imidazo[1,5-a]pyrazin-8-ylamine Prepared according to a procedure analogous to that described for 3-cyclobutyl-1-[4-(2-fluoro-phenoxy)-3-methoxy-phenyl]-imidazo[1,5-a]pyrazin-8-ylamine except using benzenethiol. $^1$H NMR (400 MHz, CDCl$_3$)-δ=1.99-2.11 (m, 1H), 2.13-2.26 (m, 1H), 2.45-2.55 (m, 2H), 2.57-2.69 (m, 2H), 3.75-3.85 (m, 1H), 3.97 (s, 3H), 5.44 (br. s., 2H), 6.82 (d, J=5.6 Hz, 1H), 7.00-7.08 (m, 3H), 7.17 (d, J=1.3 Hz, 1H), 7.34-7.43 (m, 3H), 7.45-7.51 (m, 2H). MS (ES+): m/z 402.96 (100) [MH$^+$].

Example 208

3-Cyclobutyl-1-(3-fluoro-4-o-tolyloxy-phenyl)-imidazo[1,5-a]pyrazin-8-ylamine

Prepared according to a procedure analogous to that described for synthesis of Example 171, except using 1-(4-bromo-3-fluoro-phenyl)-3-cyclobutyl-imidazo[1,5-a]pyrazin-8-ylamine and 2-methyl-phenol.

1-(4-Bromo-3-fluoro-phenyl)-3-cyclobutyl-imidazo[1,5-a]pyrazin-8-ylamine

Prepared according to a procedure analogous to that described for 1-(4-bromophenyl)-3-cyclobutylimidazo[1,5-a]pyrazin-8-ylamine, except using 4-bromo-3-fluoro-phenyl-boronic acid instead of 4-bromo-phenyl-boronic acid. MS (ES+): m/z 361.04, 363.02[MH$^+$].

Examples 209-213 were synthesized from 1-(4-bromo-3-fluoro-phenyl)-3-cyclobutyl-imidazo[1,5-a]pyrazin-8-ylamine according to the procedure described for synthesis of Example 208.

Example 214

3-Cyclobutyl-1-(4-phenylsulfanyl-phenyl)-imidazo[1,5-a]pyrazin-8-ylamine

Prepared according to a procedure analogous to that described for synthesis of Example 171 except using benzenethiol. MS (ES+): m/z 373.01 [MH$^+$].

Examples 217-222 were synthesized according to Method E:

Example 217

[4-(8-Amino-3-cyclobutylimidazo[1,5-a]pyrazin-1-yl)-3,6-dihydro-2H-pyridin-1-yl]-phenylmethanone A mixture of 3-cyclobutyl-1-(1,2,3,6-tetrahydropyridin-4-yl)-imidazo[1,5-a]pyrazin-8-ylamine (20.0 mg, 0.0742 mmol), benzoic acid (9.97 mg, 0.0817 mmol), TBTU (47.7 mg, 0.148 mmol), DIEA (0.0647 mL, 0.371 mmol) and DMF (1 mL, 0.01 mol) was stirred at rt for 10 min. The reaction mixture was directly given for Gilson HPLC purification. The fractions containing the pure product were collected and concentrated in vacuo to afford the title compound as a yellow solid. $^1$H NMR (400 MHz, CDCl$_3$): δ=1.96-2.06 (m, 1H) 2.09-2.23 (m, 1H) 2.40-2.63 (m, 4H) 2.72-2.93 (m, 2H) 3.57-3.88 (m, 3H) 3.98-4.34 (m, 1H) 4.47 (br. s., 1H) 5.13-5.45 (m, 2H) 5.72-6.14 (m, 1H) 7.04-7.08 (m, 2H) 7.42-7.51 (m, 5H). MS (ES+): m/z 374.07 (100) [MH$^+$]. HPLC: t$_R$=2.13 min (polar_5 min).

Example 218

[4-(8-Amino-3-cyclobutylimidazo[1,5-a]pyrazin-1-yl)-3,6-dihydro-2H-pyridin-1-yl]-cyclohexylmethanone Prepared according to a procedure analogous to that described for synthesis of [4-(8-amino-3-cyclobutylimidazo[1,5-a]pyrazin-1-yl)-3,6-dihydro-2H-pyridin-1-yl]-phenyl-methanone, except using cyclohexanecarboxylic acid. $^1$H NMR (400 MHz, CDCl$_3$): δ=1.25-1.40 (m, 3H) 1.60 (br. s., 2H) 1.85 (dd, J=8.97, 2.65 Hz, 5H) 2.05 (dd, J=8.84, 3.28 Hz, 1H) 2.14-2.27 (m, 1H) 2.42-2.64 (m, 5H) 2.78 (br. s., 2H) 3.69-3.97 (m, 3H) 4.31 (br. s., 2H) 6.07 (br. s., 1H) 6.83 (br.s., 1H) 7.01 (d, J=5.05 Hz, 1H). MS (ES+): m/z 380.03 (100) [MH$^+$]. HPLC: t$_R$=2.27 min (ZQ3, polar_5 min).

Example 219

[4-(8-Amino-3-cyclobutylimidazo[1,5-a]pyrazin-1-yl)-3,6-dihydro-2H-pyridin-1-yl]-(2-fluorophenyl)-methanone Prepared according to a procedure analogous to that described for synthesis of [4-(8-amino-3-cyclobutylimidazo[1,5-a]pyrazin-1-yl)-3,6-dihydro-2H-pyridin-1-yl]-phenyl-methanone except using 2-fluorobenzoic acid. $^1$H NMR (400 MHz, CDCl$_3$): δ=2.03 (ddd, J=11.75, 8.84, 3.16 Hz, 1H) 2.16 (ddd, J=14.46, 9.03, 5.56 Hz, 1H) 2.41-2.63 (m, 4H) 2.78 (br. s., 1H) 2.88 (br. s., 1H) 3.64 (t, J=5.05 Hz, 1H) 3.76 (quin, J=8.59 Hz, 1H) 4.11 (t, J=5.81 Hz, 2H) 4.51 (d, J=2.53 Hz, 1H) 5.82-6.12 (m, 1H) 6.64 (br. s., 2H) 6.87-6.98 (m, 1H) 7.04 (dd, J=5.31, 1.77 Hz, 1H) 7.15 (td, J=8.91, 3.66 Hz, 1H) 7.20-7.25 (m, 0H) 7.41-7.50 (m, 2H). MS (ES+): m/z 391.96 (100) [MH$^+$]. HPLC: t$_R$=2.16 min (OpenLynx polar_5 min).

Example 220

1-[4-(8-Amino-3-cyclobutylimidazo[1,5-a]pyrazin-1-yl)-3,6-dihydro-2H-pyridin-1-yl]-2-phenylethanone Prepared according to a procedure analogous to that described for synthesis of [4-(8-amino-3-cyclobutylimidazo[1,5-a]pyrazin-1-yl)-3,6-dihydro-2H-pyridin-1-yl]-phenyl-methanone except using phenyl-acetic acid. $^1$H NMR (400 MHz, CDCl$_3$): δ 2.03 (dd, J=8.08, 3.03 Hz, 1H) 2.11-2.25 (m, 1H) 2.41-2.60 (m, 5H) 2.74 (br. s., 1H) 3.68-3.78 (m, 2H) 3.84 (s, 2H) 3.93 (t, J=5.68 Hz, 1H) 4.17 (d, J=2.53 Hz, 1H) 4.35 (d, J=2.53 Hz, 1H) 5.78-6.08 (m, 1H) 6.81 (t, J=6.06 Hz, 1H) 6.99 (d, J=5.56 Hz, 1H) 7.22-7.40 (m, 5H). MS (ES+): m/z 388.00 (100) [MH$^+$]. HPLC: t$_R$=2.19 min (OpenLynx, polar_5 min).

Example 221

1-(1-Benzenesulfonyl-1,2,3,6-tetrahydropyridin-4-yl)-3-cyclobutyl-imidazo[1,5-a]pyrazin-8-ylamine A mixture of 3-cyclobutyl-1-(1,2,3,6-tetrahydropyridin-4-yl)-imidazo[1,5-a]pyrazin-8-ylamine (20.0 mg, 0.0742 mmol), benzenesulfonyl chloride (9.48 uL, 0.0742 mmol), DIEA (0.0647 mL, 0.371 mmol) and DMF (1 mL, 0.01 mol)

was stirred at rt for 10 min. The reaction mixture was directly given for Gilson HPLC purification. The fractions containing the pure product were concentrated in vacuo to afford the title compound as a yellow solid. $^1$H NMR (400 MHz, CDCl$_3$): δ=2.03 (dt, J=8.84, 2.65 Hz, 1H) 2.09-2.24 (m, 1H) 239-2.59 (m, 4H) 2.81 (d, J=1.77 Hz, 2H) 3.50 (t, J=5.68 Hz, 2H) 3.72 (quin, J=8.53 Hz, 1H) 3.85 (t, J=2.91 Hz, 2H) 5.93 (t, J=1.52 Hz, 1H) 6.82 (d, J=5.56 Hz, 1H) 6.99 (d, J=5.56 Hz, 1H) 7.55-7.69 (m, 3H) 7.86-7.90 (m, 2H). MS (ES+): m/z 409.99 (100) [MH$^+$]. HPLC: $t_R$=2.29 min (OpenLynx, polar_5 min).

Example 222

4-(8-Amino-3-cyclobutyl-imidazo[1,5-a]pyrazin-1-yl)-3,6-dihydro-2H-pyridine-1-carboxylic acid tert-butyl ester To a stirred mixture of 3-cyclobutyl-1-iodoimidazo[1,5-a]pyrazin-8-amine (100.00 mg, 0.318 mmol), potassium carbonate (154.0 mg, 1.11 mmol) in DME (3.0 mL) and H$_2$O (0.70 mL) was added 4-(4,4,5,5-tetramethyl-[1,3,2]dioxaborolan-2-yl)-3,6-dihydro-2H-pyridine-1-carboxylic acid tert-butyl ester (118.1 mg, 0.38 mmol). The solution was bubbled with nitrogen for 5 min. Then Pd(PPh$_3$)$_4$ (18 mg, 0.016 mmol) was added and the resulting mixture was refluxed at 100° C. for 30 min. The solvent was then removed under reduced pressure and the resulting residue was purified by a flash chromatography (2% MeOH in DCM). $^1$H NMR (400 MHz, MeOD) δ 1.53 (s, 9H), 1.95-2.07 (m, 1H), 2.14-2.28 (m, 1H), 2.44-2.54 (m, 4H), 2.62-2.71 (m, 2H), 3.73 (t, J=5.68 Hz, 2H), 3.87-3.98 (m, 1H), 4.12-421 (m, 2H), 5.94-6.00 (m, 1H), 6.96 (d, J=5.20 Hz, 1H), 7.33 (d, J=5.20 Hz, 1H). MS (ES+): m/z: 369.94, [MH$^+$], HPLC: $t_R$=2.33 min (OpenLynx, polar_5 min).

3-Cyclobutyl-1-(1,2,3,6-tetrahydro-pyridin-4-yl)-imidazo[1,5-a]pyrazin-8-ylamine To a stirred solution of 4-(8-amino-3-cyclobutyl-imidazo[1,5-a]pyrazin-1-yl)-3,6-dihydro-2H-pyridine-1-carboxylic acid tert-butyl ester (300 mg, 1.12 mmol) in 1,4-dioxane (5 mL) was added HCl (4M solution in dioxane, 10 ml) at 10° C. The resulting mixture was stirred at rt. for 3 hr. The solvent was removed under reduced pressure and the resulting residue was used for next step without any further purification. MS (ES+): m/z: 270.13 [MH$^+$], HPLC: $t_R$=1.62 min (OpenLynx, polar_5 min).

Examples 223-226 were synthesized according to Method F:

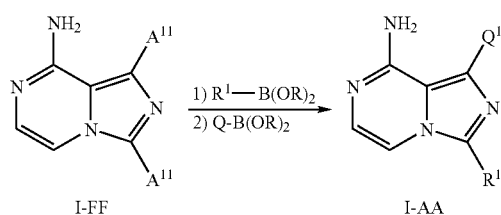

where A$^{11}$=halogen such as Cl, Br, or I and B(OR)$_2$=suitable boronic acid/ester.

Example 223

(4-{8-Amino-3-[4-(4-methyl-piperazin-1-yl)-phenyl]-imidazo[1,5-a]pyrazin-1-yl}-2-methoxy-phenyl)-phenyl-methanone To a stirred mixture of 1-bromo-3-iodo-imidazo[1,5-a]pyrazin-8-ylamine (20.00 mg, 0.05901 mmol) and 1-methyl-4-[4-(4,4,5,5-tetramethyl-[1,3,2]dioxaborolan-2-yl)-phenyl]-piperazine (17.83 mg, 0.05901 mmol) in DME (2 mL) and H$_2$O (0.5 mL) was added potassium carbonate (50.0 mg, 0.35 mmol). To the mixture nitrogen was bubbled for 5 min before Pd(PPh$_3$)$_4$ (6.82 mg, 0.00590 mmol) was added. The resulting mixture was stirred at 95° C. for 3 hr. Then, to this mixture was added [2-methoxy-4-(4,4,5,5-tetramethyl-1,3,2-dioxaborolan-2-yl)-phenyl]-phenyl-methanone (23.95 mg, 0.07081 mmol), the resulting mixture was continued stirred at 95° C. for 2 hours. Then the mixture was allowed cool down to rt, solvent was removed under reduced pressure and the product was purified by flash chromatography (1-5% MeOH in DCM). $^1$H NMR (400 MHz, MeOD) δ 2.85 (s, 3H), 3.24-3.31 (m, 4H), 3.52-3.64 (m, 4H), 3.83 (s, 3H), 7.10 (d, J=5.31 Hz, 1H), 7.25 (d, J=9.09 Hz, 2H), 7.41-7.56 (m, 5H), 7.62-7.89 (m, 6H), 8.30 (s, 2H). MS (ES+): m/z: 518.91 [MH$^+$]. HPLC: $t_R$=1.86 min (OpenLynx: polar_5 min).

Examples 224-226 were synthesized from 1-bromo-3-iodo-imidazo[1,5-a]pyrazin-8-ylamine and corresponding boronic acids or boronates according to a procedure analogous to that described for synthesis of (4-{8-Amino-3-[4-(4-methyl-piperazin-1-yl)-phenyl]-imidazo[1,5-a]pyrazin-1-yl}-2-methoxy-phenyl)-phenyl-methanone.

Example 227 trans-4-[8-Amino-1-(4-phenoxyphenyl)-imidazo[1,5-a]pyrazin-3-yl]-cyclohexanecarboxylic acid amide A mixture trans-4-[8-amino-1-(4-phenoxyphenyl)-imidazo[1,5-a]pyrazin-3-yl]-cyclohexanecarboxylic acid (15.0 mg, 0.035 mmol), 2M of NH$_3$ in i-PrOH (0.1 mL, 0.20 mmol), TBTU (22.5 mg, 0.070 mmol), DIEA (0.0647 mL, 0.371 mmol) and DMF (1 mL, 0.01 mol) was stirred at rt for 10 min. The reaction mixture was used for Gilson HPLC purification. The fractions containing the pure product were collected and concentrated in vacuo to afford the title compound as a yellow solid. $^1$H NMR (400 MHz, CDCl$_3$): δ=1.63-1.76 (m, 2H), 1.78-1.90 (m, 2H), 2.08 (t, J=13.4 Hz, 4H), 3.00-3.10 (m, 1H) 6.94 (d, J=5.6 Hz, 1H), 7.10 (d, J=7.8 Hz, 2H), 7.15 (d, J=8.6 Hz, 2H), 7.20 (t, J=7.3 Hz, 1H), 7.36-7.44 (m, 3H), 7.58 (d, J=8.6 Hz, 2H). MS (ES+): m/z 427.96 (100) [MH$^+$]. HPLC: $t_R$=2.16 min (polar_5 min).

Examples 228-230 were synthesized according to a procedure analogous to that described for synthesis of Example 227 from trans-4-[8-amino-1-(4-phenoxyphenyl)-imidazo[1,5-a]pyrazin-3-yl]-cyclohexanecarboxylic acid and corresponding amines.

Example 231 trans-4-[8-Amino-1-(4-phenoxy-phenyl)-imidazo[1,5-a]pyrazin-3-yl]-cyclohexanecarboxylic acid To a stirred mixture of trans-4-[8-amino-1-(4-phenoxyphenyl)-imidazo[1,5-a]pyrazin-3-yl]-cyclohexanecarboxylic acid methyl ester (150.00 mg, 0.33 mmol) in EtOH (3.00 mL) was added solution of sodium hydroxide (67.8 mg, 1.69 mmol) in H2O (0.500 mL) at 0° C. Then the mixture was stirred at rt. overnight. The solvent was then removed under reduced pressure to give a residue which was dissolved in H2O (3 ml). The solution was acidified to pH 1 by formic acid. The product precipitated out and was collected by filtration and dried on high vacuum pump. $^1$H NMR (400 MHz, MeOD) δ 1.59-1.88 (m, 4H), 2.03-2.21 (m, 4H), 2.35-2.46 (m, 1H), 3.09-3.20 (m, 1H), 6.99 (d, J=5.1 Hz, 1H), 7.04-7.20

(m, 5H), 7.35-7.45 (m, 2H), 7.53-7.63 (m, 3H). MS (ES+): m/z 428.97 (MH+). HPLC: $t_R$=2.25 min (OpenLynx, polar_5 min).

Example 232 trans-4-[8-amino-1-(4-phenoxy-phenyl)-imidazo[1, 5-a]pyrazin-3-yl]-cyclohexanecarboxylic acid methyl ester To a stirred mixture of trans-4-(8-amino-1-bromo-imidazo [1,5-a]pyrazin-3-yl)-cyclohexanecarboxylic acid methyl ester (2.00 g, 5.66 mmol) and 4-phenoxyphenylboronic acid (1.454 g, 6.7 mmol) in DME (25.00 mL) and $H_2O$ (8.3 mL) was added potassium fluoride dihydrate (1.865 g, 19.82 mmol). The mixture was bubbled with nitrogen for 5 min before Pd(PPh$_3$)$_4$ (330 mg, 0.28 mmol) was added to. The resulting mixture was refluxed overnight at 100° C. Solvent was removed under reduced pressure and the product was purified by flash chromatography (2% MeOH in DCM). $^1$H NMR (400 MHz, CD$_3$OD) δ 1.59-1.87 (m, 4H), 2.02-2.18 (m, 4H), 2.41-2.53 (m, 1H), 3.09-3.19 (m, 1H), 3.68 (s, 3H), 6.94-7.20 (m, 6H), 7.32-7.44 (m, 2H), 7.52-7.63 (m, 3H). MS (ES+): m/z: 442.97 [MH+]. HPLC: $t_R$=2.48 min (OpenLynx: polar_5 min).

Example 233 trans-3-(4-Aminomethyl-cyclohexyl)-1-(4-phenoxy-phenyl)-imidazo[1,5-a]pyrazin-8-ylamine trans-{4-[8-Amino-1-(4-phenoxy-phenyl)-imidazo[1,5-a] pyrazin-3-yl]-cyclohexylmethyl}-carbamic acid benzyl ester (50.00 mg, 0.091 mmol) was dissolved in concentrated HCl (2.00 mL) at 0° C. The resulting mixture was stirred at rt. overnight. The solution was washed with EtOAc (4×20 ml), the aq. solvent was then removed under reduced pressure to give a crude product which was further purified by flash chromatography (5% MeOH in DCM). $^1$H NMR (400 MHz, MeOD) δ 1.28-1.46 (m, 2H), 1.74-1.92 (m, 3H), 1.98-2.07 (m, 2H), 2.11-2.20 (m, 2H), 2.90 (d, J=7.1 Hz, 2H), 3.26-3.31 (m, 1H), 7.02-7.28 (m, 6H), 7.40-7.49 (m, 2H), 7.64-7.73 (m, 2H), 7.92 (d, J=5.8 Hz, 1H). MS (ES+): m/z: 414.00 [MH+]. HPLC: $t_R$=1.92 min (OpenLynx, polar_5 min).

Example 234 trans-3-(4-Aminomethyl-cyclohexyl)-1-(3-methoxy-4-phenoxy-phenyl)-imidazo[1,5-a]pyrazin-8-ylamine trans-{4-[8-Amino-1-(3-methoxy-4-phenoxy-phenyl)-imidazo[1,5-a]pyrazin-3-yl]-cyclohexylmethyl}-carbamic acid benzyl ester (80 mg, 0.0001 mol) was dissolved in conc. HCl (3 mL) at 0° C. The resulting mixture was allowed to stir at rt overnight. LCMS indicates the reaction is over. Water was added to the reaction mixture and the mixture was extracted with EtOAc. The aq. phase was concentrated in vacuo to give a residue which was purified by flash chromatography (eluted by 10% MeOH in DCM). $^1$H NMR (400 MHz, CDCl$_3$) δ 1.08 (dd, J=12.13, 3.28 Hz, 2H) 1.74-1.89 (m, 2H) 1.90-1.98 (m, 2H) 2.00-2.09 (m, 2H) 2.57 (d, J=6.57 Hz, 2H) 2.78-2.90 (m, 1H) 3.83 (s, 3H) 6.89-6.95 (m, 2H) 6.95-7.04 (m, 3H) 7.09 (dd, J=8.21, 1.89 Hz, 1H) 7.16 (d, J=5.05 Hz, 1H) 7.21-7.28 (m, 3H). MS (ES+): m/z: 444.17 [MH+]. HPLC: $t_R$=1.88 min (OpenLynx: polar_5 min).

Example 235 trans-{4-[8-Amino-1-(3-methoxy-4-phenoxy-phenyl)-imidazo[1,5-a]pyrazin-3-yl]-cyclohexylmethyl}-carbamic acid benzyl ester To a mixture of trans-[4-(8-amino-1-iodo-imidazo[1,5-a] pyrazin-3-yl)-cyclohexylmethyl]-carbamic acid benzyl ester (80.0 mg, 0.0002 mol), 2-(3-methoxy-4-phenoxy-phenyl)-4, 4,5,5-tetramethyl-[1,3,2]dioxaborolane (67.0 mg, 0.0002 mol), potassium carbonate (0.076 g, 0.00055 mol) in DME (3.00 mL) and $H_2O$ (0.50 mL) was added 1,1'-bis(diphenylphosphino)ferrocenepalladium(II) dichloride DCM (9.0 mg, 0.00001 mol). The resulting mixture was stirred at 100° C. for 2 h under nitrogen atmosphere. Solvent was removed under reduced pressure and the product was purified by flash chromatography (2% MeOH in DCM). MS (ES+): m/z: 577.95 [MH+]. HPLC: $t_R$=2.72 min (OpenLynx: polar_5 min).

Example 236 trans-3-(4-Methylaminomethyl-cyclohexyl)-1-(4-phenoxy-phenyl)-imidazo[1,5-a]pyrazin-8-ylamine A solution of trans-toluene-4-sulfonic acid 4-[8-amino-1-(4-phenoxyphenyl)-imidazo[1,5-a]pyrazin-3-yl]-cyclohexylmethyl ester (15.0 mg, 0.0264 mmol), 2.0 M of methylamine in MeOH (0.5 mL) and MeOH (2 mL) was microwaved at 300 watt, 100° C. for 1 h. The material was concentrated and purified by a prep TLC plate, eluting with 8% (7N NH$_3$ in MeOH) in DCM, to afford the title compound as an off-white solid. $^1$H NMR (400 MHz, CDCl$_3$): δ 1.10-1.22 (m, 2H), 1.60-1.69 (m, 1H), 1.81-1.95 (m, 2H), 1.97-2.03 (m, 2H), 2.10 (d, J=11.4 Hz, 2H), 2.46 (s, 3H), 2.51 (d, J=6.6 Hz, 2H), 2.87-2.97 (m, 1H), 5.09 (br. s., 2H), 7.04-7.18 (m, 6H), 7.23 (d, J=5.1 Hz, 1H), 7.34-7.41 (m, 2H), 7.59-7.66 (m, 2H). MS (ES+): m/z 427.89 (100) [MH+]. HPLC: $t_R$=1.89 min (polar_5 min).

trans-toluene-4-sulfonic acid 4-[8-amino-1-(4-phenoxyphenyl)-imidazo[1,5-a]pyrazin-3-yl]-cyclohexylmethyl ester To a solution of trans-{4-[8-amino-1-(4-phenoxyphenyl)-imidazo[1,5-a]pyrazin-3-yl]-cyclohexyl}-methanol (110.0 mg, 0.2654 mmol) in DCM (5 mL, 0.08 mol) and Pyridine (1 mL, 0.01 mol) at −40° C. was added a solution of toluene-4-sulfonic anhydride (95.3 mg, 0.292 mmol) in DCM and pyridine, and the mixture was warmed to rt overnight. The solution was cooled to −40° C. again, and 1 eq of toluene-4-sulfonic anhydride in DCM and pyridine was added. The reaction was allowed to warm to rt. Water (1 m) was added to quench, and the solution was transferred to a separatory funnel, and extracted using DCM and NaHCO$_3$. The organic layer was dry-loaded onto silica gel and purified via flash chromatography. Eluting with 0-2% MeOH/DCM, the fractions containing the pure product were concentrated in vacuo to afford the title compound as an off-white solid. MS (ES+): m/z 568.91 (100) [MH+]. HPLC: $t_R$=2.93 min (polar_5 min).

Example 237 trans-{4-[8-Amino-1-(4-phenoxyphenyl)-imidazo[1, 5-a]pyrazin-3-yl]-cyclohexyl}-methanol A solution of trans-4-[8-amino-1-(4-phenoxyphenyl)-imidazo[1,5-a]pyrazin-3-yl]-cyclohexanecarboxylic acid methyl ester (150.0 mg, 0.3390 mmol) in THF (10 mL, 0.1 mol) was cooled to −78° C., and 1.0 M of LiAlH₄ in THF (1.50 mL) was added dropwise. The solution was allowed to warm to rt. Sat. NaHCO₃ (10 mL) was added to quench, and the THF was removed in vacuo. DCM was added, and the mixture was transferred to a separatory funnel. The organic layer was extracted with sat. NaHCO₃, washed with brine, dried with magnesium sulfate, filtered and concentrated in vacuo to afford the title compound as an off-white solid. $^1$H NMR (400 MHz, CDCl₃): δ=1.15-1.27 (m, 2H), 1.65-1.70 (m, 1H), 1.84-1.96 (m, 2H), 1.98-2.05 (m, 2H), 2.10-2.16 (m, 2H), 2.87-2.97 (m, 1H), 3.56 (d, J=6.3 Hz, 2H), 5.06 (br. s., 2H), 7.07 (dd, J=6.9, 1.9 Hz, 3H), 7.10-7.18 (m, 3H), 7.23 (d, J=5.1 Hz, 1H), 7.35-7.40 (m, 2H), 7.60-7.63 (m, 2H). MS (ES+): m/z 416.34 (100) [MH⁺]. HPLC: $t_R$=2.34 min (polar__5 min).

Example 238

3-(4-Dimethylaminomethyl-cyclohexyl)-1-(4-phenoxy-phenyl)-imidazo[1,5-a]pyrazin-8-ylamine Prepared according to the procedure described above for the synthesis of trans-3-(4-methylaminomethyl-cyclohexyl)-1-(4-phenoxy-phenyl)-imidazo[1,5-a]pyrazin-8-ylamine, except using dimethyl-amine.

Example 239

3-[4-(4-Methyl-piperazin-1-ylmethyl)-cyclohexyl]-1-(4-phenoxy-phenyl)-imidazo[1,5-a]pyrazin-8-ylamine Prepared according to the procedure described above for the synthesis of trans-3-(4-methylaminomethyl-cyclohexyl)-1-(4-phenoxy-phenyl)-imidazo[1,5-a]pyrazin-8-ylamine, except using 1-methyl-piperazine.

cis-Toluene-4-sulfonic acid 3-[8-amino-1-(4-phenoxyphenyl)-imidazo[1,5-a]pyrazin-3-yl]-cyclobutylmethyl ester and trans-toluene-4-sulfonic acid 3-[8-amino-1-(4-phenoxyphenyl)-imidazo[1,5-a]pyrazin-3-yl]-cyclobutylmethyl ester.

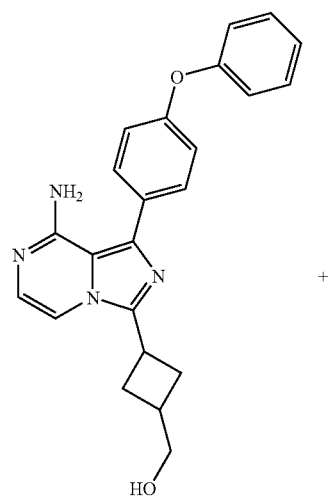

+

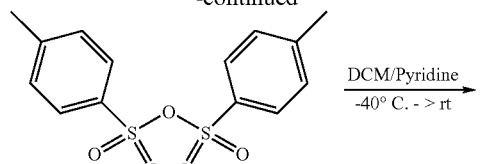

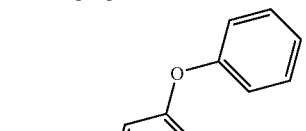

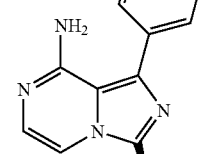

+

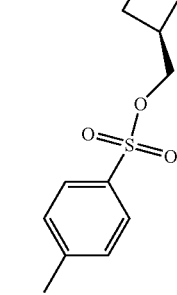

To a solution of mixture of cis- and trans-{3-[8-amino-1-(4-phenoxyphenyl)-imidazo[1,5-a]pyrazin-3-yl]-cyclobutyl}-methanol (830 mg, 2.1 mmol) in DCM (10 mL) at −40° C. was added a solution of toluene-4-sulfonic anhydride (771 mg, 2.36 mmol) in pyridine (5 mL), and the mixture was warmed to rt overnight. The solution was cooled to −40° C. again, and 1 more equivalent of toluene-4-sulfonic anhydride was added. The reaction was warmed to 0° C. This step was repeated once more. The reaction was quenched with water (10 mL), diluted with DCM, washed with NaHCO$_3$ (2×20 mL), washed with brine (1×20 mL), dried with magnesium sulfate, filtered, and concentrated in vacuo. The material was dry-loaded onto silica gel, and flash chromatography was used to purify, eluting with 0-3% MeOH/EtOAc. The fractions containing the pure cis and trans isomers were collected separately to afford the title compounds as light pink solids cis: $^1$H NMR (400 MHz, CDCl$_3$): δ=2.26-2.35 (m, 2H), 2.43 (s, 3H), 2.54-2.63 (m, 2H), 2.73-2.85 (m, 1H), 3.61-3.72 (m, 1H), 4.07 (d, J=6.8 Hz, 2H), 5.08 (s, 2H), 7.03-7.17 (m, 7H), 7.31 (d, J=8.1 Hz, 2H), 7.35-7.40 (m, 2H), 7.59-7.62 (m, 2H), 7.77 (d, J=8.3 Hz, 2H), trans: $^1$H NMR (400 MHz, CDCl$_3$): δ=2.28-2.36 (m, 2H), 2.45 (s, 3H), 2.65-2.74 (m, 2H), 2.76-2.85 (m, 1H), 3.70-3.81 (m, 1H), 4.19 (d, J=6.1 Hz, 2H), 5.49 (br. s., 2H), 6.99-7.16 (m, 7H), 7.33-7.39 (m, 4H), 7.59-7.63 (m, 2H), 7.83 (d, J=8.3 Hz, 2H).

cis- and trans-{3-[8-Amino-1-(4-phenoxyphenyl)-imidazo[1,5-a]pyrazin-3-yl]-cyclobutyl}-methanol A mixture of (cis- and trans-)[3-(8-amino-1-iodoimidazo[1,5-a]pyrazin-3-yl)-cyclobutyl]-methanol (1.50 g, 4.36 mmol), 4-phenoxyphenylboronic acid (1.21 g, 5.67 mmol), Pd(PPh$_3$)$_4$ (500 mg, 0.40 mmol), potassium carbonate (1.81 g, 13.1 mmol) and DME/Water (5:1) was microwaved at 100° C. for 4 h. The material was passed through a silica plug with 1:1 EtOAc/hexanes, followed by 10% (7N NH$_3$ in MeOH)/DCM. The DCM filtrate was dry-loaded onto silica, and the material was purified via flash chromatography, eluting with 1-3% (7N NH$_3$ in MeOH)/DCM. The fractions containing the pure product were combined and concentrated in vacuo to afford the title compound (cis- and trans-) as a white solid (830 mg, 93% purity), MS (ES+): m/z 387.01 (100) [MH$^+$]. HPLC: t$_R$=2.22 min (ZQ3, polar_5 min).

Example 240 trans-{3-[8-amino-1-(4-phenoxy-phenyl)-imidazo[1,5-a]pyrazin-3-yl]-cyclobutyl}-methanol A solution of trans-toluene-4-sulfonic acid 3-[8-amino-1-(4-phenoxy-phenyl)-imidazo[1,5-a]pyrazin-3-yl]-cyclobutylmethyl ester (10.0 mg, 0.0185 mmol), potassium hydroxide (10.4 mg, 0.185 mmol), H$_2$O (1 mL) and 1,4-dioxane (1 mL) was heated to 60° C. overnight. The mixture was titrated to pH 2 with 2M HCl. The dioxane was removed in vacuo. DCM was added to extract the product. The organics were combined, dried (Na$_2$SO$_4$) and removed under reduced pressure to give a residue which was then purified by flash chromatography (5% MeOH in DCM). MS (ES+): m/z 386.94 (100) [MH$^+$]. HPLC: t$_R$=2.23 min (polar_5 min).

Example 241 cis-3-(3-Dimethylaminomethylcyclobutyl)-1-(4-phenoxyphenyl)-imidazo[1,5-a]pyrazin-8-ylamine A mixture of cis-toluene-4-sulfonic acid 3-[8-amino-1-(4-phenoxyphenyl)-imidazo[1,5-a]pyrazin-3-yl]-cyclobutylmethyl ester (30.0 mg, 0.0555 mmol), 2 M of dimethylamine in MeOH (2 mL) and THF (5 mL, 0.06 mol) was heated to 60° C. overnight in a sealed tube. The material was concentrated in vacuo, redissolved in minimal MeOH/DCM, and loaded onto a prep TLC plate, eluting with 6% (7N NH$_3$ in MeOH)/DCM. The band containing the pure product was collected, and the product was filtered off using 1:1 MeOH/DCM. The filtrate was concentrated in vacuo, and hexanes was added. The mixture was sonicated until a white precipitate crashed out. The solid was filtered off, washing several times with hexanes, to afford the title compound as a white solid. $^1$H NMR (400 MHz, CDCl$_3$): δ=2.23 (s, 6H), 2.26-2.33 (m, 2H), 2.42 (d, J=6.3 Hz, 2H), 2.57-2.70 (m, 3H), 3.60-3.71 (m, 1H), 5.03 (s, 2H), 7.03-7.17 (m, 7H), 7.34-7.41 (m, 2H), 7.61-7.65 (m, 2H). MS (ES+): m/z 414.19 (100) [MH$^+$]. HPLC: t$_R$=1.98 min (ZQ3, polar_5 min).

Example 242

1-(4-Phenoxy-phenyl)-3-(3-pyrrolidin-1-ylmethyl-cyclobutyl)-imidazo[1,5-a]pyrazin-8-ylamine Prepared according to the procedure described above for cis-3-(3-dimethylaminomethylcyclobutyl)-1-(4-phenoxyphenyl)-imidazo[1,5-a]pyrazin-8-ylamine, except using pyrrolidine.

Example 243

3-(3 Aminomethyl-cyclobutyl)-1-(4-phenoxy-phenyl)-imidazo[1,5-a]pyrazin-8-ylamine Prepared according to the procedure described above for cis-3-(3-dimethylaminomethylcyclobutyl)-1-(4-phenoxyphenyl)-imidazo[1,5-a]pyrazin-8-ylamine, except using ammonia.

Example 244 trans-3-(3-dimethylaminomethyl-cyclobutyl)-1-(4-phenoxy-phenyl)-imidazo[1,5-a]pyrazin-8-ylamine A mixture of trans-toluene-4-sulfonic acid 3-[8-amino-1-(4-phenoxy-phenyl)-imidazo[1,5-a]pyrazin-3-yl]-cyclobutylmethyl ester (30.0 mg, 0.0555 mmol), dimethylamine in MeOH (2 M, 2 mL) and THF (5 mL) was heated to 60° C. overnight in a sealed tube. The material was concentrated in vacuo, purified by prep TLC (eluting with 5% MeOH in DCM). MS (ES+): m/z 414.19 (100) [MH$^+$]. HPLC: t$_R$=0.65 min (polar_5 min).

Example 245

1-(4-Phenoxy-phenyl)-3-(3-pyrrolidine-1-ylmethyl-cyclobutyl)-imidazo[1,5-a]pyrazin-8-ylamine Prepared according to the procedure described above for trans-3-(3-dimethylaminomethylcyclobutyl)-1-(4-phenoxy-phenyl)-imidazo[1,5-a]pyrazin-8-ylamine, except using pyrrolidine.

Example 246 cis-3-(3-Methylcyclobutyl)-1-(4-phenoxyphenyl)-imidazo[1,5-a]pyrazin-8-ylamine

To a solution of cis-toluene-4-sulfonic acid 3-[8-amino-1-(4-phenoxyphenyl)-imidazo[1,5-a]pyrazin-3-yl]-cyclobutylmethyl ester (20.0 mg, 0.0370 mmol) in THF (1 mL) at −78° C. was added 1.0 M of LiAlH$_4$ in THF (0.15 mL), and the mixture was allowed to warm to rt. Once the reaction was complete, a few drops of sat. NH$_4$Cl was added to quench. The material was transferred to a separatory funnel, and extracted using DCM and sat. NaHCO$_3$. The aqueous layer was washed twice with DCM, and the organic fractions were combined and concentrated in vacuo. The material was dissolved in minimal MeOH/DCM, and loaded onto a prep TLC plate, eluting with 2% (7N NH₃ in MeOH)/DCM. The band containing the product was collected, and the material was filtered off by washing with 1:1 MeOH I DCM. The filtrate was concentrated in vacuo to afford the title compound. ¹H NMR (400 MHz, CDCl₃): δ=1.14 (d, J=6.3 Hz, 3H), 2.13-2.23 (m, 2H), 2.46-2.57 (m, 1H), 2.58-2.67 (m, 2H), 3.52-3.62 (m, 1H), 5.07 (br. s., 2H), 7.02-7.10 (m, 3H), 7.10-7.18 (m, 4H), 7.35-7.41 (m, 2H), 7.61-7.66 (m, 2H). MS (ES+): m/z 371.06 (100) [MH⁺]. HPLC: $t_R$=2.67 min (polar_5 min).

Example 247 trans-3-(3-Methylcyclobutyl)-1-(4-phenoxyphenyl)-imidazo[1,5-a]pyrazin-8-ylamine Prepared according to the procedure described above for cis-3-(3-methylcyclobutyl)-1-(4-phenoxyphenyl)-imidazo[1,5-a]pyrazin-8-ylamine, except using trans-toluene-4-sulfonic acid 3-[8-amino-1-(4-phenoxyphenyl)-imidazo[1,5-a]pyrazin-3-yl]-cyclobutylmethyl ester.

Example 248

3-(3-Methoxymethyl-cyclobutyl)-1-(4-phenoxy-phenyl)-imidazo[1,5-a]pyrazin-8-ylamine To a stirred solution of cis-toluene-4-sulfonic acid 3-[8-amino-1-(4-phenoxy-phenyl)-imidazo[1,5-a]pyrazin-3-yl]-cyclobutylmethyl ester (20 mg, 0.04 mmol) in MeOH (2 mL) was added 25% wt. NaOMe in MeOH (25:75, MeONa: MeOH, 13 uL). The resulting mixture was stirred at 50° C. overnight. Reaction was quenched with sat. aq. NaHCO₃ solution, extracted with DCM and dried (Na₂SO₄). The solvent was removed under reduced pressure to give a residue which was then purified by flash chromatography. ¹H NMR (400 MHz, CDCl₃) δ ppm 2.28-2.43 (m, 2H), 2.54-2.65 (m, 2H), 2.65-2.75 (m, 1H), 3.34 (s, 3H), 3.40-3.46 (m, 2H), 3.59-3.75 (m, 1H), 5.03 (s, 2H), 7.02-7.09 (m, 3H), 7.08-7.18 (m, 4H), 7.33-7.40 (m, 2H), 7.59-7.65 (m, 2H).

Example 249

1-(4-Benzenesulfinylphenyl)-3-cyclobutylimidazo[1,5-a]pyrazin-8-ylamine

To a solution of 3-cyclobutyl-1-(4-phenylsulfanylphenyl)-imidazo[1,5-a]pyrazin-8-ylamine (15.0 mg, 0.0403 mmol) in DCM (3 mL, 0.05 mol) at 0° C. was added a solution of m-chloroperbenzoic acid (10.4 mg, 0.0604 mmol) in DCM. The mixture was stirred at 0° C. for 30 min. Sat. aq. NaHCO₃ solution was added to quench, and the material was transferred to a separatory funnel. The organic layer was concentrated in vacuo and redissolved in DMF (1 mL) for Gilson HPLC separation. The fractions containing the pure product were concentrated in vacuo to afford the title compound as a yellow solid. ¹H NMR (400 MHz, CDCl₃): δ=1.98-2.09 (m, 1H), 2.11-2.23 (m, 1H), 2.44-2.53 (m, 2H), 2.55-2.65 (m, 2H), 3.80 (t, J=8.5 Hz, 1H), 7.04 (d, J=5.3 Hz, 1H), 7.13 (d, J=5.3 Hz, 1H), 7.47-7.53 (m, 3H), 7.68-7.71 (m, 2H), 7.79 (s, 4H). MS (ES+): m/z 389.02 (100) [MH⁺]. HPLC: $t_R$=2.17 min (Open Lynx, polar_5 min).

Example 250

5-(8-Amino-3-cyclobutylimidazo[1,5-a]pyrazin-1-yl)-2-phenoxybenzonitrile

Into a round bottom flask was added 5-(8-amino-3-cyclobutylimidazo[1,5-a]pyrazin-1-yl)-2-fluorobenzonitrile (30 mg, 0.0001 mol), phenol (0.023 g, 0.00024 mol), potassium carbonate (0.040 g, 0.00029 mol), DMF (0.8 mL, 0.01 mol) and the reaction mixture was heated at 120° C. for 4 h. Purification by Gilson HPLC afforded 11.4 mg of the title compound as a white solid. ¹H NMR (400 MHz, CDCl₃): δ=1.98-2.11 (m, 1H), 2.12-2.26 (m, 1H), 2.44-2.55 (m, 2H), 2.55-2.67 (m, 2H), 3.82 (dq, J=8.72, 8.55 Hz, 1H), 5.04 (br. s., 2H), 6.98 (d, J=8.84 Hz, 1H), 7.09 (d, J=5.05 Hz, 1H), 7.12-7.17 (m, 3H), 7.26-7.29 (m, 1H), 7.40-7.48 (m, 2H), 7.79 (dd, J=8.59, 2.27 Hz, 1H), 8.02 (d, J=2.02 Hz, 1H). MS (ES⁺): m/z 381.94 (100)[MH⁺]. HPLC: $t_R$=2.53 min (Open Lynx, polar_5 min).

Example 251

2-[4-(8-Amino-3-cyclobutylimidazo[1,5-a]pyrazin-1-yl)-phenoxy]-benzonitrile

Into a 10 mL round bottom flask was added 4-(8-amino-3-cyclobutylimidazo[1,5-a]pyrazin-2-yl)phenol (20 mg, 0.00007 mol), benzonitrile, 2-fluoro-(0.017 g, 0.00014 mol), potassium carbonate (0.015 g, 0.00011 mol), DMF (0.6 mL, 0.007 mol) and the reaction was heated at 120° C. for 4 h. Purification by Gilson HPLC afforded 5.0 mg of the title compound as a white solid. The compound was passed through an SPE cartridge washing with NH₃ in MeOH to elute 4.8 my of the desired compound free of the TFA salt. MS(ES⁺): m/z 381.93 (100)[MH⁺]. HPLC: $t_R$=2.39 min (Open Lynx polar_5 min).

5-(8-Amino-3-cyclobutylimidazo[1,5-a]pyrazin-1-yl)-2-fluorobenzonitrile

Into a 10 mL microwave vessel were added 3-cyclobutyl-1-iodoimidazo[1,5-a]pyrazin-8-amine (100 mg, 0.0003 mol), 3-cyano-4-fluorophenylboronic acid (0.068 g, 0.00041 mol) potassium carbonate (88 mg, 0.00063 mol), Pd(PPh₃)₄ (40 my, 0.00003 mol), DME/Water (5:1) (5:1, DME:H₂O, 1 mL) and the vessel was degassed 3× with N₂. The reaction was microwaved on 300 watts, 100° C. for 45 min. The reaction vessel was resubjected to the microwave heating under the same conditions as before for 45 min. Purification by prep TLC using 4% MeOH in DCM eluting twice afforded 54 mg of the title compound as a yellow solid. MS (ES⁺): m/z 308.11 (100)[MH⁺]. HPLC: $t_R$=2.14 min (Open Lynx polar_5 min).

4-(8-Amino-3-cyclobutyl-imidazo[1,5-a]pyrazin-1-yl)-phenol

Prepared according to a Suzuki coupling procedure analogous to that described for synthesis of 5-(8-amino-3-cyclobutylimidazo[1,5-a]pyrazin-1-yl)-2-fluorobenzonitrile, except using 4 hydroxyphenylboronic acid. MS (ES⁺): m/z 281.17 (100)[MH⁺].

Example 252 cis-{4-[8-Amino-3-(3-hydroxy-cyclobutyl)-imidazo[1,5-a]pyrazin-1-yl]-phenyl}-phenyl-methanone Prepared according to a procedure analogous to that described for cis-{4-[8-amino-3-(3-hydroxy-3-methyl-cyclobutyl)-imidazo[1,5-a]pyrazin-1-yl]-phenyl}-phenyl-methanone, except using cis-3-(8-amino-1-iodo-imidazo[1,5-a]pyrazin-3-yl)-cyclobutanol.

Example 253 trans-{4-[8-Amino-3-(4-hydroxymethyl-cyclohexyl)-imidazo[1,5-a]pyrazin-1-yl]-phenyl}-phenyl-methanone Prepared according to a procedure analogous to that described for cis-{4-[8-amino-3-(3-hydroxy-3-methyl-cyclobutyl)-imidazo[1,5-a]pyrazin-1-yl]-phenyl}-phenyl-methanone, except using trans-[4-(8-amino-1-iodo-imidazo[1,5-a]pyrazin-3-yl)-cyclohexyl]-methanol.

Example 254 cis-3-{8-Amino-1-[4-(hydroxy-phenyl-methyl)-phenyl]-imidazo[1,5-a]pyrazin-3-yl}-1-methyl-cyclobutanol To a solution of cis-{4-[8-Amino-3-(3-hydroxy-3-methyl-cyclobutyl)-imidazo[1,5-a]pyrazin-1-yl]-phenyl}-phenyl-methanone (18.0 mg, 0.0452 mmol) in MeOH (3.0 mL) was added sodium borohydride (4.3 mg, 0.11 mmol) at 0° C. The reaction mixture was stirred at rt for 16 h. The reaction was quenched by sat. aq. NaHCO$_3$ solution. The solvent was removed under reduced pressure, and the material was dissolved in DCM. The organic layer was washed by sat. aq. NaHCO$_3$ solution (20 mL×2). The organic layer was dried (Na$_2$SO$_4$) and evaporated to give desired compound. MS (ES$^+$): m/z 400.86 [MH$^+$]. HPLC: t$_R$=1.97 min. (Open Lynx polar__5 min.).

Example 255 cis-3-{8-Amino-1-[4-(hydroxy-phenyl-methyl)-phenyl]-imidazo[1,5-a]pyrazin-3-yl}-cyclobutanol Prepared according to a procedure analogous to that described cis-3-{8-amino-1-[4-(hydroxy-phenyl-methyl)-phenyl]-imidazo[1,5-a]pyrazin-3-yl}-1-methyl-cyclobutanol, except using cis-{4-[8-amino-3-(3-hydroxy-cyclobutyl)-imidazo[1,5-a]pyrazin-1-yl]-phenyl}-phenyl-methanone.

Example 256 trans-4-[8-Amino-3-(4-hydroxymethylcyclohexyl)-imidazo[1,5-a]pyrazin-1-yl]-phenyl-phenylmethanol Prepared according to a procedure analogous to that described for cis-3-{8-amino-1-[4-(hydroxy-phenyl-methyl)-phenyl]-imidazo[1,5-a]pyrazin-3-yl}-1-methyl-cyclobutanol, except using trans-{4-[8-Amino-3-(4-hydroxymethylcyclohexyl)-imidazo[1,5-a]pyrazin-1-yl]-phenyl}-phenyl-methanone.

Example 257

1-[4-(3-Aminophenoxy)-phenyl]-3-cyclobutylimidazo[1,5-a]pyrazin-8-ylamine

A mixture of 3-cyclobutyl-1-[4-(3-nitrophenoxy)-phenyl]-imidazo[1,5-a]pyrazin-8-ylamine (10 mg, 0.02 mmol), iron (10 mg, 0.2 mmol), EtOH (10 mL, 0.2 mol) and conc. HCl (100 uL, 0.003 mol) was refluxed for 1 h. Sat. NaHCO$_3$ was added to quench, and the EtOH was removed in vacuo. The mixture was transferred to a separatory funnel, and DCM was used to extract the product. The organic layer was concentrated in vacuo, redissolved in minimal MeOH/DCM, and loaded onto a prep TLC plate. After eluting with 10% (7N NH$_3$ in MeOH)/DCM, the band containing the pure product was collected, and the material filtered off using 1:1 MeOH/DCM. The filtrate was concentrated in vacuo to afford the title compound as a yellow solid. $^1$H NMR (400 MHz, CDCl$_3$): δ=2.00-2.08 (m, 1H) 2.13-2.24 (m, 1H) 2.44-2.55 (m, J=8.91, 8.75, 8.75, 2.91, 2.78 Hz, 2H) 2.64 (quin, J=9.28 Hz, 2H) 3.71 (br. s., 2H) 3.82 (dq, J=8.84, 8.59 Hz, 1H) 5.05 (br. s., 2H) 6.38 (t, J=2.15 Hz, 1H) 6.46 (dd, J=8.08, 1.26 Hz, 2H) 7.05-7.16 (m, 5H) 7.63 (d, J=8.59 Hz, 2H). MS (ES+): m/z 372.10 (20) [MH$^+$]. HPLC: t$_R$=2.22 min (Open Lynx, polar__5 min).

Example 258

1-(3-Amino-4-phenoxy-phenyl)-3-cyclobutyl-imidazo[1,5-a]pyrazin-8-ylamine

Prepared according to a procedure analogous to that described for 1-[4-(3-aminophenoxy)-phenyl]-3-cyclobutyl-imidazo[1,5-a]pyrazin-8-ylamine, except using 3-cyclobutyl-1-(3-nitro-4-phenoxy-phenyl)-imidazo[1,5-a]pyrazin-8-ylamine.

Example 259 cis-3-[8-Amino-1-(3-amino-4-phenoxy-phenyl)-imidazo[1,5-a]pyrazin-3-yl]-1-methyl-cyclobutanol Prepared according to a procedure analogous to that described for 1-[4-(3-aminophenoxy)-phenyl]-3-cyclobutyl-imidazo[1,5-a]pyrazin-8-ylamine, except using cis-3-[8-amino-1-(3-nitro-4-phenoxy-phenyl)-imidazo[1,5-a]pyrazin-3-yl]-1-methyl-cyclobutanol.

Example 260

1-[4-(2-Amino-phenoxy)-phenyl]-3-cyclobutyl-imidazo[1,5-a]pyrazin-8-ylamine

Prepared according to a procedure analogous to that described for 1-[4-(3-aminophenoxy)-phenyl]-3-cyclobutyl-imidazo[1,5-a]pyrazin-8-ylamine, except using 3-cyclobutyl-1-[4-(2-nitro-phenoxy)-phenyl]-imidazo[1,5-a]pyrazin-8-ylamine.

Example 261

[2-Amino-4-(8-amino-3-cyclobutyl-imidazo[1,5-a]pyrazin-1-yl)-phenyl]-phenyl-methanone Prepared according to a procedure analogous to that described for 1-[4-(3-aminophenoxy)-phenyl]-3-cyclobutyl-imidazo[1,5-a]pyrazin-8-ylamine, except using [4-(8-amino-3-cyclobutyl-imidazo[1,5-a]pyrazin-1-yl)-2-nitro-phenyl]-phenyl-methanone.

Example 262 cis-{2-Amino-4-[8-amino-3-(3-hydroxy-3-methyl-cyclobutyl)-imidazo[1,5-a]pyrazin-1-yl]-phenyl}-phenyl-methanone Prepared according to a procedure analogous to that described for 1-[4-(3-aminophenoxy)-phenyl]-3-cyclobutylimidazo[1,5-a]pyrazin-8-ylamine, except using cis-{4-[8-amino-3-(3-hydroxy-3-methyl-cyclobutyl)-imidazo[1,5-a]pyrazin-1-yl]-2-nitro-phenyl}-phenyl-methanone.

Example 263

1-(4-Benzo[b]thiophen-2-yl-phenyl)-3-cyclobutyl-imidazo[1,5-a]pyrazin-8-ylamine

A mixture of 1-(4-bromophenyl)-3-cyclobutylimidazo[1,5-a]pyrazin-8-ylamine (30.0 mg, 0.0874 mmol), 1-benzothiophen-2-ylboronic acid (18.7 mg, 0.105 mmol) and Pd(PPh$_3$)$_4$ (5 mg, 0.004 mmol) in 1,4-dioxane (2 mL, 30 mmol) and H$_2$O (0.2 mL, 9 mmol) was degassed and refilled with nitrogen (3×). The reaction was microwaved on 300 watts, PowerMAX enabled, 100° C. for 30 min. For the workup, the reaction was concentrated in vacuo to a solid and purified by 10 g Jones Chromatography column wetted with DCM, dried loaded the product, eluted with DCM to 5% MeOH in DCM], which afford 8.4 mg (24%) of the desired product as a yellow solid. $^1$H NMR (400 MHz, CDCl$_3$); δ=2.03-2.14 (m, 1H), 2.16-2.27 (m, 1H), 2.48-2.59 (m, 2H), 2.61-2.74 (m, 2H); 3.78-3.89 (m, 1H), 6.93 (d, J=5.56 Hz, 1H), 7.14 (d, J=5.56 Hz, 1H), 7.33-7.43 (m, 2H), 7.66 (s, 1H), 7.74 (d, J=8.59 Hz, 2H), 7.80-7.92 (m, 4H). HPLC: $t_R$=2.71 min. (Open Lynx polar_5 min.). MS (ES$^+$): m/z 379.80/380.91 (100/60) [MH$^+$].

Examples 264-268 were prepared by a Suzuki coupling reaction from 1-(4-bromophenyl)-3-cyclobutylimidazo[1,5-a]pyrazin-8-ylamine according to a procedure analogous to that described for 1-(4-benzo[b]thiophen-2-yl-phenyl)-3-cyclobutyl-imidazo[1,5-a]pyrazin-8-ylamine, using corresponding boronic acids or boronates.

Example 269 trans-{4-[4-Amino-5-(4-phenoxy-phenyl)-imidazo[5,1-f][1,2,4]triazin-7-yl]-cyclohexylmethyl}-carbamic acid benzyl ester A mixture of trans-7-[({[(benzyloxy)carbonyl]amino}methyl)cyclohexyl]-5-iodoimidazo[5,1-f][1,2,4]triazin-4-amine (50.0 mg, 0.0987 mmol), 4-phenoxyphenylboronic acid (23.2 mg, 0.109 mol), Pd(PPh$_3$)$_4$ (10 mg, 0.01 mmol), potassium carbonate (41 mg, 0.30 mmol) in DME/Water (v:v=5:1, 2 mL) was irradiated with microwave at 300 watt, 100° C. for 1 h. The material was passed through a silica plug, eluting with DCM. The filtrate was concentrated in vacuo, purified by silica gel chromatography, eluting with 4% (7N NH$_3$ in MeOH) in DCM. MS (ES+): m/z 549.20 (100) [MH$^+$]. HPLC: $t_R$=3.77 min (OpenLynx, polar_5 min).

Example 270 trans-4-[4-Amino-5-(4-phenoxy-phenyl)-imidazo[5,1-f][1,2,4]triazin-7-yl]-cyclohexanecarboxylic acid methyl ester Prepared according to the procedure analogous to that described above for trans-{4-[4-amino-5-(4-phenoxy-phenyl)-imidazo[5,1-f][1,2,4]triazin-7-yl]-cyclohexylmethyl}-carbamic acid benzyl ester, except using trans-4-(4-amino-5-iodo-imidazo[5,1-f][1,2,4]triazin-7-yl)-cyclohexanecarboxylic acid methyl ester.

Example 271 trans-7-(4-Aminomethyl-cyclohexyl)-5-(4-phenoxy-phenyl)-imidazo[5,1-f][1,2,4]triazin-4-ylamine A solution of trans-{4-[4-amino-5-(4-phenoxy-phenyl)-imidazo[5,1-f][1,2,4]triazin-7-yl]-cyclohexylmethyl}-carbamic acid benzyl ester (20.0 mg, 0.0364 mmol) and 4 M of HCl in 1,4-dioxane (2 mL) was heated to reflux overnight. The solution was concentrated in vacuo and left to dry in the vacuum oven overnight to afford the title compound as a yellow solid. $^1$H NMR (400 MHz, CDCl$_3$): δ=1.23-1.37 (m, 2H), 1.83-1.99 (m, 3H), 2.03-2.09 (m, 2H), 2.15-2.24 (m, 2H), 2.86 (d, J=4.0 Hz, 2H), 3.44-3.56 (m, 1H), 7.12 (d, J=8.1 Hz, 2H), 7.17-7.26 (m, 3H), 7.44 (t, J=7.8 Hz, 3H), 7.66 (d, J=3.5 Hz, 2H), 8.00-8.10 (m, 1H). MS (ES+): m/z 415.02 (100) [MH$^+$]. HPLC: $t_R$=2.26 min (OpenLynx, polar_5 min).

Example 272 trans-{4-[4-Amino-5-(4-phenoxy-phenyl)-imidazo[5,1-f][1,2,4]triazin-7-yl]-cyclohexyl}-methanol To a stirred solution of trans-4-[4-amino-5-(4-phenoxy-phenyl)-imidazo[5,1-f][1,2,4]triazin-7-yl]-cyclohexanecarboxylic acid methyl ester (105.0 mg, 0.2368 mmol) in THF (7 mL) was added solution of LiAlH$_4$ in THF (1.0 M, 1.0 mL) at −78° C. The solution was allowed to warm to rt. Sat. aq. NaHCO$_3$ (10 mL) was added to the reaction mixture, and the THF was removed in vacuo. DCM was added, and the mixture was transferred to a separatory funnel. The organic layer was extracted with sat. aq. NaHCO$_3$, washed with brine, dried with magnesium sulfate, filtered and concentrated in vacuo to afford the title compound as an off-white solid. MS (ES+): m/z 416.09 (100) [MH$^+$]. HPLC $t_R$=3.12 min (OpenLynx, polar_5 min).

Example 273 trans-N-{4-[4-Amino-5-(4-phenoxy-phenyl)-imidazo[5,1-f][1,2,4]triazin-7-yl]-cyclohexylmethyl}-N',N'-dimethyl-ethane-1,2-diamine A solution of toluene-4-sulfonic acid 4-[4-amino-5-(4-phenoxy-phenyl)-imidazo[5,1-f][1,2,4]triazin-7-yl]-cyclohexylmethyl ester (5.0 mg, 0.0088 mmol), N,N-dimethyl-1,2-ethanediamine (1 mL, 0.009 mol) in MeOH (1 mL) was heated in microwave reactor at 300 watt, 100° C. for 2 h. The solvent and excess amine were removed in vacuo, and the material was purified by silica gel chromatography, eluting with 5% (7N NH3 in MeOH) in DCM. HPLC: $t_R$=1.99 min. (OpenLynx, polar_5 min). MS (ES$^+$): m/z 486.19 (100) [MH$^+$].

Example 274 trans-7-(4-dimethylaminomethyl-cyclohexyl)-5-(4-phenoxy-phenyl)-imidazo[5,1-f][1,2,4]triazin-4-ylamine Prepared according to the procedure analogous to that described above for trans-N-{4-[4-Amino-5-(4-phenoxy-phenyl)-imidazo[5,1-f][1,2,4]triazin-7-yl]-cyclohexylmethyl}-N',N'-dimethyl-ethane-1,2-diamine, except using dimethylamine.

Example 275 trans-2-({4-[4-Amino-5-(4-phenoxy-phenyl)-imidazo[5,1-f][1,2,4]triazin-7-yl]-cyclohexylmethyl}-amino)-ethanol Prepared according to the procedure analogous to that described above for trans-N-{4-[4-Amino-5-(4-phenoxy-phenyl)-imidazo[5,1-f][1,2,4]triazin-7-yl]-cyclohexylmethyl}-N',N'-dimethyl-ethane-1,2-diamine, except using 2-amino-ethanol.

Examples 276-287 were synthesized by a Suzuki coupling method.

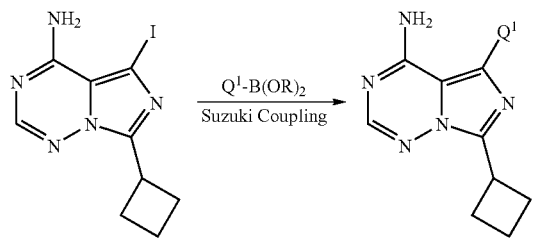

Example 276

7-Cyclobutyl-5-(4-phenoxyphenyl)-imidazo[5,1-f][1,2,4]triazin-4-ylamine

A mixture of 7-cyclobutyl-5-iodoimidazo[5,1-f][1,2,4]triazin-4-ylamine (120.0 mg, 0.3808 mmol), 4-phenoxyphenylboronic acid (97.8 mg, 0.457 mmol), potassium carbonate (0.10 g, 0.76 mmol) and Pd(PPh$_3$)$_4$ (20 mg, 0.02 mmol) in DME (5.938 mL, 57.12 mmol) and H$_2$O (1.00 mL, 55.5 mmol) was degassed and refilled with Argon (3 x). The reaction was microwaved on 300 watts, PowerMAX enabled, 100° C. for 60 min. For the workup, the reaction was concentrated in vacuo to a solid and purified by flash silica gel chromatography, eluted with 5% MeOH in DCM. $^1$H NMR (400 MHz, CDCl$_3$): δ 2.08 (1H, d) 2.16-2.26 (1H, m) 2.45-2.53 (2H, m) 2.62-2.69 (2H, m) 4.15 (1H, t, J=8.72 Hz) 7.11 (1H, d, J=7.58 Hz) 7.19 (2H, d, J=8.59 Hz) 7.43 (2H, t, J=7.96 Hz) 7.63 (2H, d, J=8.59 Hz) 7.76 (1H, s). HPLC: t$_R$=3.56 min. (OpenLynx, polar_5 min). MS (ES$^+$): m/z 357.87 (100) [MH$^+$].

Examples 277-287 were prepared by a Suzuki coupling reaction analogous to that described above for 7-cyclobutyl-5-(4-phenoxyphenyl)-imidazo[5,1-f][1,2,4]triazin-4-ylamine, using correspondent boronic acids or boronates.

Examples 288-297 were synthesized by a Suzuki coupling method.

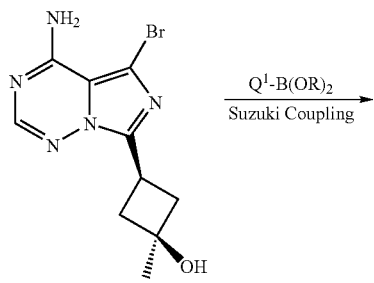

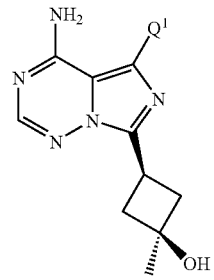

Example 288 cis-3-[4-Amino-5-(4-phenoxy-phenyl)-imidazo[5,1-t][1,2,4]triazin-7-yl]-1-methyl-cyclobutanol A mixture of cis-3-(4-amino-5-bromo-imidazo[5,1-f][1,2,4]triazin-7-yl)-1-methyl-cyclobutanol (20.0 mg, 0.0671 mmol), 4-phenoxyphenylboronic acid (15.8 mg, 0.0738 mmol), Pd(PPh$_3$)$_4$ (10 mg, 0.01 mmol), potassium carbonate (27.8 mg, 0.201 m); in DME/Water (v:v=5:1, 2 mL) was irradiated with microwave at 300 watt, 100° C. for 1 h. The material was passed through a silica plug, eluting with DCM. The filtrate was concentrated in vacuo, purified by silica gel chromatography, eluting with 4% (7N NH$_3$ in MeOH) in DCM. MS (ES+): m/z 387.95 (100) [MH$^+$]. HPLC: t$_R$=2.99 min (OpenLynx, polar_5 min).

Examples 289-297 were prepared by a Suzuki coupling reaction analogous to that described above for 7-cyclobutyl-5-(4-phenoxyphenyl)-imidazo[5,1-f][1,2,4]triazin-4-ylamine, using correspondent boronic acids or boronates.

Boronic acids and boronates:

Examples 289-297 were prepared by a Suzuki coupling reaction analogous to that described above for 7-cyclobutyl-5-(4-phenoxyphenyl)-imidazo[5,1-f][1,2,4]triazin-4-ylamine, using correspondent boronic acids or boronates.

Boronic acids and boronates:

4,4,5,5-Tetramethyl-2-(2-methyl-4-phenoxy-phenyl)-[1,3,2]dioxaborolane

To a stirred mixture of 1-bromo-2-methyl-4-phenoxybenzene (90.00 mg, 0.34 mmol), bis(pinacolato)diboron (112.9 mg, 0.44 mmol) and AcOK (117.5 mg, 1.197 mmol) in 1,4-dioxane (9.00 mL, 115 mmol) was added (1,1'bis-(diphenylphosphino)-ferrocene)palladium dichloride (10 mg, 0.02 mmol). The resulting mixture was then stirred at 80° C. under nitrogen for 3 hours. Then this mixture was passed through a short silica gel column to remove insoluble material. The solvent was then removed under reduced pressure to give crude product which was used for next step without further purification.

1-Bromo-2-methyl-4-phenoxybenzene

Into a 100 mL round bottom flask was added 4-bromo-3-methylphenol (0.90 g, 0.0048 mol), phenylboronic acid (2.4 g, 0.019 mol), cupric acetate (1.4 g, 0.0077 mol) and DCM (49.99 mL). TEA (4.0 mL, 0.029 mol) was then added followed by 4 A° molecular sieves and the reaction mixture was stirred at rt over night. Reaction mixture was then filtered through celite. The filtrate was concentrated in vacuo to give a residue which was purified by silica gel chromatography, eluting with 5% EtOAc in hexane. $^1$H NMR (400 MHz, CDCl$_3$): δ=2.35 (s, 3H), 6.72 (dd, J=8.59, 3.03 Hz, 1H), 6.91 (d, J=2.78 Hz, 1H), 6.98-7.05 (m, 2H), 7.08-7.16 (m, 1H), 7.31-7.38 (m, 2H), 7.46 (d, J=8.59 Hz, 1H).

2-[4-(3-Fluoro-phenoxy)-3-methoxy-phenyl]-4,4,5,5-tetramethyl-[1,3,2]dioxaborolane Prepared according to general Method I for borylation described above for preparation of 4,4,5,5-tetramethyl-2-(2-methyl-4-phenoxy-phenyl)-[1,3,2]dioxaborolane.

4-Bromo-1-(3-fluorophenoxy)-2-methoxybenzene

4-Bromo-2-methoxyphenol (1.4 g, 0.0071 mol), 3-fluorobenzeneboronic acid (500 mg, 0.004 mol), TEA (3.0 mL, 0.021 mol), cupric acetate (1.0 g, 0.0057 mol) and DCM (40 mL, 0.6 mol) were added to a 100 mL oven dried flask and the reaction was stirred at rt for 48 h. Reaction mixture was then filtered through celite. The filtrate was concentrated in vacuo to give a residue which was purified by silica gel chromatography, eluting with 5% EtOAc in hexane. $^1$H NMR (400 MHz, CDCl$_3$): δ=3.71 (s, 3H), 6.52 (dt, J=10.36, 2.40 Hz, 1H), 6.57-6.69 (m, 2H), 6.81 (d, J=8.34 Hz, 1H), 6.99 (dd, J=8.34, 2.27 Hz, 1H), 7.04 (d, J=2.27 Hz, 1H), 7.13 (td, J=8.34, 6.82 Hz, 1H).

2-(2-Fluoro-5-methoxy-4-phenoxy-phenyl)-4,4,5,5-tetramethyl-[1,3,2]dioxaborolane Prepared according to general Method I for borylation described above for preparation of 4,4,5,5-tetramethyl-2-(2-methyl-4-phenoxy-phenyl)-[1,3,2]dioxaborolane.

1-Bromo-2-fluoro-5-methoxy-4-phenoxybenzene

4-Bromo-5-fluoro-2-methoxyphenol (500 mg, 0.002 mol), phenylboronic acid (0.73 g, 0.0060 mol), TEA (2.0 mL, 0.014 mol), cupric acetate (0.70 g, 0.0038 mol) and DCM (20 mL, 0.4 mol) were added to a 100 mL oven dried flask and the reaction was stirred at rt for 48 h. Reaction mixture was then filtered through celite. The filtrate was concentrated in vacuo to give a residue which was purified by silica gel chromatography, eluting with 5% EtOAc in hexane. $^1$H NMR (400 MHz, CDCl$_3$): δ=3.83 (s, 3H), 6.73 (d, J=9.09 Hz, 1H), 6.94-7.00 (m, 2H), 7.07-7.15 (m, 2H), 7.34 (dd, J=8.59, 7.58 Hz, 2H).

2-(3,5-Dimethoxy-4-phenoxy-phenyl)-4,4,5,5-tetramethyl-[1,3,2]dioxaborolane

Prepared according to general Method I for borylation described above for preparation of 4,4,5,5-tetramethyl-2-(2-methyl-4-phenoxy-phenyl)-[1,3,2]dioxaborolane.

5-Bromo-1,3-dimethoxy-2-phenoxybenzene 4-bromo-2,6-dimethoxyphenol (500 mg, 0.002 mol), phenylboronic acid (0.65 g, 0.0054 mol), TEA (1.8 mL, 0.013 mol), cupric acetate (0.62 g, 0.0034 mol) and DCM (30 mL, 0.4 mol) were added to a 100 mL oven dried flask and the reaction was stirred at rt for 48 h. Reaction mixture was then filtered through celite. The filtrate was concentrated in vacuo to give a residue which was purified by silica gel chromatography, eluting with 5% EtOAc in hexane. $^1$H NMR (400 MHz, CDCl$_3$): δ=3.77 (s, 6H), 6.82 (s, 2H), 6.86 (d, J=7.83 Hz, 2H), 6.96-7.04 (m, 1H), 7.22-7.27 (m, 2H).

2-(2,3-Difluoro-4-phenoxy-phenyl)-4,4,5,5-tetramethyl-[1,3,2]dioxaborolane

Prepared according to general Method I for borylation described above for preparation of 4,4,5,5-tetramethyl-2-(2-methyl-4-phenoxy-phenyl)-[1,3,2]dioxaborolane.

1-Bromo-2,3-difluoro-4-phenoxybenzene 4-bromo-2,3-difluorophenol (1.0 g, 0.0048 mol), phenylboronic acid (1.4 g, 0.012 mol), TEA (4.0 mL, 0.029 mol), cupric acetate (1.4 g, 0.0076 mol) and DCM (60 mL, 1 mol) were added to a 100 mL oven dried flask and the reaction was stirred at rt for 48 h. Reaction mixture was then filtered through celite. The filtrate was concentrated in vacuo to give a residue which was purified by silica gel chromatography, eluting with 5% EtOAc in hexane. $^1$H NMR (400 MHz, CDCl$_3$): δ=6.70 (ddd, J=9.22, 7.33, 2.15 Hz, 1H), 6.95-7.02 (m, 2H), 7.15 (t, J=7.45 Hz, 1H), 7.23 (ddd, J=9.16, 6.88, 2.40 Hz, 1H), 7.31-7.38 (m, 2H).

2-(5-Methoxy-2-methyl-4-phenoxy-phenyl)-4,4,5,5-tetramethyl-[1,3,2]dioxaborolane Prepared according to general Method I for borylation described above for preparation of 4,4,5,5-tetramethyl-2-(2-methyl-4-phenoxy-phenyl)-[1,3,2]dioxaborolane.

1-Bromo-5-methoxy-2-methyl-4-phenoxybenzene

4-Bromo-2-methoxy-5-methylphenol (500 mg, 0.002 mol), phenylboronic acid (0.70 g, 0.0058 mol), TEA (1.9 mL, 0.014 mol), cupric acetate (0.67 g, 0.0037 mol) and DCM (30 mL) were added to a 100 mL oven dried flask and the reaction mixture was stirred at rt for 48 h. Reaction mixture was then filtered through celite. The filtrate was concentrated in vacuo to give a residue which was purified by silica gel chromatography, eluting with 5% EtOAc in hexane. $^1$H NMR (400 MHz, CDCl$_3$): δ=2.27 (s, 3H), 3.79 (s, 3H), 6.84 (s, 1H), 6.88-6.96 (m, 2H), 7.00-7.08 (m, 1H), 7.15 (s, 1H), 7.23-7.33 (m, 2H).

2-(2-Methoxy-4-phenoxy-phenyl)-4,4,5,5-tetramethyl-[1,3,2]dioxaborolane

Prepared according to general Method I for borylation described above for preparation of 4,4,5,5-tetramethyl-2-(2-methyl-4-phenoxy-phenyl)-[1,3,2]dioxaborolane.

1-Bromo-2-methoxy-4-phenoxybenzene 4-bromo-3-methoxyphenol (2.0 g, 0.0098 mol), phenylboronic acid (3.0 g, 0.025 mol), TEA (8.2 mL, 0.059 mol), cupric acetate (2.9 g, 0.016 mol) and DCM (100 mL) were added to a 100 mL oven dried flask and the reaction was stirred at rt for 48 h. Reaction mixture was then filtered through celite. The filtrate was concentrated in vacuo to give a residue which was purified by silica gel chromatography, eluting with 5% EtOAc in hexane. $^1$H NMR (400 MHz, CDCl$_3$): δ=3.81 (s, 3H), 6.45 (dd, J=8.72, 2.65 Hz, 1H), 6.61 (d, J=2.53 Hz, 1H), 7.01 (d, J=8.34 Hz, 2H), 7.12 (t, J=7.33 Hz, 1H), 7.34 (t, J=7.96 Hz, 2H), 7.42 (d, J=8.59 Hz, 1H).

2-(2-Chloro-4-phenoxy-phenyl)-4,4,5,5-tetramethyl-[1,3,2]dioxaborolane

Prepared according to general Method I for borylation described above for preparation of 4,4,5,5-tetramethyl-2-(2-methyl-4-phenoxy-phenyl)-[1,3,2]dioxaborolane.

1-Bromo-2-chloro-4-phenoxybenzene (5973-26)

4-bromo-3-chlorophenol (2.0 g, 0.0096 mol), phenylboronic acid (3.5 g, 0.029 mol), TEA (8.1 mL, 0.058 mol), cupric acetate (3.2 g, 0.017 mol) and DCM (40 mL) were added to a 100 mL oven dried flask and the reaction was stirred at rt for 24 h. Reaction mixture was then filtered through celite. The filtrate was concentrated in vacuo to give a residue which was purified by silica gel chromatography, eluting with 5% EtOAc in hexane. $^1$H NMR (400 MHz, CDCl$_3$): δ=6.74 (dd, J=8.84, 2.78 Hz, 1H), 6.94-7.02 (m, 2H), 7.06 (d, J=2.78 Hz, 1H), 7.14 (t, J=7.33 Hz, 1H), 7.29-7.38 (m, 2H), 7.48 (d, J=8.84 Hz, 1H).

4,4,5,5-Tetramethyl-2-(4-phenoxy-2-trifluoromethoxy-phenyl)-[1,3,2]dioxaborolane Prepared according to general Method I for borylation described above for preparation of 4,4,5,5-tetramethyl-2-(2-methyl-4-phenoxy-phenyl)-[1,3,2]dioxaborolane.

1-Bromo-4-phenoxy-2-trifluoromethoxybenzene

4-Bromo-3-(trifluoromethoxy)phenol (1.0 g, 0.0039 mol), phenylboronic acid (1900 mg, 0.016 mol), TEA (3.2 mL, 0.023 mol), cupric acetate (1.3 g, 0.0070 mol) and DCM (40 mL) were added to a 100 mL oven dried flask and the reaction was stirred at rt for 48 h. Reaction mixture was then filtered through celite. The filtrate was concentrated in vacuo to give a residue which was purified by silica gel chromatography, eluting with 5% EtOAc in hexane. $^1$H NMR (400 MHz, CDCl$_3$): δ=6.82 (dd, J 8.97, 2.65 Hz, 1H), 7.00 (dd, J=2.78, 1.26 Hz, 1H), 7.02-7.10 (m, 2H), 7.16-7.24 (m, 1H), 7.36-7.45 (m, 2H), 7.55 (d, J=8.84 Hz, 1H).

2-(3-Chloro-4-phenoxy-phenyl)-4,4,5,5-tetramethyl-[1,3,2]dioxaborolane

Prepared according to general Method I for borylation described above for preparation of 4,4,5,5-tetramethyl-2-(2-methyl-4-phenoxy-phenyl)-[1,3,2]dioxaborolane.

4-Bromo-2-chloro-1-phenoxybenzene

Into a 100 mL round bottom flask was added phenol, 4-bromo-2-chloro-(1.0 g, 0.0048 mol), phenylboronic acid (2.4 g, 0.019 mol), cupric acetate (1.4 g, 0.0077 mol) and DCM (50.00 mL). TEA (4.0 mL, 0.029 mol) was then added and the reaction mixture was stirred at rt for 24 h. Reaction mixture was then filtered through celite. The filtrate was concentrated in vacuo to give a residue which was purified by silica gel chromatography, eluting with 5% EtOAc in hexane. $^1$H NMR (400 MHz, CDCl$_3$): δ=6.86 (d, J=8.84 Hz, 1H), 6.94-7.07 (m, 2H), 7.10-7.19 (m, 1H), 7.30-7.41 (m, 3H), 7.63 (d, J=2.27 Hz, 1H).

2-(3-Methoxy-4-o-tolyloxy-phenyl)-4,4,5,5-tetramethyl-[1,3,2]dioxaborolane

Prepared according to general Method I for borylation described above for preparation of 4,4,5,5-tetramethyl-2-(2-methyl-4-phenoxy-phenyl)-[1,3,2]dioxaborolane.

4-Bromo-2-methoxy-1-o-tolyloxybenzene

4-Bromo-2-methoxyphenol (1.0 g, 0.0049 mol), (2-methylphenyl)boronic acid (1.7 g, 0.012 mol), TEA (4.1 mL, 0.030 mol), cupric acetate (1.4 g, 0.0079 mol) and DCM (50 mL) were added to a 100 mL oven dried flask and the reaction was stirred at rt for 48 h. Reaction mixture was then filtered through celite. The filtrate was concentrated in vacuo to give a residue which was purified by silica gel chromatography, eluting with 5% EtOAc in hexane. $^1$H NMR (400 MHz, CDCl$_3$): δ=2.28 (s, 3H), 3.88 (s, 3H), 6.61 (d, J=8.59 Hz, 1H), 6.78 (d, J=8.08 Hz, 1H), 6.99 (dd, J=8.59, 2.02 Hz, 1H), 7.04 (t, J=7.33 Hz, 1H), 7.09-7.17 (m, 2H), 7.24 (d, J=7.33 Hz, 1H).

2-(3-Methoxy-4-m-tolyloxy-phenyl)-4,4,5,5-tetramethyl-[1,3,2]dioxaborolane

Prepared according to general Method I for borylation described above for preparation of 4,4,5,5-tetramethyl-2-(2-methyl-4-phenoxy-phenyl)-[1,3,2]dioxaborolane.

4-Bromo-2-methoxy-1-m-tolyloxybenzene

4-Bromo-2-methoxyphenol (1.0 g, 0.0049 mol), 3-methylbenzeneboronic acid (1.7 g, 0.012 mol), TEA (4.1 mL, 0.030 mol), cupric acetate (1.4 g, 0.0079 mol) and DCM (50 mL) were added to a 100 mL oven dried flask and the reaction was stirred at rt for 48 h. Reaction mixture was then filtered through celite. The filtrate was concentrated in vacuo to give a residue which was purified by silica gel chromatography, eluting with 5% EtOAc in hexane. $^1$H NMR (400 MHz, CDCl$_3$): δ=2.31 (s, 3H), 3.83 (s, 3H), 6.68-6.77 (m, 2H), 6.82 (d, J=8.34 Hz, 1H), 6.87 (d, J=7.58 Hz, 1H), 7.03 (dd, J=8.46, 2.15 Hz, 1H), 7.11 (d, J=2.27 Hz, 1H), 7.17 (t, J=7.83 Hz, 1H).

2-(2,5-Difluoro-4-phenoxy-phenyl)-4,4,5,5-tetramethyl-[1,3,2]dioxaborolane

Prepared according to general Method I for borylation described above for preparation of 4,4,5,5-tetramethyl-2-(2-methyl-4-phenoxy-phenyl)-[1,3,2]dioxaborolane.

1-Bromo-2,5-difluoro-4-phenoxybenzene

4-Bromo-2,5-difluorophenol (500 my, 0.002 mol), phenylboronic acid (0.73 g, 0.0060 mol), TEA (2.0 mL, 0.014 mol), cupric acetate (0.70 g, 0.0038 mol) and DCM (20 mL) were added to a 100 mL oven dried flask and the reaction was stirred at rt for 48 h. Reaction mixture was then filtered through celite. The filtrate was concentrated in vacuo to give a residue which was purified by silica gel chromatography, eluting with 5% EtOAc in hexane. $^1$H NMR (400 MHz, CDCl$_3$): δ=6.81 (dd, J=8.84, 7.07 Hz, 1H), 6.98-7.08 (m, 2H), 7.19 (t, J=7.45 Hz, 1H), 7.31-7.48 (m, 3H).

[2-Fluoro-4-(4,4,5,5-tetramethyl-[1,3,2]dioxaborolan-2-yl)-phenyl]-phenyl-methanone Prepared according to general Method I for borylation described above for preparation of 4,4,5,5-tetramethyl-2-(2-methyl-4-phenoxy-phenyl)-[1,3,2]dioxaborolane.

(4-Bromo-2-fluorophenyl)-phenylmethanone

In an oven dried flask was added 2-fluoro-4-bromobenzoic acid (1.0 g, 0.0046 mol), thionyl chloride (0.77 mL, 0.010 mol) and a drop of DMF and the reaction was refluxed for 2 h. The excess thionyl chloride was then distilled off and the residual thionyl chloride was removed on the high vacuum pump. Benzene (20 mL, 0.2 mol) and aluminum trichloride (0.676 g, 0.00507 mol) were added to the reaction mixture. The reaction mixture was stirred at room temp for 1 h. The crude reaction mixture was poured onto ice and conc. HCl (15 mL). The organic layer was separated and the aqueous layer extracted with EtOAc. The combined organic phases were washed with 5% aq NaOH solution, water and dried (Na$_2$SO$_4$). The organic phase was concentrated in vacuo to give a residue which was purified by silica gel chromatography, eluting with 2% EtOAc in hexane. $^1$H NMR (400 MHz, CDCl$_3$): δ=7.32-7:41 (m, 1H), 7.42-7.53 (m, 4H), 7.56-7.67 (m, 1H), 7.77-7.88 (m, 2H). MS (ES$^+$): m/z 280.78 (40) [MH$^+$]. HPLC: $t_R$=3.8 min(Open Lynx polar__5 min).

Phenyl-[4-(4,4,5,5-tetramethyl-[1,3,2]dioxaborolan-2-yl)-phenyl]-amine

Prepared according to general Method I for borylation described above for preparation of 4,4,5,5-tetramethyl-2-(2-methyl-4-phenoxy-phenyl)-[1,3,2]dioxaborolane.

[3-Fluoro-4-(4,4,5,5-tetramethyl-[1,3,2]dioxaborolan-2-yl)-phenyl]-phenyl-methanone Prepared according to general Method I for borylation described above for preparation of 4,4,5,5-tetramethyl-2-(2-methyl-4-phenoxy-phenyl)-[1,3,2]dioxaborolane.

(4-Bromo-3-fluorophenyl)-phenylmethanone

In an oven dried flask was added 4-bromo-3-fluorobenzoic acid (1.0 g, 0.0046 mol), thionyl chloride (0.65 mL, 0.0089 mol) and a drop of DMF and the reaction was refluxed for 2 h. The thionyl chloride was then distilled off and benzene (20 mL, 0.2 mol) and aluminum trichloride (0.576 g, 0.00432 mol) was added to the reaction mixture and the reaction was stirred at room temp for 1 h. The crude reaction mixture was poured onto ice and conc. HCl (15 mL). The organic layer was separated and the aqueous layer extracted with EtOAc. The combined organic phases were washed with 5% aq NaOH solution, water and dried (Na$_2$SO$_4$). The organic phase was concentrated in vacuo to give a residue which was purified by silica gel chromatography, eluting with 2% EtOAc in hexane. $^1$H NMR (400 MHz, CDCl$_3$): δ=7.45-7.55 (m, 3H), 7.58 (dd, J=8.84, 1.77 Hz, 1H), 7.60-7.66 (m, 1H), 7.70 (dd, J=8.21, 6.69 Hz, 1H), 7.75-7.82 (m, 2H).

2-[4-(2,2-Difluoro-1-phenyl-vinyl)-phenyl]-4,4,5,5-tetramethyl-[1,3,2]dioxaborolane Prepared according to general Method I for borylation described above for preparation of 4,4,5,5-tetramethyl-2-(2-methyl-4-phenoxy-phenyl)-[1,3,2]dioxaborolane.

1-Bromo-4-(2,2-difluoro-1-phenylvinyl)-benzene (5973-20)

Into an oven-dried flask was added diethyl(difluoromethane)phosphonate (0.72 g, 0.0038 mol) followed by THF (30 mL, 0.4 mol) and the flask was kept at −78° C. 2 M LDA in THF (2 mL) was then added slowly and the reaction mixture was stirred at the same temp for 45 min. A solution of methanone (4-bromophenyl)phenyl-(500 mg, 0.002 mol) in THF was then slowly added via canula and the reaction was allowed to warm up to rt and stirred for 2 h. Reaction mixture was allowed to stir at 60° C. overnight. Reaction was quenched with aq. NaHCO$_3$ solution and purification by flash column chromatography using 1% EtOAc in hexanes to afforded the title compound. $^1$H NMR (400 MHz, CDCl$_3$): δ=7.05-7.16 (m, 2H), 7.19-7.26 (m, 2H), 7.26-7.37 (m, 3H), 7.42-7.49 (m, 2H).

2-(2-Ethoxy-4-phenoxy-phenyl)-4,4,5,5-tetramethyl-[1,3,2]dioxaborolane

Prepared according to general Method I for borylation described above for preparation of 4,4,5,5-tetramethyl-2-(2-methyl-4-phenoxy-phenyl)-[1,3,2]dioxaborolane.

1-Bromo-2-ethoxy-4-phenoxybenzene

To a stirred solution of 2-bromo-5-phenoxyphenol (120 mg, 0.45 mmol) in acetone (7 mL) was added potassium carbonate (0.375 g, 2.72 mol) followed by iodoethane (0.0724 mL, 0.905 mol) at rt. The mixture was stirred at rt overnight. Reaction mixture was concentrated down in vacuo and washed with brine extracting with EtOAc. The organics were combined, dried over Na$_2$SO$_4$ and concentrated to afford the title compound which was used for next step without further purification. $^1$H NMR (400 MHz, CDCl$_3$): δ=1.37 (t, J=6.95 Hz, 3H), 3.95 (q, J=7.07 Hz, 2H), 6.37 (dd, J=8.59, 2.78 Hz, 1H), 6.52 (d, J=2.53 Hz, 1H), 6.90-6.97 (m, 2H), 7.00-7.08 (m, 1H), 7.22-7.30 (m, 2H), 7.36 (d, J=8.59 Hz, 1H).

2-Bromo-5-phenoxy-phenol

To a solution of 1-bromo-2-methoxy-4-phenoxy-benzene (100.00 mg, 0.35 mmol) in DCM (5 mL) was slowly added boron tribromide (0.16 mL, 1.53 mmol) at −20° C. The reaction was stirred at that temperature for 2 h. The reaction mixture was concentrated in vacuo and dried on the pump. The crude reaction mixture was used for next step without further purification.

2-Phenoxy-5-(4,4,5,5-tetramethyl-[1,3,2]dioxaborolan-2-yl)-phenol

To a solution of 2-(3-methoxy-4-phenoxyphenyl)-4,4,5,5-tetramethyl-[1,3,2]dioxaborolane (50 mg, 0.0002 mol) in DCM (3 mL) was slowly added boron tribromide (0.145 mL, 0.00153 mol) at −20° C. The reaction was stirred at that temperature for 2 h. The reaction mixture was concentrated in vacuo and dried on the pump. The crude reaction mixture was used for next step without further purification.

(4-Dihydroxyboranyl-phenyl)-phenyl-methanone O-methyl-oxime

A solution of 4-benzoyl phenyl boronic acid (226.00 mg, 1.00 mmol) and methoxyl amine hydrochloride (101.00 mg, 1.20 mmol) in pyridine (5 mL) and EtOH (5 mL) was refluxed at 125° C. for 24 h. Reaction was then concentrated in vacuo to give a crude product which was used for next step without further purification. MS (ES$^+$): m/z 256.00 (100)[MH$^+$]. HPLC: $t_R$=3.17 min (Open Lynx polar__5 min).

2-[4-(2,6-Difluoro-phenoxy)-phenyl]-4,4,5,5-tetramethyl-[1,3,2]dioxaborolane

Prepared according to general Method I for borylation described above for preparation of 4,4,5,5-tetramethyl-2-(2-methyl-4-phenoxy-phenyl)-[1,3,2]dioxaborolane.

2-(4-Bromophenoxy)-1,3-difluorobenzene

Into a 100 mL round bottom flask was added 4-bromophenol (2.19 g, 12.7 mmol), 2,6-difluorophenylboronic acid (1.00 g, 6.33 mmol), cupric acetate (1.4 g, 7.70 mmol) and DCM (50 mL). TEA (4.0 mL, 29.0 mmol) was then added followed by 4 A° molecular sieves and the reaction mixture was stirred at rt for 48 h with an air balloon to supply oxygen. Purification by flash column chromatography using 5% EtOAc in hexanes afforded the title compound as a colorless oil.

4,4,5,5-Tetramethyl-2-(3-methyl-4-phenoxy-phenyl)-[1,3,2]dioxaborolane

Prepared according to general Method I for borylation described above for preparation of 4,4,5,5-tetramethyl-2-(2-methyl-4-phenoxy-phenyl)-[1,3,2]dioxaborolane.

4-Bromo-2-methyl-1-phenoxybenzene

Into a 100 mL round bottom flask was added 4-bromo-3-methylphenol (1.00 g, 5.35 mmol), benzeneboronic acid (1.30 g, 10.7 mmol), cupric acetate (1.4 g, 7.70 mmol) and DCM (50 mL). TEA (4.0 mL, 29.0 mmol) was then added followed by 4 A° molecular sieves and the reaction mixture was stirred at rt for 48 h. Reaction mixture was then filtered through celite. The filtrate was concentrated in vacuo to give a residue which was purified by silica gel chromatography, eluting with 5% EtOAc in hexane.

4,4,5,5-Tetramethyl-2-[4-(2-nitro-phenoxy)-phenyl]-[1,3,2]dioxaborolane

Prepared according to general Method I for borylation described above for preparation of 4,4,5,5-tetramethyl-2-(2-methyl-4-phenoxy-phenyl)-[1,3,2]dioxaborolane.

2-(4-Bromophenoxy)-nitrobenzene

Into a 100 mL round bottom flask was added 4-bromophenol (2.07 g, 12.0 mmol), 2-nitrophenylboronic acid (1.00 g, 5.99 mmol), cupric acetate (1.4 g, 7.70 mmol) and DCM (50 mL). TEA (4.0 mL, 29.0 mmol) was then added followed by 4 A° molecular sieves and the reaction mixture was stirred at rt for 48 h. Reaction mixture was then filtered through celite. The filtrate was concentrated in vacuo to give a residue which was purified by silica gel chromatography, eluting with 5% EtOAc in hexane.

2-[4-(2-Fluoro-6-methoxy-phenoxy)-phenyl]-4,4,5,5-tetramethyl-[1,3,2]dioxaborolane Prepared according to general Method I for borylation described above for preparation of 4,4,5,5-tetramethyl-2-(2-methyl-4-phenoxy-phenyl)-[1,3,2]dioxaborolane.

2-(4-Bromophenoxy)-1-fluoro-3-methoxybenzene

Into a 100 mL round bottom flask was added 4-bromophenol (2.04 g, 11.8 mmol), 6-fluoro-2-methoxyphenylboronic acid (1.00 g, 5.88 mmol), cupric acetate (1.4 g, 7.70 mmol) and DCM (50 mL). TEA (4.0 mL, 29.0 mmol) was then added followed by 4 A° molecular sieves and the reaction mixture was stirred at rt for 48 h. Reaction mixture was then filtered through celite. The filtrate was concentrated in vacuo to give a residue which was purified by silica gel chromatography, eluting with 5% EtOAc in hexane.

2-[4-(4,4,5,5-Tetramethyl-[1,3,2]dioxaborolan-2-yl)-phenoxy]-pyridine

Prepared according to general Method I for borylation described above for preparation of 4,4,5,5-tetramethyl-2-(2-methyl-4-phenoxy-phenyl)-[1,3,2]dioxaborolane.

2-(3-Chloro-5-methyl-4-phenoxy-phenyl)-4,4,5,5-tetramethyl-[1,3,2]dioxaborolane Prepared according to general Method I for borylation described above for preparation of 4,4,5,5-tetramethyl-2-(2-methyl-4-phenoxy-phenyl)-[1,3,2]dioxaborolane.

5-Bromo-1-chloro-3-methyl-2-phenoxybenzene

Into a 100 mL round bottom flask was added 4-bromo-2-chloro-6-methylphenol (1.00 g, 4.52 mmol), benzeneboronic acid (1.10 g, 9.04 mmol), cupric acetate (1.4 g, 7.70 mmol) and DCM (50 mL). TEA (4.0 mL, 29.0 mmol) was then added followed by 4 A° molecular sieves and the reaction mixture was stirred at rt for 48 h. Reaction mixture was then filtered through celite. The filtrate was concentrated in vacuo to give a residue which was purified by silica gel chromatography, eluting with 5% EtOAc in hexane.

4,4,5,5-Tetramethyl-2-(3-nitro-4-phenoxy-phenyl)-[1,3,2]dioxaborolane

Prepared according to general Method I for borylation described above for preparation of 4,4,5,5-tetramethyl-2-(2-methyl-4-phenoxy-phenyl)-[1,3,2]dioxaborolane.

4-Bromo-2-nitro-1-phenoxybenzene

A mixture of 5-bromo-2-fluoronitrobenzene (1.10 g, 5.0 mmol), phenol (0.52 g, 5.5 mmol) and $K_2CO_3$ powder (0.83 g, 5.0 mmol) in DMF (10 mL) was stirred at 80° C. for 3 h. The mixture was concentrated under reduced pressure, and the residue was partitioned between AcOEt and water. The separated organic layer was washed with 1M aqueous HCl and saturated NaCl solution. After the organic layer was dried over $Na_2SO_4$, the solvent was removed to give desired product which was used for next step without further purification.

[2-Chloro-4-(4,4,5,5-tetramethyl-[1,3,2]dioxaborolan-2-yl)-phenyl]-phenyl-methanone Prepared according to general Method I for borylation described above for preparation of 4,4,5,5-tetramethyl-2-(2-methyl-4-phenoxy-phenyl)-[1,3,2]dioxaborolane.

(4-Bromo-2-chlorophenyl)-phenylmethanone

In an oven dried flask was added 2-fluoro-4-bromobenzoic acid (1.00 g, 4.25 mmol), thionyl chloride (0.77 mL, 0.010 mol) and a drop of DMF and the reaction was refluxed for 2 h. The excess thionyl chloride was then distilled off and the residual thionyl chloride was removed on the pump. Benzene (20 mL, 0.2 mol) and aluminum trichloride (0.676 g, 5.07 mmol) were added to the reaction mixture. The reaction mixture was stirred at room temp for 1 h. The crude reaction mixture was poured onto ice and conc. HCl (15 mL). The organic layer was separated and the aqueous layer extracted with EtOAc. The combined organic phases were washed with 5% aq NaOH solution, water and dried ($Na_2SO_4$). The organic phase was concentrated in vacuo to give a residue which was purified by silica gel chromatography, eluting with 2% EtOAc in hexane.

3-Methoxy-4-(4,4,5,5-tetramethyl-[1,3,2]dioxaborolan-2-yl)-phenyl]-phenyl-methanone Prepared according to general Method I for borylation described above for preparation of 4,4,5,5tetramethyl-2-(2-methyl-4-phenoxy-phenyl)-[1,3,2]dioxaborolane.

(4-Bromo-3-methoxyphenyl)-phenylmethanone

In an oven dried flask was added 4-bromo-3-methoxybenzoic acid (1.00 g, 4.33 mmol), thionyl chloride (0.77 mL, 0.010 mol) and a drop of DMF and the reaction was refluxed for 2 h. The excess thionyl chloride was then distilled off and the residual thionyl chloride was removed oh the pump. Benzene (20 mL, 0.2 mol) and aluminum trichloride (0.676 g, 5.07 mmol) were added to the reaction mixture. The reaction mixture turned yellow in color on addition of $AlCl_3$. The reaction mixture was stirred at room temp for 1 h. The crude reaction mixture was poured onto ice and conc HCl (15 mL). The organic layer was separated and the aqueous layer extracted with EtOAc. The combined organic phases were washed with 5% aq NaOH solution, water and dried ($Na_2SO_4$). The organic phase was concentrated in vacuo to give a residue which was purified by silica gel chromatography, eluting with 2% EtOAc in hexane.

3-Methyl-4-(4,4,5,5-tetramethyl-[1,3,2]dioxaborolan-2-yl)-phenyl]-phenyl-methanone Prepared according to general Method I for borylation described above for preparation of 4,4,5,5-tetramethyl-2-(2-methyl-4-phenoxy-phenyl)-[1,3,2]dioxaborolane.

(4-Bromo-3-methylphenyl)-phenylmethanone

In an oven dried flask was added 4-bromo-3-methylbenzoic acid (1.00 g, 4.65 mmol), thionyl chloride (0.77 mL, 0.010 mol) and a drop of DMF and the reaction was refluxed for 2 h. The excess thionyl chloride was then distilled off and the residual thionyl chloride was removed on the pump. Benzene (20 mL, 0.2 mol) and aluminum trichloride (0.676 g, 5.07 mmol) were added to the reaction mixture. The reaction mixture turned yellow in color on addition of $AlCl_3$. The reaction mixture was stirred at room temp for 1 h. The crude reaction mixture was poured onto ice and conc HCl (15 mL). The organic layer was separated and the aqueous layer extracted with EtOAc. The combined organic phases were washed with 5% aq NaOH solution, water and dried ($Na_2SO_4$). The organic phase was concentrated in vacuo to give a residue which was purified by silica gel chromatography, eluting with 2% EtOAc in hexane.

[3-Chloro-4-(4,4,5,5-tetramethyl-[1,3,2]dioxaborolan-2-yl)-phenyl]-phenyl-methanone Prepared according to general Method I for borylation described above for preparation of 4,4,5,5-tetramethyl-2-(2-methyl-4-phenoxy-phenyl)-[1,3,2]dioxaborolane.

(4-Bromo-3-chlorophenyl)-phenylmethanone

In an oven dried flask was added 4-bromo-3-chlorobenzoic acid (1.00 g, 4.25 mmol), thionyl chloride (0.77 mL, 0.010 mol) and a drop of DMF and the reaction was refluxed for 2 h. The excess thionyl chloride was then distilled off and the residual thionyl chloride was removed on the pump. Benzene (20 mL, 0.2 mol) and aluminum trichloride (0.676 g, 5.07 mmol) were added to the reaction mixture. The reaction mixture turned yellow in color on addition of $AlCl_3$. The reaction mixture was stirred at room temp for 1 h. The crude reaction mixture was poured onto ice and conc HCl (15 mL). The organic layer was separated and the aqueous layer extracted with EtOAc. The combined organic phases were washed with 5% aq NaOH solution, water and dried ($Na_2SO_4$). The organic phase was concentrated in vacuo to give a residue which was purified by silica gel chromatography, eluting with 2% EtOAc in hexane.

2-(4-Cyclopentyloxy-phenyl)-4,4,5,5-tetramethyl-[1,3,2]dioxaborolane

Prepared according to general Method I for borylation described above for preparation of 4,4,5,5-tetramethyl-2-(2-methyl-4-phenoxy-phenyl)-[1,3,2]dioxaborolane.

1-Bromo-4-cyclopentyloxy-benzene

To a stirred mixture of 1-bromo-4-iodo-benzene, (1.00 g, 3.53 mmol), o-phenanthroline (255 mg, 1.41 mmol) and cyclopentanol (1.50 g, 17.44 mmol) in toluene (1.500 mL) was added copper(I) iodide (135.00 mg, 0.70 mmol) and $Cs_2CO_3$ (2.87 g, 8.83 mmol). The resulting mixture was then stirred at 120° C. in a sealed tube for 15 hours. The solvent was then removed under reduced pressure and the product was purified by flash chromatography (eluted by hexane).

2-(4-Cyclohexyloxy-phenyl)-4,4,5,5-tetramethyl-[1,3,2]dioxaborolane

Prepared according to general Method I for borylation described above for preparation of 4,4,5,5-tetramethyl-2-(2-methyl-4-phenoxy-phenyl)-[1,3,2]dioxaborolane.

1-Bromo-4-cyclohexyloxy-benzene

To a stirred mixture of 1-bromo-4-iodo-benzene, (1.00 g, 3.53 mmol), o-phenanthroline (255 mg, 1.41 mmol) and cyclohexanol (1.770 g, 17.67 mmol) in toluene (1.500 mL) was added copper(I) iodide (135 mg, 0.707 mmol) and $Cs_2CO_3$ (2.879 g, 8.837 mmol). The resulting mixture was then stirred at 120° C. in a sealed tube for 15 hours. The solvent was then removed under reduced pressure and the product was purified by flash chromatography (eluted by hexane). $^1$H NMR (400 MHz, MeOD) δ1.32-1.65 (m, 6H), 1.77-1.86 (m, 2H), 1.94-2.03 (m, 2H), 4.24-4.37 (m, 1H), 6.81-6.90 (m, 2H), 7.36-7.41 (m, 2H).

1-Phenyl-5-(4,4,5,5-tetramethyl-[1,3,2]dioxaborolan-2-yl)-1H-benzoimidazole

Prepared from 5-bromo-1-phenyl-1H-benzoimidazole according to general Method I for borylation described above for preparation of 4,4,5,5-tetramethyl-2-(2-methyl-4-phenoxy-phenyl)-[1,3,2]dioxaborolane.

4,4,5,5-Tetramethyl-2-(2-nitro-4-phenoxy-phenyl)-[1,3,2]dioxaborolane

General Procedure II for Borylation: To s a stirred mixture of 1-chloro-2-nitro-4-phenoxybenzene (58.00 mg, 0.2323 mmol), bis(pinacolato)diboron (76.70 my, 0.3020 mmol) and potassium acetate (79.80 mg, 0.8131 mmol) in 1,4-dioxane (5.00 mL) was added 1,3-bis(2,6-diisopropylphenyl)imidazol-2-ylidene hydrochloride (15.0 mg, 0.035 mmol) and palladium (II) acetate (4.0 mg, 0.02 mmol). The resulting mixture was then stirred at 80° C. under nitrogen for 15 hours. The solvent was then removed under reduced pressure and the resulting residue was passed through a silica gel plug column (5% EtOAc in hexane) to remove inorganic salts. The fractions from the column were then combined, rotovapped to give a crude material which was then used in next step without further purification.

1-Chloro-2-nitro-4-phenoxybenzene

4-Chloro-3-nitrophenol (2.0 g, 0.012 mol), phenylboronic acid (3.5 g, 0.029 mol), TEA (9.6 mL, 0.069 mol), cupric acetate (3.3 g, 0.018 mol) and DCM (100 mL, 2 mol) were added to a 100 mL oven dried flask and the reaction was stirred at rt for 48 h. The solvent was then removed under reduced pressure and the resulting residue was purified by flash chromatography (5% EtOAc in Hexane).

2-(2-Ethyl-4-phenoxy-phenyl)-4,4,5,5-tetramethyl-[1,3,2]dioxaborolane

Prepared according to general Method II for borylation described above for preparation of 4,4,5,5-tetramethyl-2-(2-nitro-4-phenoxy-phenyl)-[1,3,2]dioxaborolane.

1-Chloro-2-ethyl-4-phenoxybenzene 3-ethyl-4-chlorophenol (2.0 g, 0.013 mol), phenylboronic acid (4.7 g, 0.038 mol), TEA (11 mL, 0.077 mol), cupric acetate (4.2 g, 0.023 mol) and DCM (60 mL, 0.9 mol) were added to a 100 mL oven dried flask and the reaction was stirred at rt for 24 h. The solvent was then removed under reduced pressure and the resulting residue was purified by flash chromatography (5% EtOAc in Hexane).

[2-Methoxy-4-(4,4,5,5-tetramethyl-[1,3,2]dioxaborolan-2-yl)-phenyl]-phenyl-methanone Prepared according to general Method II for borylation described above for preparation of 4,4,5,5-tetramethyl-2-(2-nitro-4-phenoxy-phenyl)-[1,3,2]dioxaborolane.

(4-Chloro-2-methoxyphenyl)-phenylmethanone

In an oven dried flask was added 2-methoxy-4-chlorobenzoic acid (1.0 g, 0.0054 mol), thionyl chloride (0.77 mL, 0.010 mol) and a drop of DMF and the reaction was refluxed for 2 h. The thionyl chloride was then distilled off and benzene (20 mL, 0.2 mol) and aluminum trichloride (0.676 g, 0.00507 mol) was added to the reaction mixture and the reaction was stirred at room temp for 1 h. The crude reaction mixture was poured onto ice and conc HCl (15 mL). The organic layer was separated and the aqueous layer extracted with EtOAc. The combined organic phases were washed with 5% aq NaOH solution, water and dried ($Na_2SO_4$). The organic phase was concentrated in vacuo to give a residue which was purified by silica gel chromatography, eluting with 2% EtOAc in hexane. $^1$H NMR (400 MHz, $CDCl_3$): δ=3.74 (s, 3H), 7.00 (d, J=1.77 Hz, 1H) 7.05 (dd, J=8.08, 1.77 Hz, 1H), 7.32 (d, J=8.08 Hz, 1H), 7.41-7.48 (m, 2H), 7.54-7.60 (m, 1H), 7.74-7.83 (m, 2H). MS ($ES^+$): m/z 246.83 (100) [$MH^+$]. HPLC: $t_R$=3.66 min (Open Lynx polar_5 min).

(Tetrahydro-pyran-2-yl)-[4-(4,4,5,5-tetramethyl-[1,3,2]dioxaborolan-2-yl)-phenyl]-methanone Prepared according to general Method II for borylation described above for preparation of 4,4,5,5-tetramethyl-2-(2-nitro-4-phenoxy-phenyl)-[1,3,2]dioxaborolane.

(4-Chloro-phenyl)-(tetrahydro-pyran-2-yl)-methanone

To a stirred solution of (4-chloro-phenyl)-(tetrahydro-pyran-2-yl)-methanol (70.00 mg, 0.30 mmol) in DCM (10 mL) was added $NaHCO_3$ (259.4 mg, 3.08 mmol) and Dess-Martin periodinane (196.4 mg, 0.46 mmol) at 0° C. The mixture was stirred at 0° C. for 2 hrs. The solvent was then removed under reduced pressure and the resulting residue was purified by a flash chromatography (eluting with 5% AcOEt in Hexane). $^1$H NMR (400 MHz, MeOD) δ 1.52-2.02 (m, 6H), 3.65-3.77 (m, 1H), 4.04-4.17 (m, 1H), 4.82-4.88 (m, 1H), 7.54 (d, J=8.50 Hz, 2H), 8.02 (d, J=8.50 Hz, 2H).

(4-Chloro-phenyl)-(tetrahydro-pyran-2-yl)-methanol

To a stirred solution of tetrahydro-pyran-2-carbaldehyde (114.00 mg, 1.00 mmol) in THF (10 mL) was added 4-chlorophenylmagnesium bromide (1.0 M in diethyl ether, 1.5 mL, 1.50 mmol) at −78° C. The mixture was stirred at −78° C. for 2 hrs. The solvent was then removed under reduced pressure and the resulting residue was purified by a flash chromatography (eluting with 20% AcOEt in Hexane).

4-(Tetrahydro-pyran-2-ylsulfanyl)-phenyl-boronic acid

To a stirred mixture of 4-mercaptophenylboronic acid (20.7 mg, 0.135 mmol) in DCM (2.00 mL) was added dihydropyran (0.06140 mL, 0.6730 mmol) and pyridinium p-toluenesulfonate (3.38 mg, 0.0135 mmol) at 0° C. The resulting mixture was then stirred at rt overnight. Solvent was then removed under reduced pressure to give crude product which was used for next step without further purification.

2-[4-(4,4,5,5-Tetramethyl-[1,3,2]dioxaborolan-2-yl)-benzyl]-tetrahydropyran

Prepared according to general Method II for borylation described above for preparation of 4,4,5,5-tetramethyl-2-(2-nitro-4-phenoxy-phenyl)-[1,3,2]dioxaborolane.

2-(4-Chloro-benzyl)-tetrahydropyran

To a stirred mixture of (4-chlorophenyl)dihydroxyborane (524.0 mg, 3.351 mmol), 2-aminocyclohexanol hydrochloride (42 mg, 0.28 mmol) and nickel iodide (87.3 mg, 0.279 mmol) in i-PrOH (10.00 mL) was added sodium hexamethyldisilazane (1.075 g, 5.864 mmol) at 0° C. Then the mixture was stirred at rt for 5 min before, 2-(bromomethyl)tetrahydro-2-H-pyran (500.00 mg, 2.79 mmol) was added by syringe. The resulting mixture was then stirred at 60° C. for 5 h. The solvent was then removed under reduced pressure and the resulting residue was purified by a flash chromatography(5% AcOEt in hexane). $^1$H NMR (400 MHz, MeOD) δ 1.20-1.34

(m, 1H), 1.43-1.62 (m, 4H), 1.75-1.85 (m, 1H), 2.61-2.80 (m, 2H), 3.36-3.54 (m, 2H), 3.85-3.95 (m, 1H), 7.12-7.32 (m, 4H).

1-Phenyl-1-[4-(4,4,5,5-tetramethyl-[1,3,2]dioxaborolan-2-yl)-phenyl]-ethanol

Prepared according to general Method I for borylation described above for preparation of 4,4,5,5-tetramethyl-2-(2-methyl-4-phenoxy-phenyl)-[1,3,2]dioxaborolane.

1-(4-Bromo-phenyl)-1-phenyl-ethanol

To a stirred solution of (4-bromophenyl)phenyl methanone (0.750 g, 2.87 mmol) in anhydrous THF (25.00 mL) was added solution of methylmagnesium bromide in THF (3.00 M, 1.91 mL) via a syringe at −78° C. The resulting mixture was stirred for 2 hours at −78° C. The reaction was quenched with 10 mL of a saturated aqueous $NH_4Cl$ solution at −78° C. and allowed to warm to rt. The product was extracted with EtOAc (2×) and brine (2×). The aqueous layer was back-extracted with DCM several times. The organic layers were combined, dried, filtered and concentrated in vacuo to give the product which was used for next step without any further purification. $^1H$ NMR (400 MHz, $CDCl_3$): δ 1.90 (3H, s) 7.19-7.33 (5H, m) 7.33-7.43 (4H, m).

[2-Nitro-4-(4,4,5,5-tetramethyl-[1,3,2]dioxaborolan-2-yl)-phenyl]-phenyl-methanone Prepared according to general Method I for borylation described above for preparation of 4,4,5,5-tetramethyl-2-(2-methyl-4-phenoxy-phenyl)-[1,3,2]dioxaborolane.

(4-Bromo-2-nitro-phenyl)-phenyl-methanone

In an oven dried flask was added 4-Bromo-2-nitro-benzoic acid (1.33 g, 0.0054 mol), thionyl chloride (0.77 mL, 0.010 mol) and a drop of DMF and the reaction was refluxed for 2 h. The thionyl chloride was then distilled off and benzene (20 mL) and aluminum trichloride (0.676 g, 0.0051 mol) was added to the reaction mixture and the reaction was stirred at room temp for 1 h. The crude reaction mixture was poured onto ice and conc HCl (15 mL). The organic layer was separated and the aqueous layer extracted with EtOAc. The combined organic phases were washed with 5% aq NaOH solution, water and dried ($Na_2SO_4$). The organic phase was concentrated in vacuo to give a residue which was purified by silica gel chromatography, eluting with 2% EtOAc in hexane.

Phenyl-[4-(4,4,5,5-tetramethyl-[1,3,2]dioxaborolan-2-yl)-naphthalen-1-yl]-methanone Prepared according to general Method I for borylation described above for preparation of 4,4,5,5-tetramethyl-2-(2-methyl-4-phenoxy-phenyl)-[1,3,2]dioxaborolane.

(4-Bromo-naphthalen-1-yl)-phenyl-methanone an oven dried flask was added 4-bromo-naphthalene-1-carboxylic acid In (1.36 g, 0.0054 mol), thionyl chloride (0.77 mL, 0.010 mol) and a drop of DMF and the reaction was refluxed for 2 h. The thionyl chloride was then distilled off and benzene (20 mL) and aluminum trichloride (0.676 g, 0.0051 mol) was added to the reaction mixture and the reaction was stirred at room temp for 1 h. The crude reaction mixture was poured onto ice and conc HCl (15 mL). The organic layer was separated and the aqueous layer extracted with EtOAc. The combined organic phases were washed with 5% aq NaOH solution, water and dried ($Na_2SO_4$). The organic phase was concentrated in vacuo to give a residue which was purified by silica gel chromatography, eluting with 2% EtOAc in hexane.

(4-Dihydroxyboranyl-phenyl)-phenyl-methanone oxime

A solution of 4-benzoyl phenyl boronic acid (226.00 mg, 1.00 mmol) and hydroxylamine hydrochloride (84.00 mg, 1.20 mmol) in pyridine (5 mL) and EtOH (5 mL) was refluxed at 125° C. for 24 h. Reaction was then concentrated in vacuo to give a crude product which was used for next step without further purification. MS ($ES^+$): m/z 241.89 (100)[$MH^+$]. HPLC: $t_R$=2.56 min (Open Lynx polar_5 min).

4,4,5,5-Tetramethyl-2-[4-(1-methyl-1-phenyl-ethyl)-phenyl]-[1,3,2]dioxaborolane

To a stirred mixture of trifluoro-methanesulfonic acid 4-(1-methyl-1-phenyl-ethyl)-phenyl ester (117.00 mg, 0.34 mmol), bis(pinacolato)diboron (112.9 mg, 0.44 mmol) and AcOK (117.5 mg, 1.197 mmol) in 1,4-dioxane (9.00 mL, 115 mmol) was added (1,1'bis-(diphenylphosphino)-ferrocene) palladium dichloride (10 mg, 0.02 mmol). The resulting mixture was then stirred at 80° C. under nitrogen for 3 hours, LCMS indicated starting material was consumed. Then this mixture was passed through a short silica gel column to remove insoluble material. The solvent was then removed under reduced pressure to give crude product which was used for next step without further purification.

Trifluoro-methanesulfonic acid 4-(1-methyl-1-phenyl-ethyl)-phenyl ester

A solution of 4-(1-methyl-1-phenyl-ethyl)-phenol (0.850 g, 0.0040 mol) and TEA (1 mL, 0.007 mol) in DCM (10 mL) was cooled in an ice bath and charged with trifluoromethane-sulfonic anhydride (0.81 mL, 0.0048 mol). The resulting mixture was allowed to stir for 1 h while slowly warming to rt. The reaction was quenched with sat. aq. $NaHCO_3$ and then diluted with more DCM, washed with brine (20 mL), dried over $Na_2SO_4$ and concentrated to give the crude product which was then purified by flash chromatography (eluting with 5%% EtOAc in hexane).

1-Phenyl-1-[4-(4,4,5,5-tetramethyl-[1,3,2]dioxaborolan-2-yl)-phenyl]-propan-1-ol Prepared according to general Method I for borylation described above for preparation of 4,4,5,5-tetramethyl-2-(2-methyl-4-phenoxy-phenyl)-[1,3,2]dioxaborolane.

1-(4-Bromo-phenyl)-1-phenyl-propan-1-ol

To a stirred solution of ethylmagnesium chloride (153.1 mg, 1.723 mmol) in THF (10.0 mL, 123 mmol) was added zinc dichloride (47.0 mg, 0.345 mmol) at rt. The resulting mixture was stirred at rt for 1 h. Then to this mixture, (4-bromophenyl)phenyl methanone (300.00 mg, 1.1489 mmol) in THF (5 mL) was added at 0° C. The mixture was then stirred at 0° C. for 2 h. The solvent was then removed under reduced pressure and the resulting residue was purified by a flash chromatography(2% EtOAc in hexane).

4,4,5,5-Tetramethyl-2-[4-(tetrahydro-furan-2-ylmethyl)-phenyl]-[1,3,2]dioxaborolane Prepared according to general Method II for borylation described above for preparation of 4,4,5,5-tetramethyl-2-(2-nitro-4-phenoxy-phenyl)-[1,3,2]dioxaborolane.

2-(4-Chloro-benzyl)-tetrahydrofuran

To a stirred mixture of (4-chlorophenyl)dihydroxyborane (524.0 mg, 3.351 mmol), 2-aminocyclohexanol hydrochloride (42 mg, 0.28 mmol) and nickel iodide (87.3 mg, 0.279 mmol) in i-PrOH (10.00 mL) was added sodium hexamethyldisilazane (1.075 g, 5.864 mmol) at 0° C. Then the mixture was stirred at rt for 5 min before 2-bromomethyl-tetrahydrofuran (460.00 mg, 2.80 mmol) was added by syringe. The resulting mixture was then stirred at 60° C. for 5 h. The solvent was then removed under reduced pressure and the resulting residue was purified by a flash chromatography(5% AcOEt in hexane).

2-[4-(Difluoro-phenyl-methyl)-phenyl]-4,4,5,5-tetramethyl-[1,3,2]dioxaborolane Prepared according to general Method I for borylation described above for preparation of 4,4,5,5-tetramethyl-2-(2-methyl-4-phenoxy-phenyl)-[1,3,2]dioxaborolane.

1-Bromo-4-(difluoro-phenyl-methyl)-benzene

Prepared according to the Method in literature (Chemical Communications, 2005 (5), 654-656).

Phenyl-[5-(4,4,5,5-tetramethyl-[1,3,2]dioxaborolan-2-yl)-pyridin-2-yl]-methanone Prepared according to general Method I for borylation described above for preparation of 4,4,5,5-tetramethyl-2-(2-methyl-4-phenoxy-phenyl)-[1,3,2]dioxaborolane.

N-[2-Phenoxy-5-(4,4,5,5-tetramethyl-[1,3,2]dioxaborolan-2-yl)-phenyl]-formamide Prepared according to general Method II for borylation described above for preparation of 4,4,5,5-Tetramethyl-2-(2-nitro-4-phenoxy-phenyl)-[1,3,2]dioxaborolane

N-(5-Chloro-2-phenoxy-phenyl)-formamide

A mixture of 1-amino-5-chloro-2-phenoxybenzene (1.00 g, 4.55 mmol), formic acid (0.34 mL, 9.10 mmol), TBTU (1.46 g, 4.55 mmol), DIEA (2.38 mL, 13.6 mmol) and DCM (20 mL) was stirred at rt for 2 h. The solution was transferred to a separatory funnel, 20 mL of sat. aq. NaHCO$_3$ solution was added and the mixture was extracted DCM. The organics were combined and dried (Na$_2$SO$_4$). Solvent was removed under reduced pressure to give a crude residue which was purified via flash chromatography, eluting with 5% EtOAc in hexanes.

2-(3-Methoxy-4-phenoxy-phenyl)-4,4,5,5-tetramethyl-[1,3,2]dioxaborolane

Prepared according to general Method I for borylation described above for preparation of 4,4,5,5-tetramethyl-2-(2-methyl-4-phenoxy-phenyl)-[1,3,2]dioxaborolane.

4-Bromo-2-methoxy-1-phenoxy-benzene

To a stirred mixture of phenylboronic acid (1.20 g, 9.85 mmol) and 4-bromo-2-methoxyphenol (1.00 g, 4.92 mmol) in DCM (50.00 mL) was added cupric acetate (1.34 g, 7.39 mmol), powdered 4 A molecular sieves and TEA (3.43 mL, 24.6 mmol) at rt. The resulting mixture was then stirred at rt for 24 h at ambient atmosphere. The solvent was then removed under reduced pressure and the resulting residue was purified by flash chromatography (5% EtOAc in Hexane). $^1$H NMR (400 MHz, MeOD) δ ppm 3.81 (s, 3H), 6.84-6.95 (m, 3H), 7.01-7.15 (m, 2H), 7.25-7.36 (m, 3H).

2-(3-Fluoro-4-phenoxy-phenyl)-4,4,5,5-tetramethyl-[1,3,2]dioxaborolane

Prepared according to general Method I for borylation described above for preparation of 4,4,5,5-tetramethyl-2-(2-methyl-4-phenoxy-phenyl)-[1,3,2]dioxaborolane.

4-Bromo-2-fluoro-1-phenoxy-benzene

To a stirred mixture of phenylboronic acid (1.20 g, 9.85 mmol) and 4-bromo-2-fluorophenol (0.94 g, 4.92 mmol) in DCM (50.00 mL) was added cupric acetate (1.34 g, 7.39 mmol), powdered 4 A molecular sieves and TEA (3.43 mL, 24.6 mmol) at rt. The resulting mixture was then stirred at rt for 24 h at ambient atmosphere. The solvent was then removed under reduced pressure and the resulting residue was purified by flash chromatography (5% EtOAc in hexane).

4,4,5,5-Tetramethyl-2-(4-phenoxy-2-trifluoromethyl-phenyl)-[1,3,2]dioxaborolane Prepared according to general Method I for borylation described above for preparation of 4,4,5,5-tetramethyl-2-(2-methyl-4-phenoxy-phenyl)-[1,3,2]dioxaborolane.

1-Bromo-4-phenoxy-2-trifluoromethyl-benzene

To a stirred mixture of phenylboronic acid (1.20 g, 9.85 mmol) and 4-bromo-3-trifluoromethyl-phenol (1.18 g, 4.92 mmol) in DCM (50.00 mL) was added cupric acetate (1.34 g, 7.39 mmol), powdered 4 A molecular sieves and TEA (3.43 mL, 24.6 mmol) at rt. The resulting mixture was then stirred at rt for 24 h at ambient atmosphere. The solvent was then removed under reduced pressure and the resulting residue was purified by flash chromatography (5% EtOAc in hexane).

2-[4-(2-Chloro-phenoxy)-3-methoxy-phenyl]-4,4,5,5-tetramethyl-[1,3,2]dioxaborolane Prepared according to general Method I for borylation described above for preparation of 4,4,5,5-tetramethyl-2-(2-methyl-4-phenoxy-phenyl)-[1,3,2]dioxaborolane.

4-Bromo-1-(2-chloro-phenoxy)-2-methoxy-benzene

To a stirred mixture of 2-chloro-phenylboronic acid (1.54 g, 9.85 mmol) and 4-bromo-2-methoxyphenol (1.00 g, 4.92 mmol) in DCM (50.00 mL) was added cupric acetate (1.34 g, 7.39 mmol), powdered 4 A molecular sieves and TEA (3.43 mL, 24.6 mmol) at rt. The resulting mixture was then stirred at rt for 48 h at ambient atmosphere. The solvent was then removed under reduced pressure and the resulting residue was purified by flash chromatography (5% EtOAc in hexane).

1-(3-Fluoro-phenyl)-1-[4-(4,4,5,5-tetramethyl-[1,3,2]dioxaborolan-2-yl)-phenyl]-ethanol Prepared according to general Method II for borylation described above for preparation of 4,4,5,5-tetramethyl-2-(2-nitro-4-phenoxy-phenyl)-[1,3,2]dioxaborolane

1-(4-Chloro-phenyl)-1-(3-fluoro-phenyl)-ethanol

To a stirred solution of (4-chlorophenyl)-(3-fluorophenyl)-methanone (200 mg, 0.717 mmol) in THF (6 mL) was added 1.4 M of methylmagnesium bromide in THF (1.8 mL, 2.5 mmol) at −78° C. The reaction was stirred at −78° C. for 4 h. The reaction was quenched with sat. aq. NaHCO$_3$ at −78° C. The crude material was extracted with DCM and concentrated in vacuo to afford the title compound as a colorless oil which was used for next step without further purification.

(4-Chloro-phenyl)-(3-fluoro-phenyl)-methanone

In an oven dried flask was added 3-fluorobenzoic acid (1.00 g, 7.14 mmol), thionyl chloride (3 mL, 41.1 mmol) and a drop of DMF and the reaction was refluxed for 2 h. The excess thionyl chloride was then distilled off and the residual thionyl chloride was removed on the pump. Chlorobenzene (5 mL, 50 mmol) and aluminum trichloride (1.050 g, 7.85 mmol) were added to the reaction mixture. The reaction mixture turned yellow in color on addition of AlCl$_3$. The reaction mixture was stirred at room temp for 1 h. The crude reaction mixture was poured onto ice and conc HCl (15 mL). The organic layer was separated and the aqueous layer extracted with EtOAc. The combined organic phases were washed with 5% aq NaOH solution, water and dried (Na$_2$SO$_4$). The organic phase was concentrated in vacuo to give a residue which was purified by silica gel chromatography, eluting with 2% EtOAc in hexane.

1-[3-Fluoro-4-(4,4,5,5-tetramethyl-[1,3,2]dioxaborolan-2-yl)-phenyl]-1-phenyl-ethanol Prepared according to general Method I for borylation described above for preparation of 4,4,5,5-tetramethyl-2-(2-methyl-4-phenoxy-phenyl)-[1,3,2]dioxaborolane.

1-(4-Bromo-3-fluorophenyl)-1-phenylethanol

To a stirred solution of (4-bromo-3-fluorophenyl)-phenylmethanone (200 mg, 0.717 mmol) in THF (6 mL) was added 1.4 M of methylmagnesium bromide in THF (1.8 mL, 2.5 mmol) slowly at −78° C. The reaction was stirred at −78° C. for 4 h. The reaction was quenched with sat. aq. NaHCO$_3$ at −78° C. The crude material was extracted with DCM and concentrated in vacuo to afford the title compound as a colorless oil which was used for next step without further purification.

1-[3-Methyl-4-(4,4,5,5-tetramethyl-[1,3,2]dioxaborolan-2-yl)-phenyl]-1-phenyl-ethanol Prepared according to general Method I for borylation described above for preparation of 4,4,5,5-tetramethyl-2-(2-methyl-4-phenoxy-phenyl)-[1,3,2]dioxaborolane.

1-(4-Bromo-3-methylphenyl)-1-phenylethanol

To a stirred solution of (4-bromo-3-methylphenyl)-phenylmethanone (200 mg, 0.727 mmol) in THF (6 mL) was added 1.4 M of methylmagnesium bromide in THF (1.8 mL, 2.5 mmol) slowly at −78° C. The reaction was stirred at −78° C. for 4 h. The reaction was quenched with sat. aq. NaHCO$_3$ at −78° C. The crude material was extracted with DCM and concentrated in vacuo to afford the title compound as a colorless oil which was used for next step without further purification.

1-[3-Methoxy-4-(4,4,5,5-tetramethyl-[1,3,2]dioxaborolan-2-yl)-phenyl]-1-phenyl-ethanol Prepared according to general Method I for borylation described above for preparation of 4,4,5,5-tetramethyl-2-(2-methyl-4-phenoxy-phenyl)-[1,3,2]dioxaborolane.

1-(4-Bromo-3-methoxyphenyl)-1-phenylethanol

To a stirred solution of (4-bromo-3-methoxyphenyl)-phenylmethanone (200 mg, 0.687 mmol) in THF (6 mL) was added 1.4 M of methylmagnesium bromide in THF (1.8 mL, 2.5 mmol) slowly at −78° C. The reaction was stirred at −78° C. for 4 h. The reaction was quenched with sat. aq. NaHCO$_3$ at −78° C. The crude material was extracted with DCM and concentrated in vacuo to afford the title compound as a colorless oil which was used for next step without further purification.

1-[3-Chloro-4-(4,4,5,5-tetramethyl-[1,3,2]dioxaborolan-2-yl)-phenyl]-1-phenyl-ethanol Prepared according to general Method I for borylation described above for preparation of 4,4,5,5-tetramethyl-2-(2-methyl-4-phenoxy-phenyl)-[1,3,2]dioxaborolane.

1-(4-Bromo-3-chlorophenyl)-1-phenylethanol

To a stirred solution of (4-bromo-3-chlorophenyl)-phenylmethanone (200 mg, 0.677 mmol) in THF (6 mL) was added 1.4 M of methylmagnesium bromide in THF (1.8 mL, 2.5 mmol) slowly at −78° C. The reaction was stirred at −78° C. for 4 h. The reaction was quenched with sat. aq. NaHCO$_3$ at −78° C. The crude material was extracted with DCM and concentrated in vacuo to afford the title compound as a colorless oil which was used for next step without further purification.

1-(2-Fluoro-phenyl)-1-[4-(4,4,5,5-tetramethyl-[1,3,2]dioxaborolan-2-yl)-phenyl]-ethanol Prepared according to general Method II for borylation described above for preparation of 4,4,5,5-tetramethyl-2-(2-nitro-4-phenoxy-phenyl)-[1,3,2]dioxaborolane

1-(4-Chlorophenyl)-1-(2-fluorophenyl)-ethanol

To a stirred solution of (4-chlorophenyl)-(2-fluorophenyl)-methanone (200 mg, 0.717 mmol) in THF (6 mL) was added 1.4 M of methylmagnesium bromide in THF (1.8 mL, 2.5 mmol) slowly at −78° C. The reaction was stirred at −78° C. for 4 h. The reaction was quenched with sat. aq. NaHCO$_3$ at −78° C. The crude material was extracted with DCM and concentrated in vacuo to afford the title compound as a colorless oil which was used for next step without further purification.

(4-Chloro-phenyl)-(2-fluoro-phenyl)-methanone

In an oven dried flask was added 2-fluorobenzoic acid (1.00 g, 7.14 mmol), thionyl chloride (3 mL, 41.1 mmol) and a drop of DMF and the reaction was refluxed for 2 h. The excess thionyl chloride was then distilled off and the residual thionyl chloride was removed on the pump. Chlorobenzene (5 mL, 50 mmol) and aluminum trichloride (1.050 g, 7.85 mmol) were added to the reaction mixture. The reaction mixture turned yellow in color on addition of $AlCl_3$. The reaction mixture was stirred at room temp for 1 h. The crude reaction mixture was poured onto ice and conc. HCl (15 mL). The organic layer was separated and the aqueous layer extracted with EtOAc. The combined organic phases were washed with 5% aq NaOH solution, water and dried ($Na_2SO_4$). The organic phase was concentrated in vacuo to give a residue which was purified by silica gel chromatography, eluting with 2% EtOAc in hexane.

1-[2-Methoxy-4-(4,4,5,5-tetramethyl-[1,3,2]diox-aborolan-2-yl)-phenyl]-1-phenyl-ethanol Prepared according to general Method II for borylation described above for preparation of 4,4,5,5-Tetramethyl-2-(2-nitro-4-phenoxy-phenyl)-[1,3,2]dioxaborolane 1-(4-Bromo-2-ethoxy-phenyl)-1-phenyl-ethanol To a stirred solution of (4-chloro-2-methoxy-phenyl)-phenyl-methanone (180 mg, 0.687 mmol) in THF (6 mL) was added 1.4 M of methylmagnesium bromide in THF (1.8 mL, 2.5 mmol) slowly at −78° C. The reaction was stirred at −78° C. for 4 h. The reaction was quenched with sat. aq. $NaHCO_3$ at −78° C. The crude material was extracted with DCM and concentrated in vacuo to afford the title compound as a colorless oil which was used for next step without further purification.

Diethyl-{2-[4-(4,4,5,5-tetramethyl-[1,3,2]dioxaboro-lan-2-yl)-phenoxy]-ethyl}-amine Prepared from [2-(4-bromo-phenoxy)-ethyl]-diethyl-amine according to general Method I for borylation described above for preparation of 4,4,5,5-tetramethyl-2-(2-methyl-4-phenoxy-phenyl)-[1,3,2]dioxaborolane.

[2-(4-Bromo-phenoxy)-ethyl]-diethyl-amine

4-Bromophenol (0.870 g, 5.00 mmol), 2-chloro-N,N-diethylethanamine hydrochloride (0.90 mg, 5.24 mmol) and $Cs_2CO_3$ (8 g, 25 mmol) were combined in DMF (20 mL) and the mixture was heated at reflux over night. $H_2O$ (20 mL) was added and the mixture was extracted with EtOAc, then washed with 2N NaOH and brine. The organic layers were combined, dried over $Na_2SO$ and concentrated to a brown oil which was then purified by flash chromatography (eluent: 20% EtOAc in hexanes).

Dimethyl-{2-[4-(4,4,5,5-tetramethyl-[1,3,2]diox-aborolan-2-yl)-phenoxy]-ethyl}-amine Prepared from [2-(4-bromo-phenoxy)-ethyl]-dimethyl-amine according to general Method I for borylation described above for preparation of 4,4,5,5-tetramethyl-2-(2-methyl-4-phenoxy-phenyl)-[1,3,2]dioxaborolane.

[2-(4-Bromo-phenoxy)-ethyl]-dimethyl-amine

Prepared according to the procedure analogous to that described above for [2-(4-Bromo-phenoxy)-ethyl]-diethyl-amine, except using (2-chloro-ethyl)-dimethylamine hydrochloride.

Dimethyl-{2-[3-(4,4,5,5-tetramethyl-[1,3,2]diox-aborolan-2-yl)-phenoxy]-ethyl}-amine Prepared from [2-(3-bromo-phenoxy)-ethyl]-dimethyl-amine according to general Method I for borylation described above for preparation of 4,4,5,5-tetramethyl-2-(2-methyl-4-phenoxy-phenyl)-[1,3,2]dioxaborolane.

[2-(3-Bromo-phenoxy)-ethyl]-dimethyl-amine

3-Bromophenol (0.870 g, 5.00 mmol), (2-chloro-ethyl)-dimethylamine hydrochloride (0.792 g, 5.50 mmol) and $Cs_2CO_3$ (8 g, 25 mmol) were combined in DMF (20 mL) and the mixture was heated at reflux over night. $H_2O$ (20 mL) was added and the mixture was extracted with EtOAc, then washed with 2N NaOH and brine. The organic layers were combined, dried over $Na_2SO$ and concentrated to a brown oil which was then purified by flash chromatography (eluent: 20% EtOAc in hexanes).

4-[4-(4,4,5,5-Tetramethyl-[1,3,2]dioxaborolan-2-yl)-pyrazol-1-yl]-piperidine-1-carboxylic acid tert-butyl ester To a solution of 1-boc-4-hydroxypiperidine (32.2 g, 0.160 mol) in DCM (400 mL) was added TEA (26.8 mL, 0.192 mol), methanesulfonyl chloride (13.6 mL, 0.176 mol), DMAP (0.20 g, 0.0016 mol) at 0° C. under nitrogen atmosphere. The resulting mixture was slowly warmed to rt and stirred at the same temperature overnight. The mixture was washed with sat. aq. $NaHCO_3$ (3×80 mL), brine (2×80 mL), and dried over anhydrous sodium sulfate. The filtrate was concentrated to give crude 4-methanesulfonyloxypiperidine-1-carboxylic acid tert-butyl ester as a white solid, 44.7 g (yield: 100%). $^1$H-NMR ($CDCl_3$, 400 MHz): δ 1.47 (s, 9H), 1.80-1.85 (m, 2H), 1.95-1.99 (m, 2H), 3.05 (s, 3H), 3.28-3.34 (m, 2H), 3.68-3.74 (m, 2H), 4.89 (m, 1H) ppm. The crude product was used in the next step without further purification.

A mixture of 4-(4,4,5,5-tetramethyl[1,3,2]dioxaborolan-2-ly)-1H-pyrazole (30.0 g, 0.154 mol), 4-methanesulfonyloxypiperidine-1-carboxylic acid tert-butyl ester (52.2 g, 0.200 mol) and cesium carbonate (80.1 g, 0.246 mol) in DMF (400 mL.) was heated at 1.00° C. for 24 hrs. After cooled to rt, DMF was removed under high vacuum and the residue was diluted with water (200 mL). The mixture was extracted with EtOAc (3×200 mL). The combined organic phases were washed with water (3×50 mL) and brine (100 mL), dried over anhydrous sodium sulfate, filtered, and concentrated to give an orange-brown-colored oily product, which was purified by recrystallization using diisopropyl ether. $^1$H-NMR ($CDCl_3$, 300 MHz) δ 1.33 (s, 12H), 1.48 (s, 9H), 1.85-1.93 (m, 2H), 2.15-2.18 (m, 2H), 2.83-2.92 (m, 2H), 4.23-4.39 (m, 3H), 7.76 (s, 1H), 7.84 (s 1H) ppm.

Unless otherwise noted, all materials/reagents were obtained from commercial suppliers and used without further purification. $^1$H NMR (400 MHz or 300 MHz) and $^{13}$C NMR (100.6 MHz) spectra were recorded on Bruker or Varian instruments at ambient temperature with TMS or the residual solvent peak as the internal standard. The line positions or multiples are given in ppm (δ) and the coupling constants (J) are given as absolute values in Hertz (Hz). The multiplicities in $^1$H NMR spectra are abbreviated as follows: s (singlet), d (doublet), t (triplet), q (quartet), quint (quintet), m (multiplet), $m_c$ (centered multiplet), br or broad (broadened), AA'BB'. The signal multiplicities in $^{13}$C NMR spectra were determined using the DEPT135 pulse sequence and are abbreviated as follows: +($CH$ or $CH_3$), −($CH_2$), $C_{quart}$ (C).

Reactions were monitored by thin layer chromatography (TLC) on silica gel 60 $F_{254}$ (0.2 mm) precoated aluminum foil and visualized using UV light. Flash chromatography was performed with silica gel (400-230 mesh). Preparatory TLC was performed on Whatman LK6F Silica Gel 60 Å size 20×20 cm plates with a thickness of 1000 μm. Hydromatrix (=diatomaceous earth) was purchased from Varian. Mass-directed HPLC purification of compounds was performed on a Waters system composed of the following: 2767 Sample Manager, 2525 Binary Gradient Module, 600 Controller, 2487 Dual λ Absorbance Detector, Micromass ZQ2000 for ionization, Phenomenex Luna 5μ C18(2) 100 Å 150×21.2 mm 5μ column with mobile phases of 0.01% Formic Acid MeCN (A) and 0.01% Formic Acid in HPLC water (B), a flow rate of 20 mL/min, and a run time of 13 min. LC-MS data was collected on ZQ2, ZQ3 (also referred to as "OpenLynx"), or HPLC-ACQUITY. ZQ2 is an Agilent 1100 HPLC equipped with a Gilson 215 Liquid Handler, Gilson 819 Injection Module, and Waters Micromass ZQ2000 for ionization. ZQ3 is an Agilent 1100 HPLC equipped with an HP Series 1100 auto injector and Waters Micromass ZQ2000 for ionization. Both systems use the Xterra MS C18, 5μ particle size, 4.6×50 mm with a mobile phase of MeCN (A) and 0.01% Formic Acid in HPLC water (B). The flow rate is 1.3 mL/min, the run time is 5 min, and the gradient profiles are 0.00 min 5% A, 3.00 min 90% A, 3.50 min 90% A, 4.00 min 5% A, 5.00 min 5% A for polar_5 min and 0.00 min 25% A, 3.00 min 99% A, 3.50 min 99% A, 4.00 min 25% A, 5.00 min 25% A for nonpolar_5 min. All Waters Micromass ZQ2000 instruments utilized electrospray ionization in positive (ES+) or negative (ES−) mode. The Waters Micromass ZQ2000 instruments from ZQ2 and ZQ3 can also utilize atmospheric pressure chemical ionization in positive (AP+) or negative (AP−) mode. The Waters HPLC-ACQUITY system consists of an ACQUITY sample manager attached to ACQUITY SQ MS and ACQUITY PDA detectors. It uses an ACQUITY HPLC BEH® C18 2.1×50 mm 1.7 μm column with a mobile phase of 0.1% formic acid in water (A) and 0.1% formic acid in MeCN (B). The flow rate is 1.0 mL/min, run time is 2 min, and the gradient profile is 0.00 min 95% A, 1.50 min 1% A, 1.85 min 1% A, 2.0 min 95% A for analytical. UV detection is at 254 nm, and the MS utilizes electrospray ionization in positive mode (ES+). HPLC purification of compounds was performed on a Gilson system consisting of a 215 Liquid Handler, 819 Injection Module, a 322 Pump, and a 155 UV/VIS dual wavelength detector set to 254 and 210 nm. This system uses Phenomenex Luna C18(2), 5μ particle size, 50×21.2 mm or 60×21.2 mm columns with a mobile phase of MeCN and 0.1% Formic Acid in HPLC water. The flow rate is 15 mL/min and the run time is 25 min. All melting points were determined with a MeI-Temp II apparatus and are uncorrected. Elemental analyses were obtained by Atlantic Microlab, Inc., Norcross, Ga.

The tables below list the mobile phase gradients (solvent A: MeCN; solvent B: 0.01% formic acid in HPLC water) and flow rates for the analytical HPLC programs.

| Polar_5 min | | | | |
|---|---|---|---|---|
| Time | A % | B % | Flow Rate (mL/min) MicromassZQ | Flow Rate (mL/min) Platform II |
| 0.00 | 5 | 95 | 1.3 | 1.3 |
| 3.00 | 90 | 10 | 1.3 | 1.3 |
| 3.50 | 90 | 10 | 1.3 | 1.3 |
| 4.00 | 5 | 95 | 1.3 | 1.3 |
| 5.00 | 5 | 95 | 1.3 | 1.3 |

| Nonpolar_5 min | | | | |
|---|---|---|---|---|
| Time | A % | B % | Flow Rate (mL/min) MicromassZQ | Flow Rate (mL/min) Platform II |
| 0.00 | 25 | 75 | 1.3 | 1.3 |
| 3.00 | 99 | 1 | 1.3 | 1.3 |
| 3.50 | 99 | 1 | 1.3 | 1.3 |
| 4.00 | 25 | 75 | 1.3 | 1.3 |
| 5.00 | 25 | 75 | 1.3 | 1.3 |

Biological Activity

The efficacy of the Examples of the invention, compounds of Formula I, as inhibitors of protein tyrosine kinases were demonstrated and confirmed by a number of pharmacological in vitro assays. The following assays and their respective methods can be carried out with the compounds according to the present invention. Activity possessed by compounds of Formula I may be demonstrated in vivo.

Person skilled in the art will appreciate that a variety of assay formats may be used to determine the activity of the compounds of this invention. For example, AlphaScreen (Amplified Luminescent Proximity Homogeneous Assay) technology was used with the kinases described below. Assay ATP concentrations for individual kinases are included in the text.

Compounds of the invention were tested for ACK1 inhibition activity. 1 uL compounds prepared at 15× in 4 mM DMSO were combined with 9 uL ATP solution in assay buffer containing 50 mM Hepes, 1% glycerol, 1.665 mM $MnCl_2$ and Poly-(GT)-Biotin (Cisbio #61GT0BLD, 1:1500 dilution) in ProxiPlate-384 Plus plate (PerkinElmer #6008280). Final DMSO concentration was 0.25% with an ATP final concentration of 100 uM. The reaction was started by adding 5 uL ACK1 solution (Carna, 15 pg/uL final in assay) in an enzyme buffer containing 50 mM Hepes, 0.24 mM EGTA, 0.024% Brij-35, 3 mM DTT, 0.01% BSA. Reaction was allowed to occur for 20 min., shaking, at RT. Anti PT66 acceptor beads and Streptavidin donor beads (PerkinElmer #6760602R) were prepared by adding each at 1:160 dilution in a detection buffer containing 25 mM Tris-HCl, 250 mM NaCl, 100 mM EDTA, 0.25% BSA. Prepared beads were added to assay plate at 5 uL well and allowed to incubate protected from light, shaking, for 2 hrs at RT. Plates were read on AlphaQuest reader. Results are shown in Table 1.

TABLE 1

| Ex. No. | Example Structure | Example Name | Mass Data [MH+] | IC50 (μM) |
|---|---|---|---|---|
| 1 | | 3-Cyclohexyl-1-(4-phenoxy-phenyl)-imidazo[1,5-a]pyrazin-8-ylamine | 385.03 | 0.9886 |
| 2 | | 3-Cyclopropyl-1-(4-phenoxy-phenyl)-imidazo[1,5-a]pyrazin-8-ylamine | 343.15 | 0.2706 |
| 3 | | 3-Cyclopentyl-1-(4-phenoxy-phenyl)-imidazo[1,5-a]pyrazin-8-ylamine | 370.83 | 0.2120 |

TABLE 1-continued
| | | | | |
|---|---|---|---|---|
| 4 | 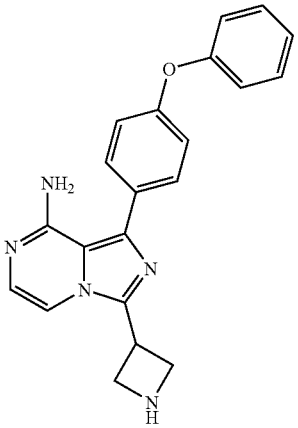 [SMILES: Nc1nccn2c(C3CNC3)nc(-c3ccc(Oc4ccccc4)cc3)c12] | 3-Azetidin-3-yl-1-(4-phenoxy-phenyl)-imidazo[1,5-a]pyrazin-8-ylamine | 358.12 | 3.7216 |
| 5 | 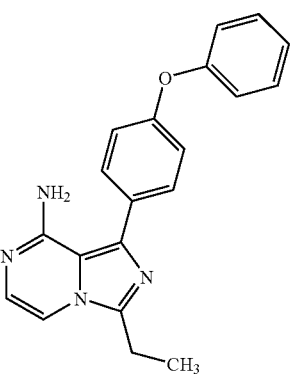 [SMILES: CCc1nc(-c2ccc(Oc3ccccc3)cc2)c2c(N)nccn12] | 3-Ethyl-1-(4-phenoxy-phenyl)-imidazo[1,5-a]pyrazin-8-ylamine | 330.92 | 0.3580 |
| 6 | 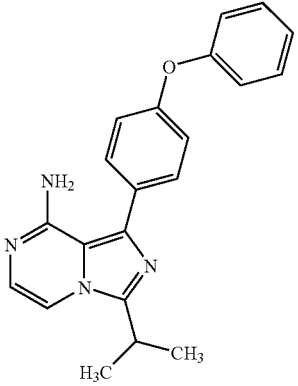 [SMILES: CC(C)c1nc(-c2ccc(Oc3ccccc3)cc2)c2c(N)nccn12] | 3-Isopropyl-1-(4-phenoxy-phenyl)-imidazo[1,5-a]pyrazin-8-ylamine | 344.96 | 0.0958 |
| 7 | 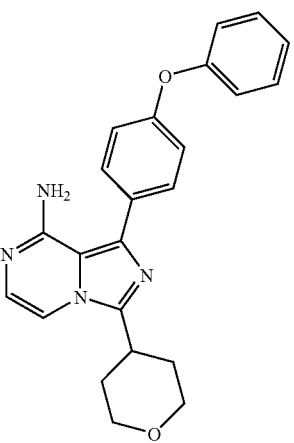 [SMILES: Nc1nccn2c(C3CCOCC3)nc(-c3ccc(Oc4ccccc4)cc3)c12] | 1-(4-Phenoxy-phenyl)-3-(tetrahydro-pyran-4-yl)imidazo[1,5-a]pyrazin-8-ylamine | 386.7 | 2.0659 |

TABLE 1-continued
| | | | | |
|---|---|---|---|---|
| 8 | 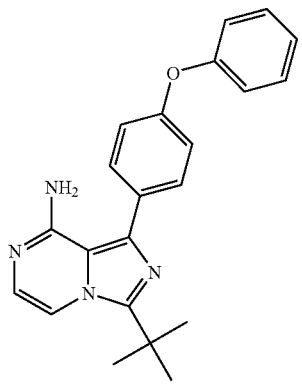 [SMILES: CC(C)(C)c1nc(-c2ccc(Oc3ccccc3)cc2)c2c(N)nccn12] | 3-tert-Butyl-1-(4-phenoxy-phenyl)-imidazo[1,5-a]pyrazin-8-ylamine | 359.11 | 0.33 |
| 9 | 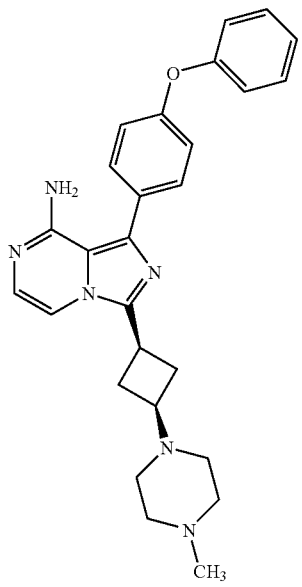 [SMILES: CN1CCN([C@H]2C[C@@H](c3nc(-c4ccc(Oc5ccccc5)cc4)c4c(N)nccn43)C2)CC1] | cis-3-[3-(4-Methyl-piperazin-1-yl)-cyclobutyl]-1-(4-phenoxy-phenyl)-imidazo[1,5-a]pyrazin-8-ylamine | 455.24 | 2.2428 |
| 10 | 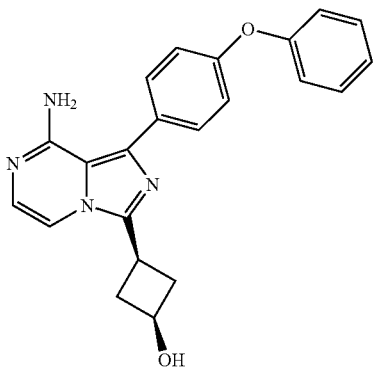 [SMILES: Nc1nccn2c1c(-c1ccc(Oc3ccccc3)cc1)nc2[C@H]1C[C@@H](O)C1] | cis-3-[8-Amino-1-(4-phenoxy-phenyl)-imidazo[1,5-a]pyrazin-3-yl]-cyclobutanol | 372.92 | 0.1526 |

| | | | | |
|---|---|---|---|---|
| 11 | 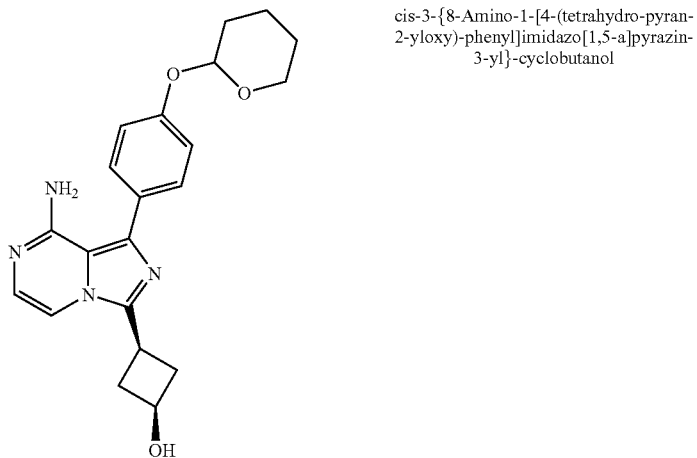 | cis-3-{8-Amino-1-[4-(tetrahydro-pyran-2-yloxy)-phenyl]imidazo[1,5-a]pyrazin-3-yl}-cyclobutanol | 380.80 | 0.050 |
| 12 | 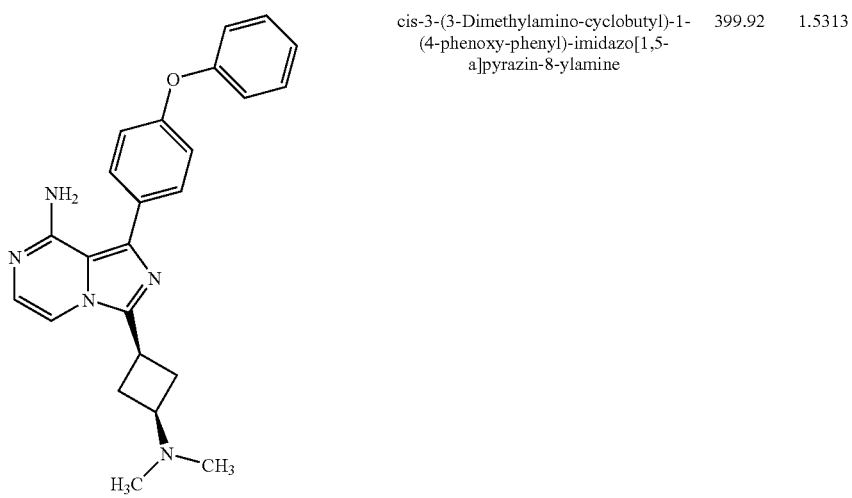 | cis-3-(3-Dimethylamino-cyclobutyl)-1-(4-phenoxy-phenyl)-imidazo[1,5-a]pyrazin-8-ylamine | 399.92 | 1.5313 |
| 13 | 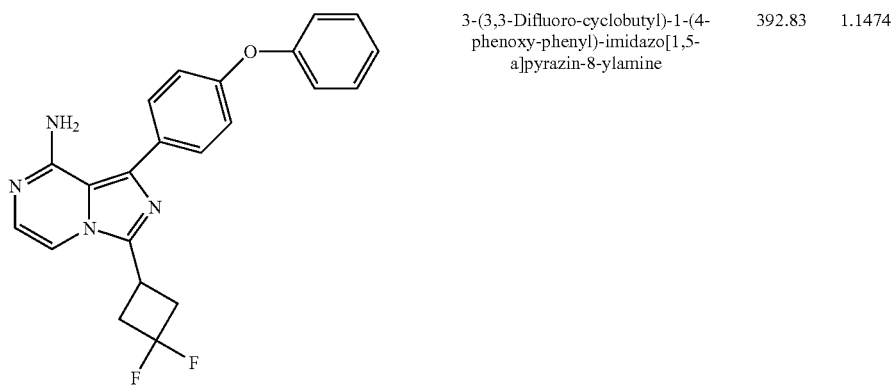 | 3-(3,3-Difluoro-cyclobutyl)-1-(4-phenoxy-phenyl)-imidazo[1,5-a]pyrazin-8-ylamine | 392.83 | 1.1474 |

TABLE 1-continued
| | | | | |
|---|---|---|---|---|
| 14 | 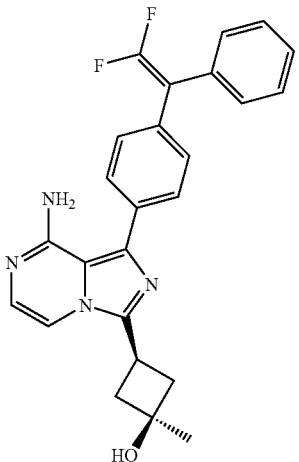 [SMILES: C[C@]1(O)C[C@@H](c2nc(-c3ccc(C(=C(F)F)c4ccccc4)cc3)c3c(N)nccn32)C1] | cis-3-{8-Amino-1-[4-(2,2-difluoro-1-phenyl-vinyl)-phenyl]-imidazo[1,5-a]pyrazin-3-yl}-1-methyl-cyclobutanol | 432.95 | 5.53 |
| 15 | 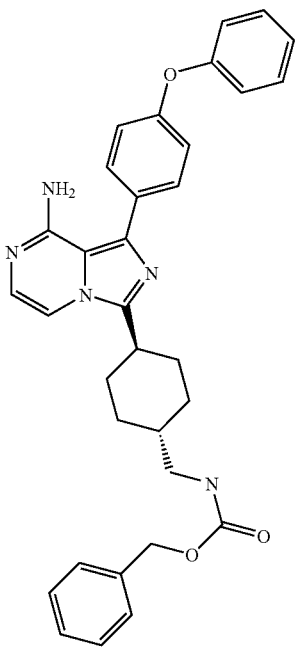 [SMILES: Nc1nccn2c1c(-c1ccc(Oc3ccccc3)cc1)nc2[C@H]1CC[C@H](CNC(=O)OCc2ccccc2)CC1] | trans-{4-[8-Amino-1-(4-phenoxy-phenyl)-imidazo[1,5-a]pyrazin-3-yl]cyclohexylmethyl}-carbamic acid benzyl ester | 547.96 | 4.9860 |

TABLE 1-continued
| | | | | |
|---|---|---|---|---|
| 16 | 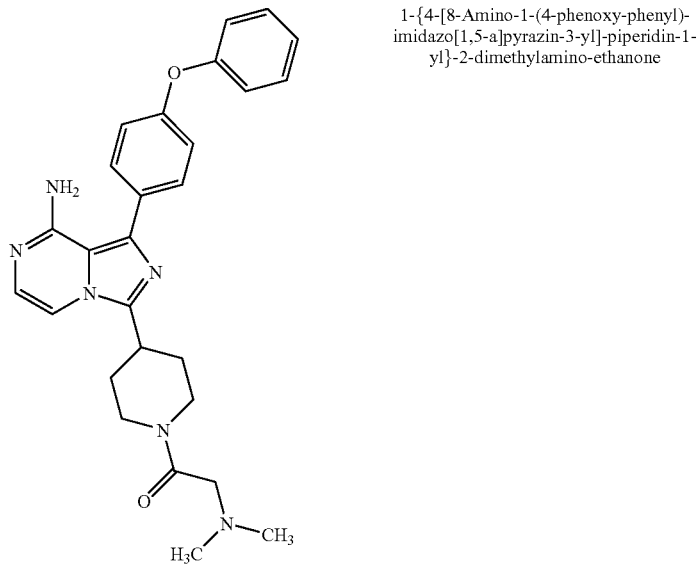 | 1-{4-[8-Amino-1-(4-phenoxy-phenyl)-imidazo[1,5-a]pyrazin-3-yl]-piperidin-1-yl}-2-dimethylamino-ethanone | 470.97 | 6.8534 |
| 17 | 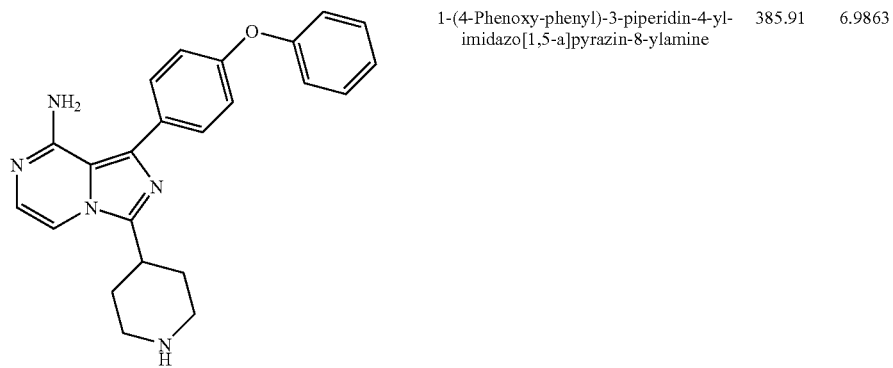 | 1-(4-Phenoxy-phenyl)-3-piperidin-4-yl-imidazo[1,5-a]pyrazin-8-ylamine | 385.91 | 6.9863 |
| 18 | 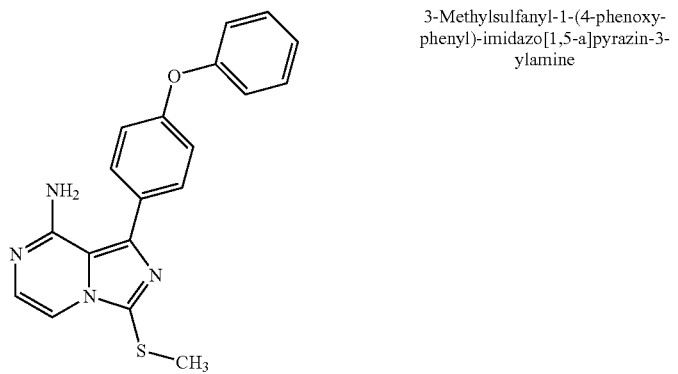 | 3-Methylsulfanyl-1-(4-phenoxy-phenyl)-imidazo[1,5-a]pyrazin-3-ylamine | 348.81 | 0.99 |

TABLE 1-continued
| | | | | |
|---|---|---|---|---|
| 20 | 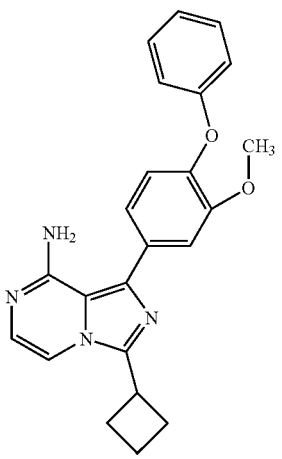 [SMILES: COc1cc(-c2nc(C3CCC3)n3ccnc(N)c23)ccc1Oc1ccccc1] | 3-Cyclobutyl-1-(3-methoxy-4-phenoxy-phenyl)-imidazo[1,5-a]pyrazin-8-ylamine | 386.88 | 0.0487 |
| 21 | 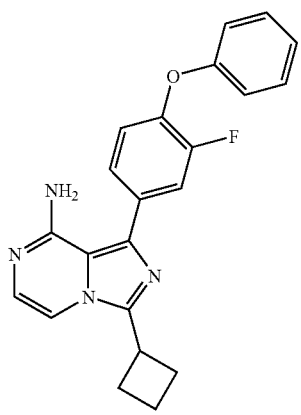 [SMILES: Nc1nccn2c(C3CCC3)nc(-c3ccc(Oc4ccccc4)c(F)c3)c12] | 3-Cyclobutyl-1-(3-fluoro-4-phenoxy-phenyl)-imidazo[1,5-a]pyrazin-8-ylamine | 374.87 | 0.0880 |
| 22 | 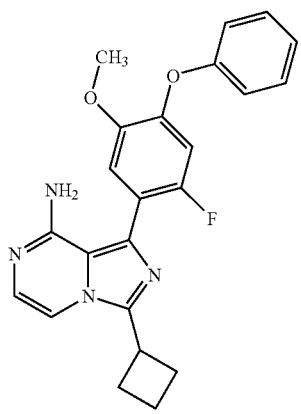 [SMILES: COc1cc(-c2nc(C3CCC3)n3ccnc(N)c23)c(F)cc1Oc1ccccc1] | 3-Cyclobutyl-1-(2-fluoro-5-methoxy-4-phenoxy-phenyl)-imidazo[1,5-a]pyrazin-8-ylamine | 405.08 | 1.7801 |

| | | | | |
|---|---|---|---|---|
| 23 | | 3-Cyclobutyl-1-(4-phenoxy-2-trifluoromethyl-phenyl)-imidazo[1,5-a]pyrazin-8-ylamine | 424.81 | 7.2249 |
| 24 | | 3-Cyclobutyl-1-(2-ethyl-4-phenoxy-phenyl)-imidazo[1,5-a]pyrazin-8-ylamine | 384.74 | 3.1211 |
| 25 | | 1-(2-Chloro-4-phenoxy-phenyl)-3-cyclobutyl-imidazo[1,5-a]pyrazin-8-ylamine | 391.08 | 1.0631 |
| 26 | | 3-Cyclobutyl-1-(2-ethoxy-4-phenoxy-phenyl)-imidazo[1,5-a]pyrazin-8-ylamine | 401.18 | 0.4745 |

TABLE 1-continued
| | | | | |
|---|---|---|---|---|
| 27 | 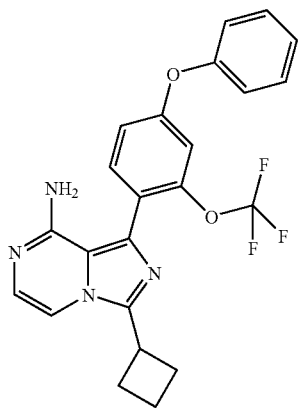 [SMILES: Nc1nccn2c(C3CCC3)nc(-c3ccc(Oc4ccccc4)cc3OC(F)(F)F)c12] | 3-Cyclobutyl-1-(4-phenoxy-2-trifluoromethoxy-phenyl)-imidazo[1,5-a]pyrazin-8-ylamine | 441.09 | 4.2200 |
| 28 | 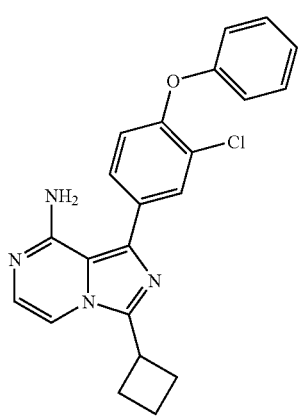 | 1-(3-Chloro-4-phenoxy-phenyl)-3-cyclobutyl-imidazo[1,5-a]pyrazin-8-ylamine | 390.82 392.84 | 1.6891 |
| 29 | 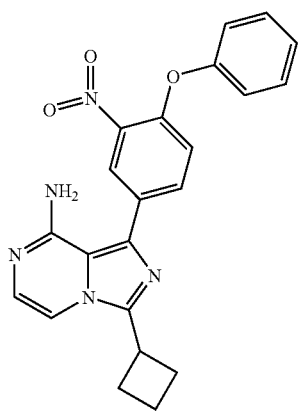 [SMILES: Nc1nccn2c(C3CCC3)nc(-c3ccc(Oc4ccccc4)c([N+](=O)[O-])c3)c12] | 3-Cyclobutyl-1-(3-nitro-4-phenoxy-phenyl)-imidazo[1,5-a]pyrazin-8-ylamine | 401.97 | 1.5214 |
| 30 | 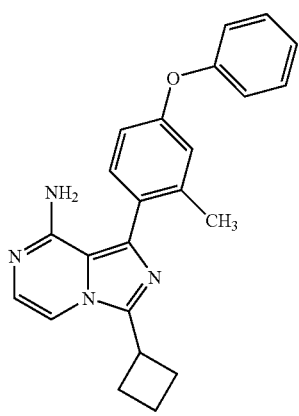 | 3-Cyclobutyl-1-(2-methyl-4-phenoxy-phenyl)-imidazo[1,5-a]pyrazin-8-ylamine | 371.07 | 0.3694 |

TABLE 1-continued
| | | | | |
|---|---|---|---|---|
| 31 | 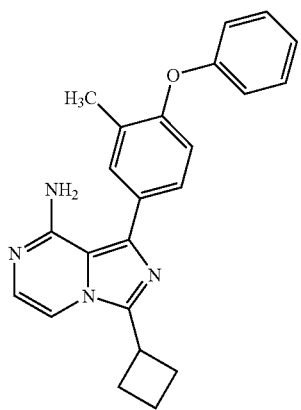 [SMILES: Cc1cc(-c2nc(C3CCC3)n3ccnc(N)c23)ccc1Oc1ccccc1] | 3-Cyclobutyl-1-(3-methyl-4-phenoxy-phenyl)-imidazo[1,5-a]pyrazin-8-ylamine | 370.96 | 6.2818 |
| 32 | 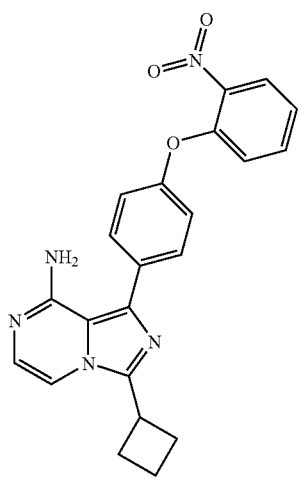 [SMILES: Nc1nccn2c(C3CCC3)nc(-c3ccc(Oc4ccccc4[N+](=O)[O-])cc3)c12] | 3-Cyclobutyl-1-[4-(2-nitro-phenoxy)-phenyl]-imidazo[1,5-a]pyrazin-8-ylamine | 402.01 | 0.9059 |
| 33 | 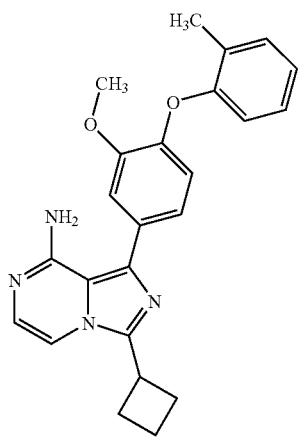 [SMILES: COc1cc(-c2nc(C3CCC3)n3ccnc(N)c23)ccc1Oc1ccccc1C] | 3-Cyclobutyl-1-(3-methoxy-4-o-tolyloxy-phenyl)-imidazo[1,5-a]pyrazin-8-ylamine | 401.04 | 1.3492 |

| | | | | |
|---|---|---|---|---|
| 34 | 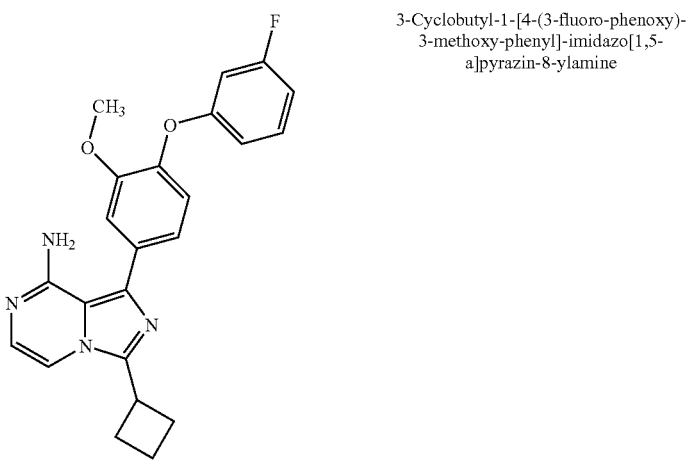 | 3-Cyclobutyl-1-[4-(3-fluoro-phenoxy)-3-methoxy-phenyl]-imidazo[1,5-a]pyrazin-8-ylamine | 405.01 | 1.1528 |
| 35 | 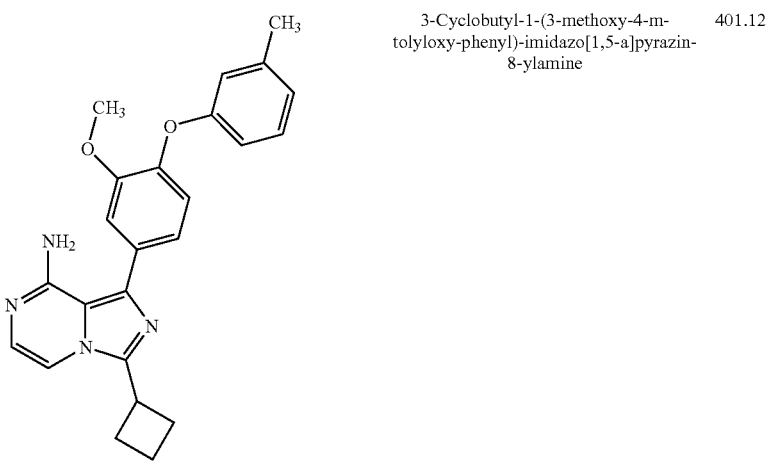 | 3-Cyclobutyl-1-(3-methoxy-4-m-tolyloxy-phenyl)-imidazo[1,5-a]pyrazin-8-ylamine | 401.12 | 0.9974 |
| 36 | 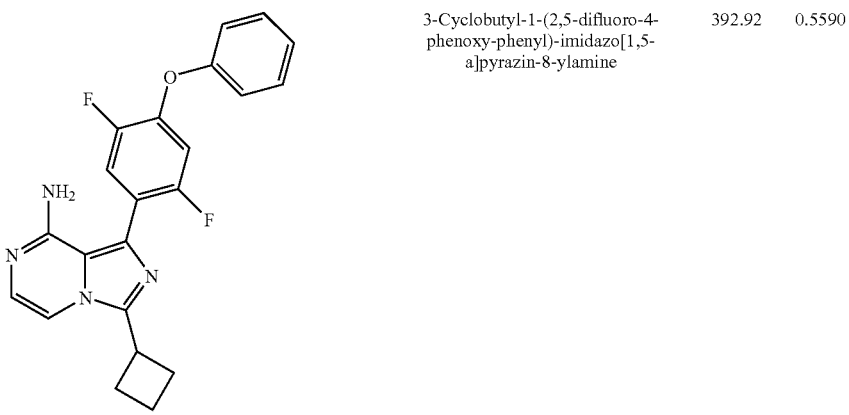 | 3-Cyclobutyl-1-(2,5-difluoro-4-phenoxy-phenyl)-imidazo[1,5-a]pyrazin-8-ylamine | 392.92 | 0.5590 |

TABLE 1-continued
| | | | | |
|---|---|---|---|---|
| 37 | 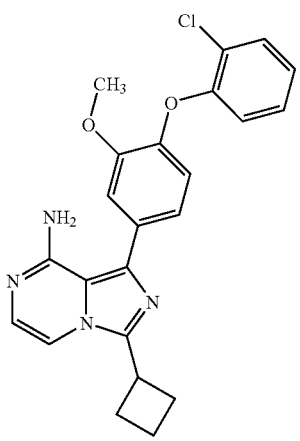 [SMILES: COc1cc(-c2nc(C3CCC3)n3ccnc(N)c23)ccc1Oc1ccccc1Cl] | 1-[4-(2-Chloro-phenoxy)-3-methoxy-phenyl]-3-cyclobutyl-imidazo[1,5-a]pyrazin-8-ylamine | 421.08 | 0.6213 |
| 38 | 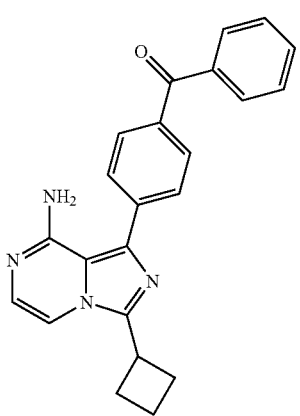 | [4-(8-Amino-3-cyclobutyl-imidazo[1,5-a]pyrazin-1-yl)-phenyl]-phenyl-methanone | 369.08 | 0.0865 |
| 39 | 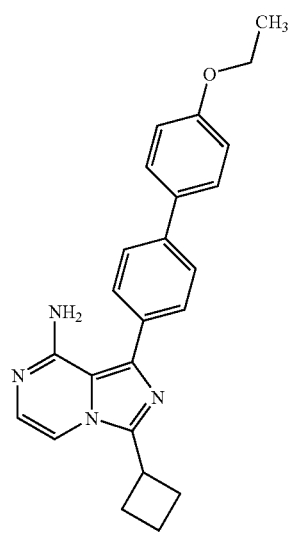 [SMILES: CCOc1ccc(-c2ccc(-c3nc(C4CCC4)n4ccnc(N)c34)cc2)cc1] | 3-Cyclobutyl-1-(4'-ethoxy-biphenyl-4-yl)-imidazo[1,5-a]pyrazin-8-ylamine | 385.17 | 10.3013 |

TABLE 1-continued
| | | | | |
|---|---|---|---|---|
| 40 | 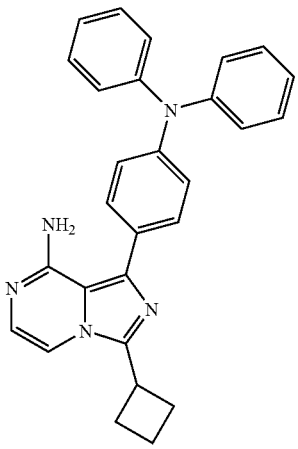 [SMILES: Nc1nccn2c(C3CCC3)nc(-c3ccc(N(c4ccccc4)c4ccccc4)cc3)c12] | 3-Cyclobutyl-1-(4-diphenylamino-phenyl)-imidazo[1,5-a]pyrazin-8-ylamine | 431.81 | 9.0264 |
| 41 | 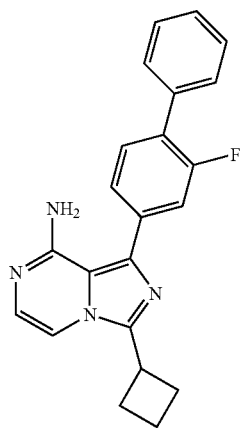 [SMILES: Nc1nccn2c(C3CCC3)nc(-c3ccc(-c4ccccc4)c(F)c3)c12] | 3-Cyclobutyl-1-(2-fluoro-biphenyl-4-yl)-imidazo[1,5-a]pyrazin-8-ylamine | 359 | 1.3952 |
| 42 | 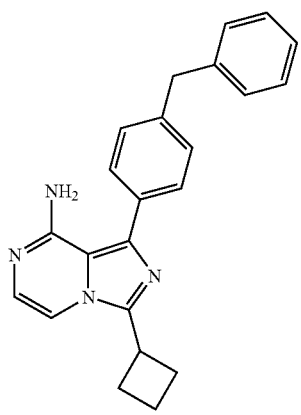 [SMILES: Nc1nccn2c(C3CCC3)nc(-c3ccc(Cc4ccccc4)cc3)c12] | 1-(4-Benzyl-phenyl)-3-cyclobutyl-imidazo[1,5-a]pyrazin-8-ylamine | 354.93 | 0.5729 |

TABLE 1-continued
| | | | | |
|---|---|---|---|---|
| 43 | 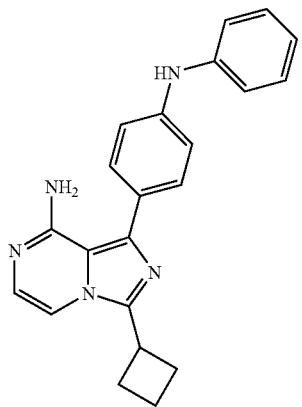 [SMILES: Nc1nccn2c(C3CCC3)nc(-c3ccc(Nc4ccccc4)cc3)c12] | 3-Cyclobutyl-1-(4-phenylamino-phenyl)-imidazo[1,5-a]pyrazin-8-ylamine | 355.82 | 0.3806 |
| 44 | 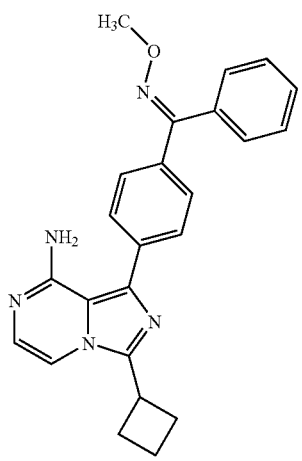 [SMILES: CO/N=C(\c1ccccc1)c1ccc(-c2nc(C3CCC3)n3ccnc(N)c23)cc1] | [4-(8-Amino-3-cyclobutyl-imidazo[1,5-a]pyrazin-1-yl)-phenyl]-phenyl-methanone O-methyl-oxime | 397.97 | 6.4348 |
| 45 | 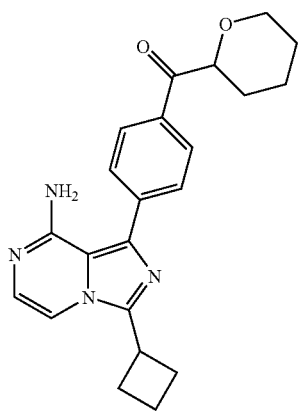 [SMILES: Nc1nccn2c(C3CCC3)nc(-c3ccc(C(=O)C4CCCCO4)cc3)c12] | [4-(8-Amino-3-cyclobutyl-imidazo[1,5-a]pyrazin-1-yl)-phenyl]-(tetrahydro-pyran-2-yl)-methanone | 376.98 | 0.6122 |

TABLE 1-continued
| | | | | |
|---|---|---|---|---|
| 46 | 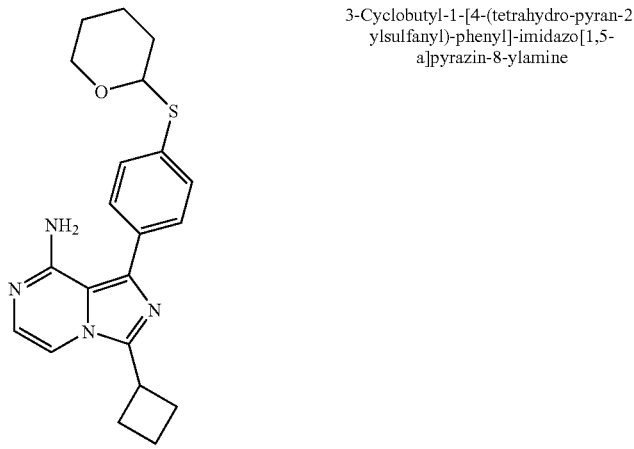 | 3-Cyclobutyl-1-[4-(tetrahydro-pyran-2-ylsulfanyl)-phenyl]-imidazo[1,5-a]pyrazin-8-ylamine | 380.84 | 0.2053 |
| 47 | 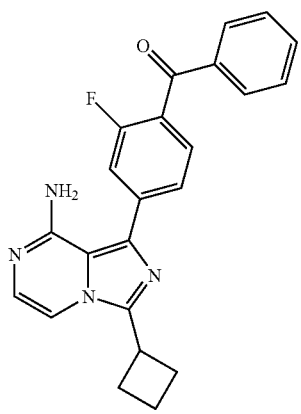 [SMILES: Nc1nccn2c(C3CCC3)nc(-c3ccc(C(=O)c4ccccc4)c(F)c3)c12] | [4-(8-Amino-3-cyclobutyl-imidazo[1,5-a]pyrazin-1-yl)-2-fluoro-phenyl]-phenyl-methanone | 386.93 | 0.1813 |
| 48 | 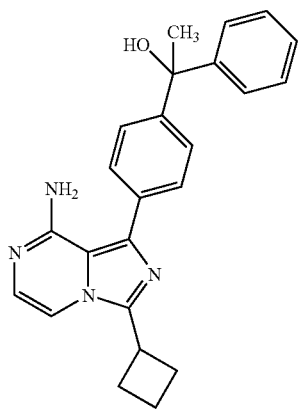 [SMILES: CC(O)(c1ccccc1)c1ccc(-c2nc(C3CCC3)n3ccnc(N)c23)cc1] | 1-[4-(8-Amino-3-cyclobutyl-imidazo[1,5-a]pyrazin-1-yl)-phenyl]1-phenyl-ethanol | 385.09 | 0.0900 |

TABLE 1-continued
| | | | | |
|---|---|---|---|---|
| 49 | 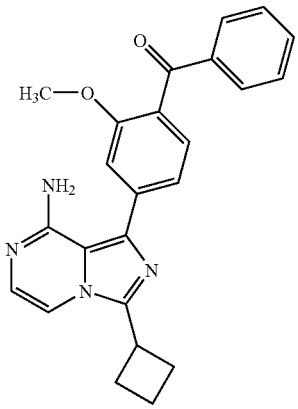 [SMILES: COc1cc(-c2nc(C3CCC3)n3ccnc(N)c23)ccc1C(=O)c1ccccc1] | [4-(8-Amino-3-cyclobutyl-imidazo[1,5-a]pyrazin-1-yl)-2-methoxy-phenyl]phenyl-methanone | 398.99 | 0.0352 |
| 50 | 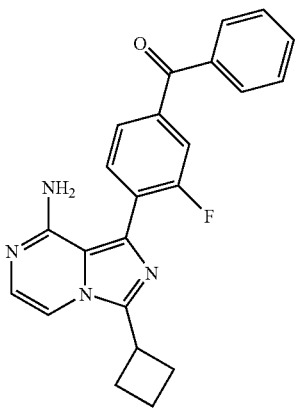 [SMILES: Nc1nccn2c(C3CCC3)nc(-c3ccc(C(=O)c4ccccc4)cc3F)c12] | [4-(8-Amino-3-cyclobutyl-imidazo[1,5-a]pyrazin-1-yl)-3-fluoro-phenyl]phenyl-methanone | 387.02 | 0.0604 |
| 51 | 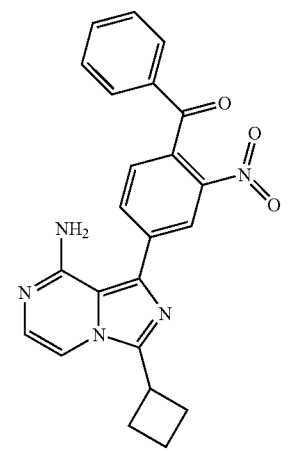 [SMILES: Nc1nccn2c(C3CCC3)nc(-c3ccc(C(=O)c4ccccc4)c([N+](=O)[O-])c3)c12] | [4-(8-Amino-3-cyclobutyl-imidazo[1,5-a]pyrazin-1-yl)-2-nitro-phenyl]-phenyl-methanone | 414.99 | 0.5823 |

TABLE 1-continued
| | | | | |
|---|---|---|---|---|
| 52 | 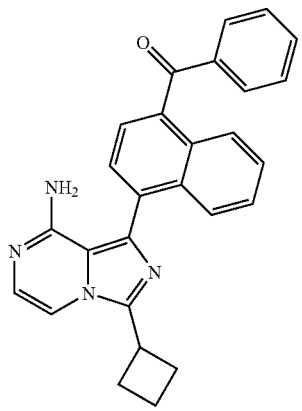 [SMILES: Nc1nccn2c(C3CCC3)nc(-c3ccc(C(=O)c4ccccc4)c4ccccc34)c12] | [4-(8-Amino-3-cyclobutyl-imidazo[1,5-a]pyrazin-1-yl)-naphthalen-1-yl]-phenyl-methanone | 419.01 | 1.5973 |
| 53 | 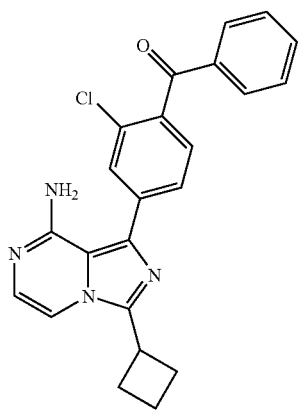 [SMILES: Nc1nccn2c(C3CCC3)nc(-c3ccc(C(=O)c4ccccc4)c(Cl)c3)c12] | [4-(8-Amino-3-cyclobutyl-imidazo[1,5-a]pyrazin-1-yl)-2-chloro-phenyl]-phenyl-methanone | 403.14 | 0.2330 |
| 54 | 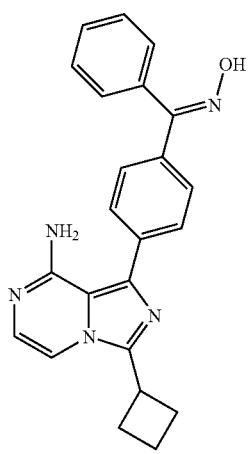 [SMILES: Nc1nccn2c(C3CCC3)nc(-c3ccc(/C(=N/O)c4ccccc4)cc3)c12] | [4-(8-Amino-3-cyclobutyl-imidazo[1,5-a]pyrazin-1-yl)-phenyl]-phenyl-methanone oxime | 383.96 | 3.7827 |

TABLE 1-continued
| | | | | |
|---|---|---|---|---|
| 55 | 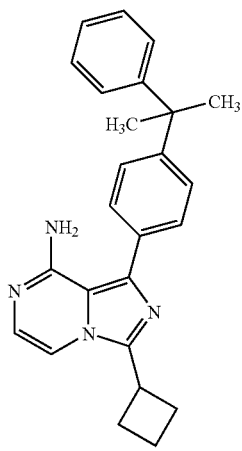 [SMILES: CC(C)(c1ccccc1)c1ccc(-c2nc(C3CCC3)n3ccnc(N)c23)cc1] | 3-Cyclobutyl-1-[4-(1-methyl-1-phenyl-ethyl)-phenyl]-imidazo[1,5-a]pyrazin-8-ylamine | 383.11 | 7.5627 |
| 56 | 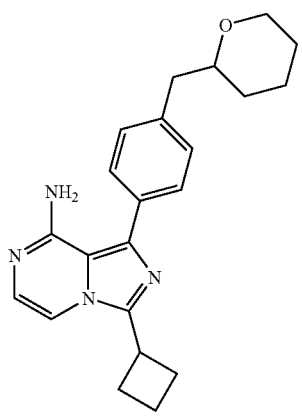 [SMILES: Nc1nccn2c(C3CCC3)nc(-c3ccc(CC4CCCCO4)cc3)c12] | 3-Cyclobutyl-1-[4-(tetrahydro-pyran-2-ylmethyl)-phenyl]-imidazo[1,5-a]pyrazin-8-ylamine | 362.76 | 2.7840 |
| 57 | 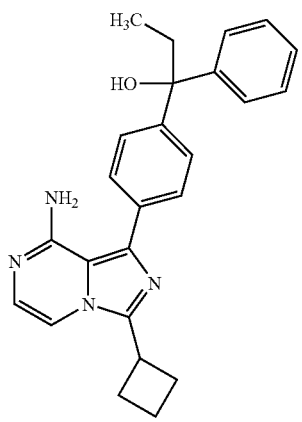 [SMILES: CCC(O)(c1ccccc1)c1ccc(-c2nc(C3CCC3)n3ccnc(N)c23)cc1] | 1-[4-(8-Amino-3-cyclobutyl-imidazo[1,5-a]pyrazin-1-yl)-phenyl]-1-phenyl-propan-1-ol | 399.04 | 9.8248 |

TABLE 1-continued
| | | | | |
|---|---|---|---|---|
| 58 | 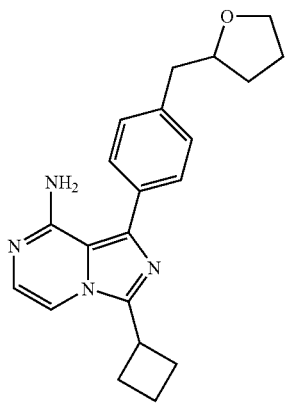 [SMILES: Nc1nccn2c(C3CCC3)nc(-c3ccc(CC4CCCO4)cc3)c12] | 3-Cyclobutyl-1-[4-(tetrahydro-furan-2-ylmethyl)-phenyl]-imidazo[1,5-a]pyrazin-8-ylamine | 349.15 | 2.9491 |
| 59 | 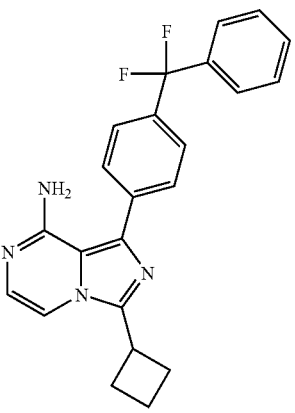 [SMILES: Nc1nccn2c(C3CCC3)nc(-c3ccc(C(F)(F)c4ccccc4)cc3)c12] | 3-Cyclobutyl-1-[4-(difluoro-phenyl-methyl)-phenyl]-imidazo[1,5-a]pyrazin-8-ylamine | 391.01 | 2.2948 |
| 60 | 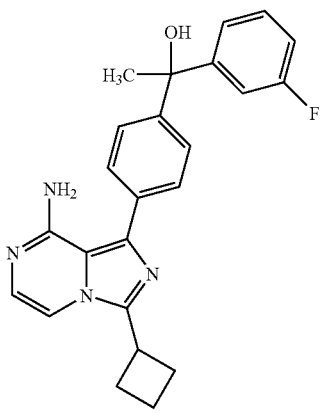 [SMILES: CC(O)(c1ccc(-c2nc(C3CCC3)n3ccnc(N)c23)cc1)c1cccc(F)c1] | 1-[4-(8-Amino-3-cyclobutyl-imidazo[1,5-a]pyrazin-1-yl)-phenyl]-1-(3-fluoro-phenyl)-ethanol | 402.92 | 2.1247 |

TABLE 1-continued
| | | | | |
|---|---|---|---|---|
| 61 | 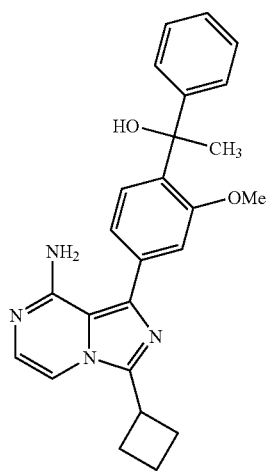 [SMILES: COc1cc(-c2nc(C3CCC3)n3ccnc(N)c23)ccc1C(C)(O)c1ccccc1] | 1-[4-(8-Amino-3-cyclobutyl-imidazo[1,5-a]pyrazin-1-yl)-2-methoxy-phenyl]-1-phenyl-ethanol | 415.11 | 0.6312 |
| 62 | 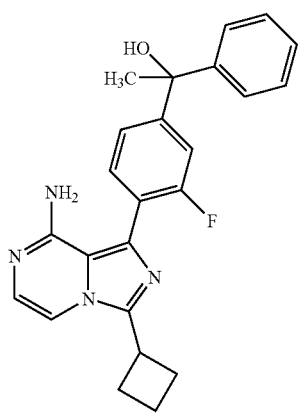 [SMILES: CC(O)(c1ccccc1)c1ccc(-c2nc(C3CCC3)n3ccnc(N)c23)c(F)c1] | 1-[4-(8-Amino-3-cyclobutyl-imidazo[1,5-a]pyrazin-1-yl)-3-fluoro-phenyl]-1-phenyl-ethanol | 403.02 | 0.3645 |
| 63 | 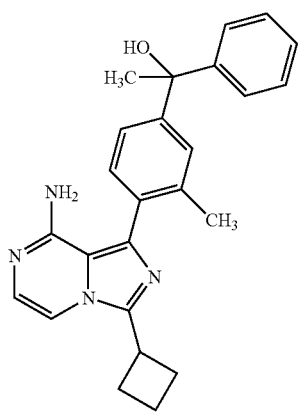 [SMILES: Cc1cc(C(C)(O)c2ccccc2)ccc1-c1nc(C2CCC2)n2ccnc(N)c12] | 1-[4-(8-Amino-3-cyclobutyl-imidazo[1,5-a]pyrazin-1-yl)-3-methyl-phenyl]-1-phenyl-ethanol | 399.11 | 0.8532 |

TABLE 1-continued

| | | | | |
|---|---|---|---|---|
| 64 | | 1-[4-(8-Amino-3-cyclobutyl-imidazo[1,5-a]pyrazin-1-yl)-phenyl]-1-(2-fluoro-phenyl)-ethanol | 403.14 | 1.0965 |
| 65 | | 1-[4-(8-Amino-3-cyclobutyl-imidazo[1,5-a]pyrazin-1-yl)-3-methoxy-phenyl]-1-phenyl-ethanol | 416.33 | 0.1883 |
| 66 | | 1-[4-(8-Amino-3-cyclobutyl-imidazo[1,5-a]pyrazin-1-yl)-3-chloro-phenyl]-1-phenyl-ethanol | 419.13 | 0.3151 |
| 67 | | [4-(8-Amino-3-cyclobutyl-imidazo[1,5-a]pyrazin-1-yl)-3-methoxy-phenyl]-phenyl-methanone | 399.09 | 0.2031 |

TABLE 1-continued
| | | | | |
|---|---|---|---|---|
| 68 | 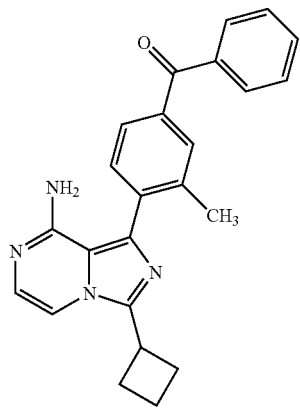 [SMILES: Cc1cc(C(=O)c2ccccc2)ccc1-c1nc(C2CCC2)n2ccnc(N)c12] | [4-(8-Amino-3-cyclobutyl-imidazo[1,5-a]pyrazin-1-yl)-3-methyl-phenyl]-phenyl-methanone | 383.04 | 0.4046 |
| 69 | 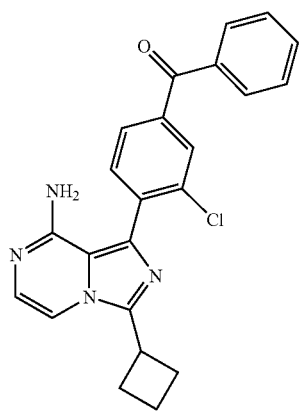 | [4-(8-Amino-3-cyclobutyl-imidazo[1,5-a]pyrazin-1-yl)-3-chloro-phenyl]-phenyl-methanone | 403.10<br>405.10 | 0.1810 |
| 70 | 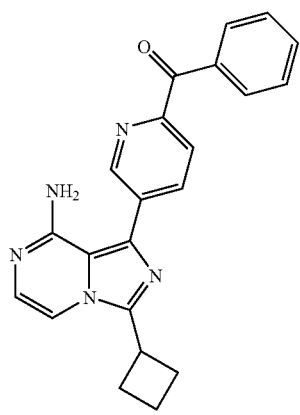 [SMILES: Nc1nccn2c(C3CCC3)nc(-c3ccc(C(=O)c4ccccc4)nc3)c12] | [5-(8-Amino-3-cyclobutyl-imidazo[1,5-a]pyrazin-1-yl)-pyridin-2-yl]-phenyl-methanone | 370.16 | 1.97 |
| 71 | 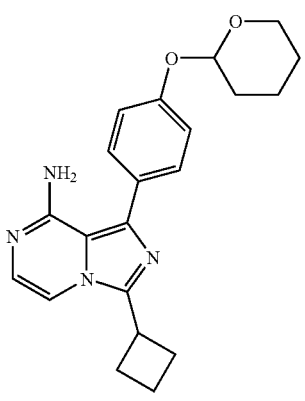 [SMILES: Nc1nccn2c(C3CCC3)nc(-c3ccc(OC4CCCCO4)cc3)c12] | -Cyclobutyl-1-[4-(tetrahydro-pyran-2-yloxy)-phenyl]-imidazo[1,5-a]pyrazin-8-ylamine | 366.22 | 0.1 |

TABLE 1-continued
| | | | | |
|---|---|---|---|---|
| 72 | 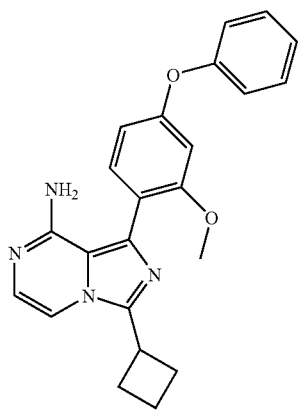 | 3-Cyclobutyl-1-(2-methoxy-4-phenoxy-phenyl)-imidazo[1,5-a]pyrazin-8-ylamine | 387.98 | 0.075 |
| 73 | 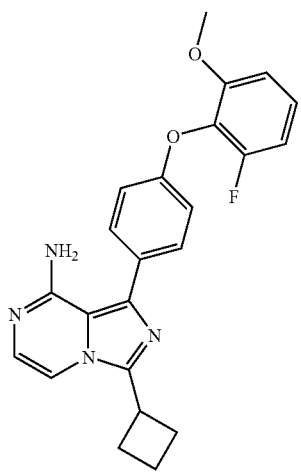 [SMILES: COc1cccc(F)c1Oc1ccc(-c2nc(C3CCC3)n3ccnc(N)c23)cc1] | 3-Cyclobutyl-1-[4-(2-fluoro-6-methoxy-phenoxy)-phenyl]-imidazo[1,5-a]pyrazin-8-ylamine | 405.11 | 2.5 |
| 74 | 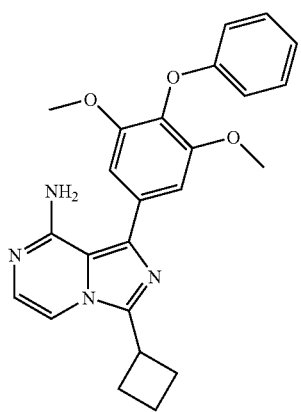 [SMILES: COc1cc(-c2nc(C3CCC3)n3ccnc(N)c23)cc(OC)c1Oc1ccccc1] | 3-Cyclobutyl-1-(3,5-dimethoxy-4-phenoxy-phenyl)-imidazo[1,5-a]pyrazin-8-ylamine | 516.70 | 0.77 |

TABLE 1-continued
| 75 | 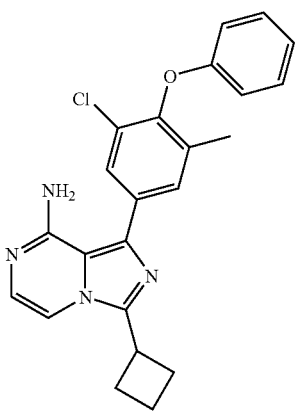 [SMILES: Cc1cc(-c2nc(C3CCC3)n3ccnc(N)c23)cc(Cl)c1Oc1ccccc1] | 1-(3-Chloro-5-methyl-4-phenoxy-phenyl)-3-cyclobutyl-imidazo[1,5-a]pyrazin-8-ylamine | 405.08 407.08 | 6.37 |
| --- | --- | --- | --- | --- |
| 76 | 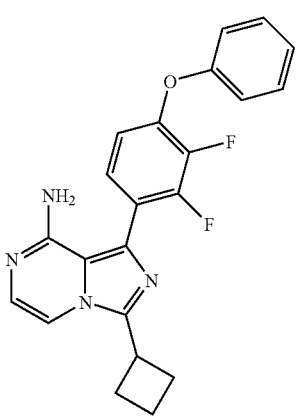 [SMILES: Nc1nccn2c(C3CCC3)nc(-c3ccc(Oc4ccccc4)c(F)c3F)c12] | 3-Cyclobutyl-1-(2,3-difluoro-4-phenoxy-phenyl)-imidazo[1,5-a]pyrazin-8-ylamine | 393.01 | 0.23 |
| 77 | 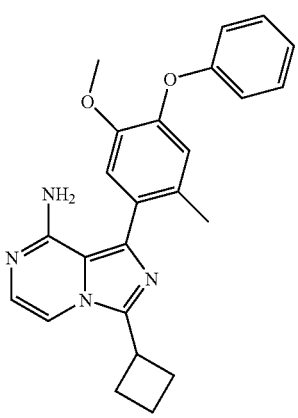 [SMILES: COc1cc(-c2nc(C3CCC3)n3ccnc(N)c23)c(C)cc1Oc1ccccc1] | 3-Cyclobutyl-1-(5-methoxy-2-methyl-4-phenoxy-phenyl)-imidazo[1,5-a]pyrazin-8-ylamine | 401.00 | 0.55 |
| 78 | 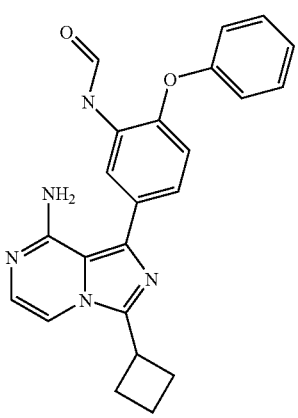 [SMILES: Nc1nccn2c(C3CCC3)nc(-c3ccc(Oc4ccccc4)c(NC=O)c3)c12] | N-[5-(8-Amino-3-cyclobutyl-imidazo[1,5-a]pyrazin-1-yl)-2-phenoxy-phenyl]-formamide | 399.65 | 2.35 |

TABLE 1-continued
| 79 | 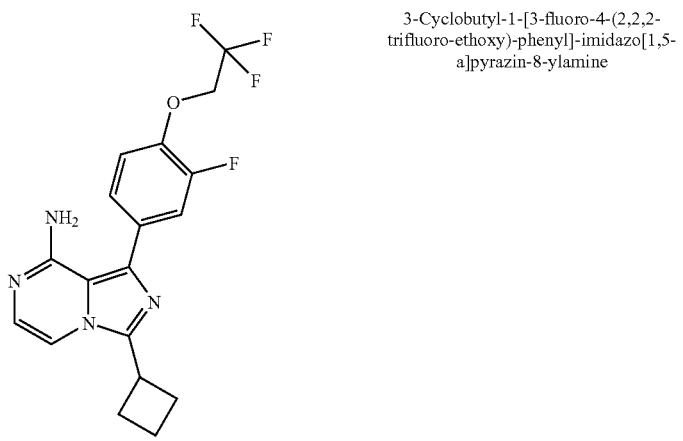 | 3-Cyclobutyl-1-[3-fluoro-4-(2,2,2-trifluoro-ethoxy)-phenyl]-imidazo[1,5-a]pyrazin-8-ylamine | 380.93 | 9.56 |
| --- | --- | --- | --- | --- |
| 80 | 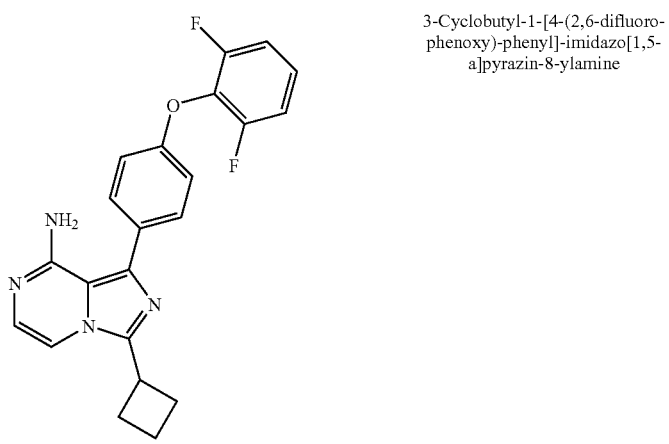 | 3-Cyclobutyl-1-[4-(2,6-difluoro-phenoxy)-phenyl]-imidazo[1,5-a]pyrazin-8-ylamine | 393.07 | 0.32 |
| 81 | 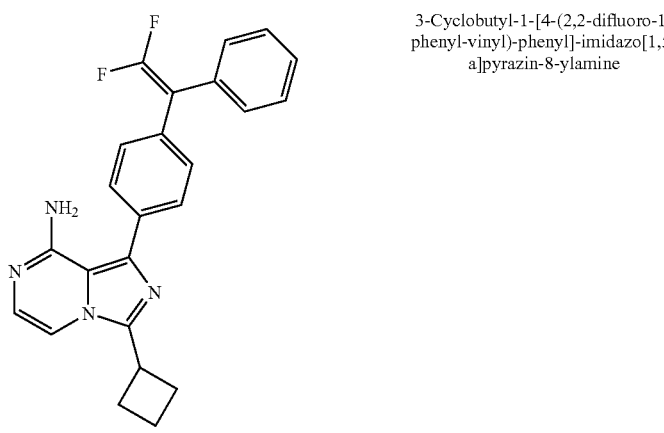 | 3-Cyclobutyl-1-[4-(2,2-difluoro-1-phenyl-vinyl)-phenyl]-imidazo[1,5-a]pyrazin-8-ylamine | 402.84 | 7.95 |

TABLE 1-continued
| 82 | 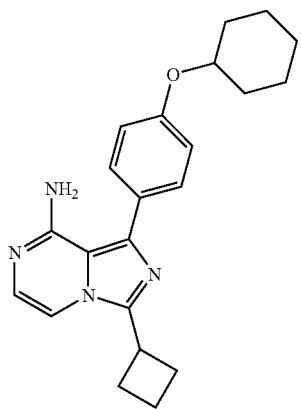 [SMILES: Nc1nccn2c(C3CCC3)nc(-c3ccc(OC4CCCCC4)cc3)c12] | 3-Cyclobutyl-1-(4-cyclohexyloxy-phenyl)-imidazo[1,5-a]pyrazin-8-ylamine | 363.01 | 0.8 |
| --- | --- | --- | --- | --- |
| 83 | 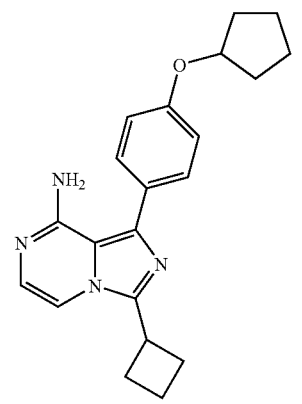 [SMILES: Nc1nccn2c(C3CCC3)nc(-c3ccc(OC4CCCC4)cc3)c12] | 3-Cyclobutyl-1-(4-cyclopentyloxy-phenyl)-imidazo[1,5-a]pyrazin-8-ylamine | 349.01 | 5.19 |
| 84 | 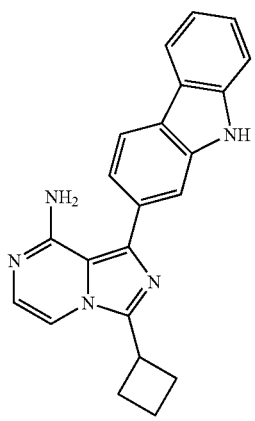 [SMILES: Nc1nccn2c(C3CCC3)nc(-c3ccc4c(c3)[nH]c3ccccc34)c12] | 1-(9H-Carbazol-2-yl)-3-cyclobutyl-imidazo[1,5-a]pyrazin-8-ylamine | 354.10 | 6.75 |

TABLE 1-continued
| | | | | |
|---|---|---|---|---|
| 85 | 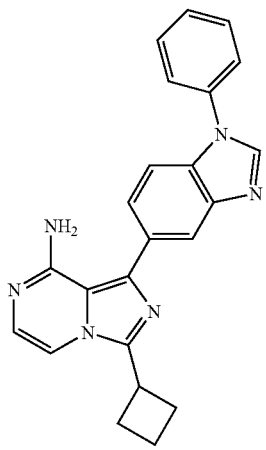 [SMILES: Nc1nccn2c(C3CCC3)nc(-c3ccc4c(c3)ncn4-c3ccccc3)c12] | 3-Cyclobutyl-1-(1-phenyl-1H-benzoimidazol-5-yl)-imidazo[1,5-a]pyrazin-8-ylamine | 380.91 | 3.35 |
| 86 | 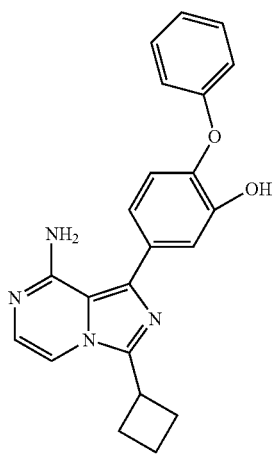 [SMILES: Nc1nccn2c(C3CCC3)nc(-c3ccc(Oc4ccccc4)c(O)c3)c12] | 5-(8-Amino-3-cyclobutyl-imidazo[1,5-a]pyrazin-1-yl)-2-phenoxy-phenol | 373.11 | 0.0589 |
| 87 | 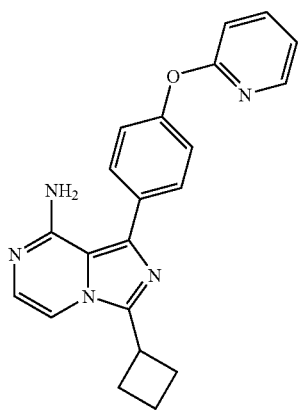 [SMILES: Nc1nccn2c(C3CCC3)nc(-c3ccc(Oc4ccccn4)cc3)c12] | 3-Cyclobutyl-1-[4-(pyridin-2-yloxy)-phenyl]-imidazo[1,5-a]pyrazin-8-ylamine | 358.13 | 1.9 |

TABLE 1-continued
| | | | | |
|---|---|---|---|---|
| 88 | 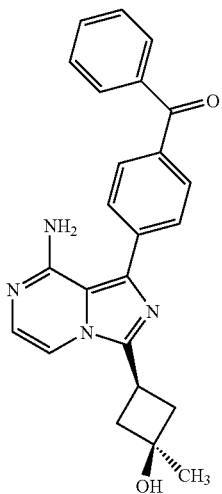 [SMILES: C[C@]1(O)C[C@@H](c2nc(-c3ccc(C(=O)c4ccccc4)cc3)c3c(N)nccn32)C1] | cis-{4-[8-Amino-3-(3-hydroxy-3-methyl-cyclobutyl)-imidazo[1,5-a]pyrazin-1-yl]-phenyl}-phenyl-methanone | 398.78 | 0.1832 |
| 89 | 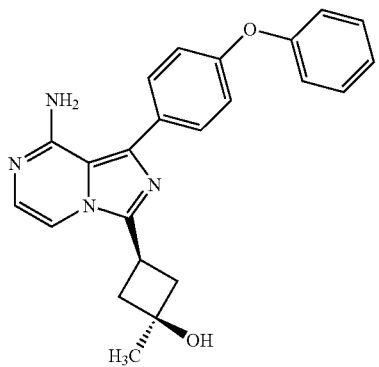 [SMILES: C[C@]1(O)C[C@@H](c2nc(-c3ccc(Oc4ccccc4)cc3)c3c(N)nccn32)C1] | cis-3-[8-Amino-1-(4-phenoxy-phenyl)-imidazo[1,5-a]pyrazin-3-yl]-1-methyl-cyclobutanol | 386.87 | 0.4920 |
| 90 | 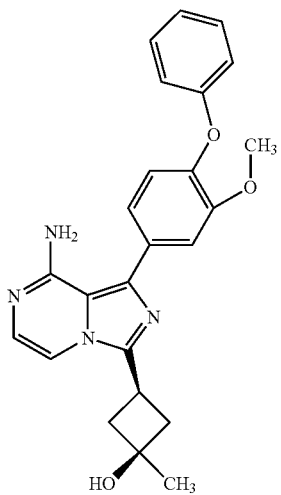 [SMILES: COc1cc(-c2nc([C@H]3C[C@@](C)(O)C3)n3ccnc(N)c23)ccc1Oc1ccccc1] | cis-3-[8-Amino-1-(3-methoxy-4-phenoxy-phenyl)-imidazo[1,5-a]pyrazin-3-yl]-1-methyl-cyclobutanol | 416.86 | 0.4590 |

TABLE 1-continued
| | | | | |
|---|---|---|---|---|
| 91 | 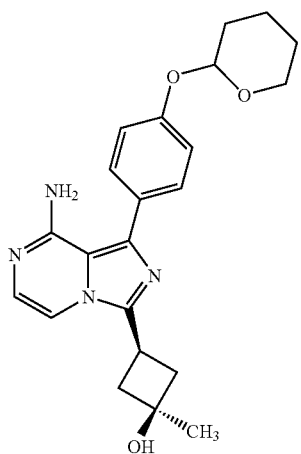 [SMILES: C[C@]1(O)C[C@@H](c2nc(-c3ccc(OC4CCCCO4)cc3)c3c(N)nccn32)C1] | cis-3-{8-Amino-1-[4-(tetrahydro-pyran-2-yloxy)-phenyl]-imidazo[1,5-a]pyrazin-3-yl}-1-methyl-cyclobutanol | 394.88 | 0.1782 |
| 92 | 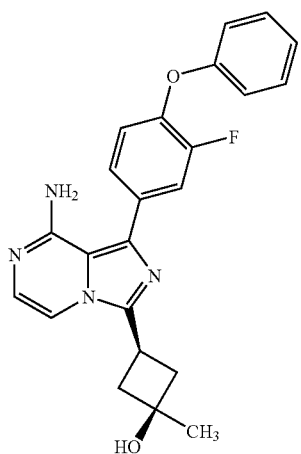 [SMILES: C[C@]1(O)C[C@@H](c2nc(-c3ccc(Oc4ccccc4)c(F)c3)c3c(N)nccn32)C1] | cis-3-[8-Amino-1-(3-fluoro-4-phenoxy-phenyl)-imidazol[1,5-a]pyrazin-3-yl]-1-methyl-cyclobutanol | 404.85 | 0.1146 |
| 93 | 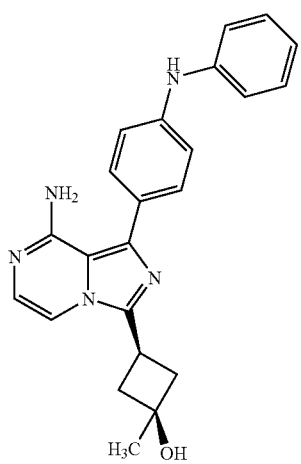 [SMILES: C[C@]1(O)C[C@@H](c2nc(-c3ccc(Nc4ccccc4)cc3)c3c(N)nccn32)C1] | cis-3-[8-Amino-1-(4-phenylamino-phenyl)-imidazo[1,5-a]pyrazin-3-yl]-1-methyl-cyclobutanol | 385.75 | 1.4599 |

TABLE 1-continued
| | | | | |
|---|---|---|---|---|
| 94 | 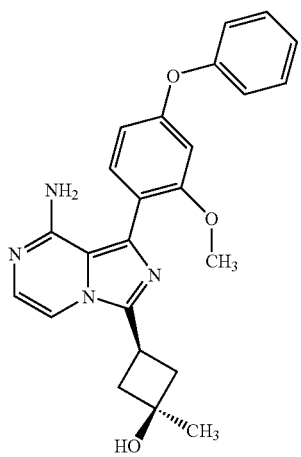 [SMILES: COc1cc(Oc2ccccc2)ccc1-c1nc([C@H]2C[C@@](C)(O)C2)n2ccnc(N)c12] | cis-3-[8-Amino-1-(2-methoxy-4-phenoxy-phenyl)-imidazo[1,5-a]pyrazin-3-yl]-1-methyl-cyclobutanol | 416.91 | 0.1188 |
| 95 | 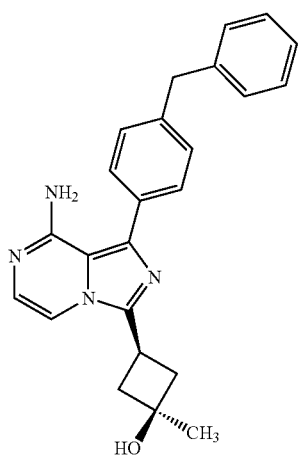 | cis-3-[8-Amino-1-(4-benzyl-phenyl)-imidazo[1,5-a]pyrazin-3-yl]-1-methyl-cyclobutanol | 384.87 | 0.2338 |
| 96 | 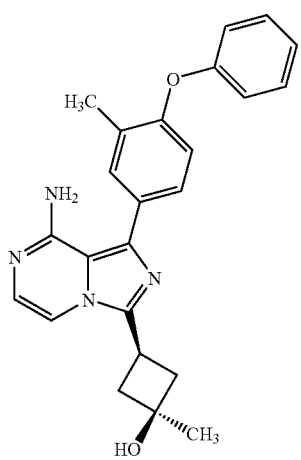 [SMILES: Cc1cc(-c2nc([C@H]3C[C@@](C)(O)C3)n3ccnc(N)c23)ccc1Oc1ccccc1] | cis-3-[8-Amino-1-(3-methyl-4-phenoxy-phenyl)-imidazo[1,5-a]pyrazin-3-yl]-1-methyl-cyclobutanol | 400.99 | 1.9796 |

TABLE 1-continued
| 97 | 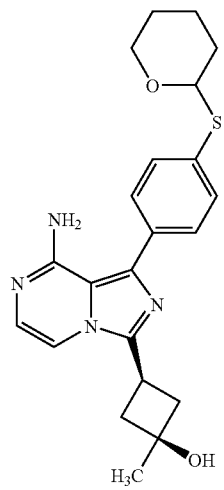 [SMILES: C[C@]1(O)C[C@@H](c2nc(-c3ccc(SC4CCCCO4)cc3)c3c(N)nccn32)C1] | cis-3-{8-Amino-1-[4-(tetrahydro-pyran-2-ylsulfanyl)-phenyl]-imidazo[1,5-a]pyrazin-3-yl}-1-methyl-cyclobutanol | 410.89 | 0.2424 |
| --- | --- | --- | --- | --- |
| 98 | 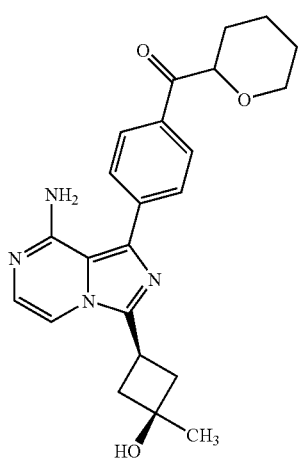 [SMILES: C[C@]1(O)C[C@@H](c2nc(-c3ccc(C(=O)C4CCCCO4)cc3)c3c(N)nccn32)C1] | cis-{4-[8-Amino-3-(3-hydroxy-3-methyl-cyclobutyl)-imidazo[1,5-a]pyrazin-1-yl]-phenyl}-(tetrahydro-pyran-2-yl)-methanone | 407.12 | 2.5401 |
| 99 | 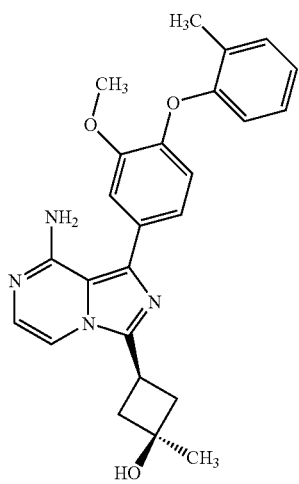 [SMILES: COc1cc(-c2nc([C@H]3C[C@@](C)(O)C3)n3ccnc(N)c23)ccc1Oc1ccccc1C] | cis-3-[8-Amino-1-(3-methoxy-4-o-tolyloxy-phenyl)-imidazo[1,5-a]pyrazin-3-yl]-1-methyl-cyclobutanol | 431.06 | 1.4700 |

TABLE 1-continued

| | | | | |
|---|---|---|---|---|
| 100 | | cis-3-{8-Amino-1-[4-(3-fluoro-phenoxy)-3-methoxy-phenyl]-imidazo[1,5a]pyrazin-3-yl}-1-methyl-cyclobutanol | 435.06 | 4.0831 |
| 101 | | cis-3-[8-Amino-1-(3-methoxy-4-m-tolyloxy-phenyl)-imidazo[1,5-a]pyrazin-3-yl]-1-methyl-cyclobutanol | 431.12 | 1.2054 |
| 102 | | cis-3-{8-Amino-1-[4-(2-fluoro-6-methoxy-phenoxy)-phenyl]-imidazo[1,5-a]pyrazin-3-yl}-1-methyl-cyclobutanol | 435.02 | 7.8495 |

TABLE 1-continued
| | | | | |
|---|---|---|---|---|
| 103 | 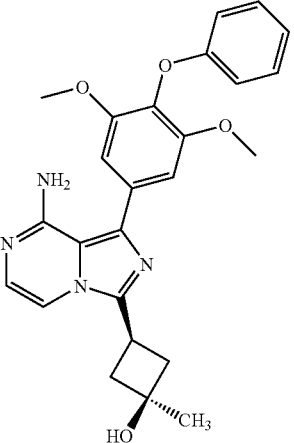 [SMILES: COc1cc(-c2nc([C@H]3C[C@@](C)(O)C3)n3ccnc(N)c23)cc(OC)c1Oc1ccccc1] | cis-3-[8-Amino-1-(3,5-dimethoxy-4-phenoxy-phenyl)-imidazo[1,5-a]pyrazin-3-yl[-1-methyl-cyclobutanol | 447.02 | 2.6246 |
| 104 | 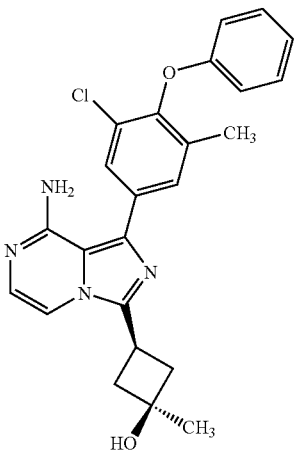 [SMILES: Cc1cc(-c2nc([C@H]3C[C@@](C)(O)C3)n3ccnc(N)c23)cc(Cl)c1Oc1ccccc1] | cis-3-[8-Amino-1-(3-chloro-5-methyl-4-phenoxy-phenyl)-imidazo[1,5-a]pyrazin-3-yl]-1-methyl-cyclobutanol | 434.95 | 6.8650 |
| 105 | 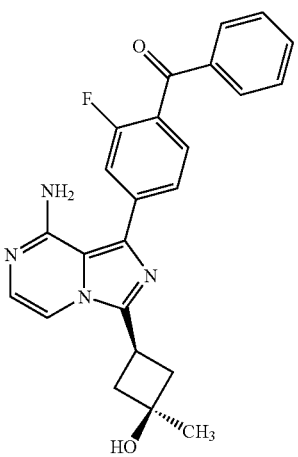 | cis-{4-[8-Amino-3-(3-hydroxy-3-methyl-cyclobutyl)-imidazo[1,5-a]pyrazin-1-yl]-2-fluoro-phenyl}-phenyl-methanone | 416.96 | 0.1396 |

TABLE 1-continued
| 106 | 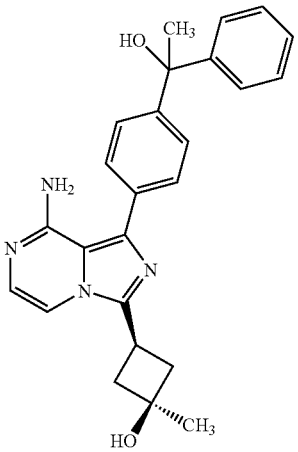 [SMILES: CC(O)(c1ccccc1)c1ccc(-c2nc([C@H]3C[C@@](C)(O)C3)n3ccnc(N)c23)cc1] | cis-3-{8-Amino-1-[4-(1-hydroxy-1-phenyl-ethyl)-phenyl]-imidazo[1,5-a]pyrazin-3-yl}-1-methyl-cyclobutanol | 415.02 | 0.2161 |
| 107 | 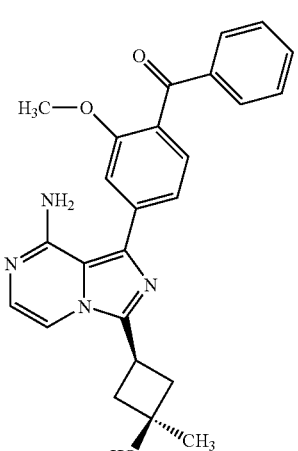 | cis-{4-[8-Amino-3-(3-hydroxy-3-methyl-cyclobutyl)-imidazo[1,5-a]pyrazin-1-yl]-2-methoxy-phenyl}-phenyl-methanone | 429.02 | 0.1168 |
| 108 | 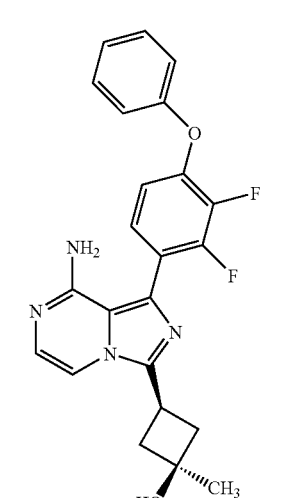 | cis-3-[8-Amino-1-(2,3-difluoro-4-phenoxy-phenyl)-imidazo[1,5-a]pyrazin-3-yl]-1-methyl-cyclobutanol | 423.03 | 0.1371 |

TABLE 1-continued
| | | | | |
|---|---|---|---|---|
| 109 | 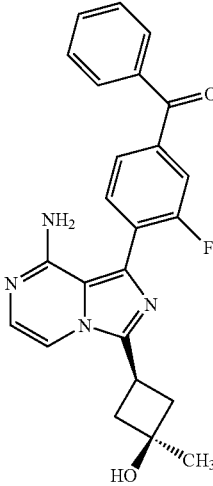 | cis-{4-[8-Amino-3-(3-hydroxy-3-methyl-cyclobutyl)-imidazo[1,5-a]pyrazin-1-yl]-3-fluoro-phenyl}-phenyl-methanone | 416.97 | 0.0886 |
| 110 | 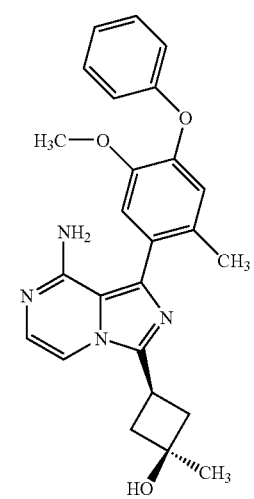 [SMILES: COc1cc(-c2nc([C@H]3C[C@@](C)(O)C3)n3ccnc(N)c23)c(C)cc1Oc1ccccc1] | cis-3-[8-Amino-1-(5-methoxy-2-methyl-4-phenoxy-phenyl)-imidazo[1,5-a]pyrazin-3-yl]-1-methyl-cyclobutanol | 431.04 | 0.8914 |
| 111 | 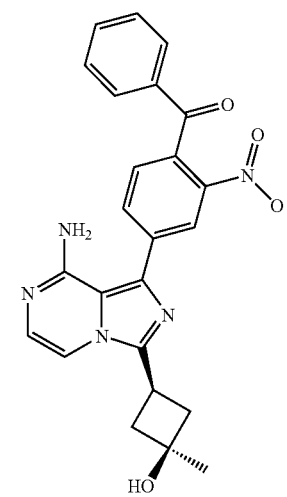 | cis-{4-[8-Amino-3-(3-hydroxy-3-methyl-cyclobutyl)-imidazo[1,5-a]pyrazin-1-yl]-2-nitro-phenyl}-phenyl-methanone | 444.94 | 1.1883 |

TABLE 1-continued
| 112 | 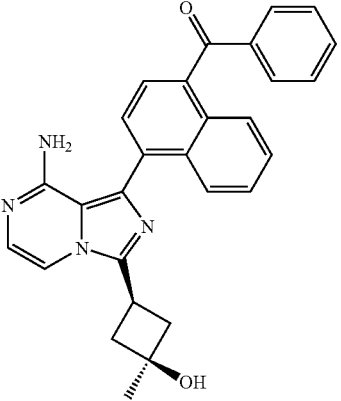 [SMILES: C[C@]1(O)C[C@@H](c2nc(-c3ccc(C(=O)c4ccccc4)c4ccccc34)c3c(N)nccn32)C1] | cis-{4-[8-Amino-3-(3-hydroxy-3-methyl-cyclobutyl)-imidazo[1,5-a]pyrazin-1-yl]-naphthalen-1-yl}-phenyl-methanone | 449.03 | 1.5141 |
|---|---|---|---|---|
| 113 | 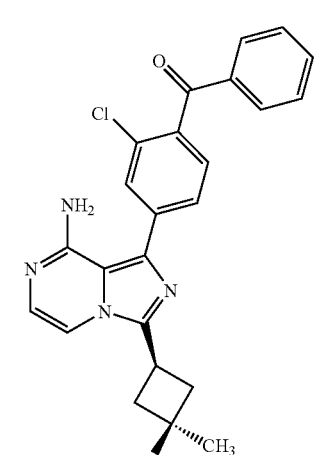 | cis-{4-[8-Amino-3-(3-hydroxy-3-methyl-cyclobutyl)-imidazo[1,5-a]pyrazin-1-yl]-2-chloro-phenyl}-phenyl-methanone | 433.08 | 0.2211 |
| 114 | 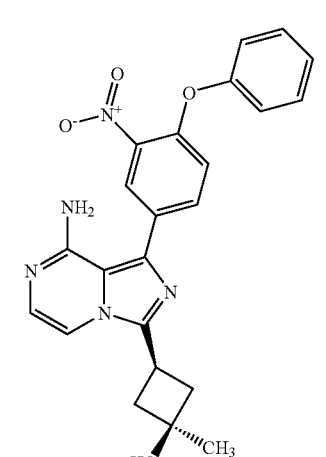 | cis-3-[8-Amino-1-(3-nitro-4-phenoxy-phenyl)-imidazo[1,5-a]pyrazin-3-yl]-1-methyl-cyclobutanol | 433.31 | 3.2634 |

TABLE 1-continued

| | | | | |
|---|---|---|---|---|
| 115 | | cis-3-{8-Amino-1-[3-fluoro-4-(2,2,2-trifluoro-ethoxy)-phenyl]-imidazo[1,5-a]pyrazin-3-yl}-1-methyl-cyclobutanol | 411.09 | 6.8229 |
| 116 | | cis-{4-[8-Amino-3-(3-hydroxy-3-methyl-cyclobutyl)-imidazo[1,5-a]pyrazin-1-yl]-phenyl}-phenyl-methanone oxime | 414.02 | 5.5878 |
| 117 | | cis-3-{8-Amino-1-[4-(tetrahydro-furan-2-ylmethyl)-phenyl]-imidazo[1,5-a]pyrazin-3-yl}-1-methyl-cyclobutanol | 379.1 | 5.3251 |

TABLE 1-continued
| 118 | 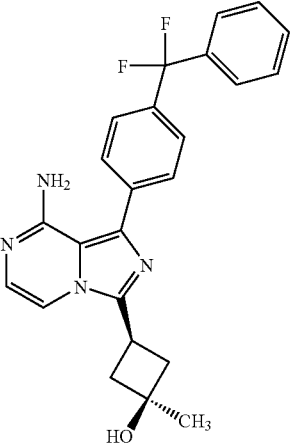 [SMILES: C[C@]1(O)C[C@@H](c2nc(-c3ccc(C(F)(F)c4ccccc4)cc3)c3c(N)nccn32)C1] | cis-3-{8-Amino-1-[4-(difluoro-phenyl-methyl)-phenyl]-imidazo[1,5-a]pyrazin-3-yl}-1-methyl-cyclobutanol | 420.99 | 0.4518 |
| --- | --- | --- | --- | --- |
| 119 | 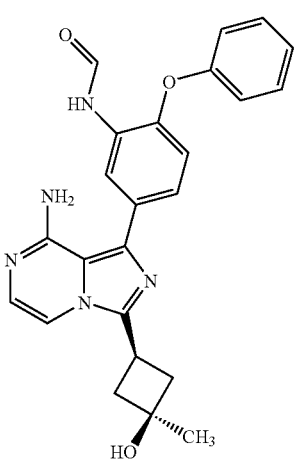 [SMILES: C[C@]1(O)C[C@@H](c2nc(-c3ccc(Oc4ccccc4)c(NC=O)c3)c3c(N)nccn32)C1] | cis-N-{5-[8-Amino-3-(3-hydroxy-3-methyl-cyclobutyl)-imidazo[1,5-a]pyrazin-1-yl]-2-phenoxy-phenyl}-formamide | 429.68 | 8.5279 |
| 120 | 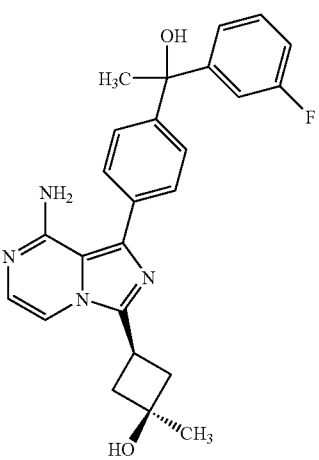 [SMILES: CC(O)(c1ccc(-c2nc([C@H]3C[C@@](C)(O)C3)n3ccnc(N)c23)cc1)c1cccc(F)c1] | cis-3-(8-Amino-1-{4-[1-(3-fluoro-phenyl)-1-hydroxy-ethyl]-phenyl}-imidazo[1,5-a]pyrazin-3-yl)-1-methyl-cyclobutanol | 433.16 | 5.5782 |

TABLE 1-continued

| 121 | | cis-3-[8-Amino-1-(2-chloro-4-phenoxy-phenyl)-imidazo[1,5-a]pyrazin-3-yl]-1-methyl-cyclobutanol | 420.84 | 0.7576 |
| --- | --- | --- | --- | --- |
| 122 | | cis-3-{8-Amino-1-[2-fluoro-4-(1-hydroxy-1-phenyl-ethyl)-phenyl]-imidazo[1,5-a]pyrazin-3-yl}-1-methyl-cyclobutanol | 433.07 | 0.4293 |
| 123 | | cis-3-{8-Amino-1-[4-(1-hydroxy-1-phenyl-ethyl)-2-methyl-phenyl]-imidazo[1,5-a]pyrazin-3-yl}-1-methyl-cyclobutanol | 429.04 | 1.0481 |

TABLE 1-continued
| | | | | |
|---|---|---|---|---|
| 124 | 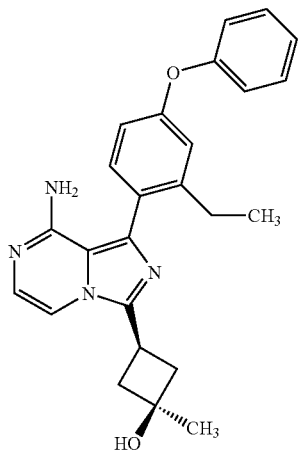 [SMILES: CCc1cc(Oc2ccccc2)ccc1-c1nc([C@H]2C[C@@](C)(O)C2)n2ccnc(N)c12] | cis-3-[8-Amino-1-(2-ethyl-4-phenoxy-phenyl)-imidazo[1,5-a]pyrazin-3-yl]-1-methyl-cyclobutanol | 415.07 | 1.8817 |
| 125 | 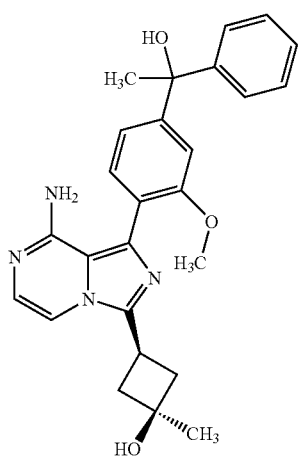 [SMILES: COc1cc(C(C)(O)c2ccccc2)ccc1-c1nc([C@H]2C[C@@](C)(O)C2)n2ccnc(N)c12] | cis-3-{8-Amino-1-[4-(1-hydroxy-1-phenyl-ethyl)-2-methoxy-phenyl]-imidazo[1,5-a]pyrazin-3-yl}-1-methyl-cyclobutanol | 445.06 | 0.3447 |
| 126 | 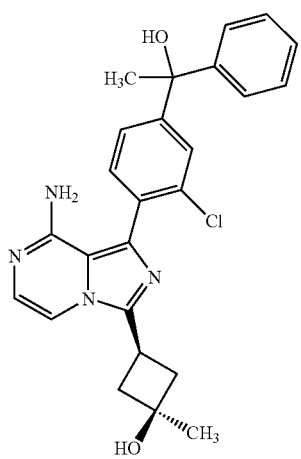 | cis-3-{8-Amino-1-[2-chloro-4-(1-hydroxy-1-phenyl-ethyl)-phenyl]-imidazo[1,5-a]pyrazin-3-yl}-1-methyl-cyclobutanol | 449.14 | 0.4779 |

| | | | | |
|---|---|---|---|---|
| 127 | 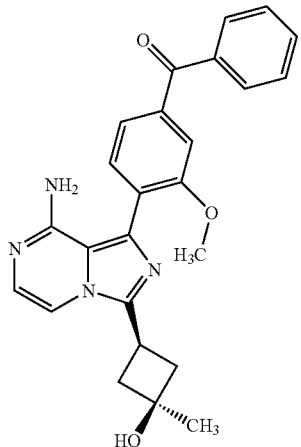 [SMILES: COc1cc(C(=O)c2ccccc2)ccc1-c1nc([C@H]2C[C@@](C)(O)C2)n2ccnc(N)c12] | cis-{4-[8-Amino-3-(3-hydroxy-3-methyl-cyclobutyl)-imidazo[1,5-a]pyrazin-1-yl]-3-methoxy-phenyl}-phenyl-methanone | 429.06 | 0.4157 |
| 128 | 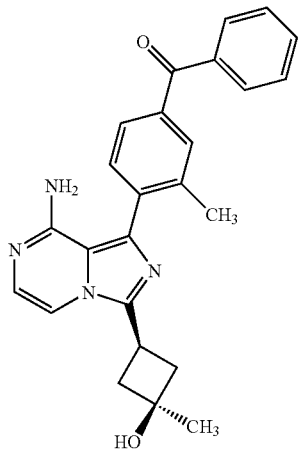 [SMILES: Cc1cc(C(=O)c2ccccc2)ccc1-c1nc([C@H]2C[C@@](C)(O)C2)n2ccnc(N)c12] | cis-{4-[8-Amino-3-(3-hydroxy-3-methyl-cyclobutyl)-imidazo[1,5-a]pyrazin-1-yl]-3-methyl-phenyl}-phenyl-methanone | 413.06 | 0.5244 |
| 129 | 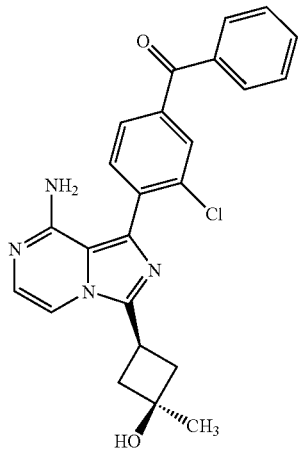 [SMILES: C[C@]1(O)C[C@@H](c2nc(-c3ccc(C(=O)c4ccccc4)cc3Cl)c3c(N)nccn32)C1] | cis-{4-[8-Amino-3-(3-hydroxy-3-methyl-cyclobutyl)-imidazo[1,5-a]pyrazin-1-yl]-3-chloro-phenyl}-phenyl-methanone | 433.07 | 0.2172 |

TABLE 1-continued
| | | | | |
|---|---|---|---|---|
| 130 | 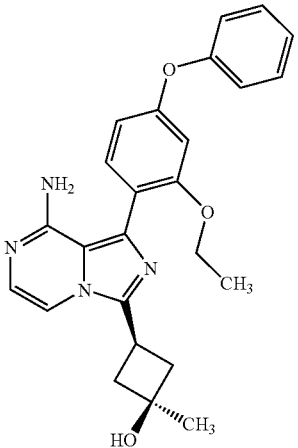 [SMILES: CCOc1cc(Oc2ccccc2)ccc1-c1nc([C@H]2C[C@@](C)(O)C2)n2ccnc(N)c12] | cis-3-[8-Amino-1-(2-ethoxy-4-phenoxy-phenyl)-imidazo[1,5-a]pyrazin-3-yl]-1-methyl-cyclobutanol | 431.13 | 0.3504 |
| 131 | 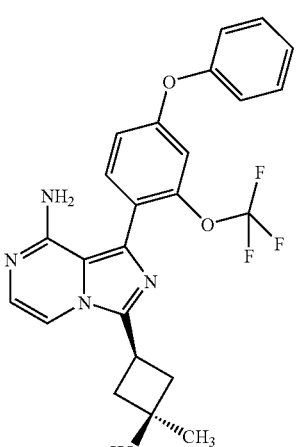 | cis-3-[8-Amino-1-(4-phenoxy-2-trifluoromethoxy-phenyl)-imidazo[1,5-a]pyrazin-3-yl]-1-methyl-cyclobutanol | 471.09 | 2.1590 |
| 132 | 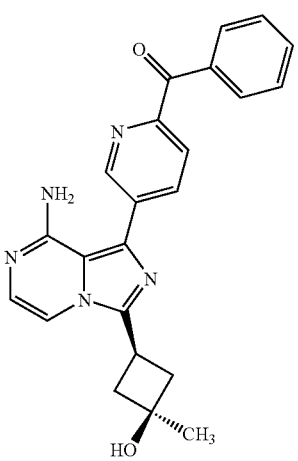 [SMILES: C[C@]1(O)C[C@@H](c2nc(-c3ccc(C(=O)c4ccccc4)nc3)c3c(N)nccn32)C1] | cis-{5-[8-Amino-3-(3-hydroxy-3-methyl-cyclobutyl)-imidazo[1,5-a]pyrazin-1-yl]-pyridin-2-yl}-phenyl-methanone | 400.16 | 3.7969 |

TABLE 1-continued

| | | | | |
|---|---|---|---|---|
| 133 | | cis-3-{8-Amino-1-[4-(2,6-difluoro-phenoxy)-phenyl]-imidazo[1,5-a]pyrazin-3-yl}-1-methyl-cyclobutanol | 422.98 | 0.73 |
| 134 | | 1-(4-Phenoxy-phenyl)-3-(1H-pyrazol-3-yl)-imidazo[1,5-a]pyrazin-3-ylamine | 369.1 | 0.2552 |
| 135 | | 1-(4-Phenoxy-phenyl)-3-thiophen-3-yl-imidazo[1,5-a]pyrazin-8-ylamine | 384.94 | 3.3435 |

TABLE 1-continued
| 136 | 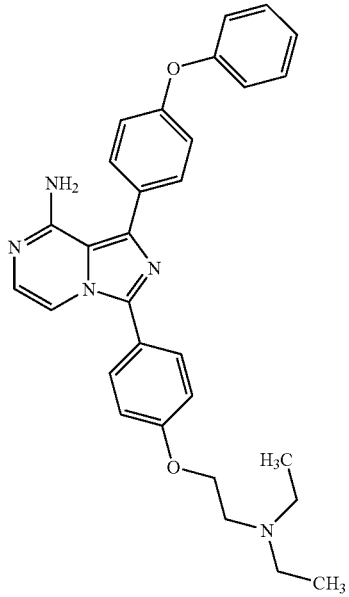 [SMILES: CCN(CC)CCOc1ccc(-c2nc(-c3ccc(Oc4ccccc4)cc3)c3c(N)nccn23)cc1] | 3-[4-(2-Diethylamino-ethoxy)-phenyl]-1-(4-phenoxy-phenyl)-imidazo[1,5-a]pyrazin-8-ylamine | 494.02 | 0.3525 |
| --- | --- | --- | --- | --- |
| 137 | 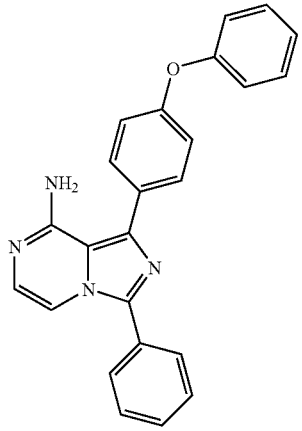 [SMILES: Nc1nccn2c(-c3ccccc3)nc(-c3ccc(Oc4ccccc4)cc3)c12] | 1-(4-Phenoxy-phenyl)-3-phenyl-imidazo[1,5-a]pyrazin-8-ylamino | 378.8 | 2.5874 |
| 138 | 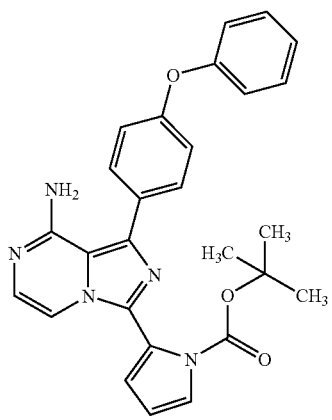 [SMILES: CC(C)(C)OC(=O)n1cccc1-c1nc(-c2ccc(Oc3ccccc3)cc2)c2c(N)nccn12] | 2-[8-Amino-1-(4-phenoxy-phenyl)-imidazo[1,5-a]pyrazin-3-yl]pyrrole-1-carboxylic acid tert-butyl ester | 469.31 | 5.9753 |

TABLE 1-continued

| | | | | |
|---|---|---|---|---|
| 139 | | 3-(4-Dimethylaminomethyl-phenyl)-1-(4-phenoxy-phenyl)-imidazo[1,5-a]pyrazin-8-ylamine | 436.13 | 0.6505 |
| 140 | | 4-[8-Amino-1-(4-phenoxy-phenyl)-imidazo[1,5-a]pyrazin-3-yl]-phenol | 394.94 | 0.3920 |
| 141 | | 3-(4-Amino-phenyl)-1-(4-phenoxy-phenyl)-imidazo[1,5-a]pyrazin-8-ylamine | 395.36 | 0.1834 |

TABLE 1-continued
| 142 | 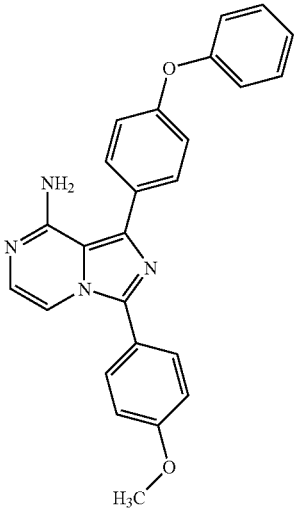 [SMILES: COc1ccc(-c2nc(-c3ccc(Oc4ccccc4)cc3)c3c(N)nccn23)cc1] | 3-(4-Methoxy-phenyl)-1-(4-phenoxy-phenyl)-imidazo[1,5-a]pyrazin-8-ylamine | 408.95 | 0.9927 |
| --- | --- | --- | --- | --- |
| 143 | 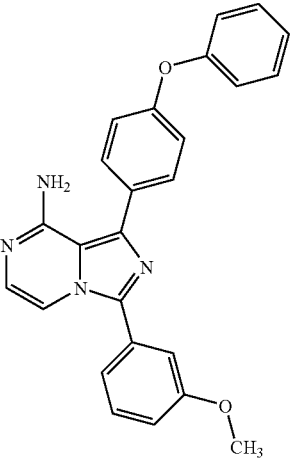 [SMILES: COc1cccc(-c2nc(-c3ccc(Oc4ccccc4)cc3)c3c(N)nccn23)c1] | 3-(3-Methoxy-phenyl)-1-(4-phenoxy-phenyl)-imidazo[1,5-a]pyrazin-8-ylamine | 409.00 | 1.4192 |
| 144 | 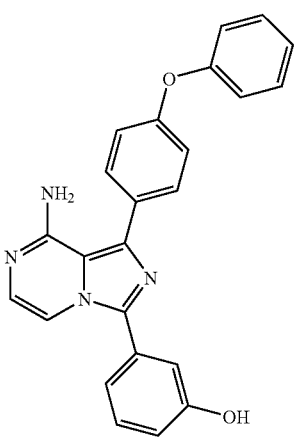 [SMILES: Nc1nccn2c(-c3cccc(O)c3)nc(-c3ccc(Oc4ccccc4)cc3)c12] | 3-[8-Amino-1-(4-phenoxy-phenyl)-imidazo[1,5-a]pyrazin-3-yl]-phenol | 394.98 | 0.3478 |

TABLE 1-continued
| | | | | |
|---|---|---|---|---|
| 145 | 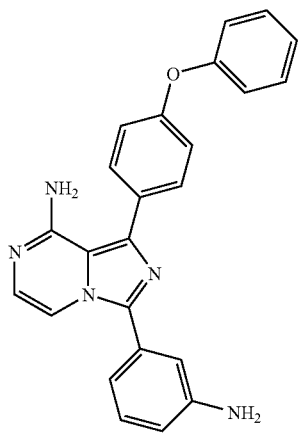 [SMILES: Nc1cccc(-c2nc(-c3ccc(Oc4ccccc4)cc3)c3c(N)nccn23)c1] | 3-(3-Amino-phenyl)-1-(4-phenoxy-phenyl)-imidazo[1,5-a]pyrazin-8-ylamine | 394.05 | 0.3353 |
| 146 | 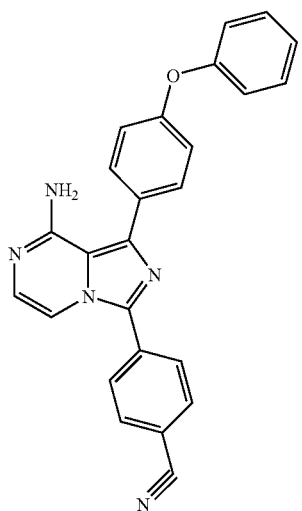 [SMILES: N#Cc1ccc(-c2nc(-c3ccc(Oc4ccccc4)cc3)c3c(N)nccn23)cc1] | 4-[8-Amino-1-(4-phenoxy-phenyl)-imidazo[1,5-a]pyrazin-3-yl]-benzonitrile | 403.96 | 5.6704 |
| 147 | 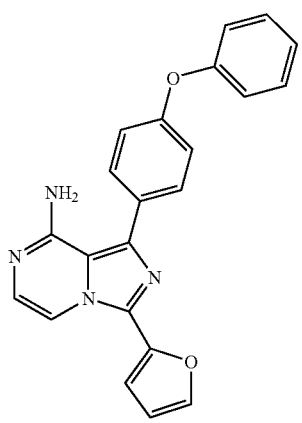 [SMILES: Nc1nccn2c(-c3ccco3)nc(-c3ccc(Oc4ccccc4)cc3)c12] | 3-Furan-2-yl-1-(4-phenoxy-phenyl)-imidazo[1,5-a]pyrazin-8-ylamine | 368.95 | 0.2861 |

| | | | | |
|---|---|---|---|---|
| 148 | 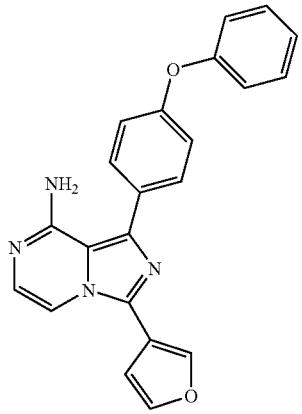 [SMILES: Nc1nccn2c(-c3ccoc3)nc(-c3ccc(Oc4ccccc4)cc3)c12] | 3-Furan-3-yl-1-(4-phenoxy-phenyl)-imidazo[1,5-a]pyrazin-8-ylamine | 369.01 | 0.1450 |
| 149 | 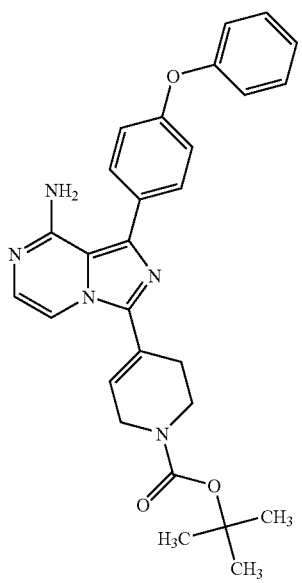 [SMILES: CC(C)(C)OC(=O)N1CC=C(c2nc(-c3ccc(Oc4ccccc4)cc3)c3c(N)nccn23)CC1] | 4-[8-Amino-1-(4-phenoxy-phenyl)-imidazo[1,5-a]pyrazin-3-yl]-3,6-dihydro-2H-pyridine-1-carboxylic acid tert-butyl ester | 485.37 | 1.9696 |
| 150 | 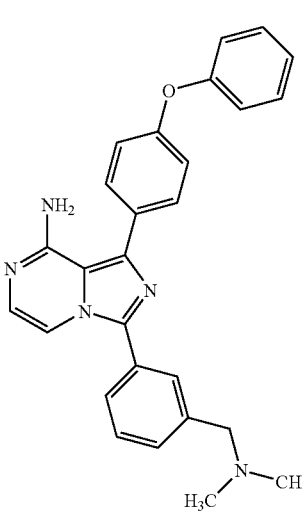 | 3-(3-Dimethylaminomethyl-phenyl)-1-(4-phenoxy-phenyl)-imidazo[1,5-a]pyrazin-8-ylamine | 436.11 | 2.7171 |

TABLE 1-continued
| | | | | |
|---|---|---|---|---|
| 151 | 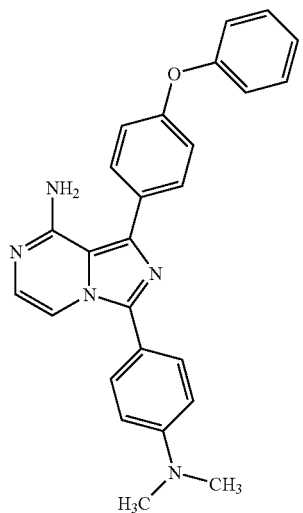 [SMILES: CN(C)c1ccc(-c2nc(-c3ccc(Oc4ccccc4)cc3)c3c(N)nccn23)cc1] | 3-(4-Dimethylamino-phenyl)-1-(4-phenoxy-phenyl)-imidazo[1,5-a]pyrazin-8-ylamine | 421.93 | 0.6693 |
| 152 | 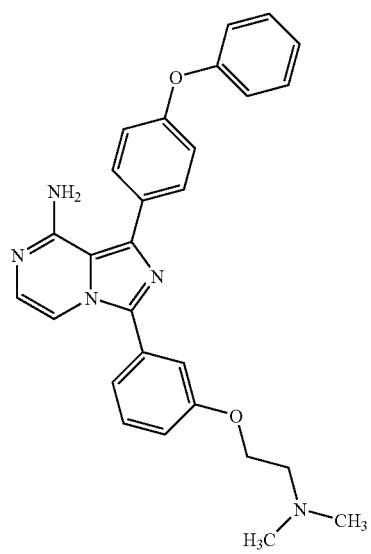 [SMILES: CN(C)CCOc1cccc(-c2nc(-c3ccc(Oc4ccccc4)cc3)c3c(N)nccn23)c1] | 3-[3-(2-Dimethylamino-ethoxy)-phenyl]-1-(4-phenoxy-phenyl)-imidazo[1,5a]pyrazin-8-ylamine | 466.14 | 0.4280 |

| | | | | |
|---|---|---|---|---|
| 153 | 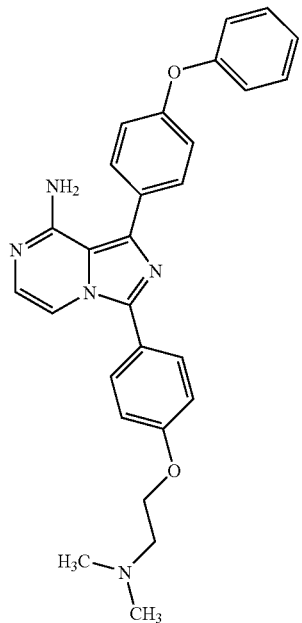 [SMILES: CN(C)CCOc1ccc(-c2nc(-c3ccc(Oc4ccccc4)cc3)c3c(N)nccn23)cc1] | 3-[4-(2-Dimethylamino-ethoxy)-phenyl]-1-(4-phenoxy-phenyl)-imidazo[1,5a]pyrazin-8-ylamine | 466.15 | 0.0439 |
| 154 | 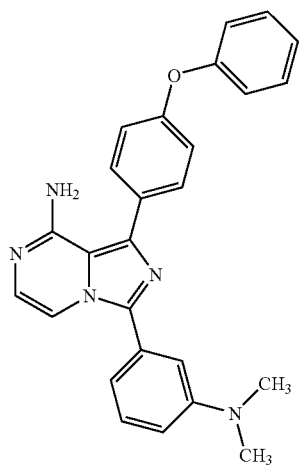 [SMILES: CN(C)c1cccc(-c2nc(-c3ccc(Oc4ccccc4)cc3)c3c(N)nccn23)c1] | 3-(3-Dimethylamino-phenyl)-1-(4-phenoxy-phenyl)-imidazo[1,5-a]pyrazin-8-ylamine | 422.01 | 0.9978 |

TABLE 1-continued
| 155 | 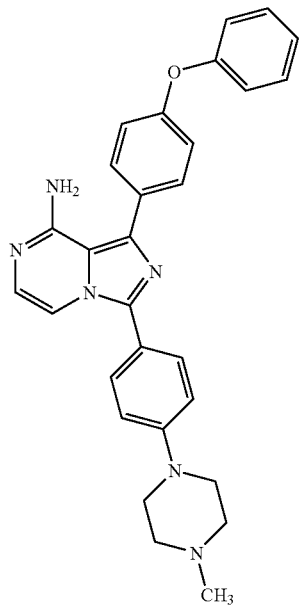 [SMILES: CN1CCN(c2ccc(-c3nc(-c4ccc(Oc5ccccc5)cc4)c4c(N)nccn34)cc2)CC1] | 3-[4-(4-Methyl-piperazin-1-yl)-phenyl]-1-(4-phenoxy-phenyl)-imidazo[1,5-a]pyrazin-8-ylamine | 477.15 | 0.0667 |
|---|---|---|---|---|
| 156 | 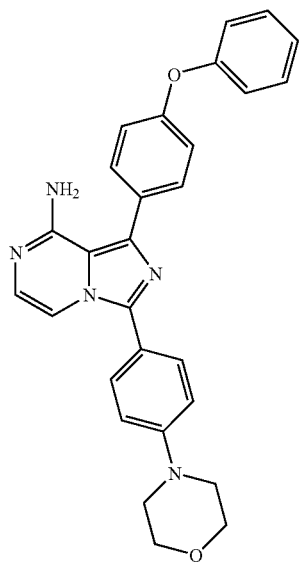 [SMILES: Nc1nccn2c(-c3ccc(N4CCOCC4)cc3)nc(-c3ccc(Oc4ccccc4)cc3)c12] | 3-(4-Morpholin-4-yl-phenyl)-1-(4-phenoxy-phenyl)-imidazo[1,5-a]pyrazin-8-ylamine | 465.42 | 3.6840 |

TABLE 1-continued

| 157 | | 4-{4-[8-Amino-1-(4-phenoxy-phenyl)-imidazo[1,5-a]pyrazin-3-yl]-pyrazol-1-yl}-piperidine-1-carboxylic acid tert-butyl ester | 552.14 | 3.6285 |
|---|---|---|---|---|
| 158 | | 3-[4-(2-Morpholin-4-yl-ethoxy)-phenyl]-1-(4-phenoxy-phenyl)-imidazo[1,5-a]pyrazin-8-ylamine | 507.93 | 0.6767 |
| 159 | | 1-(4-Phenoxy-phenyl)-3-(1H-pyrrol-3-yl)-imidazo[1,5-a]pyrazin-8-ylamine | 367.85 | 0.1217 |

TABLE 1-continued

| | | | | |
|---|---|---|---|---|
| 160 | | 1-(4-Phenoxy-phenyl)-3-pyridin-4-yl-imidazo[1,5-a]pyrazin-8-ylamine | 380.11 | 2.6267 |
| 161 | | 3-(1H-Indol-6-yl)-1-(4-phenoxy-phenyl)-imidazo[1,5-a]pyrazin-8-ylamine | 418.1 | 3.3449 |
| 162 | | 4-[8-Amino-1-(4-phenoxy-phenyl)-imidazo[1,5-a]pyrazin-3-yl]-benzoic acid | 423.09 | 2.2695 |

TABLE 1-continued
| 163 | 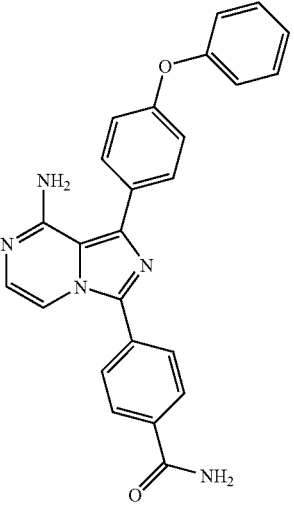 [SMILES: NC(=O)c1ccc(-c2nc(-c3ccc(Oc4ccccc4)cc3)c3c(N)nccn23)cc1] | 4-[8-Amino-1-(4-phenoxy-phenyl)-imidazo[1,5-a]pyrazin-3-yl]-benzamide | 422.05 | 0.1880 |
| 164 | 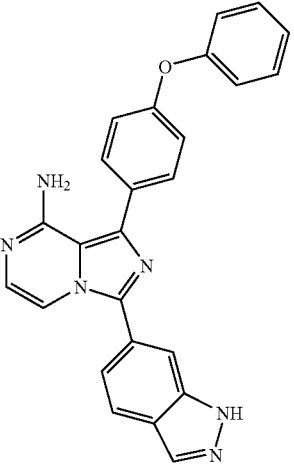 [SMILES: Nc1nccn2c(-c3ccc4cn[nH]c4c3)nc(-c3ccc(Oc4ccccc4)cc3)c12] | 3-(1H-Indazol-6-yl)-1-(4-phenoxy-phenyl)-imidazo[1,5-a]pyrazin-8-ylamine | 419.03 | 3.8730 |
| 165 | 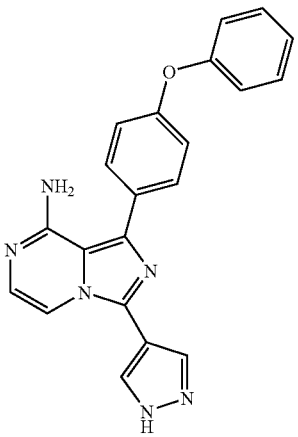 | 1-(4-Phenoxy-phenyl)-3-(1H-pyrazol-4-yl)-imidazo[1,5-a]pyrazin-8-ylamine | 369.13 | 0.3918 |

TABLE 1-continued

| | | | | |
|---|---|---|---|---|
| 166 | | 3-(1-Methyl-1H-pyrazol-4-yl)-1-(4-phenoxy-phenyl)-imidazo[1,5-a]pyrazin-8-ylamine | 383.01 | 0.8114 |
| 167 | | 3-(2-Amino-phenyl)-1-(4-phenoxy-phenyl)-imidazo[1,5-a]pyrazin-8-ylamine | 394.07 | 6.8762 |
| 168 | | 3-[8-Amino-1-(4-phenoxy-phenyl)-imidazo[1,5-a]pyrazin-3-yl]-benzoic acid | 423.09 | 1.6774 |

TABLE 1-continued
| 169 | 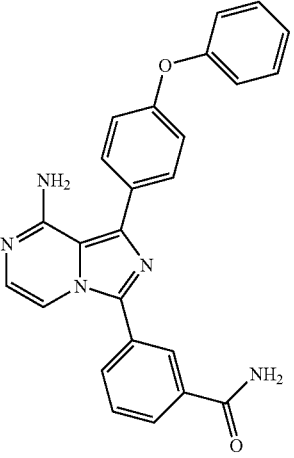 [SMILES: NC(=O)c1cccc(-c2nc(-c3ccc(Oc4ccccc4)cc3)c3c(N)nccn23)c1] | 3-[8-Amino-1-(4-phenoxy-phenyl)-imidazo[1,5-a]pyrazin-3-yl]-benzamide | 422.13 | 4.4235 |
| --- | --- | --- | --- | --- |
| 170 | 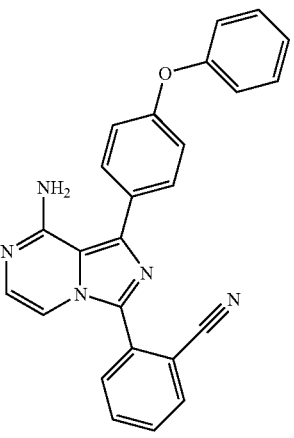 [SMILES: N#Cc1ccccc1-c1nc(-c2ccc(Oc3ccccc3)cc2)c2c(N)nccn12] | 2-[8-Amino-1-(4-phenoxy-phenyl)-imidazo[1,5-a]pyrazin-3-yl]-benzonitrile | 404.09 | 1.8536 |
| 171 | 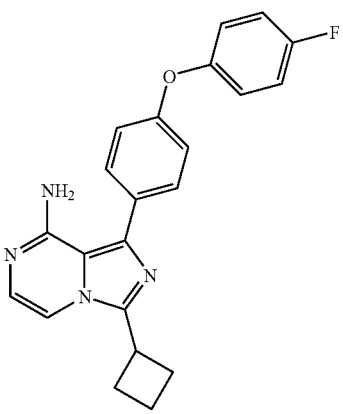 [SMILES: Nc1nccn2c(C3CCC3)nc(-c3ccc(Oc4ccc(F)cc4)cc3)c12] | 3-Cyclobutyl-1-[4-[4-(4-fluoro-phenoxy)-phenyl]-imidazo[1,5-a]pyrazin-8-ylamine | 374.98 | 5.4554 |

TABLE 1-continued
| 172 | 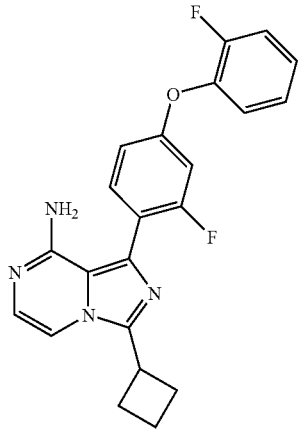 [SMILES: Nc1nccn2c(C3CCC3)nc(-c3ccc(Oc4ccccc4F)cc3F)c12] | 3-Cyclobutyl-1-[2-fluoro-4-(2-fluoro-phenoxy)-phenyl]-imidazo[1,5-a]pyrazin-8-ylamine | 392.85 | 0.6980 |
| --- | --- | --- | --- | --- |
| 173 | 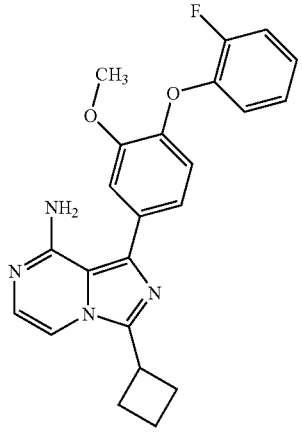 [SMILES: COc1cc(-c2nc(C3CCC3)n3ccnc(N)c23)ccc1Oc1ccccc1F] | 3-Cyclobutyl-1-[4-fluoro-phenoxy)-3-methoxy-phenyl]-imidazo[1,5-a]pyrazin-8-ylamine | 404.94 | 0.3553 |
| 174 | 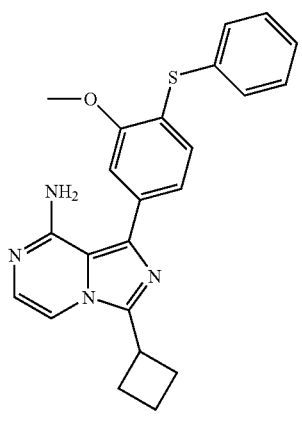 [SMILES: COc1cc(-c2nc(C3CCC3)n3ccnc(N)c23)ccc1Sc1ccccc1] | 3-Cyclobutyl-1-(3-methoxy-4-phenylsulfanyl-phenyl)-imidazo[1,5-a]pyrazin-8-ylamine | 402.96 | 1.13 |

TABLE 1-continued
| | | | | |
|---|---|---|---|---|
| 175 | 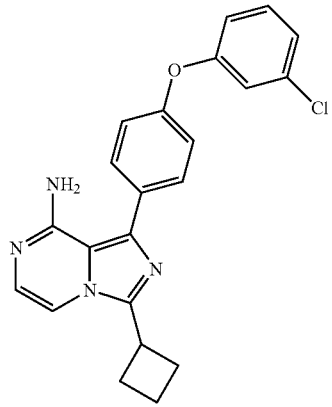 [SMILES: Nc1nccn2c(C3CCC3)nc(-c3ccc(Oc4cccc(Cl)c4)cc3)c12] | 1-[4-(3-Chloro-phenoxy)-phenyl]-3-cyclobutyl-imidazo[1,5-a]pyrazin-8-ylamine | 391.06 393.04 | 3.1959 |
| 176 | 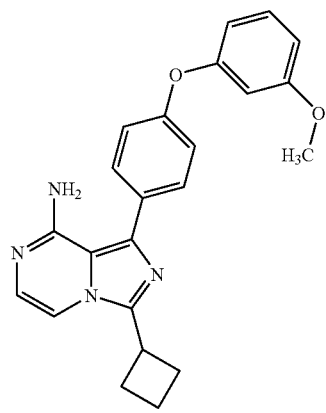 [SMILES: COc1cccc(Oc2ccc(-c3nc(C4CCC4)n4ccnc(N)c34)cc2)c1] | 3-Cyclobutyl-1-[4-(3-methoxy-phenoxy)-phenyl[-imidazo[1,5-a]pyrazin-8-ylamine | 387.00 | 3.8763 |
| 177 | 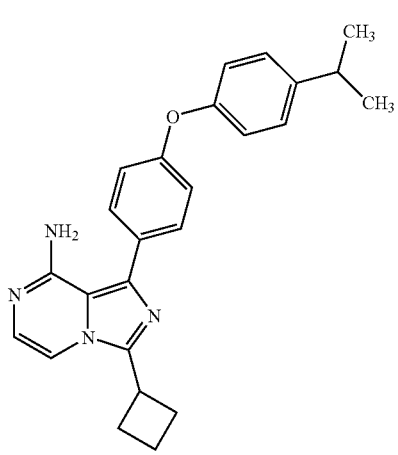 [SMILES: CC(C)c1ccc(Oc2ccc(-c3nc(C4CCC4)n4ccnc(N)c34)cc2)cc1] | 3-Cyclobutyl-1-[4-(4-isopropyl-phenoxy)-phenyl]-imidazo[1,5-a]pyrazin-8-ylamine | 399.14 | 1.4196 |

TABLE 1-continued
| | | | | |
|---|---|---|---|---|
| 178 | 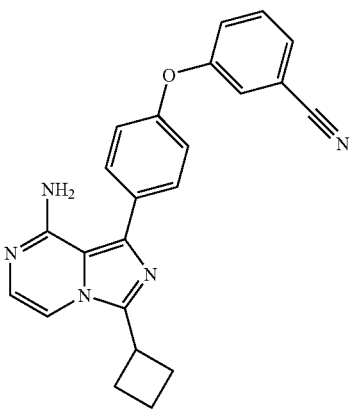 [SMILES: N#Cc1cccc(Oc2ccc(-c3nc(C4CCC4)n4ccnc(N)c34)cc2)c1] | 3-[4-(8-Amino-3-cyclobutyl-imidazo[1,5-a]pyrazin-1-yl)-phenoxy]-benzonitrile | 382.06 | 2.1614 |
| 179 | 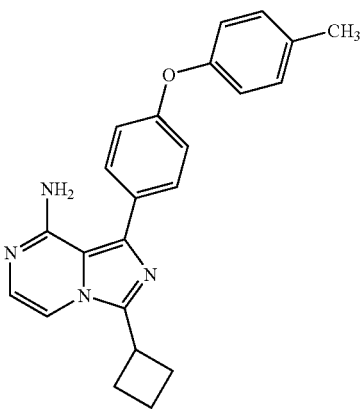 [SMILES: Cc1ccc(Oc2ccc(-c3nc(C4CCC4)n4ccnc(N)c34)cc2)cc1] | 3-Cyclobutyl-1-(4-p-tolyloxy-phenyl)-imidazo[1,5-a]pyrazin-8-ylamine | 371.11 | 0.8986 |
| 180 | 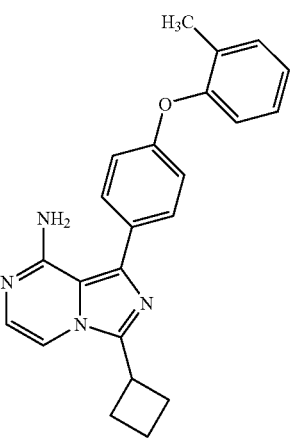 | 3-Cyclobutyl-1-(4-o-tolyloxy-phenyl)-imidazo[1,5-a]pyrazin-8-ylamine | 371.11 | 0.2430 |

TABLE 1-continued
| | | | | |
|---|---|---|---|---|
| 181 | 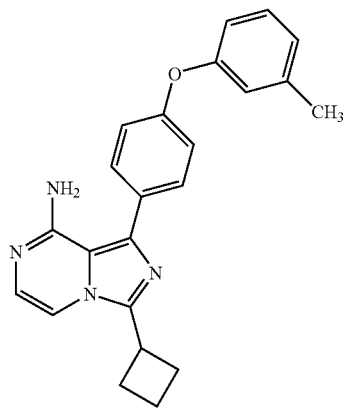 [SMILES: Cc1cccc(Oc2ccc(-c3nc(C4CCC4)n4ccnc(N)c34)cc2)c1] | 3-Cyclobutyl-1-(4-m-tolyloxy-phenyl)-imidazo[1,5-a]pyrazin-8-ylamine | 371 | 0.2380 |
| 182 | 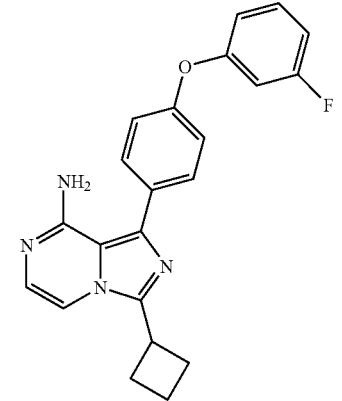 [SMILES: Nc1nccn2c(C3CCC3)nc(-c3ccc(Oc4cccc(F)c4)cc3)c12] | 3-Cyclobutyl-1-[4-(3-fluoro-phenoxy)-phenyl]-imidazo[1,5-a]pyrazin-8-ylamine | 374.96 | 0.1090 |
| 183 | 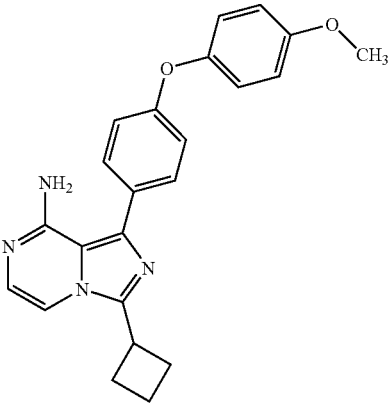 [SMILES: COc1ccc(Oc2ccc(-c3nc(C4CCC4)n4ccnc(N)c34)cc2)cc1] | 3-Cyclobutyl-1-[4-(4-methoxy-phenoxy)-phenyl]-imidazo[1,5-a]pyrazin-8-ylamine | 386.99 | 1.5100 |

| | | | | |
|---|---|---|---|---|
| 184 | 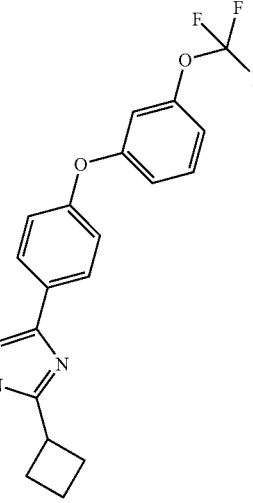 | 3-Cyclobutyl-1-[4-(3-trifluoromethoxy-phenoxy)-phenyl]-imidazo[1,5-a]pyrazin-8-ylamine | 440.87 | 5.5624 |
| 185 | 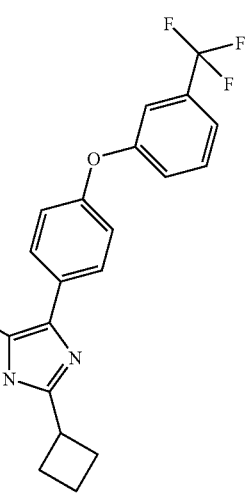 | 3-Cyclobutyl-1-[4-(3-trifluoromethyl-phenoxy)-phenyl]-imidazo[1,5-a]pyrazin-8-ylamine | 424.91 | 2.1681 |
| 186 | 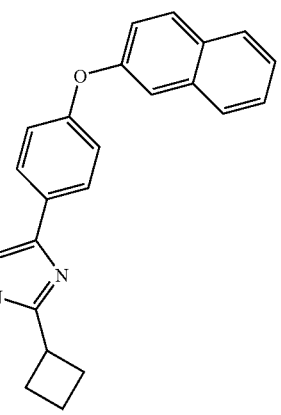 | 3-Cyclobutyl-1-[4-(naphthalen-2-yloxy)-phenyl]-imidazo[1,5-a]pyrazin-8-ylamine | 406.94 | 6.9288 |

TABLE 1-continued

| | | | | |
|---|---|---|---|---|
| 187 | | 1-[4-(Benzo[1,3]dioxol-5-yloxy)-phenyl]-3-cyclobutyl-imidazo[1,5-a]pyrazin-8-ylamine | 400.97 | 1.7291 |
| 188 | | 3-Cyclobutyl-1-[4-(2-fluoro-phenoxy)-phenyl]-imidazo[1,5-a]pyrazin-8-ylamine | 375.01 | 0.0952 |
| 189 | | 1-[4-(4-Chloro-phenoxy)-phenyl]-3-cyclobutyl-imidazo[1,5-a]pyrazin-8-ylamine | 391.04 | 1.8685 |

TABLE 1-continued
| | | | | |
|---|---|---|---|---|
| 190 | 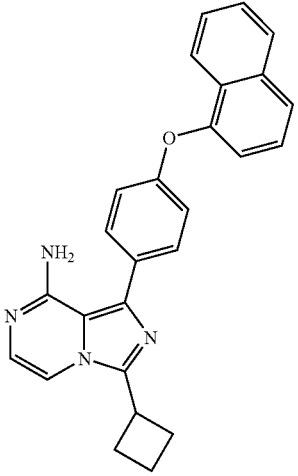 | 3-Cyclobutyl-1-[4-(naphthalen-1-yloxy)-phenyl]-imidazo[1,5-a]pyrazin-8-ylamine | 406.95 | 5.9542 |
| 191 | 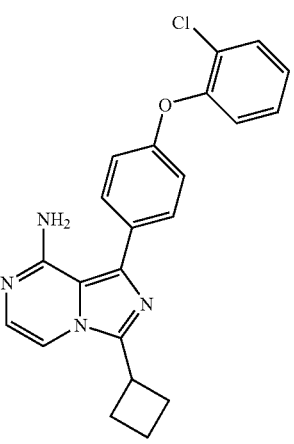 [SMILES: Nc1nccn2c(C3CCC3)nc(-c3ccc(Oc4ccccc4F)cc3)c12] | 1-[4-(2-Chloro-phenoxy)-phenyl]-3-cyclobutyl-imidazo[1,5-a]pyrazin-8-ylamine | 391.04 | 0.7379 |
| 192 | 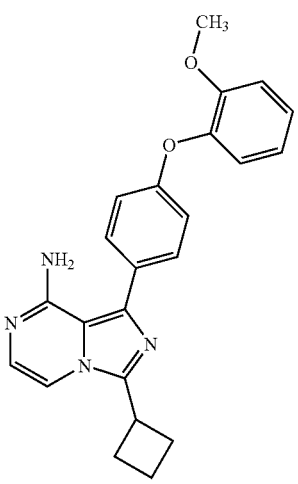 [SMILES: COc1ccccc1Oc1ccc(-c2nc(C3CCC3)n3ccnc(N)c23)cc1] | 3-Cyclobutyl-1-[4-(2-methoxy-phenoxy)-phenyl]-imidazo[1,5-a]pyrazin-8-ylamine | 386.99 | 9.4295 |

TABLE 1-continued

| | | | | |
|---|---|---|---|---|
| 193 | | 3-Cyclobutyl-1-[4-(4-trifluoromethoxy-phenoxy)-phenyl]-imidazo[1,5-a]pyrazin-8-ylamine | 440.86 | 6.5756 |
| 194 | | 3-[4-(8-Amino-3-cyclobutyl-imidazo[1,5-a]pyrazin-1-yl)-phenoxy]-benzoic acid methyl ester | 415.04 | 12.8530 |
| 195 | | 3-Cyclobutyl-1-[4-(3-nitro-phenoxy)-phenyl]-imidazo[1,5-a]pyrazin-8-ylamine | 401.95 | 0.8411 |

TABLE 1-continued
| | | | | |
|---|---|---|---|---|
| 196 | 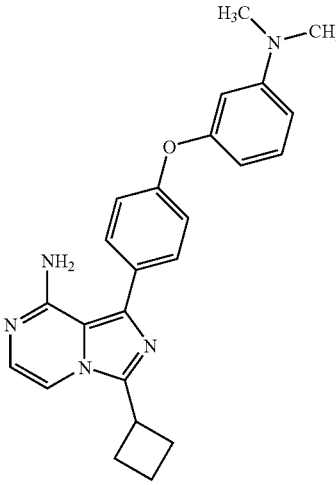 | 3-Cyclobutyl-1-[4-(3-dimethylamino-phenoxy)-phenyl]-imidazo[1,5-a]pyrazin-8-ylamine | 399.92 | 2.9648 |
| 197 | 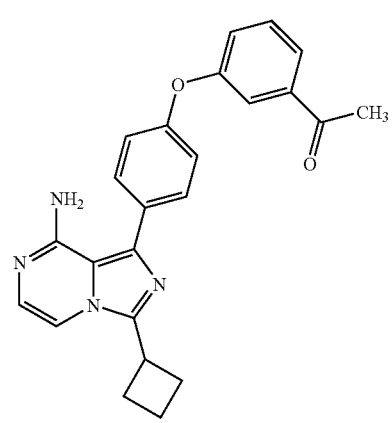 [SMILES: CC(=O)c1cccc(Oc2ccc(-c3nc(C4CCC4)n4ccnc(N)c34)cc2)c1] | 1-{3-[4-(8-Amino-3-cyclobutyl-imidazo[1,5-a]pyrazin-1-yl)-phenoxy]-phenyl}-ethanone | 399.01 | 3.4663 |
| 198 | 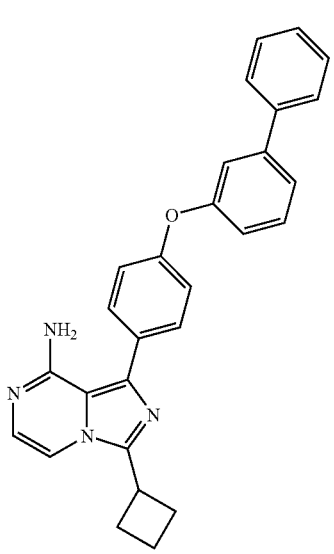 [SMILES: Nc1nccn2c(C3CCC3)nc(-c3ccc(Oc4cccc(-c5ccccc5)c4)cc3)c12] | 1-[4-(Biphenyl-3-yloxy)-phenyl]-3-cyclobutyl-imidazo[1,5-a]pyrazin-8-ylamine | 432.93 | 3.8789 |

TABLE 1-continued

| | | | | |
|---|---|---|---|---|
| 199 | | 3-Cyclobutyl-1-[4-(2-methyl-benzothiazol-5-yloxy)-phenyl]-imidazo[1,5-a]pyrazin-8-ylamine | 428.05 | 3.3040 |
| 200 | | 3-Cyclobutyl-1-[4-(3-isopropyl-phenoxy)-phenyl]-imidazo[1,5-a]pyrazin-8-ylamine | 398.97 | 8.4759 |
| 201 | | 3-Cyclobutyl-1-[4-(2-trifluoromethoxy-phenoxy)-phenyl]-imidazo[1,5-a]pyrazin-8-ylamine | 440.84 | 4.2450 |

TABLE 1-continued
| | | | | |
|---|---|---|---|---|
| 202 | 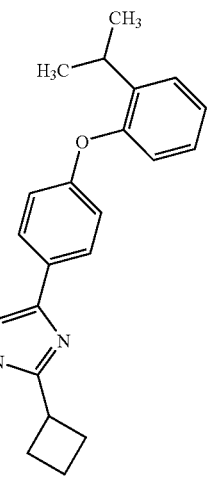 | 3-Cyclobutyl-1-[4-(2-isopropyl-phenoxy)-phenyl]-imidazo[1,5-a]pyrazin-8-ylamine | 399.03 | 4.5277 |
| 203 | 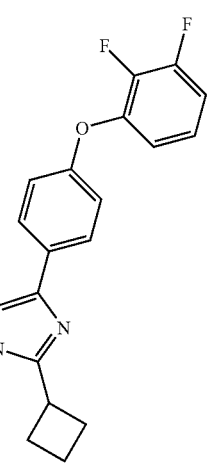 | 3-Cyclobutyl-1-[4-(2,3-difluoro-phenoxy)-phenyl]-imidazo[1,5-a]pyrazin-8-ylamine | 392.98 | 4.0193 |
| 204 | 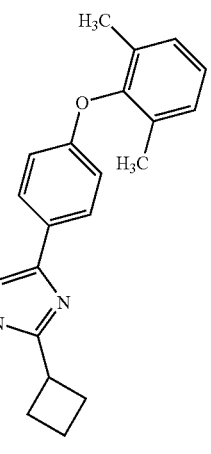 | 3-Cyclobutyl-1-[4-(2,6-dimethyl-phenoxy)-phenyl]-imidazo[1,5-a]pyrazin-8-ylamine | 385.03 | 3.6165 |

TABLE 1-continued
| 205 | 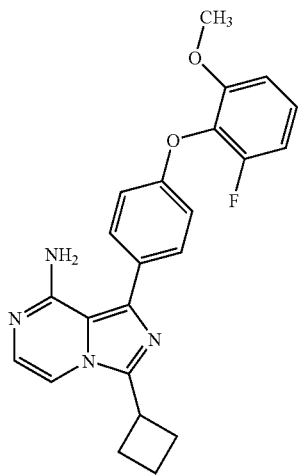 [SMILES: COc1cccc(F)c1Oc1ccc(-c2nc(C3CCC3)n3ccnc(N)c23)cc1] | 3-Cyclobutyl-1-[4-(2-fluoro-6-methoxy-phenoxy)-phenyl]-imidazo[1,5-a]pyrazin-8-ylamine | 405.11 | 2.5276 |
| 206 | 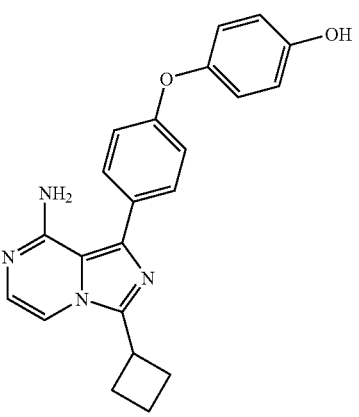 | 4-[4-(8-Amino-3-cyclobutyl-imidazo[1,5-a]pyrazin-1-yl)-phenoxy]-phenol | 373.05 | 3.5830 |
| 207 | 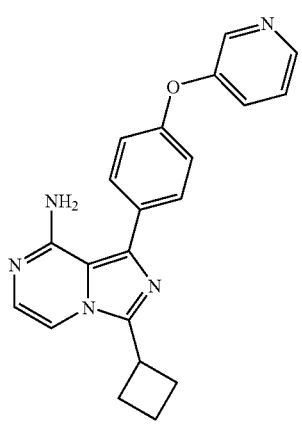 [SMILES: Nc1nccn2c(C3CCC3)nc(-c3ccc(Oc4cccnc4)cc3)c12] | 3-Cyclobutyl-1-[4-(pyridin-3-yloxy)-phenyl]-imidazo[1,5-a]pyrazin-8-ylamine | 358.12 | 11.6 |

TABLE 1-continued
| | | | | |
|---|---|---|---|---|
| 208 | 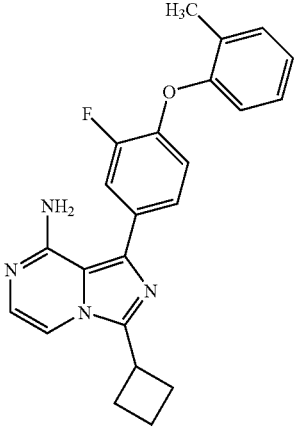 [SMILES: Cc1ccccc1Oc1ccc(-c2nc(C3CCC3)n3ccnc(N)c23)cc1F] | 3-Cyclobutyl-1-(3-fluoro-4-o-tolyloxy-phenyl)-imidazo[1,5-a]pyrazin-8-ylamine | 388.98 | 3.9017 |
| 209 | 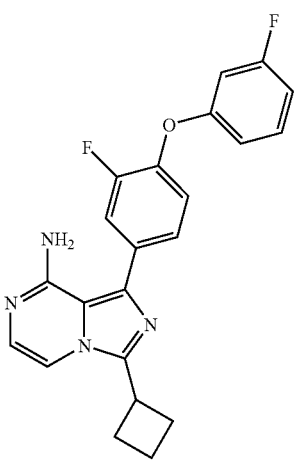 [SMILES: Nc1nccn2c(C3CCC3)nc(-c3ccc(Oc4cccc(F)c4)c(F)c3)c12] | 3-Cyclobutyl-1-[3-fluoro-4-(3-fluoro-phenoxy)-phenyl]-imidazo[1,5-a]pyrazin-8-ylamine | 394.25 | 3.3086 |
| 210 | 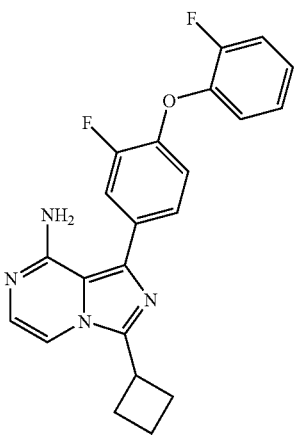 [SMILES: Nc1nccn2c(C3CCC3)nc(-c3ccc(Oc4ccccc4F)c(F)c3)c12] | 3-Cyclobutyl-1-[3-fluoro-4-(2-fluoro-phenoxy)-phenyl]-imidazo[1,5-a]pyrazin-8-ylamine | 392.94 | 1.9507 |

| | | | | |
|---|---|---|---|---|
| 211 | 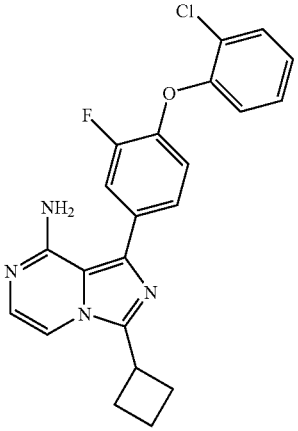 [SMILES: Nc1nccn2c(C3CCC3)nc(-c3ccc(Oc4ccccc4Cl)c(F)c3)c12] | 1-[4-(2-Chloro-phenoxy)-3-fluoro-phenyl]-3-cyclobutyl-imidazo[1,5-a]pyrazin-8-ylamine | 409.07 | 7.3784 |
| 212 | 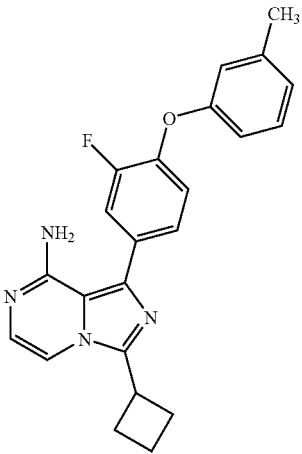 [SMILES: Cc1cccc(Oc2ccc(-c3nc(C4CCC4)n4ccnc(N)c34)cc2F)c1] | 3-Cyclobutyl-1-(3-fluoro-4-m-tolyloxy-phenyl)-imidazo[1,5-a]pyrazin-8-ylamine | 389.05 | 4.1463 |
| 213 | 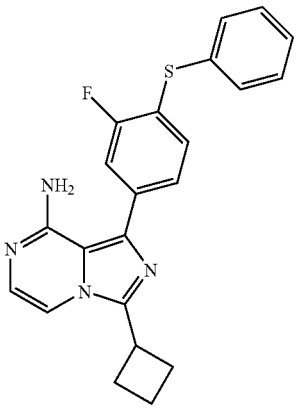 [SMILES: Nc1nccn2c(C3CCC3)nc(-c3ccc(Sc4ccccc4)c(F)c3)c12] | 3-Cyclobutyl-1-(3-fluoro-4-phenylsulfanyl-phenyl)-imidazo[1,5-a]pyrazin-8-ylamine | 390.96 | 2.21 |

| | | | | |
|---|---|---|---|---|
| 214 | 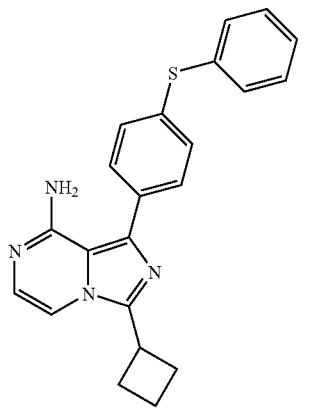 [SMILES: Nc1nccn2c(C3CCC3)nc(-c3ccc(Sc4ccccc4)cc3)c12] | 3-Cyclobutyl-1-(4-phenylsulfanyl-phenyl)-imidazo[1,5-a]pyrazin-8-ylamine | 373.01 | 0.33 |
| 215 | 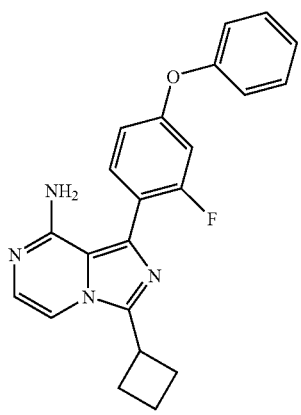 [SMILES: Nc1nccn2c(C3CCC3)nc(-c3ccc(Oc4ccccc4)cc3F)c12] | 3-Cyclobutyl-1-(2-fluoro-4-phenoxy-phenyl)-imidazo[1,5-a]pyrazin-8-ylamine | 374.97 | 0.2194 |
| 216 | 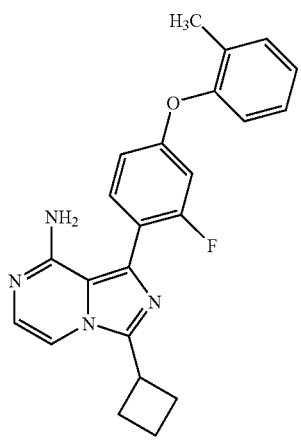 [SMILES: Cc1ccccc1Oc1ccc(-c2nc(C3CCC3)n3ccnc(N)c23)c(F)c1] | 3-Cyclobutyl-1-(2-fluoro-4-o-tolyloxy-phenyl)-imidazo[1,5-a]pyrazin-8-ylamine | 388.96 | 2.9880 |

TABLE 1-continued
| | | | | |
|---|---|---|---|---|
| 217 | 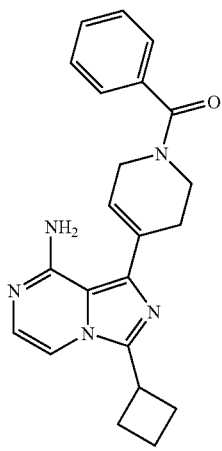 [SMILES: Nc1nccn2c(C3CCC3)nc(C3=CCN(C(=O)c4ccccc4)CC3)c12] | [4-(8-Amino-3-cyclobutyl-imidazo[1,5-a]pyrazin-1-yl)-3,6-dihydro-2H-pyridin-1-yl]-phenyl-methanone | 374.07 | 2.3533 |
| 218 | 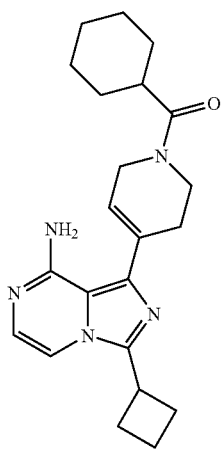 [SMILES: Nc1nccn2c(C3CCC3)nc(C3=CCN(C(=O)C4CCCCC4)CC3)c12] | [4-(8-Amino-3-cyclobutyl-imidazo[1,5-a]pyrazin-1-yl)-3,6-dihydro-2H-pyridin-1-yl]-cyclohexyl-methanone | 380.03 | 5.0120 |
| 219 | 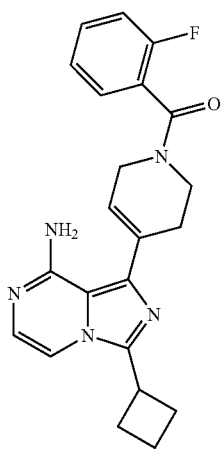 [SMILES: Nc1nccn2c(C3CCC3)nc(C3=CCN(C(=O)c4ccccc4F)CC3)c12] | [4-(8-Amino-3-cyclobutyl-imidazo[1,5-a]pyrazin-1-yl)-3,6-dihydro-2H-pyridin-1-yl]-(2-fluoro-phenyl)-methanone | 391.96 | 6.4142 |

US 8,481,733 B2
TABLE 1-continued
| 220 | 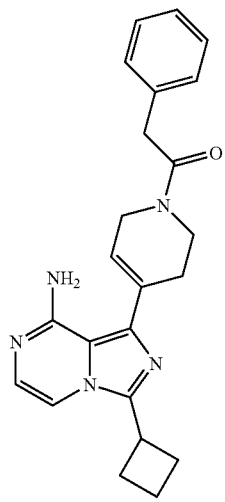 [SMILES: Nc1nccn2c(C3CCC3)nc(C3=CCN(C(=O)Cc4ccccc4)CC3)c12] | 1-[4-(8-Amino-3-cyclobutyl-imidazo[1,5-a]pyrazin-1-yl)-3,6-dihydro-2H-pyridin-1-yl]-2-phenyl-ethanone | 388.00 | 7.0551 |
| 221 | 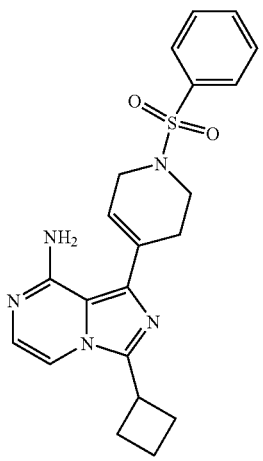 [SMILES: Nc1nccn2c(C3CCC3)nc(C3=CCN(S(=O)(=O)c4ccccc4)CC3)c12] | 1-(1-Benzenesulfonyl-1,2,3,6-tetrahydro-pyridin-4-yl)-3-cyclobutyl-imidazo[1,5-a]pyrazin-8-ylamine | 409.99 | 1.1723 |
| 222 | 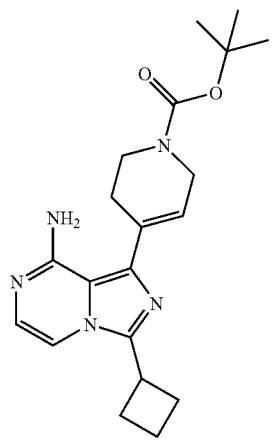 [SMILES: CC(C)(C)OC(=O)N1CC=C(c2nc(C3CCC3)n3ccnc(N)c23)CC1] | 4-(8-Amino-3-cyclobutyl-imidazo[1,5-a]pyrazin-1-yl)-3,6-dihydro-2H-pyridine-1-carboxylic acid tert-butyl ester | 369.94 | 1.8617 |

TABLE 1-continued
| 223 | 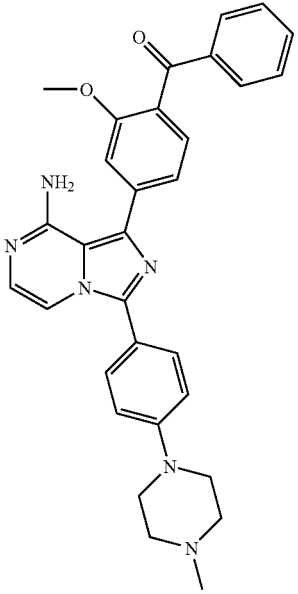 [SMILES: COc1cc(-c2nc(-c3ccc(N4CCN(C)CC4)cc3)n3ccnc(N)c23)ccc1C(=O)c1ccccc1] | (4-{8-Amino-3-[4-(4-methyl-piperazin-1-yl)-phenyl]-imidazo[1,5-a]pyrazin-1-yl}-2-methoxy-phenyl)-phenyl-methanone | 518.91 | 0.030 |
| 224 | 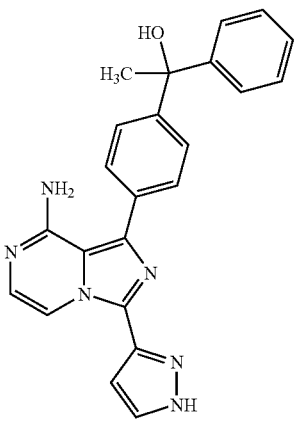 [SMILES: CC(O)(c1ccccc1)c1ccc(-c2nc(-c3cc[nH]n3)n3ccnc(N)c23)cc1] | 1-{4-[8-Amino-3-(1H-pyrazol-3-yl)-imidazo[1,5-a]pyrazin-1-yl]-phenyl}-1-phenyl-ethanol | 397.17 | 0.64 |
| 225 | 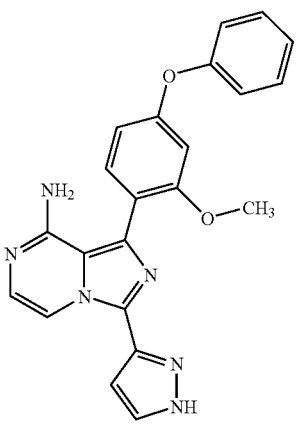 [SMILES: COc1cc(Oc2ccccc2)ccc1-c1nc(-c2cc[nH]n2)n2ccnc(N)c12] | 1-(2-Methoxy-4-phenoxy-phenyl)-3-(1H-pyrazol-3-yl)-imidazo[1,5-a]pyrazin-8-ylamine | 399.14 | 0.66 |

TABLE 1-continued
| 226 | 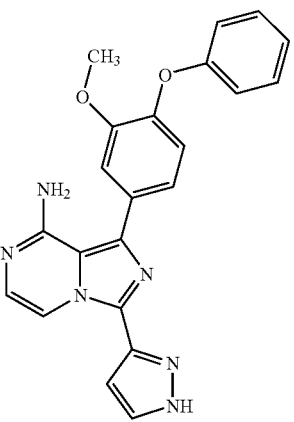 [SMILES: COc1cc(-c2nc(-c3cc[nH]n3)n3ccnc(N)c23)ccc1Oc1ccccc1] | 1-(3-Methoxy-4-phenoxy-phenyl)-3-(1H-pyrazol-3-yl)-imidazo[1,5-a]pyrazin-8-ylamine | 399.16 | 0.74 |
| --- | --- | --- | --- | --- |
| 227 | 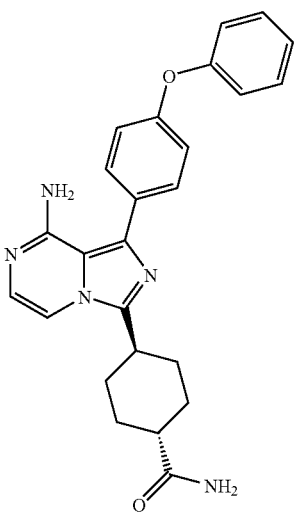 [SMILES: Nc1nccn2c1c(-c1ccc(Oc3ccccc3)cc1)nc2[C@H]1CC[C@H](C(N)=O)CC1] | trans-4-[8-Amino-1-(4-phenoxy-phenyl)-imidazo[1,5-a]pyrazin-3-yl]-cyclohexanecarboxylic acid amide | 427.96 | 0.634 |
| 228 | 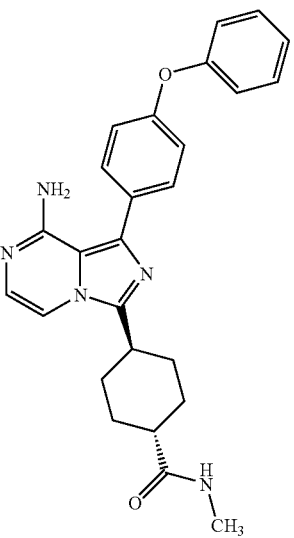 [SMILES: CNC(=O)[C@H]1CC[C@H](c2nc(-c3ccc(Oc4ccccc4)cc3)c3c(N)nccn32)CC1] | trans-4-[8-Amino-1-(4-phenoxy-phenyl)-imidazo[1,5-a]pyrazin-3-yl]-cyclohexanecarboxylic acid methylamide | 441.97 | 1.0113 |

TABLE 1-continued
| 229 | 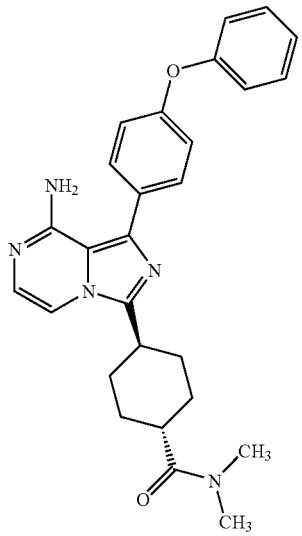 [SMILES: CN(C)C(=O)[C@H]1CC[C@H](c2nc(-c3ccc(Oc4ccccc4)cc3)c3c(N)nccn32)CC1] | trans-4-[8-Amino-1-(4-phenoxy-phenyl)-imidazo[1,5-a]pyrazin-3-yl]-cyclohexanecarboxylic acid dimethylamide | 456.12 | 3.3028 |
| 230 | 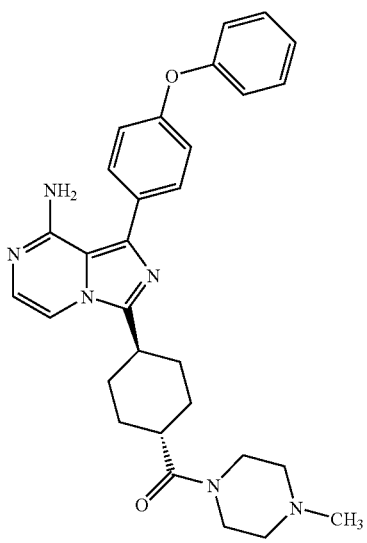 [SMILES: CN1CCN(C(=O)[C@H]2CC[C@H](c3nc(-c4ccc(Oc5ccccc5)cc4)c4c(N)nccn43)CC2)CC1] | trans-{4-[8-Amino-1-(4-phenoxy-phenyl)-imidazo[1,5-a]pyrazin-3-yl]-cyclohexyl}-(4-methyl-piperazin-1-yl)-methanone | 511.01 | 1.6794 |
| 231 | 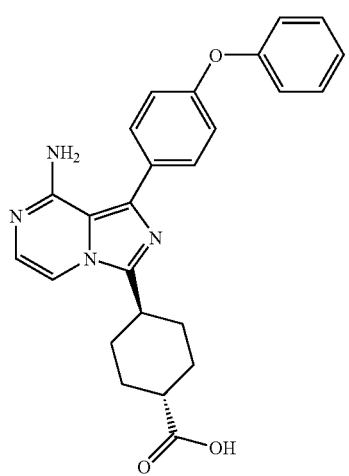 [SMILES: Nc1nccn2c1c(-c1ccc(Oc3ccccc3)cc1)nc2[C@H]1CC[C@H](C(=O)O)CC1] | trans-4-[8-Amino-1-(4-phenoxy-phenyl)-imidazo[1,5-a]pyrazin-3-yl]-cyclohexanecarboxylic acid | 428.97 | 3.5025 |

TABLE 1-continued

| | | | | |
|---|---|---|---|---|
| 232 | | trans-4-[8-Amino-1-(4-phenoxy-phenyl)-imidazo[1,5-a]pyrazin-3-yl]-cyclohexanecarboxylic acid methyl ester | 442.97 | 5.4816 |
| 233 | | trans-3-(4-Aminomethyl-cyclohexyl)-1-(4-phenoxy-phenyl)-imidazo[1,5-a]pyrazin-8-ylamine | 414.00 | 0.4011 |
| 234 | | trans-3-(4-Aminomethyl-cyclohexyl)-1-(3-methoxy-4-phenoxy-phenyl)-imidazo[1,5-a]pyrazin-8-ylamine | 444.17 | 0.4 |

TABLE 1-continued
| 235 | 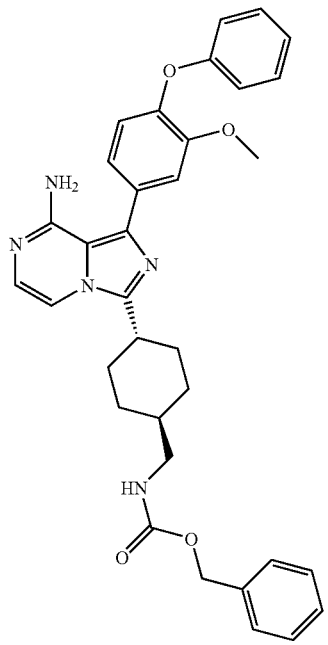 [SMILES: COc1cc(-c2nc([C@H]3CC[C@H](CNC(=O)OCc4ccccc4)CC3)n3ccnc(N)c23)ccc1Oc1ccccc1] | trans-{4-[8-Amino-1-(3-methoxy-4-phenoxy-phenyl)-imidazo[1,5-a]pyrazin-3-yl]-cyclohexylmethyl}-carbamic acid benzyl ester | 577.95 | 3.19 |
| 236 | 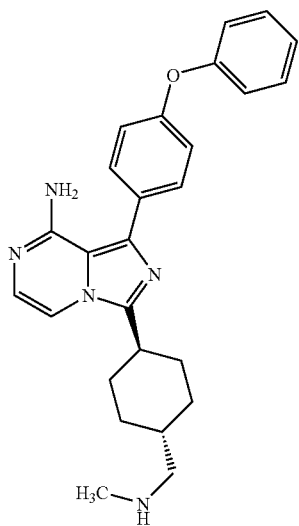 [SMILES: CNC[C@H]1CC[C@H](c2nc(-c3ccc(Oc4ccccc4)cc3)c3c(N)nccn32)CC1] | trans-3-(4-Methylaminomethyl-cyclohexyl)-1-(4-phenoxy-phenyl)-imidazo[1,5-a]pyrazin-8-ylamine | 427.89 | 0.1536 |

TABLE 1-continued
| | | | | |
|---|---|---|---|---|
| 237 | 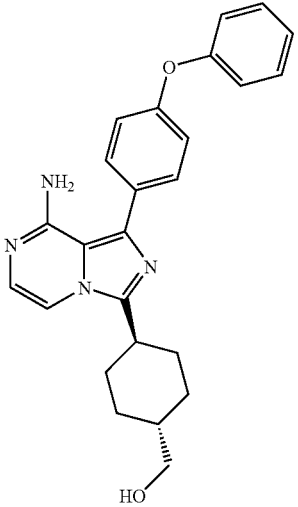 | trans-{4-[8-Amino-1-(4-phenoxy-phenyl)-imidazo[1,5-a]pyrazin-3-yl]-cyclohexyl}-methanol | 416.34 | 0.2194 |
| 238 | 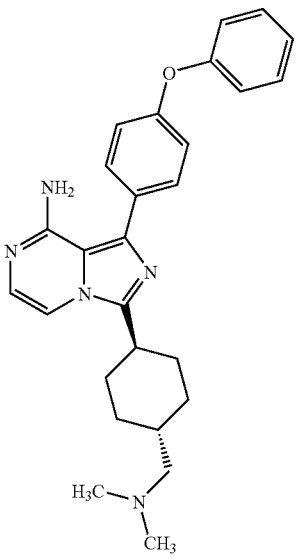 [SMILES: CN(C)C[C@H]1CC[C@H](c2nc(-c3ccc(Oc4ccccc4)cc3)c3c(N)nccn32)CC1] | trans-3-(4-Dimethylaminomethyl-cyclohexyl)-1-(4-phenoxy-phenyl)-imidazo[1,5-a]pyrazin-8-ylamine | 441.93 | 0.0751 |
| 239 | 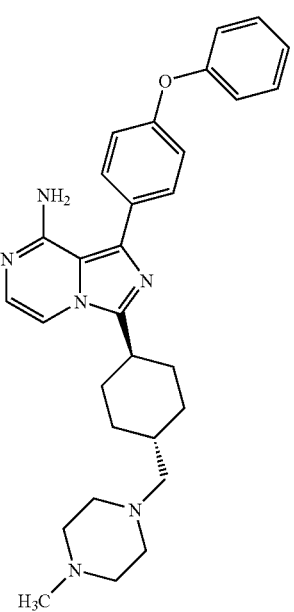 [SMILES: CN1CCN(C[C@H]2CC[C@H](c3nc(-c4ccc(Oc5ccccc5)cc4)c4c(N)nccn43)CC2)CC1] | trans-3-[4-(4-Methyl-piperazin-1-ylmethyl)-cyclohexyl]-1-(4-phenoxy-phenyl)-imidazo[1,5-a]pyrazin-8-ylamine | 496.95 | 0.5034 |

TABLE 1-continued
| # | Structure | Name | MW | Value |
|---|---|---|---|---|
| 240 | 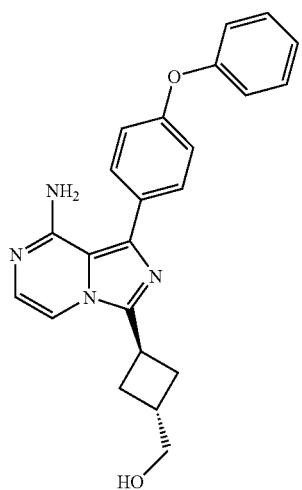 [SMILES: Nc1nccn2c1c(-c1ccc(Oc3ccccc3)cc1)nc2[C@H]1C[C@H](CO)C1] | trans-3-[8-Amino-1-(4-phenoxy-phenyl)-imidazo[1,5-a]pyrazin-3-yl]-cyclobutyl}-methanol | 386.94 | 0.1387 |
| 241 | 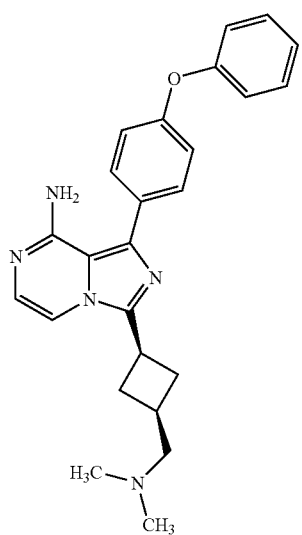 [SMILES: CN(C)C[C@H]1C[C@@H](c2nc(-c3ccc(Oc4ccccc4)cc3)c3c(N)nccn32)C1] | cis-3-(3-Dimethylaminomethyl-cyclobutyl)-1-(4-phenoxy-phenyl)-imidazo[1,5-a]pyrazin-8-ylamine | 414.19 | 1.1579 |
| 242 | 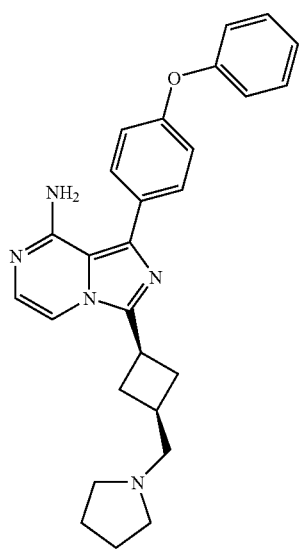 [SMILES: Nc1nccn2c1c(-c1ccc(Oc3ccccc3)cc1)nc2[C@H]1C[C@@H](CN2CCCC2)C1] | cis-1-(4-Phenoxy-phenyl)-3-(3-pyrrolidin-1-ylmethyl-cyclobutyl)-imidazo[1,5-a]pyrazin-8-ylamine | 440.18 | 2.4981 |

TABLE 1-continued
| | | | | |
|---|---|---|---|---|
| 243 | 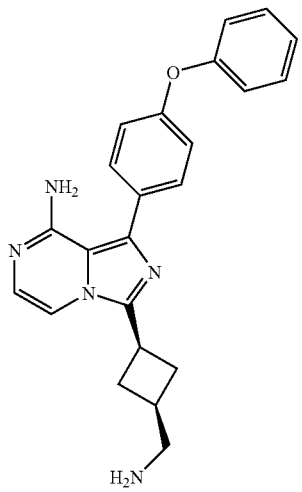 [SMILES: NC[C@H]1C[C@@H](c2nc(-c3ccc(Oc4ccccc4)cc3)c3c(N)nccn32)C1] | cis-3-(3-Aminomethyl-cyclobutyl)-1-(4-phenoxy-phenyl)-imidazo[1,5-a]pyrazin-8-ylamine | 387.17 | 0.3280 |
| 244 | 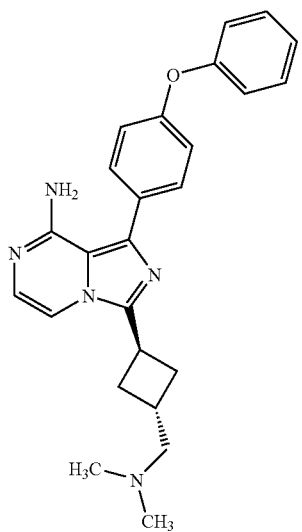 [SMILES: CN(C)C[C@H]1C[C@H](c2nc(-c3ccc(Oc4ccccc4)cc3)c3c(N)nccn32)C1] | trans-3-(3-Dimethylaminomethyl-cyclobutyl)-1-(4-phenoxy-phenyl)-imidazo[1,5-a]pyrazin-8-ylamine | 414.19 | 4.0073 |
| 245 | 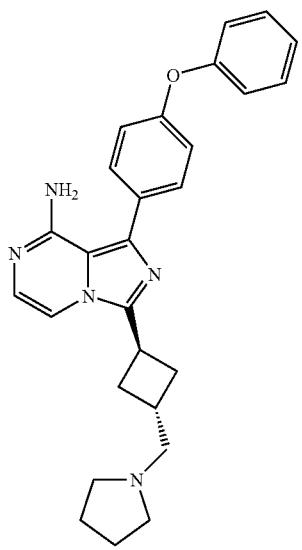 [SMILES: Nc1nccn2c1c(-c1ccc(Oc3ccccc3)cc1)nc2[C@H]1C[C@H](CN2CCCC2)C1] | trans-1-(4-Phenoxy-phenyl)-3-(3-pyrrolidin-1-ylmethyl-cyclobutyl)-imidazo[1,5-a]pyrazin-8-ylamine | 440.18 | 4.2052 |

TABLE 1-continued
| 246 | 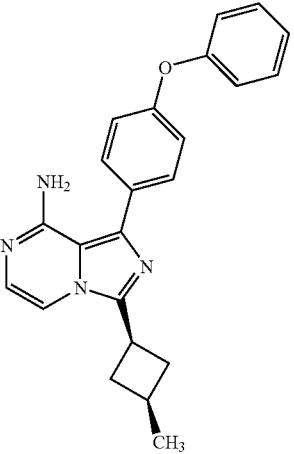 [SMILES: C[C@H]1C[C@@H](c2nc(-c3ccc(Oc4ccccc4)cc3)c3c(N)nccn32)C1] | cis-3-(3-Methyl-cyclobutyl)-1-(4-phenoxy-phenyl)-imidazo[1,5-a]pyrazin-8-ylamine | 371.06 | 0.4336 |
| 247 | 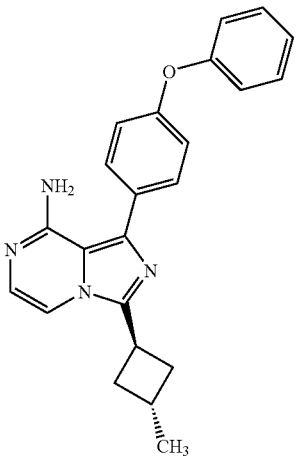 [SMILES: C[C@H]1C[C@H](c2nc(-c3ccc(Oc4ccccc4)cc3)c3c(N)nccn32)C1] | trans-3-(3-Methyl-cyclobutyl)-1-(4-phenoxy-phenyl)-imidazo[1,5-a]pyrazin-8-ylamine | 371.14 | 0.7028 |
| 248 | 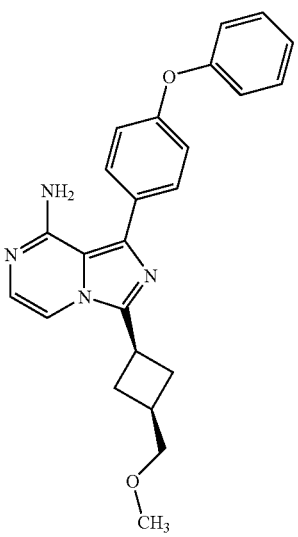 [SMILES: COC[C@H]1C[C@@H](c2nc(-c3ccc(Oc4ccccc4)cc3)c3c(N)nccn32)C1] | cis-3-(3-Methoxymethyl-cyclobutyl)-1-(4-phenoxy-phenyl)-imidazo[1,5-a]pyrazin-8-ylamine | 400.93 | 1.3527 |

TABLE 1-continued
| 249 | 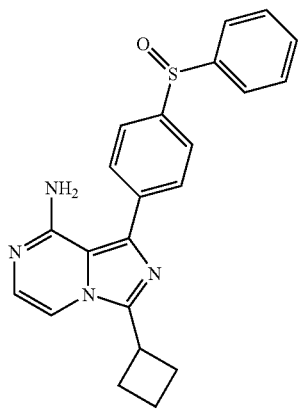 [SMILES: Nc1nccn2c(C3CCC3)nc(-c3ccc(S(=O)c4ccccc4)cc3)c12] | 1-(4-Benzenesulfinyl-phenyl)-3-cyclobutyl-imidazo[1,5-a]pyrazin-8-ylamine | 389.02 | 6.9180 |
| --- | --- | --- | --- | --- |
| 250 | 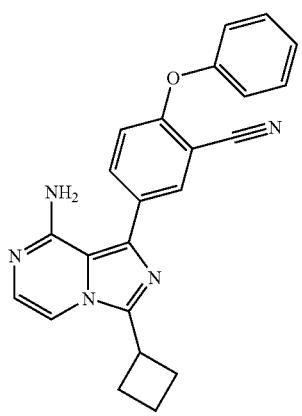 [SMILES: N#Cc1cc(-c2nc(C3CCC3)n3ccnc(N)c23)ccc1Oc1ccccc1] | 5-(8-Amino-3-cyclobutylimidazo[1,5-a]pyrazin-1-yl)-2-phenoxybenzonitrile | 381.94 | 1.78 |
| 251 | 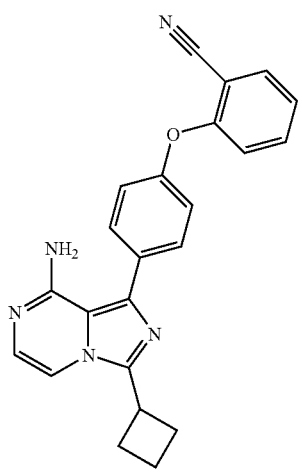 [SMILES: N#Cc1ccccc1Oc1ccc(-c2nc(C3CCC3)n3ccnc(N)c23)cc1] | 2-[4-(8-Amino-3-cyclobutylimidazo[1,5-a]pyrazin-1-yl)-phenoxy]-benzonitrile | 381.93 | 0.36 |

TABLE 1-continued
| | | | | |
|---|---|---|---|---|
| 252 | 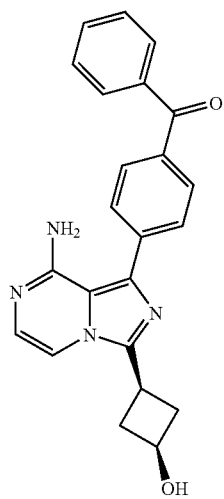 [SMILES: Nc1nccn2c1c(-c1ccc(C(=O)c3ccccc3)cc1)nc2[C@H]1C[C@@H](O)C1] | cis-{4-[8-Amino-3-(3-hydroxy-cyclobutyl)-imidazo[1,5-a]pyrazin-1-yl]-phenyl}-phenyl-methanone | 384.85 | 0.112 |
| 253 | 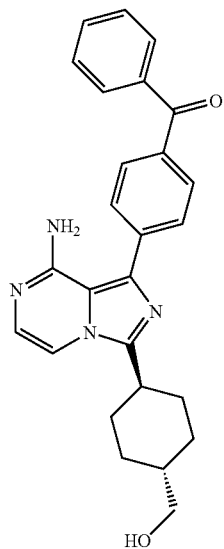 [SMILES: Nc1nccn2c1c(-c1ccc(C(=O)c3ccccc3)cc1)nc2[C@H]1CC[C@H](CO)CC1] | trans-{4-[8-Amino-3-(4-hydroxymethyl-cyclohexyl)-imidazo[1,5-a]pyrazin-1-yl]-phenyl}-phenyl-methanone | 426.88 | 0.297 |
| 254 | 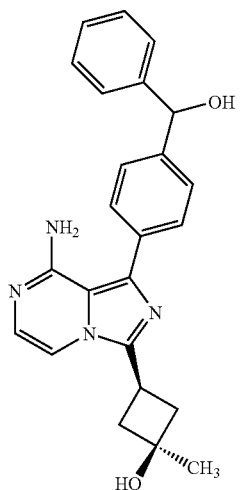 [SMILES: C[C@]1(O)C[C@@H](c2nc(-c3ccc(C(O)c4ccccc4)cc3)c3c(N)nccn32)C1] | cis-3-{8-Amino-1-[4-(hydroxy-phenyl-methyl)-phenyl]-imidazo[1,5-a]pyrazin-3-yl}-1-methyl-cyclobutanol | 400.86 | 0.6823 |

TABLE 1-continued
| | | | | |
|---|---|---|---|---|
| 255 | 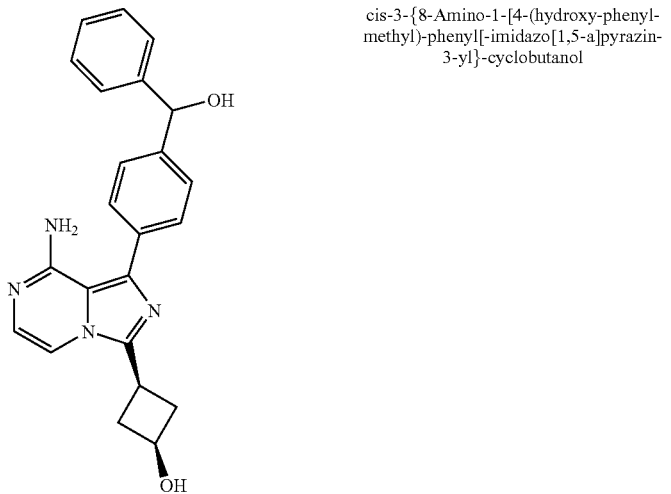 | cis-3-{8-Amino-1-[4-(hydroxy-phenyl-methyl)-phenyl[-imidazo[1,5-a]pyrazin-3-yl}-cyclobutanol | 386.91 | 2.76 |
| 256 | 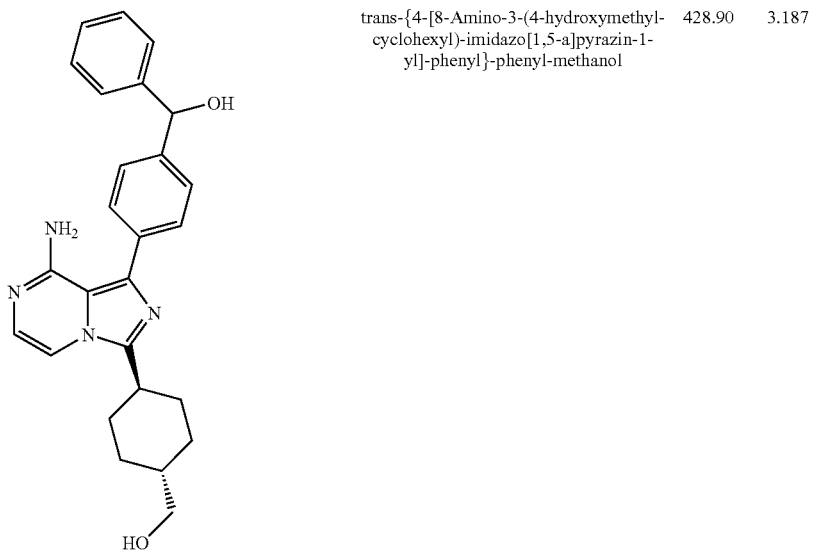 | trans-{4-[8-Amino-3-(4-hydroxymethyl-cyclohexyl)-imidazo[1,5-a]pyrazin-1-yl]-phenyl}-phenyl-methanol | 428.90 | 3.187 |
| 257 | 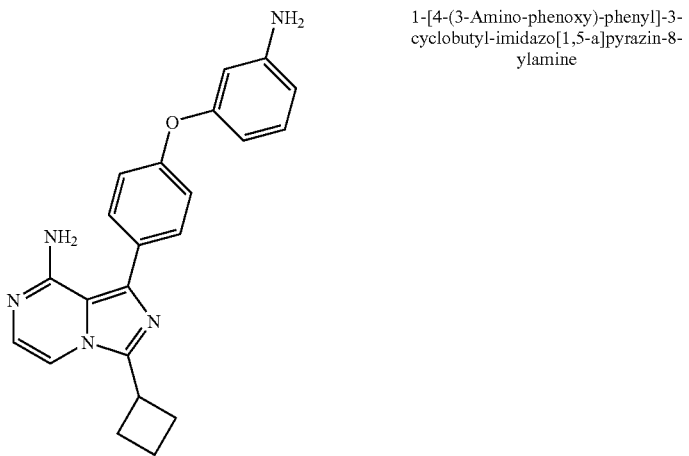 | 1-[4-(3-Amino-phenoxy)-phenyl]-3-cyclobutyl-imidazo[1,5-a]pyrazin-8-ylamine | 372.10 | 0.43 |

TABLE 1-continued
| 258 | 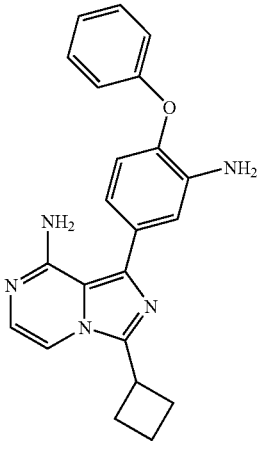 [SMILES: Nc1cc(-c2nc(C3CCC3)n3ccnc(N)c23)ccc1Oc1ccccc1] | 1-(3-Amino-4-phenoxy-phenyl)-3-cyclobutyl-imidazo[1,5-a]pyrazin-8-ylamine | 371.96 | 0.1098 |
| 259 | 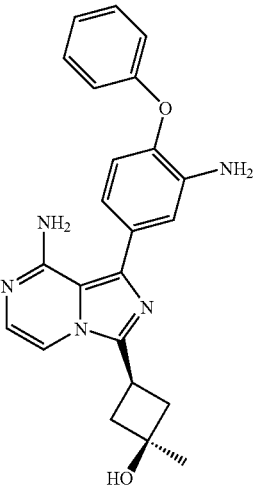 [SMILES: C[C@]1(O)C[C@@H](c2nc(-c3ccc(Oc4ccccc4)c(N)c3)c3c(N)nccn32)C1] | cis-3-[8-Amino-1-(3-amino-4-phenoxy-phenyl)-imidazo[1,5-a]pyrazin-3-yl]-1-methyl-cyclobutanol | 402.02 | 0.4646 |
| 260 | 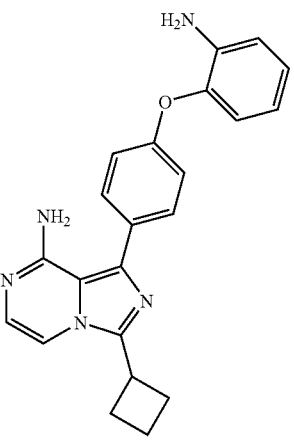 [SMILES: Nc1ccccc1Oc1ccc(-c2nc(C3CCC3)n3ccnc(N)c23)cc1] | 1-[4-(2-Amino-phenoxy)-phenyl]-3-cyclobutyl-imidazo[1,5-a]pyrazin-8-ylamine | 372.16 | 4.8319 |

TABLE 1-continued
| | | | | |
|---|---|---|---|---|
| 261 | 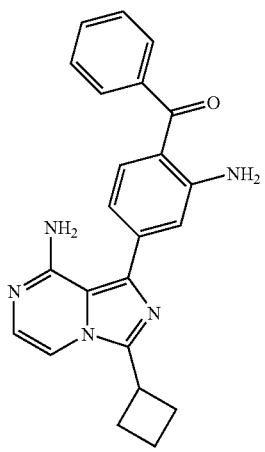 [SMILES: Nc1cc(-c2nc(C3CCC3)n3ccnc(N)c23)ccc1C(=O)c1ccccc1] | [2-Amino-4-(8-amino-3-cyclobutyl-imidazo[1,5-a]pyrazin-1-yl)-phenyl]-phenyl-methanone | 383.9 | 0.0369 |
| 262 | 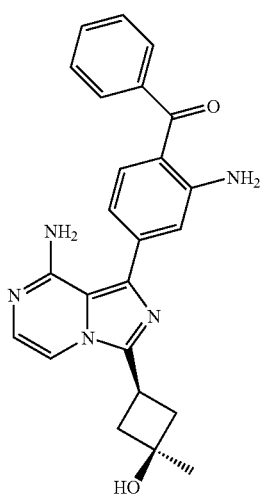 [SMILES: C[C@]1(O)C[C@@H](c2nc(-c3ccc(C(=O)c4ccccc4)c(N)c3)c3c(N)nccn32)C1] | cis-{2-Amino-4-[8-amino-3-(3-hydroxy-3-methyl-cyclobutyl)-imidazo[1,5-a]pyrazin-1-yl]-phenyl}-phenyl-methanone | 413.87 | 0.0500 |
| 263 | 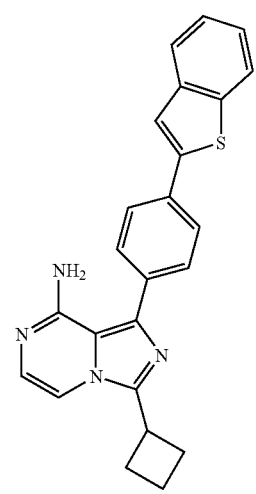 [SMILES: Nc1nccn2c(C3CCC3)nc(-c3ccc(-c4cc5ccccc5s4)cc3)c12] | 1-(4-Benzo[b]thiophen-2-yl-phenyl)-3-cyclobutyl-imidazo[1,5-a]pyrazin-8-ylamine | 397.07 | 9.9505 |

TABLE 1-continued
| 264 | 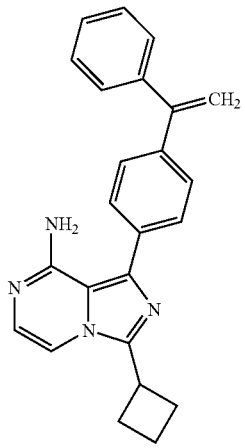 [SMILES: C=C(c1ccccc1)c1ccc(-c2nc(C3CCC3)n3ccnc(N)c23)cc1] | 3-Cyclobutyl-1-[4-(1-phenyl-vinyl)-phenyl]-imidazo[1,5-a]pyrazin-8-ylamine | 366.98 | 0.4439 |
| --- | --- | --- | --- | --- |
| 265 | 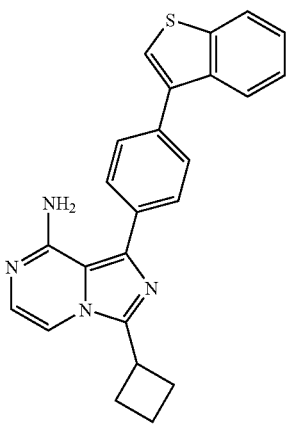 [SMILES: Nc1nccn2c(C3CCC3)nc(-c3ccc(-c4csc5ccccc45)cc3)c12] | 1-(4-Benzo[b]thiophen-3-yl-phenyl)-3-cyclobutyl-imidazo[1,5-a]pyrazin-8-ylamine | 396.75 | 4.0910 |
| 266 | 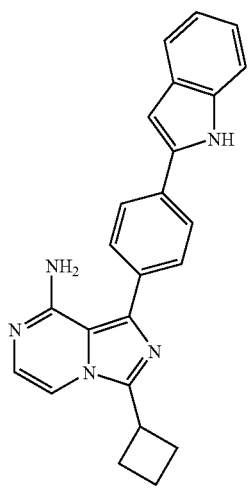 [SMILES: Nc1nccn2c(C3CCC3)nc(-c3ccc(-c4cc5ccccc5[nH]4)cc3)c12] | 3-Cyclobutyl-1-[4-(1H-indol-2-yl)-phenyl]imidazo[1,5-a]pyrazin-8-ylamine | 379.9 | 4.7026 |

TABLE 1-continued
| | | | | |
|---|---|---|---|---|
| 267 | 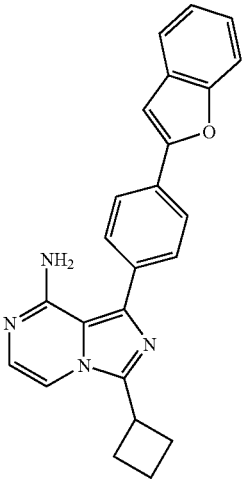 [SMILES: Nc1nccn2c(C3CCC3)nc(-c3ccc(-c4cc5ccccc5o4)cc3)c12] | 1-(4-Benzofuran-2-yl-phenyl)-3-cyclobutyl-imidazo[1,5-a]pyrazin-8-ylamine | 380.84 | 1.0770 |
| 268 | 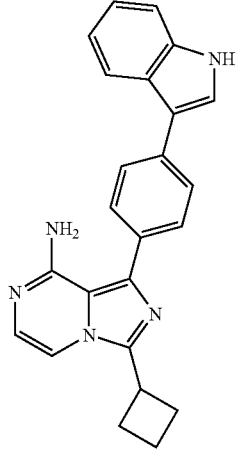 [SMILES: Nc1nccn2c(C3CCC3)nc(-c3ccc(-c4c[nH]c5ccccc45)cc3)c12] | 3-Cyclobutyl-1-[4-(1H-indol-3-yl)-phenyl]-imidazo[1,5-a]pyrazin-8-ylamine | 380.15 | 3.4934 |
| 269 | 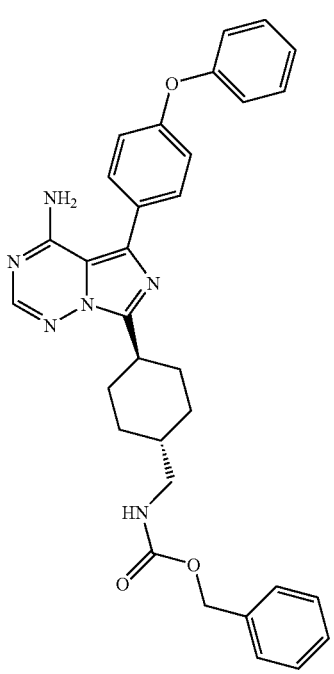 [SMILES: Nc1ncnn2c1c(-c1ccc(Oc3ccccc3)cc1)nc2[C@H]1CC[C@H](CNC(=O)OCc2ccccc2)CC1] | trans-{4-[4-Amino-5-(4-phenoxy-phenyl)-imidazo[5,1-f][1,2,4]triazin-7-yl]-cyclohexylmethyl}-carbamic acid benzyl ester | 549.20 | 4.9300 |

TABLE 1-continued
| | | | | |
|---|---|---|---|---|
| 270 | 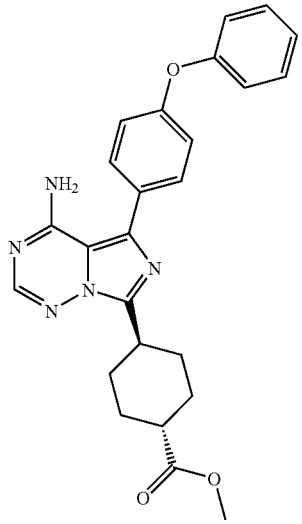 [SMILES: COC(=O)[C@H]1CC[C@H](c2nc(-c3ccc(Oc4ccccc4)cc3)c3c(N)ncnn32)CC1] | trans-4-[4-Amino-5-(4-phenoxy-phenyl)-imidazo[5,1-f][1,2,4]triazin-7-yl]-cyclohexanecarboxylic acid methyl ester | 444.29 | 17.0 |
| 271 | 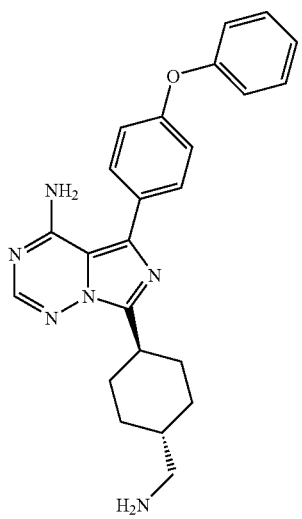 [SMILES: NC[C@H]1CC[C@H](c2nc(-c3ccc(Oc4ccccc4)cc3)c3c(N)ncnn32)CC1] | trans-7-(4-Aminomethyl-cyclohexyl)-5-(4-phenoxy-phenyl)-imidazo[5,1-f][1,2,4]triazin-4-ylamine | 415.02 | 0.1759 |
| 272 | 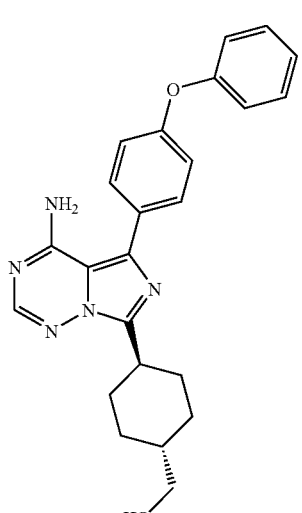 | trans-{4-[4-Amino-5-(4-phenoxy-phenyl)-imidazo[5,1-f][1,2,4]triazin-7-yl]-cyclohexyl}-methanol | 416.09 | 0.1991 |

TABLE 1-continued
| 273 | 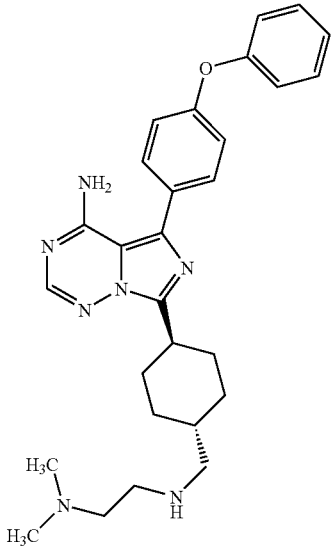 [SMILES: CN(C)CCNC[C@H]1CC[C@H](c2nc(-c3ccc(Oc4ccccc4)cc3)c3c(N)ncnn32)CC1] | trans-N-{4-[4-Amino-5-(4-phenoxy-phenyl)-imidazo[5,1-f][1,2,4]triazin-7-yl]-cyclohexylmethyl}-N',N'-dimethyl-ethane-1,2-diamine | 486.19 | 0.2164 |
| 274 | 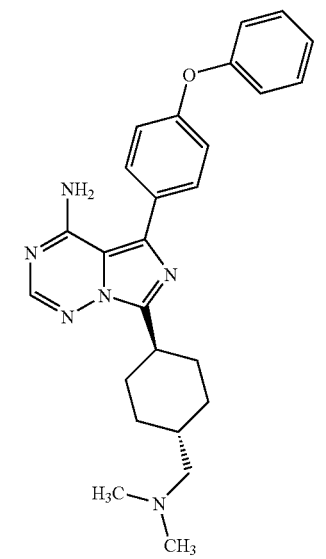 [SMILES: CN(C)C[C@H]1CC[C@H](c2nc(-c3ccc(Oc4ccccc4)cc3)c3c(N)ncnn32)CC1] | trans-7-(4-Dimethylaminomethyl-cyclohexyl)-5-(4-phenoxy-phenyl)-imidazo[5,1-f][1,2,4]triazin-4-ylamine | 443.02 | 0.4046 |
| 275 | 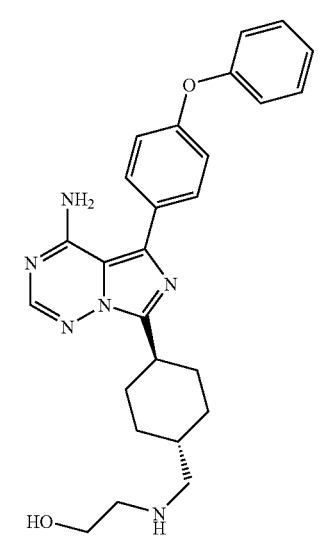 [SMILES: Nc1ncnn2c1c(-c1ccc(Oc3ccccc3)cc1)nc2[C@H]1CC[C@H](CNCCO)CC1] | trans-2-({4-[4-Amino-5-(4-phenoxy-phenyl)-imidazo[5,1-f][1,2,4]triazin-7-yl]-cyclohexylmethyl}-amino)-ethanol | 459.05 | 0.6097 |

TABLE 1-continued
| | | | | |
|---|---|---|---|---|
| 276 | 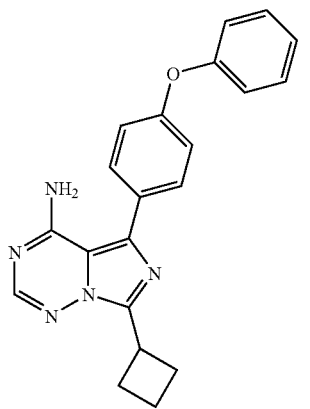 [SMILES: Nc1ncnn2c(C3CCC3)nc(-c3ccc(Oc4ccccc4)cc3)c12] | 7-Cyclobutyl-5-(4-phenoxy-phenyl)-imidazo[5,1-f][1,2,4]triazin-4-ylamine | 358.01 | 0.2014 |
| 277 | 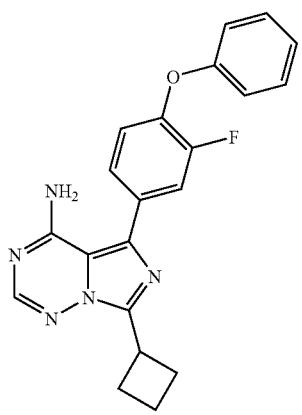 | 4-Cyclobutyl-5-(3-fluoro-4-phenoxy-phenyl)-imidazo[5,1-f][1,2,4]triazin-4-ylamine | 376.12 | 0.1967 |
| 278 | 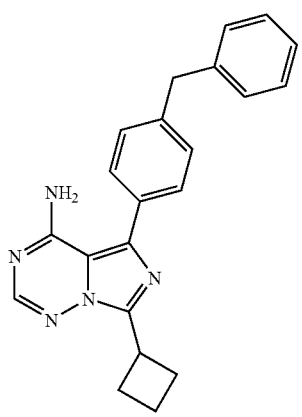 [SMILES: Nc1ncnn2c(C3CCC3)nc(-c3ccc(Cc4ccccc4)cc3)c12] | 5-(4-Benzyl-phenyl)-7-cyclobutyl-imidazo[5,1-f][1,2,4]triazin-4-ylamine | 356.15 | 1.9798 |

| | | | | |
|---|---|---|---|---|
| 279 | | 7-Cyclobutyl-5-[4-(2,6-difluoro-phenoxy)-phenyl]-imidazo[5,1-f][1,2,4]triazin-4-ylamine | 394.02 | 4.1139 |
| 280 | | 7-Cyclobutyl-5-(3-methoxy-4-o-tolyloxy-phenyl)-imidazo[5,1-f][1,2,4]triazin-4-ylamine | 401.97 | 3.2471 |
| 281 | | 7-Cyclobutyl-5-(3-methoxy-4-phenoxy-phenyl)-imidazo[5,1-f][1,2,4]triazin-4-ylamine | 387.92 | 1.1706 |

TABLE 1-continued
| | | | | |
|---|---|---|---|---|
| 282 | 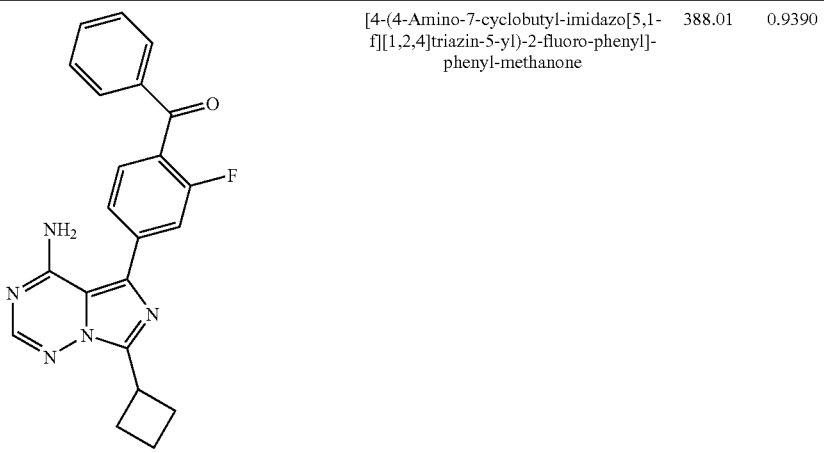 | [4-(4-Amino-7-cyclobutyl-imidazo[5,1-f][1,2,4]triazin-5-yl)-2-fluoro-phenyl]-phenyl-methanone | 388.01 | 0.9390 |
| 283 | 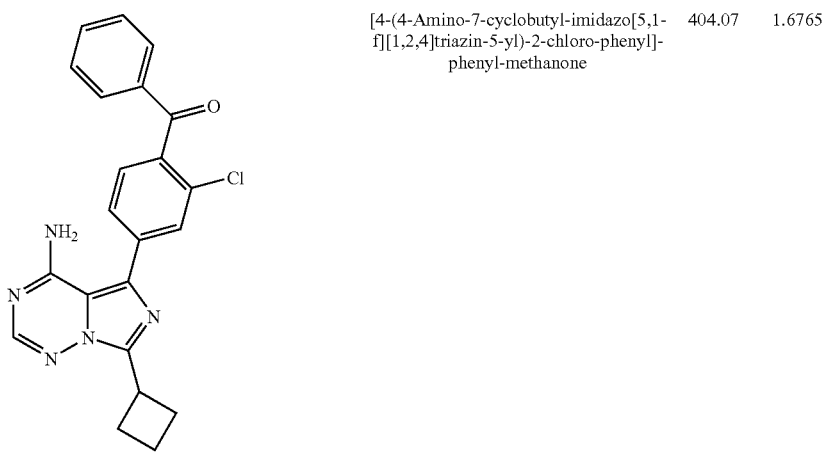 | [4-(4-Amino-7-cyclobutyl-imidazo[5,1-f][1,2,4]triazin-5-yl)-2-chloro-phenyl]-phenyl-methanone | 404.07 | 1.6765 |
| 284 | 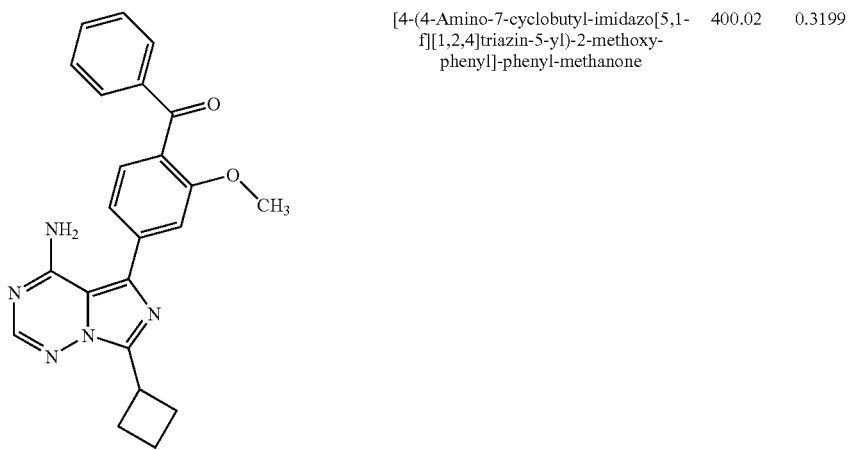 | [4-(4-Amino-7-cyclobutyl-imidazo[5,1-f][1,2,4]triazin-5-yl)-2-methoxy-phenyl]-phenyl-methanone | 400.02 | 0.3199 |

TABLE 1-continued
| | | | | |
|---|---|---|---|---|
| 285 | 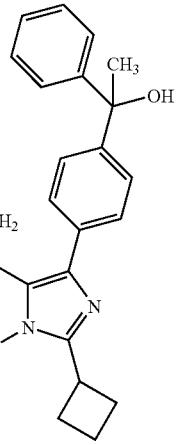 | 1-[4-(4-Amino-7-cyclobutyl-imidazo[5,1-f][1,2,4]triazin-5-yl)-phenyl]-1-phenyl-ethanol | 386.15 | 0.2630 |
| 286 | 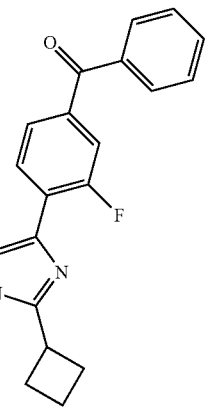 | [4-(4-Amino-7-cyclobutyl-imidazo[5,1-f][1,2,4]triazin-5-yl)-3-fluoro-phenyl]-phenyl-methanone | 387.94 | 0.1360 |
| 287 | 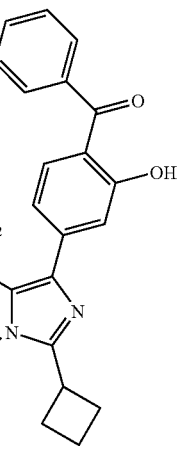 | [4-(4-Amino-7-cyclobutyl-imidazo[5,1-f][1,2,4]triazin-5-yl)-2-hydroxy-phenyl]-phenyl-methanone | 386.15 | 1.2277 |

| | | | | |
|---|---|---|---|---|
| 288 | 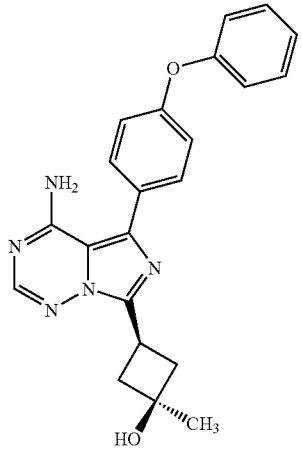 [SMILES: C[C@]1(O)C[C@@H](c2nc(-c3ccc(Oc4ccccc4)cc3)c3c(N)ncnn32)C1] | cis-3-[4-Amino-5-(4-phenoxy-phenyl)-imidazo[5,1-f][1,2,4]triazin-7-yl]-1-methyl-cyclobutanol | 387.95 | 0.8314 |
| 289 | 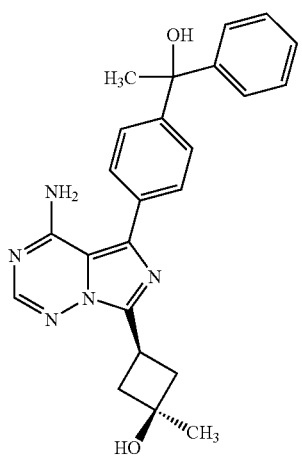 [SMILES: CC(O)(c1ccccc1)c1ccc(-c2nc([C@H]3C[C@@](C)(O)C3)n3ncnc(N)c23)cc1] | cis-3-{4-Amino-5-[4-(1-hydroxy-1-phenyl-ethyl)-phenyl]-imidazo[5,1-f][1,2,4]triazin-7-yl}-1-methyl-cyclobutanol | 416.04 | 0.7974 |
| 290 | 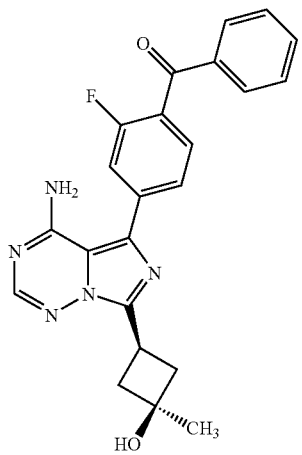 [SMILES: C[C@]1(O)C[C@@H](c2nc(-c3ccc(C(=O)c4ccccc4)c(F)c3)c3c(N)ncnn32)C1] | cis-{4-[4-Amino-7-(3-hydroxy-3-methyl-cyclobutyl)-imidazo[5,1-f][1,2,4]triazin-5-yl]-2-fluoro-phenyl}-phenyl-methanone | 418.11 | 0.9756 |

| | | | | |
|---|---|---|---|---|
| 291 | 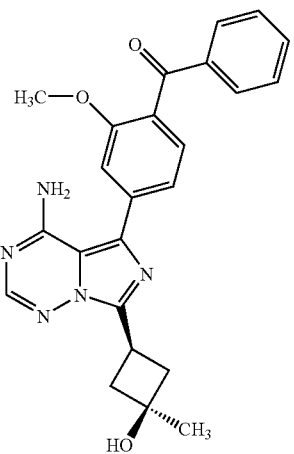 | cis-{4-[4-Amino-7-(3-hydroxy-3-methyl-cyclobutyl)-imidazo[5,1-f][1,2,4]triazin-5-yl]-2-methoxy-phenyl}-phenyl-methanone | 430.01 | 0.5984 |
| 292 | 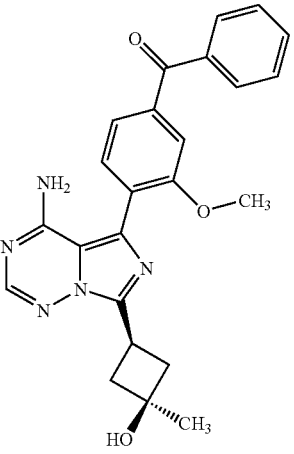 [SMILES: COc1cc(C(=O)c2ccccc2)ccc1-c1nc([C@H]2C[C@@](C)(O)C2)n2ncnc(N)c12] | cis-3-[4-Amino-5-(2-methoxy-4-phenoxy-phenyl)-imidazo[5,1-f][1,2,4]triazin-7-yl]-1-methyl-cyclobutanol | 418.18 | 1.3649 |
| 293 | 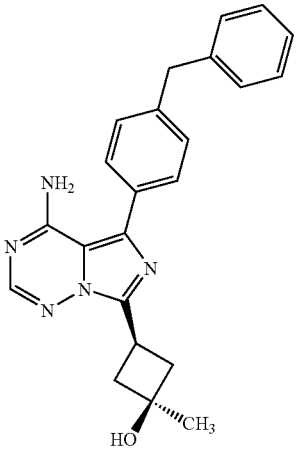 [SMILES: C[C@]1(O)C[C@@H](c2nc(-c3ccc(Cc4ccccc4)cc3)c3c(N)ncnn32)C1] | cis-3-[4-Amino-5-(4-benzyl-phenyl)-imidazo[5,1-f][1,2,4]triazin-7-yl]-1-methyl-cyclobutanol | 387.31 | 0.6228 |

| | | | | |
|---|---|---|---|---|
| 294 | 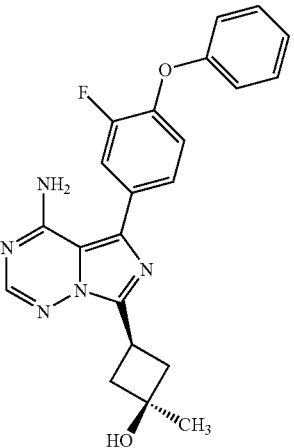 [SMILES: C[C@]1(O)C[C@@H](c2nc(-c3ccc(Oc4ccccc4)c(F)c3)c3c(N)ncnn32)C1] | cis-3-[4-Amino-5-(3-fluoro-4-phenoxy-phenyl)-imidazo[5,1-f][1,2,4]triazin-7-yl]-1-methyl-cyclobutanol | 406.35 | 1.2520 |
| 295 | 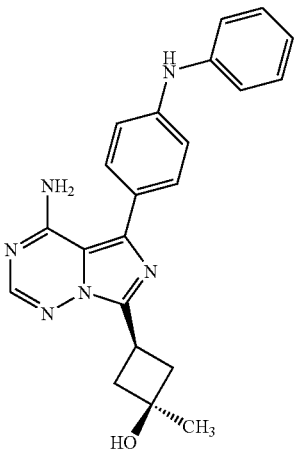 [SMILES: C[C@]1(O)C[C@@H](c2nc(-c3ccc(Nc4ccccc4)cc3)c3c(N)ncnn32)C1] | cis-3-[4-Amino-5-(4-phenylamino-phenyl)-imidazo[5,1-f][1,2,4]triazin-7-yl]-1-methyl-cyclobutanol | 387.06 | 3.8037 |
| 296 | 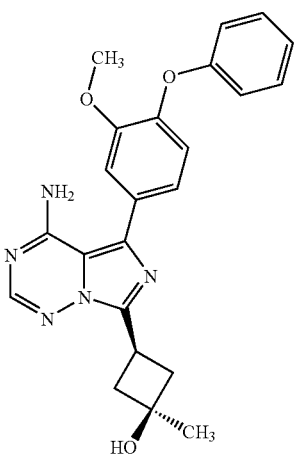 [SMILES: COc1cc(-c2nc([C@H]3C[C@@](C)(O)C3)n3ncnc(N)c23)ccc1Oc1ccccc1] | cis-3-[4-Amino-5-(3-methoxy-4-phenoxy-phenyl)-imidazo[5,1-f][1,2,4]triazin-7-yl]-1-methyl-cyclobutanol | 417.98 | 2.0467 |

| Ex. | Structure | | ACK1 Biochemical IC50 (μM) |
|---|---|---|---|
| 297 | 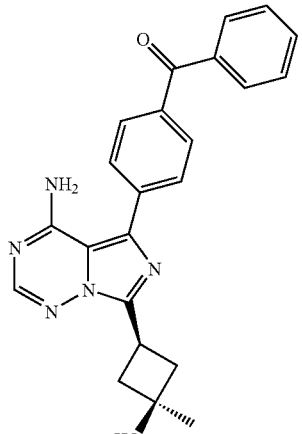 | cis-{4-[4-Amino-7-(3-hydroxy-3-methyl-cyclobutyl)-imidazo[5,1-f][1,2,4]triazin-5-yl]phenyl}-phenyl-methanone  399.99 | 0.4879 |
| Ex. | Structure | ACK1 Biochemical IC50 (μM) |
|---|---|---|
| 298. | 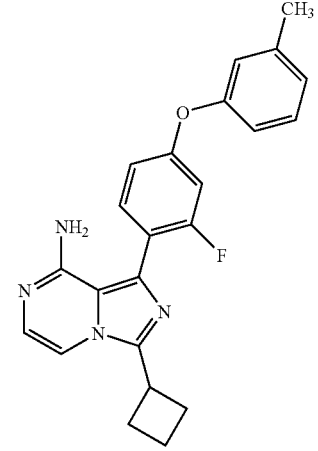 [SMILES: Cc1cccc(Oc2ccc(-c3nc(C4CCC4)n4ccnc(N)c34)c(F)c2)c1] | >10 |
| 299. | 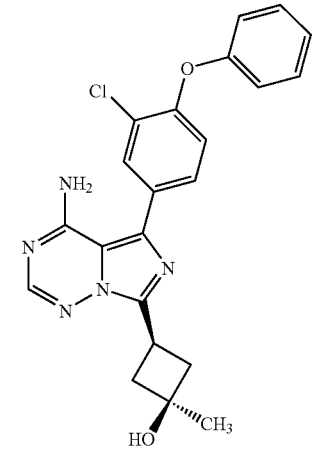 [SMILES: C[C@]1(O)C[C@@H](c2nc(-c3ccc(Oc4ccccc4)c(Cl)c3)c3c(N)ncnn32)C1] | >10 |

TABLE 1-continued
| 300. | 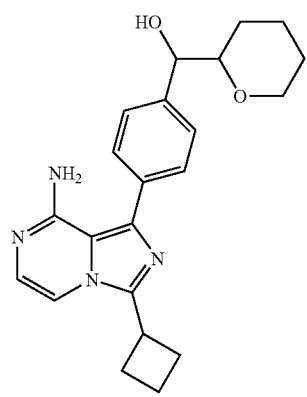 [SMILES: Nc1nccn2c(C3CCC3)nc(-c3ccc(C(O)C4CCCCO4)cc3)c12] | >10 |
| 301. | 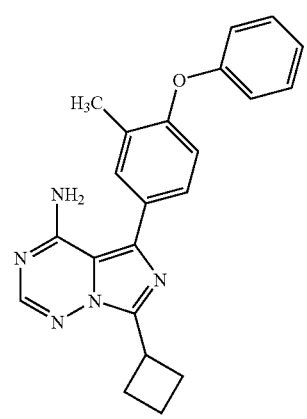 | >10 |
| 302. | 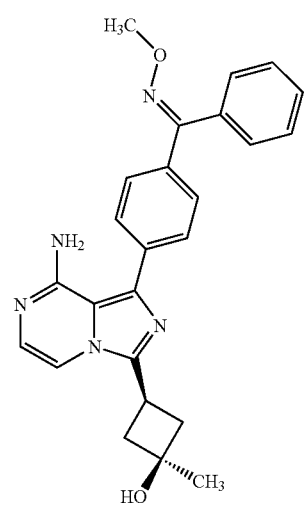 [SMILES: CO/N=C(\c1ccccc1)c1ccc(-c2nc([C@H]3C[C@@](C)(O)C3)n3ccnc(N)c23)cc1] | >10 |
| 303. | 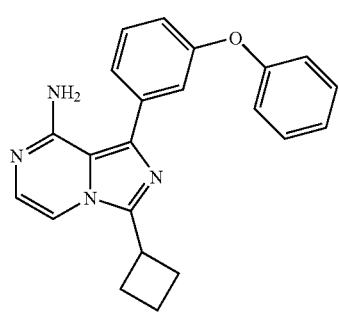 | >10 |

TABLE 1-continued
| 304. | 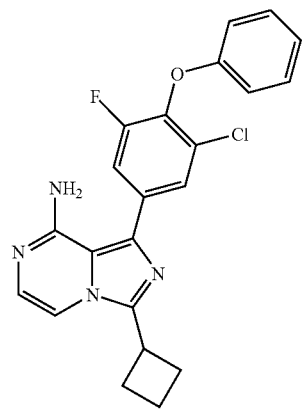 | >10 |
| 305. | 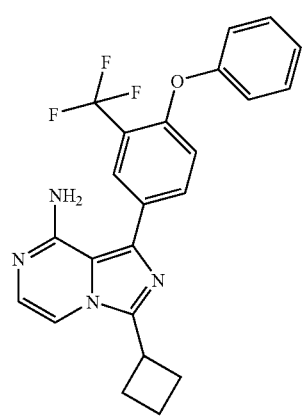 [SMILES: Nc1nccn2c(C3CCC3)nc(-c3ccc(Oc4ccccc4)c(C(F)(F)F)c3)c12] | >10 |
| 306. | 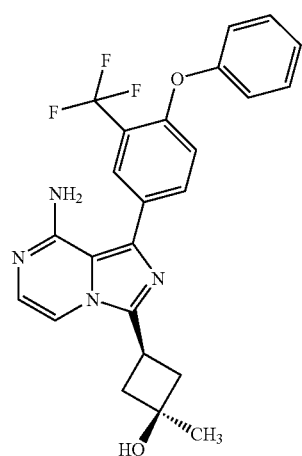 [SMILES: C[C@]1(O)C[C@@H](c2nc(-c3ccc(Oc4ccccc4)c(C(F)(F)F)c3)c3c(N)nccn32)C1] | >10 |

TABLE 1-continued
| 307. | 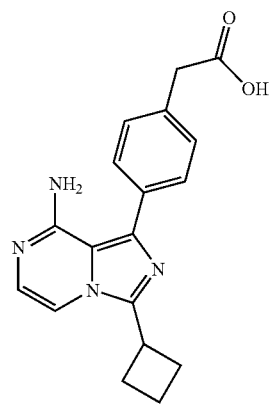 [SMILES: Nc1nccn2c(C3CCC3)nc(-c3ccc(CC(=O)O)cc3)c12] | >10 |
| 308. | 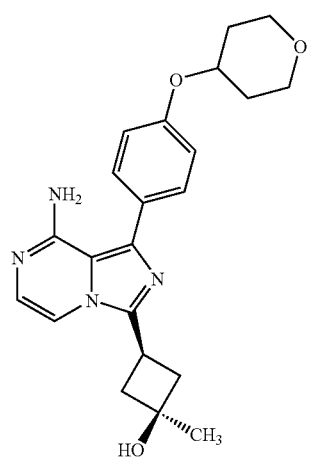 [SMILES: C[C@]1(O)C[C@@H](c2nc(-c3ccc(OC4CCOCC4)cc3)c3c(N)nccn32)C1] | >10 |
| 309. | 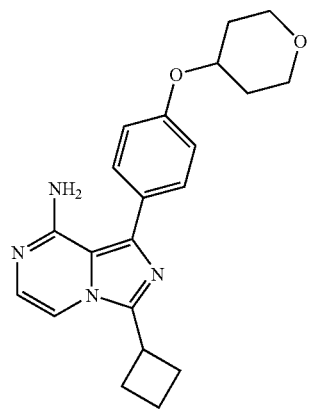 [SMILES: Nc1nccn2c(C3CCC3)nc(-c3ccc(OC4CCOCC4)cc3)c12] | >10 |

TABLE 1-continued
| 310. | 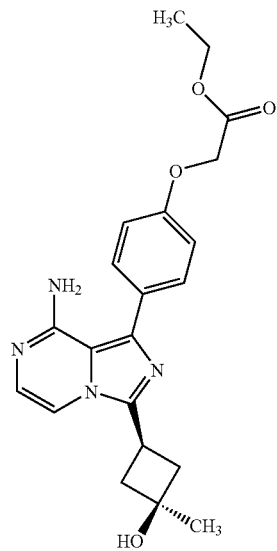 | >10 |
| 311. | 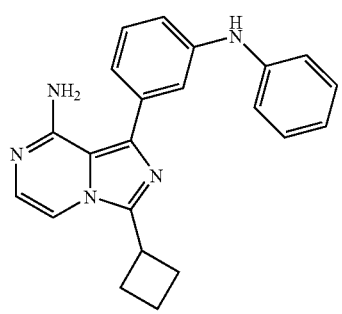 [SMILES: Nc1nccn2c(C3CCC3)nc(-c3cccc(Nc4ccccc4)c3)c12] | >10 |
| 312. | 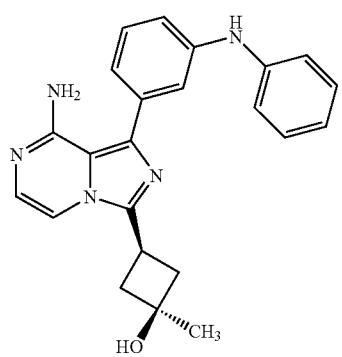 [SMILES: C[C@]1(O)C[C@@H](c2nc(-c3cccc(Nc4ccccc4)c3)c3c(N)nccn32)C1] | >10 |

TABLE 1-continued
| 313. | 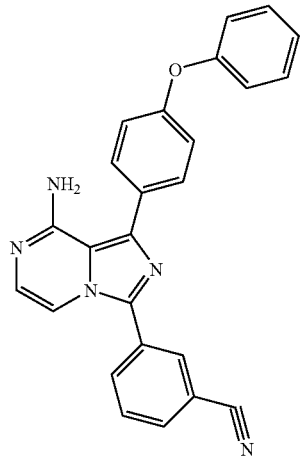 [SMILES: N#Cc1cccc(-c2nc(-c3ccc(Oc4ccccc4)cc3)c3c(N)nccn23)c1] | >10 |
| --- | --- | --- |
| 314. | 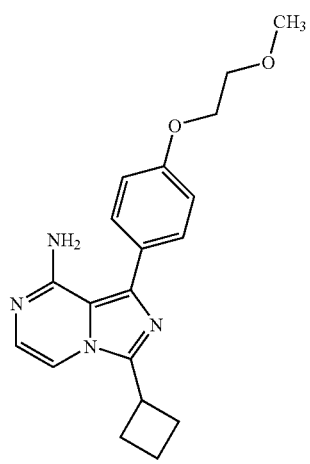 [SMILES: COCCOc1ccc(-c2nc(C3CCC3)n3ccnc(N)c23)cc1] | >10 |
| 315. | 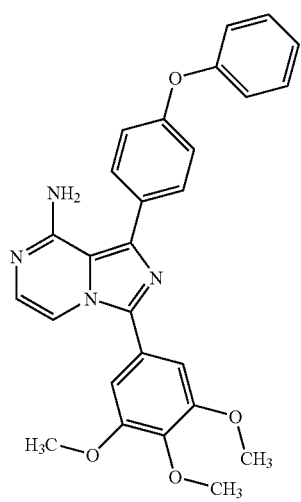 [SMILES: COc1cc(-c2nc(-c3ccc(Oc4ccccc4)cc3)c3c(N)nccn23)cc(OC)c1OC] | >10 |

TABLE 1-continued
| 316. | 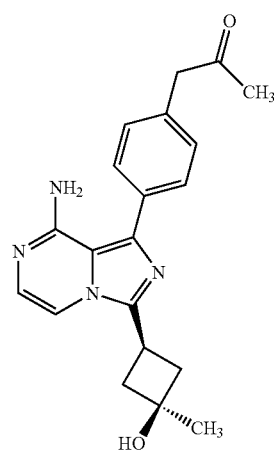 [SMILES: CC(=O)Cc1ccc(-c2nc([C@H]3C[C@@](C)(O)C3)n3ccnc(N)c23)cc1] | >10 |
| 317. | 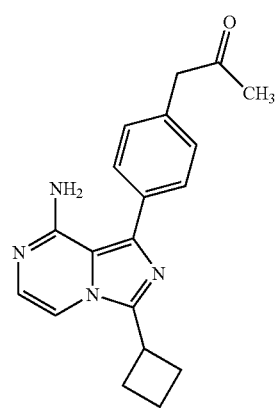 [SMILES: CC(=O)Cc1ccc(-c2nc(C3CCC3)n3ccnc(N)c23)cc1] | >10 |
| 318. | 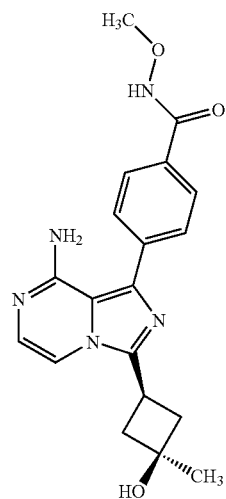 [SMILES: CONC(=O)c1ccc(-c2nc([C@H]3C[C@@](C)(O)C3)n3ccnc(N)c23)cc1] | >10 |

TABLE 1-continued
| | | |
|---|---|---|
| 319. | 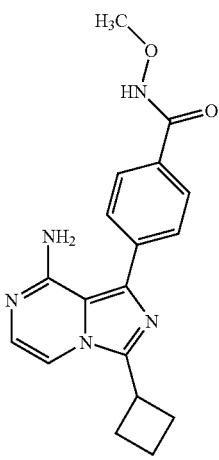 [SMILES: CONC(=O)c1ccc(-c2nc(C3CCC3)n3ccnc(N)c23)cc1] | >10 |
| 320. | 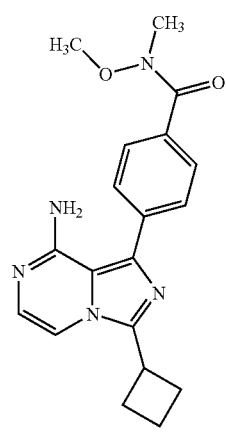 [SMILES: CON(C)C(=O)c1ccc(-c2nc(C3CCC3)n3ccnc(N)c23)cc1] | >10 |
| 321. | 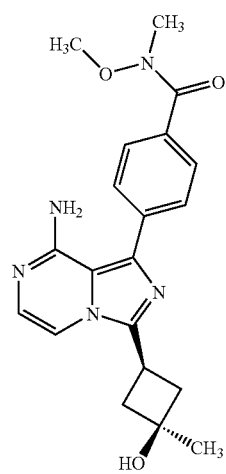 [SMILES: CON(C)C(=O)c1ccc(-c2nc([C@H]3C[C@@](C)(O)C3)n3ccnc(N)c23)cc1] | >10 |

TABLE 1-continued
| 322. | 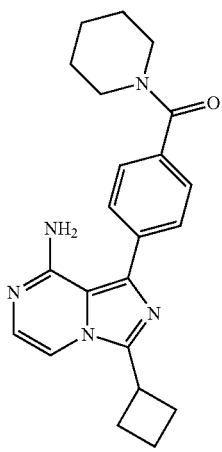 [SMILES: Nc1nccn2c(C3CCC3)nc(-c3ccc(C(=O)N4CCCCC4)cc3)c12] | >10 |
| 323. | 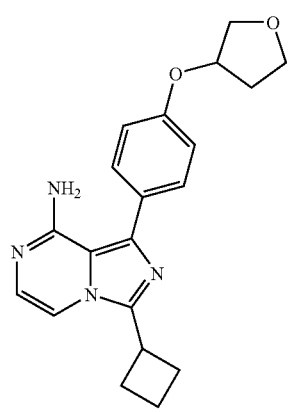 [SMILES: Nc1nccn2c(C3CCC3)nc(-c3ccc(OC4CCOC4)cc3)c12] | >10 |
| 324. | 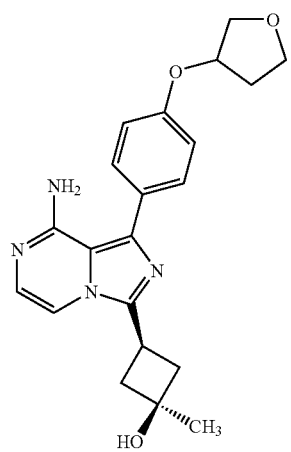 [SMILES: C[C@]1(O)C[C@@H](c2nc(-c3ccc(OC4CCOC4)cc3)c3c(N)nccn32)C1] | >10 |

TABLE 1-continued
| 325. | 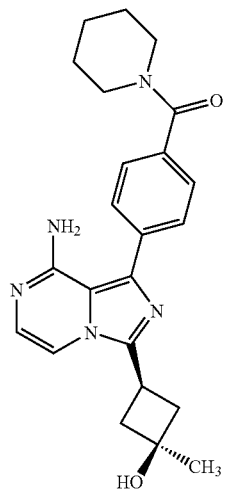 [SMILES: C[C@]1(O)C[C@@H](c2nc(-c3ccc(C(=O)N4CCCCC4)cc3)c3c(N)nccn32)C1] | >10 |
| 326. | 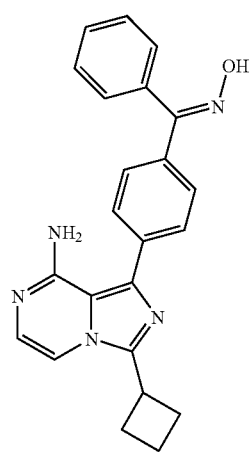 | >10 |
| 327. | 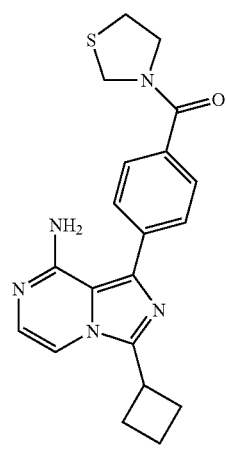 [SMILES: Nc1nccn2c(C3CCC3)nc(-c3ccc(C(=O)N4CCSC4)cc3)c12] | >10 |

TABLE 1-continued
| | | |
|---|---|---|
| 328. | 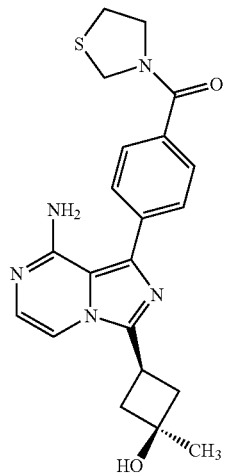 [SMILES: C[C@]1(O)C[C@@H](c2nc(-c3ccc(C(=O)N4CCSC4)cc3)c3c(N)nccn32)C1] | >10 |
| 329. | 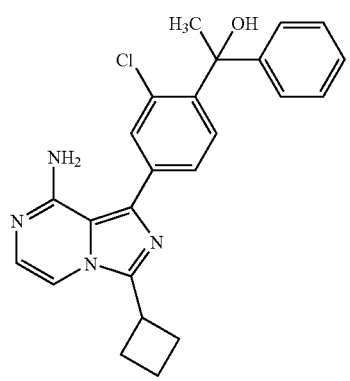 [SMILES: CC(O)(c1ccccc1)c1ccc(-c2nc(C3CCC3)n3ccnc(N)c23)cc1Cl] | >10 |
| 330. | 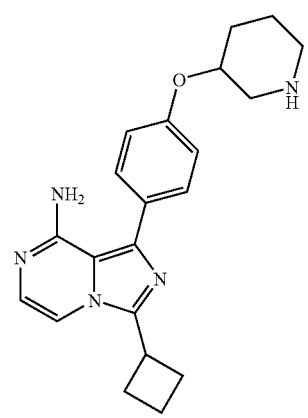 [SMILES: Nc1nccn2c(C3CCC3)nc(-c3ccc(OC4CCCNC4)cc3)c12] | >10 |

TABLE 1-continued
| | | |
|---|---|---|
| 331. | 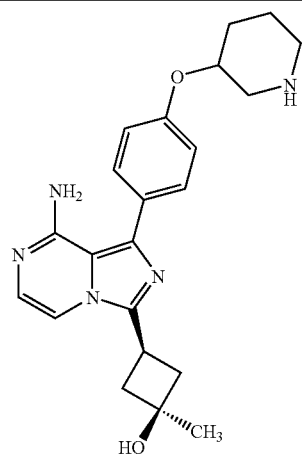 | >10 |
| 332. | 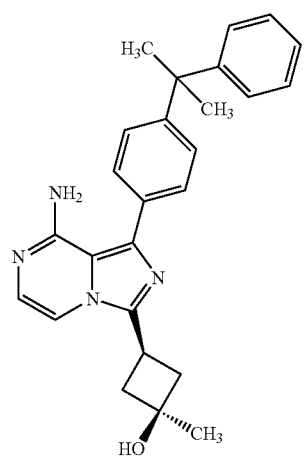 [SMILES: CC(C)(c1ccccc1)c1ccc(-c2nc([C@H]3C[C@@](C)(O)C3)n3ccnc(N)c23)cc1] | >10 |
| 333. | 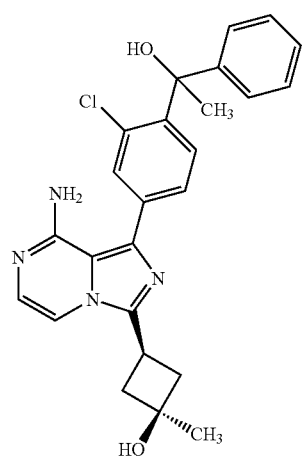 [SMILES: CC(O)(c1ccccc1)c1ccc(-c2nc([C@H]3C[C@@](C)(O)C3)n3ccnc(N)c23)cc1Cl] | >10 |

TABLE 1-continued
| | | |
|---|---|---|
| 334. | 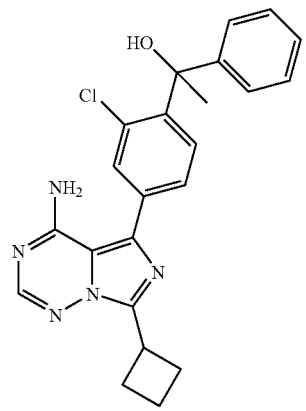 [SMILES: CC(O)(c1ccccc1)c1ccc(-c2nc(C3CCC3)n3ncnc(N)c23)cc1Cl] | >10 |
| 335. | 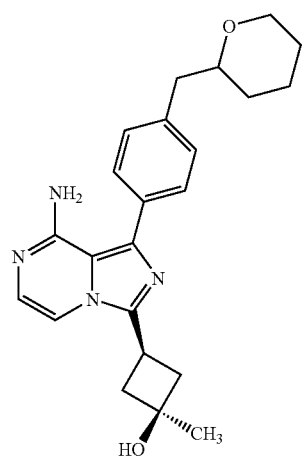 [SMILES: C[C@]1(O)C[C@@H](c2nc(-c3ccc(CC4CCCCO4)cc3)c3c(N)nccn32)C1] | >10 |
| 336. | 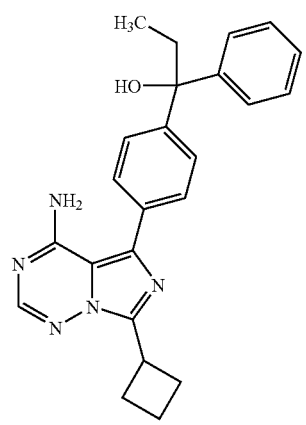 | >10 |

TABLE 1-continued
| 337. | 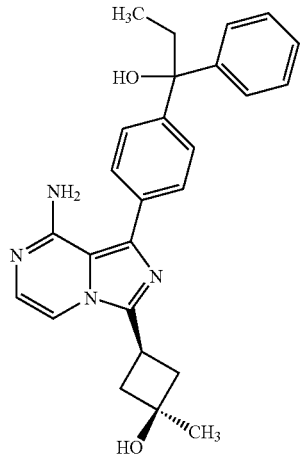 [SMILES: CCC(O)(c1ccccc1)c1ccc(-c2nc([C@H]3C[C@@](C)(O)C3)n3ccnc(N)c23)cc1] | >10 |
| 338. | 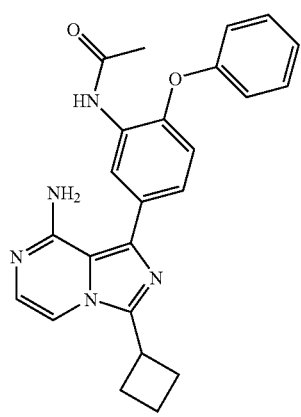 [SMILES: CC(=O)Nc1cc(-c2nc(C3CCC3)n3ccnc(N)c23)ccc1Oc1ccccc1] | >10 |
| 339. | 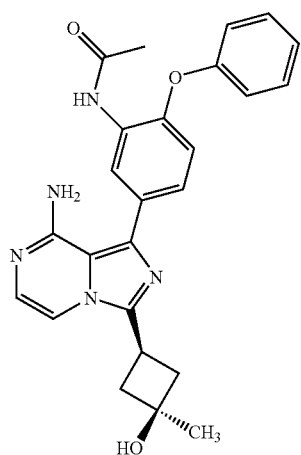 [SMILES: CC(=O)Nc1cc(-c2nc([C@H]3C[C@@](C)(O)C3)n3ccnc(N)c23)ccc1Oc1ccccc1] | >10 |

TABLE 1-continued
| 340. | 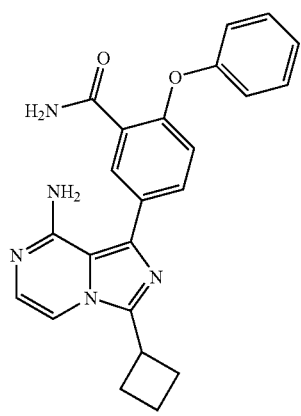 [SMILES: NC(=O)c1cc(-c2nc(C3CCC3)n3ccnc(N)c23)ccc1Oc1ccccc1] | >10 |
| 341. | 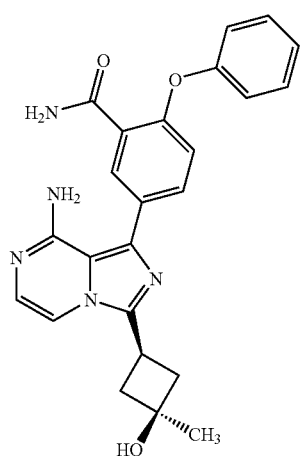 [SMILES: C[C@]1(O)C[C@@H](c2nc(-c3ccc(Oc4ccccc4)c(C(N)=O)c3)c3c(N)nccn32)C1] | >10 |
| 342. | 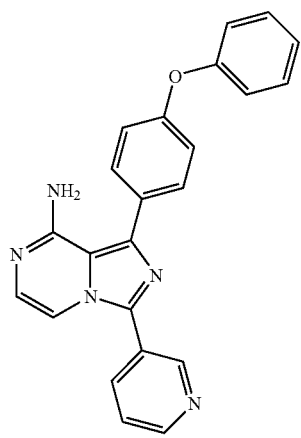 [SMILES: Nc1nccn2c(-c3cccnc3)nc(-c3ccc(Oc4ccccc4)cc3)c12] | >10 |

TABLE 1-continued
| 343. | 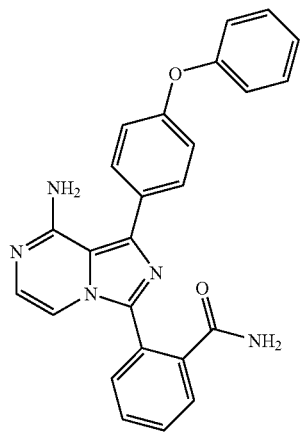 [SMILES: NC(=O)c1ccccc1-c1nc(-c2ccc(Oc3ccccc3)cc2)c2c(N)nccn12] | >10 |
| --- | --- | --- |
| 344. | 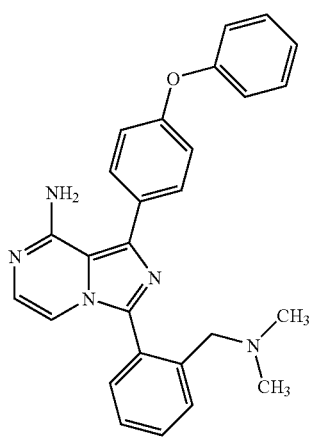 [SMILES: CN(C)Cc1ccccc1-c1nc(-c2ccc(Oc3ccccc3)cc2)c2c(N)nccn12] | >10 |
Comparator compounds were also tested in the ACK1 biochemical assay:
Comparator 1:
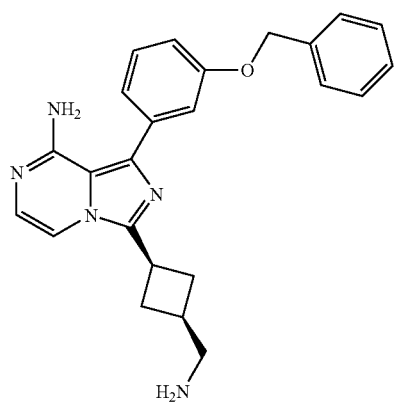
IC$_{50}$: 10.2 µM (100 µM ATP)
-continued
Comparator 2:
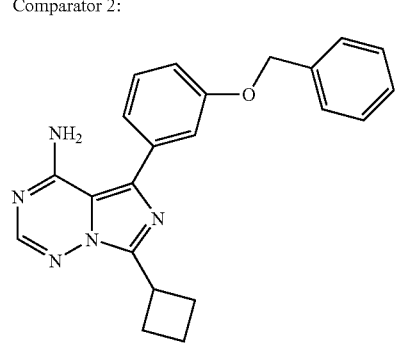
IC$_{50}$: >10 µM (10 µM ATP)

Comparator 3:

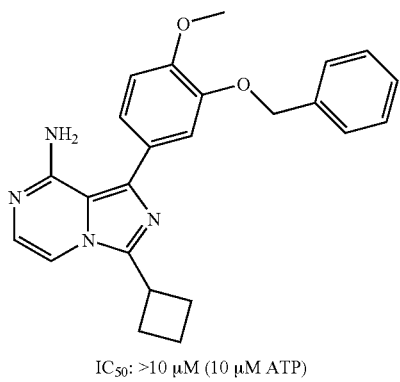

IC$_{50}$: >10 μM (10 μM ATP)

Comparator 4:

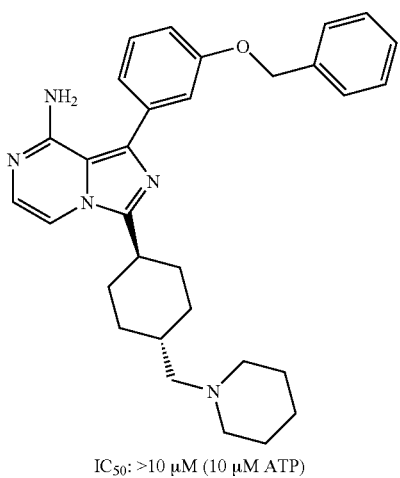

IC$_{50}$: >10 μM (10 μM ATP)

Comparator 5:

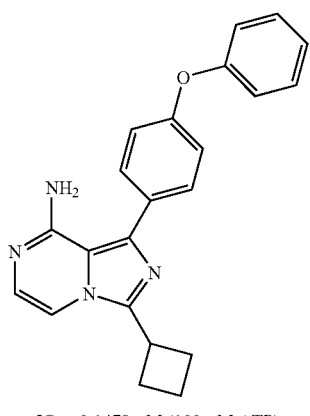

IC$_{50}$: 0.1478 μM (100 μM ATP)

Preparation of Comparator 5: To a stirred mixture of 3-cyclobutyl-1-iodo-imidazo[1,5a]pyrazin-8-ylamine (22.6 mg, 0.072 mmol), potassium carbonate (35.2 mg, 0.25 mmol) in DME (2.0 mL) and H$_2$O (0.50 mL, 28 mmol;) in a microwave reactor vessel was added 4-phenoxyphenylboronic acid (18.69 mg, 0.087 mmol). The solution was bubbled with nitrogen for 5 min. Then Pd(PPh$_3$)$_4$ (4.2 mg, 0.0036 mmol) was added and the resulting mixture was irradiated by microwave at 300 watt, at 100° C. for 30 min. The solvent was then removed under reduced pressure and the resulting residue was purified by flash chromatography (5% MeOH in DCM). MS (ES+): m/z: 357.13 [MH$^+$].

The invention includes the compounds described which exhibit an IC$_{50}$ against ACK1 as described herein of about 0.05 μM or lower, 0.1 μM or lower, 0.2 μM or lower, 0.5 μM or lower, or 1 μM or lower, or 10 μM or lower.

Cell-based Assay for Inhibition of ACK1 (aka TNK2): The ability of compounds to inhibit the ACK1 kinase activity was determined in a cell-based capture ELISA assay using NCI-H1703 cells (ATCC# CRL-5889), which was originally derived from adenocarcinoma of a non-small cell lung cancer patient. The assay determines the ability of compounds to block phosphorylation (including autophosphorylation) of ACK1 that is endogenously expressed in NCI-H1703 cells. Cells are pre-incubated with compounds at various concentrations in the complete growth medium. Cell lysates are then prepared and ACK1 protein is captured on to ACK1 antibody-coated 96-well ELISA plate. The phospho-tyrosine content of ACK1 protein is then monitored by quantitation of degree of binding of an antibody that recognizes phosphorylated ACK1 at tyrosine residues within the captured protein. The antibody used has a reporter enzyme (e.g. horseradish peroxidase, HRP) covalently attached, such that binding of antibody to phosphorylated ACK1 can be determined quantitatively by incubation with an appropriate HRP substrate.

The stock reagents used are as follows: Cell Lysis Buffer (CST, cat#9803): 20 mM Tris-HCl (pH 7.5); 150 mM NaCl; 1 mM Na$_2$EDTA; 1 mM EGTA; 1% Triton; 2.5 mM Sodium pyrophosphate; 1 mM μ-glycerophosphate; 1 mM Na$_3$VO$_4$; 1 μg/ml leupeptin. Anti-ACK1 antibody: 0.5 μg/mL anti-ACK1 antibody (Abcam, cat#ab37367) in 50 mM sodium bicarbonate buffer, pH 9.2. ELISA assay plates: ELISA assay plates are prepared by addition of 100 μL of anti-ACK1 antibodies to each well of a 96-well plate (Costar, catalog #3922), followed by incubation at 4° C. overnight. The wells are then washed three times with 300 μL wash buffer. Plate wash buffer: PBS containing 0.5% Tween-20 (PBST). Cell assay medium: DMEM, 10% FBS, 1% L-Glut. Anti-Phospho-Tyrosine (PY20) Antibody HRP conjugated: 1:3500 dilution of PY20 antibody (Zymed, catalog #03-7720) in PBST containing 3% BSA. HRP substrate: ELISA Femto Chemiluminescence reagent (Pierce, catalog#37075A/B).

Assay protocol: Cultures of NCI-H1703 cells growing in RPMI medium containing 10% fetal bovine serum, 1% L-glutamine, 10 mM HEPES, 1 mM sodium pyruvate, 1.5 g/L sodium bicarbonate and 4.5 g/L glucose were detached by trypsin-EDTA, washed with PBS and collected by centrifugation. The cells are then suspended in cell assay medium. Cells are then plated in to 96-well flat bottom plates at 5×10$^5$ cells per well in 100 μL cell assay medium and incubated overnight at 37° C. in a CO$_2$ incubator.

Compound dilutions were prepared from 10 mM DMSO stocks by dilution in cell assay medium, the final concentration of DMSO in the assay being 0.5%. To compound incubation wells, 10 μL of test compound was added (compounds are assayed at concentrations between 30 μM to 1 nM); to positive control wells, 10 μL of cell assay medium containing 0.5% DMSO was added. The cells were then incubated with compounds at 37° C. for 3 h. The medium was removed by aspiration and the cells were lysed by addition of 120 μL of ice-cold cell lysis buffer per well. The plate was kept on ice for 15 min and 100 μL of the cell lysates from each well were then transferred to the wells of a capture ELISA assay plate and incubated at 4° C. for overnight.

Following incubation of the cell lysates in the ELISA plate, the wells were washed 3 times with 200 μL of wash buffer, then 100 μL of the phospho-tyrosine (PY20) antibody HRP conjugate solution was added to each well, and the plate was incubated at RT for 2 h. The wells were then washed 3 times with 200 μL of wash buffer and 50 μL of the chemiluminescent HRP substrate was added to each well for luminometric quantitation of the amount of phospho-tyrosine antibody, which is already bound to the plate.

Comparison of the assay signals obtained in the presence of compound with those of positive and negative controls (cells with no compound and no cell lysate being added), allows the degree of inhibition of tyrosine phosphorylation to be determined over a range of compound concentrations. These inhibition values were fitted to a sigmoidal dose-response inhibition curve to determine the $IC_{50}$ values (i.e. the concentration of the compound that inhibits tyrosine phosphorylation of ACK1 by 50%).

ACK1 cellular $IC_{50}$ data: Example 106A: IC50>4.0 μM; Example 106B: IC50=0.20 μM.

Pharmaceutical Compositions

The present invention includes pharmaceutical compositions formulated from a therapeutically effective amount of any active agent(s)/compound(s) of the invention with or without at least one suitable excipient and/or carrier and with or without additional active agent(s).

The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art.

The active agent(s) of the invention can be combined with a pharmaceutical carrier according to conventional pharmaceutical compounding techniques. The carrier may take a wide variety of forms depending on the form of preparation desired for administration. e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion, or as a water-in-oil liquid emulsion. In addition to the common dosage forms set out above, the active agent may also be administered by delayed, sustained, or controlled release means and/or delivery devices. Also included are spray-dried dispersions. The compositions may be prepared by any of the methods of pharmacy, such as bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Use

The invention includes methods of inhibiting protein kinase activity, such as nonreceptor protein kinase activity, such as ACK1 activity, comprising administering one or more active agents/compounds of the invention in a therapeutically effective amount in an effective overall treatment that may include other active agents.

The invention includes treating hyperproliferative disorders such as cancer, such as cancerous tumors mediated by ACK1 or overexpressing ACK1, according to the above.

The invention includes any of the above methods, wherein the cancer is a solid tumor, which can be a late or advanced-stage tumor or metastatic tumor.

The invention includes any of the above methods wherein the cancer can be breast, esophageal, lung, melanoma, ovarian, pancreatic, or prostate.

The invention includes a method of mitigating tumor metastasis or reducing cancer invasiveness comprising administering one or more active agents/compounds of the invention in a therapeutically effective amount in an effective overall treatment that may include other active agents.

The invention includes a method of inhibiting epithelial-to-mesenchymal transition in a tumor comprising administering one or more active agents/compounds of the invention in a therapeutically effective amount in an effective overall treatment that may include other active agents.

The invention includes combination treatments, wherein a compound/active agent of the present invention is administered in combination or sequentially with another active agent. Any effective agent for a desired indication, such as an EGFR inhibitor, can be used.

Generally, dosage levels on the order of from about 0.1 mg/kg to about 150 mg/kg of body weight per day are useful in the treatment of the above-indicated conditions. It is understood, however, that the specific dose level for any particular patient will depend upon a variety of factors including the age, body weight, general health, sex, diet, time of administration, route of administration, rate of excretion, drug combination and the severity of the particular disease undergoing therapy.

Abbreviations

Unless otherwise indicated in context, the following abbreviations may be used:
BOC t-Butyloxycarbonyl
CBZ Carbobenzyloxy
$CDCl_3$ Deuterated chloroform
$CD_3OD$ Deuterated methanol
$CHCl_3$ Chloroform
DCM methylene chloride
DIEA N,N-diisopropylethylamine
DMAP 4-Dimethylaminopyridine
DMF N,N-Dimethylformamide
DMSO Dimethylsulfoxide
EDCI or EDC1-(3-Dimethylaminopropyl)-3-ethylcarbodiimide
EtOAc Ethyl acetate
EtOH Ethanol
Fmoc Fluorene methyloxycarbonyl
HOBt 1-Hydroxybenzotriazole
HPLC High performance liquid chromatography
LC/MS Liquid chromatography mass spectrometry
MS Mass spectroscopy
MeCN Acetonitrile
MeOH Methanol
TBTU O-(Benzotriazol-1-yl)-N,N,N',N'-tetramethyluronium tetrafluoroborate
TEA triethylamine
TFA Trifluoroacetic acid
THF Tetrahydrofuran
TLC Thin layer chromatography
d Day(s)
RT or rt Room temperature
$t_R$ Retention time General Definitions Any section headings or subheadings herein are for the reader's convenience or formal compliance and are non-limiting.

Unless otherwise indicated in context, the following general definitions apply.

Language and terms refer to their broadest reasonable interpretation as understood by the skilled artisan.

In that a salt, solvate, or hydrate of a compound necessarily includes the compound itself, a recitation of a compound is intended to embrace such forms thereof.

The term "active agent" of the invention refers to a compound of the invention in any salt, polymorph, crystal, solvate, or hydrated form.

Unless otherwise indicated in context (such as by a connecting "1"), the connections of compound name moieties are at the rightmost recited moiety. That is, the substituent name starts with a terminal moiety, continues with any bridging moieties, and ends with the connecting moiety. For example, "heteroarylthioC$_{1-4}$alkyl is a heteroaryl group connected through a thio sulfur to a C$_{1-4}$ alkyl, which alkyl connects to the chemical species bearing the substituent.

The term "halo" or "halogen" refers to fluoro, chloro, bromo, or iodo.

The term "alkyl" refers to any saturated hydrocarbon group, including branched, straight chain, cyclic, including bi- and polycyclic, bridged, and spiro groups, or any combination of the above. The term "alkenyl" refers to any ethylenically unsaturated hydrocarbon group. The term "alkynyl" refers to any acetylenically unsaturated hydrocarbon group. "C$_{x-y}$" may be used to define number of carbons in a group. For example, "C$_{0-12}$alkyl" means alkyl having 0-12 carbons, wherein C$_0$alkyl means a single covalent chemical bond when a linking group and means hydrogen when a terminal group.

The term "alkoxy" refers to any alkyl group attached through a bridging oxygen atom.

The term "cyclic" refers to any ring system, i.e., carbocyclic or heterocyclic. The size of ring systems may be described using terminology such as "x-cyclic," which means a cyclic ring system that can have from x to y ring atoms.

The term "carbocyclic" refers to any aryl, cycloalkyl, or unsaturated carbocyclic.

The term "aryl" refers to any all-carbon monocyclic, bicyclic, or polycyclic groups having an aromaticity. The terms "aryl-alkyl" or "arylalkyl" or "aralkyl" refer to any alkyl that forms a bridging portion with a terminal aryl.

The term "cycloalkyl" refers to any saturated hydrocarbon ring system. Such includes bi- and poly cycloalkyl, bridged systems, and spiros.

The term "unsaturated carbocyclic" refers to any unsaturated hydrocarbon ring system including aryl.

The term "heterocyclic" refers to any heteroaryl, heterocycloalkyl, or unsaturated heterocyclic ring system.

The terms "heteroaryl" or "hetaryl" refer to any ring system containing at least one ring having one or more ring atoms selected from N, O, and S and having aromaticity.

The term "heterocycloalkyl" refers to any saturated ring system containing at least one ring having one or more ring atoms selected from N, O, and S.

The term "unsaturated heterocyclic" refers to any ring system that is not carbocyclic, heteroaryl, or heterocycloalkyl.

One in the art understands that an "oxo" requires a second bond from the atom to which the oxo is attached. Accordingly, it is understood that oxo cannot be substituted onto an aryl or heteroaryl ring.

The invention claimed is:

1. A compound according to Formula I:

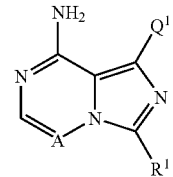

wherein:
A is CH;
Q$^1$ is —X$^1$—Y$^1$—Z$^1$;
or Q$^1$ is:

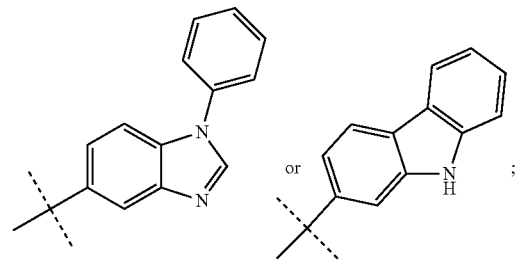

Y$^1$ is selected from >C(R$^2$)R$^3$, >C(OR$^2$)R$^3$, >C=O, >C=C(R$^2$)R$^3$, >C=NR$^2$, >C=NOR$^2$, >NR$^2$, >O, or >S(O)$_m$;

and wherein when Y$^1$ is >O and R$^1$ is cyclobutyl, at least one of X$^1$ or Z$^1$ is substituted;

X$^1$ is phenyl which can be substituted by 1 to 3 independently selected G$^1$ groups;

Z$^1$ is phenyl which can be substituted by 1 to 3 independently selected G$^1$ groups;

each instance of G$^1$ is independently selected from halo —CN, —CF$_3$, —OCF$_3$, —NO$_2$, C$_{1-4}$alkyl, phenylC$_{0-3}$alkyl, $_{5-6}$heteroarylC$_{0-3}$alkyl, —OR$^4$, —NR$^4$R$^5$, —C(O)R$^4$, —C(O)NR$^4$R$^5$, —C(O)OR$^4$, or —NR$^4$C(O)R$^5$, any of which can be substituted by 1 to 3 independently selected G$^2$ groups;

each instance of G$^2$ is independently selected from halo, —CN, —OH, —NH$_2$, oxo, —CF$_3$, —OCF$_3$, or C$_{1-4}$alkyl, an of which can be substituted by 1 to 3 groups independently selected from halo, —CN, —OH, —NH$_2$, C$_{1-4}$alkyl (which may be partially or fully halogenated), —N(C$_{1-6}$alkyl)C$_{1-6}$alkyl (which may be partially or fully halogenated), or —OC$_{1-4}$alkyl (which may be partially or fully halogenated);

each instance of G$^3$ is independently selected from halo oxo —CN, —CF$_3$, —OCF$_3$, C$_{1-4}$alkyl, $_{5-6}$heterocyclicC$_{0-3}$alkyl, phenylC$_{0-3}$alkyl, —OR$^8$, —NR$^8$R$^9$, —C(O)R$^8$, —C(O)NR$^8$R$^9$, —C(O)OR$^8$, —NR$^8$C(O)R$^9$, —(CR$^8$R$^9$)$_n$NR$^6$R$^7$, —(CR$^8$R$^9$)$_n$OR$^6$, —NR$^8$C(O)OR$^9$, —O(CR$^8$R$^9$)$_n$NR$^6$R$^7$, —N(CR$^8$R$^9$)$_n$OR$^6$, or —(CR$^8$R$^9$)$_n$NR$^6$C(O)OR$^7$, any of which can be substituted by 1 to 3 independently selected G$^2$ substituents;

R$^1$ is selected from C$_{3-12}$alkyl, $_{3-6}$cycloalkyl, phenyl, or $_{5-6}$heterocyclic, any of which can be substituted by 1 to 3 independently selected G$^3$ groups;

each instance of $R^2$ and $R^3$ is independently selected from H, halo, or —$C_{1-6}$alkyl;

each instance of $R^4$ and $R^5$ can be independently selected from H, $C_{1-4}$alkyl, $_{5-6}$cyclic$C_{0-3}$alkyl; and each instance of $R^6$, $R^7$, $R^8$, and $R^9$ is independently selected from H, $C_{1-6}$alkyl, or $_{3-6}$cyclic$C_{0-6}$alkyl; wherein any $R^4/R^5$, $R^6/R^7$, $R^8/R^9$ pair, together with the atom to which they are attached, can form a $_{3-6}$cyclic that can include one or more heteroatoms selected from O, $N(C_{0-3}$alkyl), or $S(O)_m$;

each m is independently selected from 0-2; and each n is independently selected from 0-3;

or a pharmaceutically acceptable salt thereof.

2. The compound of claim 1, wherein:

$X^1$ is phenyl, which can be substituted by 1 to 2 independently selected $G^1$ groups;

$Y^1$ is selected from >O, >C(O), >NH, >N(CH$_3$), >C(OR$^2$)(R$^3$), >C(R$^2$)(R$^3$), or $S(O)_m$;

$Z^1$ is phenyl, which can be substituted by 1 to 2 independently selected $G^1$ groups;

each instance of $G^1$ is independently selected from halo, —CN, —CF$_3$, —OCF$_3$, —NO$_2$, $C_{1-4}$alkyl, —OR$^4$, —NR$^4$R$^5$, —C(O)R$^4$, —C(O)NR$^4$R$^5$, —C(O)OR$^4$, or —NR$^4$C(O)R$^5$, any of which can be substituted by 1 to 2 independently selected $G^2$ groups;

each instance of $G^2$ is independently selected from halo, —CN, —OH, —NH$_2$, oxo, —CF$_3$, —OCF$_3$, or $C_{1-4}$alkyl;

$R^1$ is selected from phenyl, $_{5-6}$heteroaryl, $_{3-6}$cycloalkyl, or $C_{3-6}$alkyl, any of which can be substituted by 1 to 2 independently selected $G^3$ groups;

each instance of $R^2$ and $R^3$ is independently selected from H, halo, or $C_{1-3}$alkyl;

each instance of $R^4$ and $R^5$ is independently selected from H or $C_{1-4}$alkyl;

each instance of $R^6$, $R^7$, $R^8$, and $R^9$ is independently selected from H or $C_{1-4}$alkyl; wherein any $R^8/R^9$ or $R^6/R^7$ pair, together with the atom to which they are attached, can form a $_{3-6}$cyclic that can include one or more heteroatoms selected from O, $N(C_{0-3}$alkyl), or $S(O)_m$; and each n is independently selected from 0-2; or a pharmaceutically acceptable salt thereof.

3. The compound of claim 1, wherein:

$Q^1$ is —$X^1$—$Y^1$—$Z^1$;

$X^1$ is phenyl which can be substituted by 1 to 2 of —OH, $C_{1-3}$alkyl, halo, $C_{1-3}$alkoxy, or NH$_2$;

$Y^1$ is selected from >S, >O, >C(O), >C(OR$^2$)R$^3$, or >C(R$^2$)R$^3$;

$Z^1$ is phenyl which can be substituted by 1 to 2 independently selected from halo, methyl, —OH, or NH$_2$;

$R^1$ is selected from $_{5-6}$heteroaryl, phenyl, or $_{3-6}$cycloalkyl, any of which can be substituted with 1 to 2 independently selected from —OH, —C(O)NH$_2$, $C_{1-2}$alkyl, —(CH$_2$)$_{0-2}$NH$_2$, —$C_{1-2}$alkoxyNH$_2$, or piperazin-1-yl, wherein any amine hydrogen or hydroxy hydrogen can be replaced with methyl, ethyl, or with —(CH$_2$)$_2$N(CH$_3$)$_2$; and each instance of $R^2$ and $R^3$ is independently selected from H, halo, methyl, or OH; or a pharmaceutically acceptable salt thereof.

4. The compound of claim 3, wherein:

$X^1$ is phenyl which can be substituted with 1 to 2 of halo, NH$_2$, ethoxy, or methoxy;

$Z^1$ is phenyl which can be substituted by 1-2 of halo, —OH, or NH$_2$; and $R^1$ is $C_{4-6}$cycloalkyl which can be substituted with 1 to 2 independently selected from methyl, hydroxy, or aminomethyl; or a pharmaceutically acceptable salt thereof.

5. The compound of claim 4, wherein:

$X^1$ is phenyl which can be substituted with 1 to 2 independently selected from halo, NH$_2$, or methoxy;

$Y^1$ is selected from >O, >C(OR$^2$)R$^3$, or >C(R$^2$)R$^3$; and $R^2$ and $R^3$ are independently selected from H, F or methyl;

$Z^1$ is phenyl; or a pharmaceutically acceptable salt thereof.

6. The compound of claim 1, wherein $Q^1$ is one of:

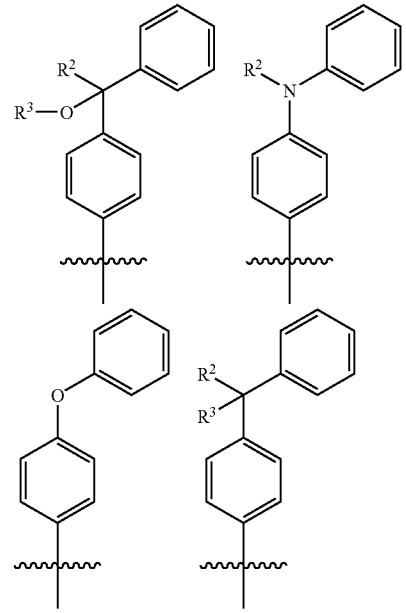

wherein each phenyl group in $Q^1$ can be substituted by up to two $G^1$ substituents; or a pharmaceutically acceptable salt thereof.

7. The compound of claim 6, wherein $R^1$ is cyclobutyl which can be substituted with 1 to 2 independent hydroxy or methyl; or a pharmaceutically acceptable salt thereof.

8. The compound of claim 6, wherein $R^1$ is cyclohexyl or phenyl, either optionally substituted with 4-methylpiperazin-1-yl, —(CH$_2$)$_{1-3}$N(CH$_3$)$_2$, or —O(CH$_2$)$_{1-3}$N(CH$_3$)$_2$, or a pharmaceutically acceptable salt thereof.

9. The compound of claim 6, wherein: $R^1$ is phenyl or $_{5-6}$heteroaryl, either optionally substituted by $G^3$; or a pharmaceutically acceptable salt thereof.

10. The compound of claim 6, wherein $R^1$ is $_{5-6}$heterocyclic; or a pharmaceutically acceptable salt thereof.

11. The compound of claim 7, wherein $R^1$ is:

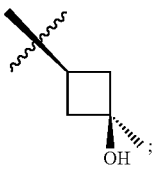

or a pharmaceutically acceptable salt thereof.

12. The compound of claim 6, wherein each instance of $R^2$ and $R^3$ is independently selected from H, halo, or $C_{1-3}$alkyl; or a pharmaceutically acceptable salt thereof.

13. The compound of claim 1, represented by the formula:

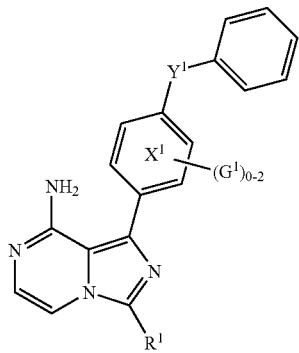

wherein $Y^1$ is >O or >C(CH$_3$)OH or >CF$_2$; each $G^1$ group is independently selected from C$_{1-3}$alkyl, halo or C$_{1-3}$alkoxy; and $R^1$ is selected from:

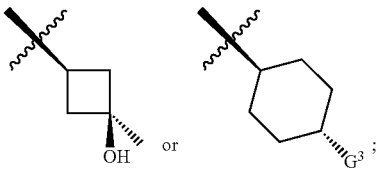

wherein $G^3$ is —CH$_2$NR$^6$R$^7$; and R$^6$ and R$^7$ are independently selected from H, C$_{1-4}$alkyl,
or a pharmaceutically acceptable salt thereof.

14. The compound of claim 1, represented by the formula:

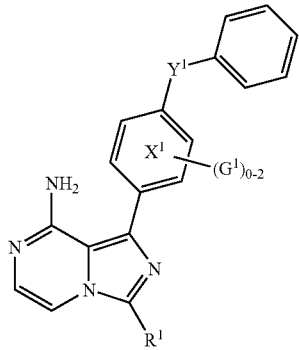

wherein $Y^1$ is >O or >C(CH$_3$)OH or >CF$_2$; each $G^1$ group is independently selected from C$_{1-3}$alkyl, halo or C$_{1-3}$alkoxy; and $R^1$ is selected from phenyl or $_{5-6}$heteroaryl; or
a pharmaceutically acceptable salt thereof.

15. A compound selected from:
3-Cyclohexyl-1-(4-phenoxy-phenyl)-imidazo[1,5-a]pyrazin-8-ylamine
3-Cyclopropyl-1-(4-phenoxy-phenyl)-imidazo[1,5-a]pyrazin-8-ylamine
3-Cyclopentyl-1-(4-phenoxy-phenyl)-imidazo[1,5-a]pyrazin-8-ylamine
3-Azetidin-3-yl-1-(4-phenoxy-phenyl)-imidazo[1,5-a]pyrazin-8-ylamine
3-Ethyl-1-(4-phenoxy-phenyl)-imidazo[1,5-a]pyrazin-8-ylamine
3-Isopropyl-1-(4-phenoxy-phenyl)-imidazo[1,5-a]pyrazin-8-ylamine
1-(4-Phenoxy-phenyl)-3-(tetrahydro-pyran-4-yl)imidazo[1,5-a]pyrazin-8-ylamine
3-tert-Butyl-1-(4-phenoxy-phenyl)-imidazo[1,5-a]pyrazin-8-ylamine
cis-3-[3-(4-Methyl-piperazin-1-yl)-cyclobutyl]-1-(4-phenoxy-phenyl)-imidazo[1,5-a]pyrazin-8-ylamine
cis-3-[8-Amino-1-(4-phenoxy-phenyl)-imidazo[1,5-a]pyrazin-3-yl]-cyclobutanol
cis-3-{8-Amino-1-[4-(tetrahydro-pyran-2-yloxy)-phenyl]-imidazo[1,5-a]pyrazin-3-yl}-cyclobutanol
cis-3-(3-Dimethylamino-cyclobutyl)-1-(4-phenoxy-phenyl)-imidazo[1,5-a]pyrazin-8-ylamine
3-(3,3-Difluoro-cyclobutyl)-1-(4-phenoxy-phenyl)-imidazo[1,5-a]pyrazin-8-ylamine
cis-3-{8-Amino-1-[4-(2,2-difluoro-1-phenyl-vinyl)-phenyl]-imidazo[1,5-a]pyrazin-3-yl}-1-methyl-cyclobutanol
trans-{4-[8-Amino-1-(4-phenoxy-phenyl)-imidazo[1,5-a]pyrazin-3-yl]cyclohexylmethyl}-carbamic acid benzyl ester
1-{4-[8-Amino-1-(4-phenoxy-phenyl)-imidazo[1,5-a]pyrazin-3-yl]-piperidin-1-yl}-2-dimethylamino-ethanone
1-(4-Phenoxy-phenyl)-3-piperidin-4-yl-imidazo[1,5-a]pyrazin-8-ylamine
3-Methylsulfanyl-1-(4-phenoxy-phenyl)-imidazo[1,5-a]pyrazin-8-ylamine
3-Cyclobutyl-1-(3-methoxy-4-phenoxy-phenyl)-imidazo[1,5-a]pyrazin-8-ylamine
3-Cyclobutyl-1-(3-fluoro-4-phenoxy-phenyl)-imidazo[1,5-a]pyrazin-8-ylamine
3-Cyclobutyl-1-(2-fluoro-5-methoxy-4-phenoxy-phenyl)-imidazo[1,5-a]pyrazin-8-ylamine
3-Cyclobutyl-1-(4-phenoxy-2-trifluoromethyl-phenyl)-imidazo[1,5-a]pyrazin-8-ylamine
3-Cyclobutyl-1-(2-ethyl-4-phenoxy-phenyl)-imidazo[1,5-a]pyrazin-8-ylamine
1-(2-Chloro-4-phenoxy-phenyl)-3-cyclobutyl-imidazo[1,5-a]pyrazin-8-ylamine
3-Cyclobutyl-1-(2-ethoxy-4-phenoxy-phenyl)-imidazo[1,5-a]pyrazin-8-ylamine
3-Cyclobutyl-1-(4-phenoxy-2-trifluoromethoxy-phenyl)-imidazo[1,5-a]pyrazin-8-ylamine
1-(3-Chloro-4-phenoxy-phenyl)-3-cyclobutyl-imidazo[1,5-a]pyrazin-8-ylamine
3-Cyclobutyl-1-(3-nitro-4-phenoxy-phenyl)-imidazo[1,5-a]pyrazin-8-ylamine
3-Cyclobutyl-1-(2-methyl-4-phenoxy-phenyl)-imidazo[1,5-a]pyrazin-8-ylamine
3-Cyclobutyl-1-(3-methyl-4-phenoxy-phenyl)-imidazo[1,5-a]pyrazin-8-ylamine
3-Cyclobutyl-1-[4-(2-nitro-phenoxy)-phenyl]-imidazo[1,5-a]pyrazin-8-ylamine
3-Cyclobutyl-1-(3-methoxy-4-o-tolyloxy-phenyl)-imidazo[1,5-a]pyrazin-8-ylamine
3-Cyclobutyl-1-[4-(3-fluoro-phenoxy)-3-methoxy-phenyl]-imidazo[1,5-a]pyrazin-8-ylamine
3-Cyclobutyl-1-(3-methoxy-4-m-tolyloxy-phenyl)-imidazo[1,5-a]pyrazin-8-ylamine
3-Cyclobutyl-1-(2,5-difluoro-4-phenoxy-phenyl)-imidazo[1,5-a]pyrazin-8-ylamine
1-[4-(2-Chloro-phenoxy)-3-methoxy-phenyl]-3-cyclobutyl-imidazo[1,5-a]pyrazin-8-ylamine
[4-(8-Amino-3-cyclobutyl-imidazo[1,5-a]pyrazin-1-yl)-phenyl]-phenyl-methanone 3-Cyclobutyl-1-(4'-ethoxy-biphenyl-4-yl)-imidazo[1,5-a]pyrazin-8-ylamine
3-Cyclobutyl-1-(4-diphenylamino-phenyl)-imidazo[1,5-a]pyrazin-8-ylamine
1-(4-Benzyl-phenyl)-3-cyclobutyl-imidazo[1,5-a]pyrazin-8-ylamine
3-Cyclobutyl-1-(4-phenylamino-phenyl)-imidazo[1,5-a]pyrazin-8-ylamine
[4-(8-Amino-3-cyclobutyl-imidazo[1,5-a]pyrazin-1-yl)-phenyl]-phenyl-methanone O-methyl-oxime
[4-(8-Amino-3-cyclobutyl-imidazo[1,5-a]pyrazin-1-yl)-phenyl]-(tetrahydro-pyran-2-yl)-methanone
3-Cyclobutyl-1-[4-(tetrahydro-pyran-2-ylsulfanyl)-phenyl]-imidazo[1,5-a]pyrazin-8-ylamine
[4-(8-Amino-3-cyclobutyl-imidazo[1,5-a]pyrazin-1-yl)-2-fluoro-phenyl]-phenyl-methanone
1-[4-(8-Amino-3-cyclobutyl-imidazo[1,5-a]pyrazin-1-yl)-phenyl]-1-phenyl-ethanol
[4-(8-Amino-3-cyclobutyl-imidazo[1,5-a]pyrazin-1-yl)-2-methoxy-phenyl]-phenyl-methanone
[4-(8-Amino-3-cyclobutyl-imidazo[1,5-a]pyrazin-1-yl)-3-fluoro-phenyl]-phenyl-methanone
[4-(8-Amino-3-cyclobutyl-imidazo[1,5-a]pyrazin-1-yl)-2-nitro-phenyl]-phenyl-methanone
[4-(8-Amino-3-cyclobutyl-imidazo[1,5-a]pyrazin-1-yl)-naphthalen-1-yl]-phenyl-methanone
[4-(8-Amino-3-cyclobutyl-imidazo[1,5-a]pyrazin-1-yl)-2-chloro-phenyl]-phenyl-methanone
[4-(8-Amino-3-cyclobutyl-imidazo[1,5-a]pyrazin-1-yl)-phenyl]-phenyl-methanone oxime
3-Cyclobutyl-1-[4-(1-methyl-1-phenyl-ethyl)-phenyl]-imidazo[1,5-a]pyrazin-8-ylamine
3-Cyclobutyl-1-[4-(tetrahydro-pyran-2-ylmethyl)-phenyl]-imidazo[1,5-a]pyrazin-8-ylamine
1-[4-(8-Amino-3-cyclobutyl-imidazo[1,5-a]pyrazin-1-yl)-phenyl]-1-phenyl-propan-1-ol
3-Cyclobutyl-1-[4-(tetrahydro-furan-2-ylmethyl)-phenyl]-imidazo[1,5-a]pyrazin-8-ylamine
3-Cyclobutyl-1-[4-(difluoro-phenyl-methyl)-phenyl]-imidazo[1,5-a]pyrazin-8-ylamine  1-[4-(8-Amino-3-cyclobutyl-imidazo[1,5-a]pyrazin-1-yl)-phenyl]-1-(3-fluoro-phenyl)-ethanol
1-[4-(8-Amino-3-cyclobutyl-imidazo[1,5-a]pyrazin-1-yl)-2-methoxy-phenyl]-1-phenyl-ethanol
1-[4-(8-Amino-3-cyclobutyl-imidazo[1,5-a]pyrazin-1-yl)-3-fluoro-phenyl]-1-phenyl-ethanol
1-[4-(8-Amino-3-cyclobutyl-imidazo[1,5-a]pyrazin-1-yl)-3-methyl-phenyl]-1-phenyl-ethanol
1-[4-(8-Amino-3-cyclobutyl-imidazo[1,5-a]pyrazin-1-yl)-phenyl]-1-(2-fluoro-phenyl)-ethanol
1-[4-(8-Amino-3-cyclobutyl-imidazo[1,5-a]pyrazin-1-yl)-3-methoxy-phenyl]-1-phenyl-ethanol
1-[4-(8-Amino-3-cyclobutyl-imidazo[1,5-a]pyrazin-1-yl)-3-chloro-phenyl]-1-phenyl-ethanol
[4-(8-Amino-3-cyclobutyl-imidazo[1,5-a]pyrazin-1-yl)-3-methoxy-phenyl]-phenyl-methanone
[4-(8-Amino-3-cyclobutyl-imidazo[1,5-a]pyrazin-1-yl)-3-methyl-phenyl]-phenyl-methanone
[4-(8-Amino-3-cyclobutyl-imidazo[1,5-a]pyrazin-1-yl)-3-chloro-phenyl]-phenyl-methanone
[5-(8-Amino-3-cyclobutyl-imidazo[1,5-a]pyrazin-1-yl)-pyridin-2-yl]-phenyl-methanone
-Cyclobutyl-1-[4-(tetrahydro-pyran-2-yloxy)-phenyl]-imidazo[1,5-a]pyrazin-8-ylamine
3-Cyclobutyl-1-(2-methoxy-4-phenoxy-phenyl)-imidazo[1,5-a]pyrazin-8-ylamine
3-Cyclobutyl-1-[4-(2-fluoro-6-methoxy-phenoxy)-phenyl]-imidazo[1,5-a]pyrazin-8-ylamine
3-Cyclobutyl-1-(3,5-dimethoxy-4-phenoxy-phenyl)-imidazo[1,5-a]pyrazin-8-ylamine
1-(3-Chloro-5-methyl-4-phenoxy-phenyl)-3-cyclobutyl-imidazo[1,5-a]pyrazin-8-ylamine
3-Cyclobutyl-1-(2,3-difluoro-4-phenoxy-phenyl)-imidazo[1,5-a]pyrazin-8-ylamine
3-Cyclobutyl-1-(5-methoxy-2-methyl-4-phenoxy-phenyl)-imidazo[1,5-a]pyrazin-8-ylamine
N-[5-(8-Amino-3-cyclobutyl-imidazo[1,5-a]pyrazin-1-yl)-2-phenoxy-phenyl]-formamide
3-Cyclobutyl-1-[3-fluoro-4-(2,2,2-trifluoro-ethoxy)-phenyl]-imidazo[1,5-a]pyrazin-8-ylamine
3-Cyclobutyl-1-[4-(2,6-difluoro-phenoxy)-phenyl]-imidazo[1,5-a]pyrazin-8-ylamine
3-Cyclobutyl-1-[4-(2,2-difluoro-1-phenyl-vinyl)-phenyl]-imidazo[1,5-a]pyrazin-8-ylamine
3-Cyclobutyl-1-(4-cyclohexyloxy-phenyl)-imidazo[1,5-a]pyrazin-8-ylamine
3-Cyclobutyl-1-(4-cyclopentyloxy-phenyl)-imidazo[1,5-a]pyrazin-8-ylamine
1-(9H-Carbazol-2-yl)-3-cyclobutyl-imidazo[1,5-a]pyrazin-8-ylamine
5-(8-Amino-3-cyclobutyl-imidazo[1,5-a]pyrazin-1-yl)-2-phenoxy-phenol
3-Cyclobutyl-1-[4-(pyridin-2-yloxy)-phenyl]-imidazo[1,5-a]pyrazin-8-ylamine
cis-{-4-[8-Amino-3-(3-hydroxy-3-methyl-cyclobutyl)-imidazo[1,5-a]pyrazin-1-yl]-phenyl}-phenyl-methanone
cis-3-[8-Amino-1-(4-phenoxy-phenyl)-imidazo[1,5-a]pyrazin-3-yl]-1-methyl-cyclobutanol
cis-3-[8-Amino-1-(3-methoxy-4-phenoxy-phenyl)-imidazo[1,5-a]pyrazin-3-yl]-1-methyl-cyclobutanol
cis-3-{8-Amino-1-[4-(tetrahydro-pyran-2-yloxy)-phenyl]-imidazo[1,5-a]pyrazin-3-yl}-1-methyl-cyclobutanol
cis-3-[8-Amino-1-(3-fluoro-4-phenoxy-phenyl)-imidazo[1,5-a]pyrazin-3-yl]-1-methyl-cyclobutanol
cis-3-[8-Amino-1-(4-phenylamino-phenyl)-imidazo[1,5-a]pyrazin-3-yl]-1-methyl-cyclobutanol
cis-3-[8-Amino-1-(2-methoxy-4-phenoxy-phenyl)-imidazo[1,5-a]pyrazin-3-yl]-1-methyl-cyclobutanol
cis-3-[8-Amino-1-(4-benzyl-phenyl)-imidazo[1,5-a]pyrazin-3-yl]-1-methyl-cyclobutanol
cis-3-[8-Amino-1-(3-methyl-4-phenoxy-phenyl)-imidazo[1,5-a]pyrazin-3-yl]-1-methyl-cyclobutanol
cis-3-{8-Amino-1-[4-(tetrahydro-pyran-2-ylsulfanyl)-phenyl]-imidazo[1,5-a]pyrazin-3-yl}-1-methyl-cyclobutanol
cis-{-4-[8-Amino-3-(3-hydroxy-3-methyl-cyclobutyl)-imidazo[1,5-a]pyrazin-1-yl]-phenyl}-(tetrahydro-pyran-2-yl)-methanone
cis-3-[8-Amino-1-(3-methoxy-4-o-tolyloxy-phenyl)-imidazo[1,5-a]pyrazin-3-yl]-1-methyl-cyclobutanol
cis-3-{8-Amino-1-[4-(3-fluoro-phenoxy)-3-methoxy-phenyl]-imidazo[1,5a]pyrazin-3-yl}-1-methyl-cyclobutanol
cis-3-[8-Amino-1-(3-methoxy-4-m-tolyloxy-phenyl)-imidazo[1,5-a]pyrazin-3-yl]-1-methyl-cyclobutanol
cis-3-{8-Amino-1-[4-(2-fluoro-6-methoxy-phenoxy)-phenyl]-imidazo[1,5-a]pyrazin-3-yl}-1-methyl-cyclobutanol
cis-3-[8-Amino-1-(3,5-dimethoxy-4-phenoxy-phenyl)-imidazo[1,5-a]pyrazin-3-yl]-1-methyl-cyclobutanol cis-3-[8-Amino-1-(3-chloro-5-methyl-4-phenoxy-phenyl)-imidazo[1,5-a]pyrazin-3-yl]-1-methyl-cyclobutanol
cis-{4-[8-Amino-3-(3-hydroxy-3-methyl-cyclobutyl)-imidazo[1,5-a]pyrazin-1-yl]-2-fluoro-phenyl}-phenyl-methanone
cis-3-{8-Amino-1-[4-(1-hydroxy-1-phenyl-ethyl)-phenyl]-imidazo[1,5-a]pyrazin-3-yl}-1-methyl-cyclobutanol
cis-{4-[8-Amino-3-(3-hydroxy-3-methyl-cyclobutyl)-imidazo[1,5-a]pyrazin-1-yl]-2-methoxy-phenyl}-phenyl-methanone
cis-3-[8-Amino-1-(2,3-difluoro-4-phenoxy-phenyl)-imidazo[1,5-a]pyrazin-3-yl]-1-methyl-cyclobutanol
cis-{4-[8-Amino-3-(3-hydroxy-3-methyl-cyclobutyl)-imidazo[1,5-a]pyrazin-1-yl]-3-fluoro-phenyl}-phenyl-methanone
cis-3-[8-Amino-1-(5-methoxy-2-methyl-4-phenoxy-phenyl)-imidazo[1,5-a]pyrazin-3-yl]-1-methyl-cyclobutanol
cis-{4-[8-Amino-3-(3-hydroxy-3-methyl-cyclobutyl)-imidazo[1,5-a]pyrazin-1-yl]-2-nitro-phenyl}-phenyl-methanone
cis-{4-[8-Amino-3-(3-hydroxy-3-methyl-cyclobutyl)-imidazo[1,5-a]pyrazin-1-yl]-naphthalen-1-yl}-phenyl-methanone
cis-{4-[8-Amino-3-(3-hydroxy-3-methyl-cyclobutyl)-imidazo[1,5-a]pyrazin-1-yl]-2-chloro-phenyl}-phenyl-methanone
cis-3-[8-Amino-1-(3-nitro-4-phenoxy-phenyl)-imidazo[1,5-a]pyrazin-3-yl]-1-methyl-cyclobutanol
cis-3-{8-Amino-1-[3-fluoro-4-(2,2,2-trifluoro-ethoxy)-phenyl]-imidazo[1,5-a]pyrazin-3-yl}-1-methyl-cyclobutanol
cis-{4-[8-Amino-3-(3-hydroxy-3-methyl-cyclobutyl)-imidazo[1,5-a]pyrazin-1-yl]-phenyl}-phenyl-methanone oxime
cis-3-{8-Amino-1-[4-(tetrahydro-furan-2-ylmethyl)-phenyl]-imidazo[1,5-a]pyrazin-3-yl}-1-methyl-cyclobutanol
cis-3-{8-Amino-1-[4-(difluoro-phenyl-methyl)-phenyl]-imidazo[1,5-a]pyrazin-3-yl}-1-methyl-cyclobutanol
cis-N-{5-[8-Amino-3-(3-hydroxy-3-methyl-cyclobutyl)-imidazo[1,5-a]pyrazin-1-yl]-2-phenoxy-phenyl}-formamide
cis-3-(8-Amino-1-{4-[1-(3-fluoro-phenyl)-1-hydroxy-ethyl]-phenyl}-imidazo[1,5-a]pyrazin-3-yl)-1-methyl-cyclobutanol
cis-3-[8-Amino-1-(2-chloro-4-phenoxy-phenyl)-imidazo[1,5-a]pyrazin-3-yl]-1-methyl-cyclobutanol
cis-3-{8-Amino-1-[2-fluoro-4-(1-hydroxy-1-phenyl-ethyl)-phenyl]-imidazo[1,5-a]pyrazin-3-yl}-1-methyl-cyclobutanol
cis-3-{8-Amino-1-[4-(1-hydroxy-1-phenyl-ethyl)-2-methyl-phenyl]-imidazo[1,5-a]pyrazin-3-yl}-1-methyl-cyclobutanol
cis-3-[8-Amino-1-(2-ethyl-4-phenoxy-phenyl)-imidazo[1,5-a]pyrazin-3-yl]-1-methyl-cyclobutanol
cis-3-{8-Amino-1-[4-(1-hydroxy-1-phenyl-ethyl)-2-methoxy-phenyl]-imidazo[1,5-a]pyrazin-3-yl}-1-methyl-cyclobutanol
cis-3-{8-Amino-1-[2-chloro-4-(1-hydroxy-1-phenyl-ethyl)-phenyl]-imidazo[1,5-a]pyrazin-3-yl}-1-methyl-cyclobutanol
cis-{4-[8-Amino-3-(3-hydroxy-3-methyl-cyclobutyl)-imidazo[1,5-a]pyrazin-1-yl]-3-methoxy-phenyl}-phenyl-methanone
cis-{4-[8-Amino-3-(3-hydroxy-3-methyl-cyclobutyl)-imidazo[1,5-a]pyrazin-1-yl]-3-methyl-phenyl}-phenyl-methanone
cis-{4-[8-Amino-3-(3-hydroxy-3-methyl-cyclobutyl)-imidazo[1,5-a]pyrazin-1-yl]-3-chloro-phenyl}-phenyl-methanone
cis-3-[8-Amino-1-(2-ethoxy-4-phenoxy-phenyl)-imidazo[1,5-a]pyrazin-3-yl]-1-methyl-cyclobutanol
cis-3-[8-Amino-1-(4-phenoxy-2-trifluoromethoxy-phenyl)-imidazo[1,5-a]pyrazin-3-yl]-1-methyl-cyclobutanol
cis-{5-[8-Amino-3-(3-hydroxy-3-methyl-cyclobutyl)-imidazo[1,5-a]pyrazin-1-yl]-pyridin-2-yl}-phenyl-methanone
cis-3-{8-Amino-1-[4-(2,6-difluoro-phenoxy)-phenyl]-imidazo[1,5-a]pyrazin-3-yl}-1-methyl-cyclobutanol
1-(4-Phenoxy-phenyl)-3-(1H-pyrazol-3-yl)-imidazo[1,5-a]pyrazin-8-ylamine
1-(4-Phenoxy-phenyl)-3-thiophen-3-yl-imidazo[1,5-a]pyrazin-8-ylamine
3-[4-(2-Diethylamino-ethoxy)-phenyl]-1-(4-phenoxy-phenyl)-imidazo[1,5-a]pyrazin-8-ylamine
1-(4-Phenoxy-phenyl)-3-phenyl-imidazo[1,5-a]pyrazin-8-ylamine
2-[8-Amino-1-(4-phenoxy-phenyl)-imidazo[1,5-a]pyrazin-3-yl]-pyrrole-1-carboxylic acid tert-butyl ester
3-(4-Dimethylaminomethyl-phenyl)-1-(4-phenoxy-phenyl)-imidazo[1,5-a]pyrazin-8-ylamine
4-[8-Amino-1-(4-phenoxy-phenyl)-imidazo[1,5-a]pyrazin-3-yl]-phenol
3-(4-Amino-phenyl)-1-(4-phenoxy-phenyl)-imidazo[1,5-a]pyrazin-8-ylamine
3-(4-Methoxy-phenyl)-1-(4-phenoxy-phenyl)-imidazo[1,5-a]pyrazin-8-ylamine
3-(3-Methoxy-phenyl)-1-(4-phenoxy-phenyl)-imidazo[1,5-a]pyrazin-8-ylamine
3-[8-Amino-1-(4-phenoxy-phenyl)-imidazo[1,5-a]pyrazin-3-yl]-phenol
3-(3-Amino-phenyl)-1-(4-phenoxy-phenyl)-imidazo[1,5-a]pyrazin-8-ylamine
4-[8-Amino-1-(4-phenoxy-phenyl)-imidazo[1,5-a]pyrazin-3-yl]-benzonitrile
3-Furan-2-yl-1-(4-phenoxy-phenyl)-imidazo[1,5-a]pyrazin-8-ylamine
3-Furan-3-yl-1-(4-phenoxy-phenyl)-imidazo[1,5-a]pyrazin-8-ylamine
4-[8-Amino-1-(4-phenoxy-phenyl)-imidazo[1,5-a]pyrazin-3-yl]-3,6-dihydro-2H-pyridine-1-carboxylic acid tert-butyl ester
3-(3-Dimethylaminomethyl-phenyl)-1-(4-phenoxy-phenyl)-imidazo[1,5-a]pyrazin-8-ylamine
3-(4-Dimethylamino-phenyl)-1-(4-phenoxy-phenyl)-imidazo[1,5-a]pyrazin-8-ylamine
3-[3-(2-Dimethylamino-ethoxy)-phenyl]-1-(4-phenoxy-phenyl)-imidazo[1,5a]pyrazin-8-ylamine
3-[4-(2-Dimethylamino-ethoxy)-phenyl]-1-(4-phenoxy-phenyl)-imidazo[1,5a]pyrazin-8-ylamine
3-(3-Dimethylamino-phenyl)-1-(4-phenoxy-phenyl)-imidazo[1,5-a]pyrazin-8-ylamine
3-[4-(4-Methyl-piperazin-1-yl)-phenyl]-1-(4-phenoxy-phenyl)-imidazo[1,5-a]pyrazin-8-ylamine
3-(4-Morpholin-4-yl-phenyl)-1-(4-phenoxy-phenyl)-imidazo[1,5-a]pyrazin-8-ylamine
4-{4-[8-Amino-1-(4-phenoxy-phenyl)-imidazo[1,5-a]pyrazin-3-yl]-pyrazol-1-yl}-piperidine-1-carboxylic acid tert-butyl ester 3-[4-(2-Morpholin-4-yl-ethoxy)-phenyl]-1-(4-phenoxy-phenyl)-imidazo[1,5-a]pyrazin-8-ylamine
1-(4-Phenoxy-phenyl)-3-(1H-pyrrol-3-yl)-imidazo[1,5-a]pyrazin-8-ylamine
1-(4-Phenoxy-phenyl)-3-pyridin-4-yl-imidazo[1,5-a]pyrazin-8-ylamine
3-(1H-Indol-6-yl)-1-(4-phenoxy-phenyl)-imidazo[1,5-a]pyrazin-8-ylamine
4-[8-Amino-1-(4-phenoxy-phenyl)-imidazo[1,5-a]pyrazin-3-yl]-benzoic acid
4-[8-Amino-1-(4-phenoxy-phenyl)-imidazo[1,5-a]pyrazin-3-yl]-benzamide
3-(1H-Indazol-6-yl)-1-(4-phenoxy-phenyl)-imidazo[1,5-a]pyrazin-8-ylamine
1-(4-Phenoxy-phenyl)-3-(1H-pyrazol-4-yl)-imidazo[1,5-a]pyrazin-8-ylamine
3-(1-Methyl-1H-pyrazol-4-yl)-1-(4-phenoxy-phenyl)-imidazo[1,5-a]pyrazin-8-ylamine
3-(2-Amino-phenyl)-1-(4-phenoxy-phenyl)-imidazo[1,5-a]pyrazin-8-ylamine
3-[8-Amino-1-(4-phenoxy-phenyl)-imidazo[1,5-a]pyrazin-3-yl]-benzoic acid
3-[8-Amino-1-(4-phenoxy-phenyl)-imidazo[1,5-a]pyrazin-3-yl]-benzamide
2-[8-Amino-1-(4-phenoxy-phenyl)-imidazo[1,5-a]pyrazin-3-yl]-benzonitrile
3-Cyclobutyl-1-[4-(4-fluoro-phenoxy)-phenyl]-imidazo[1,5-a]pyrazin-8-ylamine
3-Cyclobutyl-1-[2-fluoro-4-(2-fluoro-phenoxy)-phenyl]-imidazo[1,5-a]pyrazin-8-ylamine
3-Cyclobutyl-1-[4-(2-fluoro-phenoxy)-3-methoxy-phenyl]-imidazo[1,5-a]pyrazin-8-ylamine
3-Cyclobutyl-1-(3-methoxy-4-phenylsulfanyl-phenyl)-imidazo[1,5-a]pyrazin-8-ylamine
1-[4-(3-Chloro-phenoxy)-phenyl]-3-cyclobutyl-imidazo[1,5-a]pyrazin-8-ylamine
3-Cyclobutyl-1-[4-(3-methoxy-phenoxy)-phenyl]-imidazo[1,5-a]pyrazin-8-ylamine
3-Cyclobutyl-1-[4-(4-isopropyl-phenoxy)-phenyl]-imidazo[1,5-a]pyrazin-8-ylamine
3-[4-(8-Amino-3-cyclobutyl-imidazo[1,5-a]pyrazin-1-yl)-phenoxy]-benzonitrile
3-Cyclobutyl-1-(4-p-tolyloxy-phenyl)-imidazo[1,5-a]pyrazin-8-ylamine
3-Cyclobutyl-1-(4-o-tolyloxy-phenyl)-imidazo[1,5-a]pyrazin-8-ylamine
3-Cyclobutyl-1-(4-m-tolyloxy-phenyl)-imidazo[1,5-a]pyrazin-8-ylamine
3-Cyclobutyl-1-[4-(3-fluoro-phenoxy)-phenyl]-imidazo[1,5-a]pyrazin-8-ylamine
3-Cyclobutyl-1-[4-(4-methoxy-phenoxy)-phenyl]-imidazo[1,5-a]pyrazin-8-ylamine
3-Cyclobutyl-1-[4-(3-trifluoromethoxy-phenoxy)-phenyl]-imidazo[1,5-a]pyrazin-8-ylamine
3-Cyclobutyl-1-[4-(3-trifluoromethyl-phenoxy)-phenyl]-imidazo[1,5-a]pyrazin-8-ylamine
3-Cyclobutyl-1-[4-(naphthalen-2-yloxy)-phenyl]-imidazo[1,5-a]pyrazin-8-ylamine
1-[4-(Benzo[1,3]dioxol-5-yloxy)-phenyl]-3-cyclobutyl-imidazo[1,5-a]pyrazin-8-ylamine
3-Cyclobutyl-1-[4-(2-fluoro-phenoxy)-phenyl]-imidazo[1,5-a]pyrazin-8-ylamine
1-[4-(4-Chloro-phenoxy)-phenyl]-3-cyclobutyl-imidazo[1,5-a]pyrazin-8-ylamine
3-Cyclobutyl-1-[4-(naphthalen-1-yloxy)-phenyl]-imidazo[1,5-a]pyrazin-8-ylamine
1-[4-(2-Chloro-phenoxy)-phenyl]-3-cyclobutyl-imidazo[1,5-a]pyrazin-8-ylamine
3-Cyclobutyl-1-[4-(2-methoxy-phenoxy)-phenyl]-imidazo[1,5-a]pyrazin-8-ylamine
3-Cyclobutyl-1-[4-(4-trifluoromethoxy-phenoxy)-phenyl]-imidazo[1,5-a]pyrazin-8-ylamine
3-[4-(8-Amino-3-cyclobutyl-imidazo[1,5-a]pyrazin-1-yl)-phenoxy]-benzoic acid methyl ester
3-Cyclobutyl-1-[4-(3-nitro-phenoxy)-phenyl]-imidazo[1,5-a]pyrazin-8-yl-amine
3-Cyclobutyl-1-[4-(3-dimethylamino-phenoxy)-phenyl]-imidazo[1,5-a]pyrazin-8-ylamine
1-{3-[4-(8-Amino-3-cyclobutyl-imidazo[1,5-a]pyrazin-1-yl)-phenoxy]-phenyl}-ethanone
1-[4-(Biphenyl-3-yloxy)-phenyl]-3-cyclobutyl-imidazo[1,5-a]pyrazin-8-ylamine
3-Cyclobutyl-1-[4-(2-methyl-benzothiazol-5-yloxy)-phenyl]-imidazo[1,5-a]pyrazin-8-ylamine
3-Cyclobutyl-1-[4-(3-isopropyl-phenoxy)-phenyl]-imidazo[1,5-a]pyrazin-8-ylamine
3-Cyclobutyl-1-[4-(2-trifluoromethoxy-phenoxy)-phenyl]-imidazo[1,5-a]pyrazin-8-ylamine
3-Cyclobutyl-1-[4-(2-isopropyl-phenoxy)-phenyl]-imidazo[1,5-a]pyrazin-8-ylamine
3-Cyclobutyl-1-[4-(2,3-difluoro-phenoxy)-phenyl]-imidazo[1,5-a]pyrazin-8-ylamine
3-Cyclobutyl-1-[4-(2,6-dimethyl-phenoxy)-phenyl]-imidazo[1,5-a]pyrazin-8-ylamine
3-Cyclobutyl-1-[4-(2-fluoro-6-methoxy-phenoxy)-phenyl]-imidazo[1,5-a]pyrazin-8-ylamine
4-[4-(8-Amino-3-cyclobutyl-imidazo[1,5-a]pyrazin-1-yl)-phenoxy]-phenol
3-Cyclobutyl-1-[4-(pyridin-3-yloxy)-phenyl]-imidazo[1,5-a]pyrazin-8-yl-amine
3-Cyclobutyl-1-(3-fluoro-4-o-tolyloxy-phenyl)-imidazo[1,5-a]pyrazin-8-ylamine
3-Cyclobutyl-1-[3-fluoro-4-(3-fluoro-phenoxy)-phenyl]-imidazo[1,5-a]pyrazin-8-ylamine
3-Cyclobutyl-1-[3-fluoro-4-(2-fluoro-phenoxy)-phenyl]-imidazo[1,5-a]pyrazin-8-ylamine
1-[4-(2-Chloro-phenoxy)-3-fluoro-phenyl]-3-cyclobutyl-imidazo[1,5-a]pyrazin-8-ylamine
3-Cyclobutyl-1-(3-fluoro-4-m-tolyloxy-phenyl)-imidazo[1,5-a]pyrazin-8-ylamine
3-Cyclobutyl-1-(3-fluoro-4-phenylsulfanyl-phenyl)-imidazo[1,5-a]pyrazin-8-ylamine
3-Cyclobutyl-1-(4-phenylsulfanyl-phenyl)-imidazo[1,5-a]pyrazin-8-ylamine
3-Cyclobutyl-1-(2-fluoro-4-phenoxy-phenyl)-imidazo[1,5-a]pyrazin-8-ylamine
3-Cyclobutyl-1-(2-fluoro-4-o-tolyloxy-phenyl)-imidazo[1,5-a]pyrazin-8-ylamine
[4-(8-Amino-3-cyclobutyl-imidazo[1,5-a]pyrazin-1-yl)-3,6-dihydro-2H-pyridin-1-yl]-phenyl-methanone
[4-(8-Amino-3-cyclobutyl-imidazo[1,5-a]pyrazin-1-yl)-3,6-dihydro-2H-pyridin-1-yl]-cyclohexyl-methanone
[4-(8-Amino-3-cyclobutyl-imidazo[1,5-a]pyrazin-1-yl)-3,6-dihydro-2H-pyridin-1-yl]-(2-fluoro-phenyl)-methanone
1-[4-(8-Amino-3-cyclobutyl-imidazo[1,5-a]pyrazin-1-yl)-3,6-dihydro-2H-pyridin-1-yl]-2-phenyl-ethanone
1-(1-Benzenesulfonyl-1,2,3,6-tetrahydro-pyridin-4-yl)-3-cyclobutyl-imidazo[1,5-a]pyrazin-8-ylamine
4-(8-Amino-3-cyclobutyl-imidazo[1,5-a]pyrazin-1-yl)-3,6-dihydro-2H-pyridine-1-carboxylic acid tert-butylester (4-{8-Amino-3-[4-(4-methyl-piperazin-1-yl)-phenyl]-imidazo[1,5-a]pyrazin-1-yl}-2-methoxy-phenyl)-phenyl-methanone
1-{-4-[8-Amino-3-(1H-pyrazol-3-yl)-imidazo[1,5-a]pyrazin-1-yl]-phenyl}-1-phenyl-ethanol
1-(2-Methoxy-4-phenoxy-phenyl)-3-(1H-pyrazol-3-yl)-imidazo[1,5-a]pyrazin-8-ylamine
1-(3-Methoxy-4-phenoxy-phenyl)-3-(1H-pyrazol-3-yl)-imidazo[1,5-a]pyrazin-8-ylamine
trans-4-[8-Amino-1-(4-phenoxy-phenyl)-imidazo[1,5-a]pyrazin-3-yl]-cyclohexanecarboxylic acid amide
trans-4-[8-Amino-1-(4-phenoxy-phenyl)-imidazo[1,5-a]pyrazin-3-yl]-cyclohexanecarboxylic acid methylamide
trans-4-[8-Amino-1-(4-phenoxy-phenyl)-imidazo[1,5-a]pyrazin-3-yl]-cyclohexanecarboxylic acid dimethylamide
trans-{-4-[8-Amino-1-(4-phenoxy-phenyl)-imidazo[1,5-a]pyrazin-3-yl-cyclohexyl}-(4-methyl-piperazin-1-yl)-methanone
trans-4-[8-Amino-1-(4-phenoxy-phenyl)-imidazo[1,5-a]pyrazin-3-yl]-cyclohexanecarboxylic acid
trans-4-[8-Amino-1-(4-phenoxy-phenyl)-imidazo[1,5-a]pyrazin-3-yl]-cyclohexanecarboxylic acid methyl ester
trans-3-(4-Aminomethyl-cyclohexyl)-1-(4-phenoxy-phenyl)-imidazo[1,5-a]pyrazin-8-ylamine
trans-3-(4-Aminomethyl-cyclohexyl)-1-(3-methoxy-4-phenoxy-phenyl)-imidazo[1,5-a]pyrazin-8-ylamine
trans-{4-[8-Amino-1-(3-methoxy-4-phenoxy-phenyl)-imidazo[1,5-a]pyrazin-3-yl]cyclohexylmethyl}-carbamic acid benzyl ester
trans-3-(4-Methylaminomethyl-cyclohexyl)-1-(4-phenoxy-phenyl)-imidazo[1,5-a]pyrazin-8-ylamine
trans-{4-[8-Amino-1-(4-phenoxy-phenyl)-imidazo[1,5-a]pyrazin-3-yl]-cyclohexyl}-methanol
trans-3-(4-Dimethylaminomethyl-cyclohexyl)-1-(4-phenoxy-phenyl)-imidazo[1,5-a]pyrazin-8-ylamine
trans-3-[4-(4-Methyl-piperazin-1-ylmethyl)-cyclohexyl]-1-(4-phenoxy-phenyl)-imidazo[1,5-a]pyrazin-8-ylamine
trans-3-[8-Amino-1-(4-phenoxy-phenyl)-imidazo[1,5-a]pyrazin-3-yl]-cyclobutyl}-methanol
cis-3-(3-Dimethylaminomethyl-cyclobutyl)-1-(4-phenoxy-phenyl)-imidazo[1,5-a]pyrazin-8-ylamine
cis-1-(4-Phenoxy-phenyl)-3-(3-pyrrolidin-1-ylmethyl-cyclobutyl)-imidazo[1,5-a]pyrazin-8-ylamine
cis-3-(3-Aminomethyl-cyclobutyl)-1-(4-phenoxy-phenyl)-imidazo[1,5-a]pyrazin-8-ylamine
trans-3-(3-Dimethylaminomethyl-cyclobutyl)-1-(4-phenoxy-phenyl)-imidazo[1,5-a]pyrazin-8-ylamine
trans-1-(4-Phenoxy-phenyl)-3-(3-pyrrolidin-1-ylmethyl-cyclobutyl)-imidazo[1,5-a]pyrazin-8-ylamine
cis-3-(3-Methyl-cyclobutyl)-1-(4-phenoxy-phenyl)-imidazo[1,5-a]pyrazin-8-ylamine
trans-3-(3-Methyl-cyclobutyl)-1-(4-phenoxy-phenyl)-imidazo[1,5-a]pyrazin-8-ylamine
cis-3-(3-Methoxymethyl-cyclobutyl)-1-(4-phenoxy-phenyl)-imidazo[1,5-a]pyrazin-8-ylamine
1-(4-Benzenesulfinyl-phenyl)-3-cyclobutyl-imidazo[1,5-a]pyrazin-8-ylamine
5-(8-Amino-3-cyclobutylimidazo[1,5-a]pyrazin-1-yl)-2-phenoxybenzonitrile
2-[4-(8-Amino-3-cyclobutylimidazo[1,5-a]pyrazin-1-yl)-phenoxy]-benzonitrile
cis-{-4-[8-Amino-3-(3-hydroxy-cyclobutyl)-imidazo[1,5-a]pyrazin-1-yl]-phenyl}-phenyl-methanone
trans-{4-[8-Amino-3-(4-hydroxymethyl-cyclohexyl)-imidazo[1,5-a]pyrazin-1-yl]-phenyl}-phenyl-methanone
cis-3-{8-Amino-1-[4-(hydroxy-phenyl-methyl)-phenyl]-imidazo[1,5-a]pyrazin-3-yl}-1-methyl-cyclobutanol
cis-3-{8-Amino-1-[4-(hydroxy-phenyl-methyl)-phenyl]-imidazo[1,5-a]pyrazin-3-yl}-cyclobutanol
trans-{4-[8-Amino-3-(4-hydroxymethyl-cyclohexyl)-imidazo[1,5-a]pyrazin-1-yl]-phenyl}-phenyl-methanol
1-[4-(3-Amino-phenoxy)-phenyl]-3-cyclobutyl-imidazo[1,5-a]pyrazin-8-ylamine
1-(3-Amino-4-phenoxy-phenyl)-3-cyclobutyl-imidazo[1,5-a]pyrazin-8-ylamine
cis-3-[8-Amino-1-(3-amino-4-phenoxy-phenyl)-imidazo[1,5-a]pyrazin-3-yl]-1-methyl-cyclobutanol
1-[4-(2-Amino-phenoxy)-phenyl]-3-cyclobutyl-imidazo[1,5-a]pyrazin-8-ylamine
[2-Amino-4-(8-amino-3-cyclobutyl-imidazo[1,5-a]pyrazin-1-yl)-phenyl]-phenyl-methanone
cis-{2-Amino-4-[8-amino-3-(3-hydroxy-3-methyl-cyclobutyl)-imidazo[1,5-a]pyrazin-1-yl]-phenyl}-phenyl-methanone
3-Cyclobutyl-1-[4-(1-phenyl-vinyl)-phenyl]-imidazo[1,5-a]pyrazin-8-ylamine
trans-{4-[4-Amino-5-(4-phenoxy-phenyl)-imidazo[5,1-f][1,2,4]triazin-7-yl]-cyclohexylmethyl}-carbamic acid benzyl ester
trans-4-[4-Amino-5-(4-phenoxy-phenyl)-imidazo[5,1-f][1,2,4]triazin-7-yl]-cyclohexanecarboxylic acid methyl ester
trans-7-(4-Aminomethyl-cyclohexyl)-5-(4-phenoxy-phenyl)-imidazo[5,1-f][1,2,4]triazin-4-ylamine
trans-{4-[4-Amino-5-(4-phenoxy-phenyl)-imidazo[5,1-f][1,2,4]triazin-7-yl]-cyclohexyl}-methanol
trans-N-{4-[4-Amino-5-(4-phenoxy-phenyl)-imidazo[5,1-f][1,2,4]triazin-7-yl]-cyclohexylmethyl}-N',N'-dimethyl-ethane-1,2-diamine
trans-7-(4-Dimethylaminomethyl-cyclohexyl)-5-(4-phenoxy-phenyl)-imidazo[5,1-f][1,2,4]triazin-4-ylamine
trans-2-({4-[4-Amino-5-(4-phenoxy-phenyl)-imidazo[5,1-f][1,2,4]triazin-7-yl]-cyclohexylmethyl}-amino)-ethanol
7-Cyclobutyl-5-(4-phenoxy-phenyl)-imidazo[5,1-f][1,2,4]triazin-4-ylamine
7-Cyclobutyl-5-(3-fluoro-4-phenoxy-phenyl)-imidazo[5,1-f][1,2,4]triazin-4-ylamine
5-(4-Benzyl-phenyl)-7-cyclobutyl-imidazo[5,1-f][1,2,4]triazin-4-ylamine
7-Cyclobutyl-5-[4-(2,6-difluoro-phenoxy)-phenyl]-imidazo[5,1-f][1,2,4]triazin-4-ylamine
7-Cyclobutyl-5-(3-methoxy-4-o-tolyloxy-phenyl)-imidazo[5,1-f][1,2,4]triazin-4-ylamine
7-Cyclobutyl-5-(3-methoxy-4-phenoxy-phenyl)-imidazo[5,1-f][1,2,4]triazin-4-ylamine
[4-(4-Amino-7-cyclobutyl-imidazo[5,1-f][1,2,4]triazin-5-yl)-2-fluoro-phenyl]-phenyl-methanone
[4-(4-Amino-7-cyclobutyl-imidazo[5,1-f][1,2,4]triazin-5-yl)-2-chloro-phenyl]-phenyl-methanone
[4-(4-Amino-7-cyclobutyl-imidazo[5,1-f][1,2,4]triazin-5-yl)-2-methoxy-phenyl]-phenyl-methanone
1-[4-(4-Amino-7-cyclobutyl-imidazo[5,1-f][1,2,4]triazin-5-yl)-phenyl]-1-phenyl-ethanol
[4-(4-Amino-7-cyclobutyl-imidazo[5,1-f][1,2,4]triazin-5-yl)-3-fluoro-phenyl]-phenyl-methanone
[4-(4-Amino-7-cyclobutyl-imidazo[5,1-f][1,2,4]triazin-5-yl)-2-hydroxy-phenyl]-phenyl-methanone
cis-3-[4-Amino-5-(4-phenoxy-phenyl)-imidazo[5,1-f][1,2,4]triazin-7-yl]-1-m ethyl-cyclobutanol cis-3-{4-Amino-5-[4-(1-hydroxy-1-phenyl-ethyl)-phenyl]-imidazo[5,1-f][1,2,4]triazin-7-yl}-1-methyl-cyclobutanol cis-{4-[4-Amino-7-(3-hydroxy-3-methyl-cyclobutyl)-imidazo[5,1-f][1,2,4]triazin-5-yl]-2-fluoro-phenyl}-phenyl-methanone cis-{4-[4-Amino-7-(3-hydroxy-3-methyl-cyclobutyl)-imidazo[5,1-f][1,2,4]triazin-5-yl]-2-methoxy-phenyl}-phenyl-methanone cis-3-[4-Amino-5-(2-methoxy-4-phenoxy-phenyl)-imidazo[5,1-f][1,2,4]triazin-7-yl]-1-methyl-cyclobutanol cis-3-[4-Amino-5-(4-benzyl-phenyl)-imidazo[5,1-f][1,2,4]triazin-7-yl]-1-methyl-cyclobutanol cis-3-[4-Amino-5-(3-fluoro-4-phenoxy-phenyl)-imidazo[5,1-f][1,2,4]triazin-7-yl]-1-methyl-cyclobutanol cis-3-[4-Amino-5-(4-phenylamino-phenyl)-imidazo[5,1-f][1,2,4]triazin-7-yl]-1-methyl-cyclobutanol cis-3-[4-Amino-5-(3-methoxy-4-phenoxy-phenyl)-imidazo[5,1-f][1,2,4]triazin-7-yl]-1-methyl-cyclobutanol; or cis-{4-[4-Amino-7-(3-hydroxy-3-methyl-cyclobutyl)-imidazo[5,1-f][1,2,4]triazin-5-yl]-phenyl}-phenyl-methanone;

or a pharmaceutically acceptable salt thereof.

16. A compound selected from:

cis-3-[8-Amino-1-(3-methoxy-4-phenoxy-phenyl)-imidazo[1,5-a]pyrazin-3-yl]-1-methyl-cyclobutanol cis-3-[8-Amino-1-(3-fluoro-4-phenoxy-phenyl)-imidazo[1,5-a]pyrazin-3-yl]-1-methyl-cyclobutanol cis-3-[8-Amino-1-(2-methoxy-4-phenoxy-phenyl)-imidazo[1,5-a]pyrazin-3-yl]-1-methyl-cyclobutanol cis-3-{8-Amino-1-[4-(1-hydroxy-1-phenyl-ethyl)-phenyl]-imidazo[1,5-a]pyrazin-3-yl}-1-methyl-cyclobutanol cis-3-{8-Amino-1-[4-(1-hydroxy-1-phenyl-ethyl)-phenyl]-imidazo[1,5-a]pyrazin-3-yl}-1-methyl-cyclobutanol cis-3-[8-Amino-1-(2,3-difluoro-4-phenoxy-phenyl)-imidazo[1,5-a]pyrazin-3-yl]-1-methyl-cyclobutanol cis-3-{8-Amino-1-[4-(difluoro-phenyl-methyl)-phenyl]-imidazo[1,5-a]pyrazin-3-yl}-1-methyl-cyclobutanol cis-3-{8-Amino-1-[2-fluoro-4-(1-hydroxy-1-phenyl-ethyl)-phenyl]-imidazo[1,5-a]pyrazin-3-yl}-1-methyl-cyclobutanol cis-3-{8-Amino-1-[4-(1-hydroxy-1-phenyl-ethyl)-2-methoxy-phenyl]-imidazo[1,5-a]pyrazin-3-yl}-1-methyl-cyclobutanol cis-3-{8-Amino-1-[2-chloro-4-(1-hydroxy-1-phenyl-ethyl)-phenyl]-imidazo[1,5-a]pyrazin-3-yl}-1-methyl-cyclobutanol cis-3-[8-Amino-1-(2-ethoxy-4-phenoxy-phenyl)-imidazo[1,5-a]pyrazin-3-yl]-1-methyl-cyclobutanol 1-(4-Phenoxy-phenyl)-3-(1H-pyrazol-3-yl)-imidazo[1,5-a]pyrazin-8-ylamine 3-(4-Amino-phenyl)-1-(4-phenoxy-phenyl)-imidazo[1,5-a]pyrazin-8-ylamine 3-Furan-2-yl-1-(4-phenoxy-phenyl)-imidazo[1,5-a]pyrazin-8-ylamine 3-Furan-3-yl-1-(4-phenoxy-phenyl)-imidazo[1,5-a]pyrazin-8-ylamine 3-[4-(2-Dimethylamino-ethoxy)-phenyl]-1-(4-phenoxy-phenyl)-imidazo[1,5a]pyrazin-8-ylamine 3-[4-(4-Methyl-piperazin-1-yl)-phenyl]-1-(4-phenoxy-phenyl)-imidazo[1,5-a]pyrazin-8-ylamine trans-3-(4-Aminomethyl-cyclohexyl)-1-(4-phenoxy-phenyl)-imidazo[1,5-a]pyrazin-8-ylamine trans-3-(4-Aminomethyl-cyclohexyl)-1-(3-methoxy-4-phenoxy-phenyl)-imidazo[1,5-a]pyrazin-8-ylamine trans-3-(4-Methylaminomethyl-cyclohexyl)-1-(4-phenoxy-phenyl)-imidazo[1,5-a]-pyrazin-8-ylamine trans-3-(4-Dimethylaminomethyl-cyclohexyl)-1-(4-phenoxy-phenyl)-imidazo[1,5-a]pyrazin-8-ylamine; or cis-3-[8-Amino-1-(3-amino-4-phenoxy-phenyl)-imidazo[1,5-a]pyrazin-3-yl]-1-methyl-cyclobutanol;

or a pharmaceutically acceptable salt thereof.

* * * * *